(12) United States Patent
Cremer et al.

(10) Patent No.: US 7,828,858 B2
(45) Date of Patent: Nov. 9, 2010

(54) MIXTURE OF SULFIDE DYES

(75) Inventors: Christian Cremer, Lörrach (DE); Victor Paul Eliu, Lörrach (DE); Beate Fröhling, Grenzach-Wyhlen (DE); Olof Wallquist, Bottmingen (CH)

(73) Assignee: Ciba Corporation, Tarrytown, NY (US)

( * ) Notice: Subject to any disclaimer, the term of this patent is extended or adjusted under 35 U.S.C. 154(b) by 258 days.

(21) Appl. No.: 11/992,929

(22) PCT Filed: Sep. 13, 2006

(86) PCT No.: PCT/EP2006/066325

§ 371 (c)(1), (2), (4) Date: Apr. 1, 2008

(87) PCT Pub. No.: WO2006/136617

PCT Pub. Date: Dec. 28, 2006

(65) Prior Publication Data

US 2009/0100610 A1    Apr. 23, 2009

(30) Foreign Application Priority Data

Oct. 11, 2005    (EP) ................................ 05109445

(51) Int. Cl.
*A61Q 5/10*    (2006.01)
*C07D 277/26*    (2006.01)

(52) U.S. Cl. ........................ 8/405; 8/409; 8/426; 8/432; 8/435; 8/565; 8/566; 8/567; 8/568; 8/570; 8/571; 8/575; 548/169; 132/202; 132/208

(58) Field of Classification Search .................... 8/405, 8/409, 426, 432, 565, 566, 567, 568, 570, 8/571, 575; 132/202, 208; 548/169
See application file for complete search history.

(56) References Cited

U.S. PATENT DOCUMENTS 3,225,025 A * 12/1965 Jeremias et al. ............. 534/745
4,783,393 A    11/1988 Brazas, Jr. et al. .......... 430/270

FOREIGN PATENT DOCUMENTS

EP    0224175    6/1987
WO    2005/097051    10/2005

OTHER PUBLICATIONS

STIC Search Report dated Jun. 21, 2010.*
English Language Abstract of EP 0224175, Jun. 3, 1987.

* cited by examiner

*Primary Examiner*—Eisa B Elhilo
(74) *Attorney, Agent, or Firm*—Mervin G. Wood

(57) ABSTRACT

Disclosed are mixtures of sulfide dyes and dyeing compositions comprising mixtures of sulfide dyes. The dye mixtures are useful for the dyeing of organic materials, such as keratin fibers, preferably human hair.

15 Claims, No Drawings

MIXTURE OF SULFIDE DYES

The present invention relates to mixtures of sulfide dyes, compositions thereof, and to their use for the dyeing of organic materials, such as keratin fibers, wool, leather, silk, cellulose or polyamides, especially keratin-containing fibers, cotton or nylon, and preferably hair, more preferably human hair.

It is known, for example, from WO 95/01772 that cationic dyes can be used for the dyeing of organic material, for example keratin, silk, cellulose or cellulose derivatives, and also synthetic fibers, for example polyamides. Cationic dyes exhibit very brilliant shades. A disadvantage is their unsatisfactory fastness to washing.

The technical problem is to provide dyes that are distinguished by deep dying having good fastness properties with respect to washing, light, shampooing and rubbing.

Accordingly, the present invention relates to a dye composition comprising a mixture of dyes selected from the compounds of formula $$D_1\text{-}(Z_1)_r\text{—}Y_1\text{—}S\text{-}A, \qquad (1)$$

wherein

A is hydrogen; a radical of formula (1a) $*$—S—$Y_2$—$(Z_2)_r$-$D_2$; or a thio ester group of formula (1b)

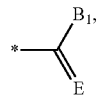

wherein

E is O; S; or N—$R_a$;

$B_1$ is —$OR_b$; —$NR_bR_c$; or —$SR_b$;

$R_a$, $R_b$ and $R_c$, independently from each other are hydrogen; $C_1$-$C_{12}$alkyl; $C_6$-$C_{12}$aryl; or $C_6$-$C_{12}$aryl-$C_1$-$C_{12}$alkyl;

$D_1$ and $D_2$ independently from each other is a radical of formula ($1a_1$)

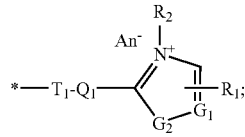

($1a_2$)

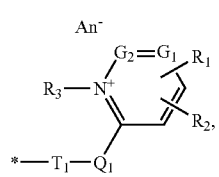

($1a_3$)

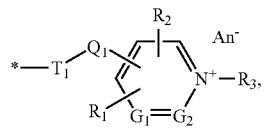

($1a_4$)

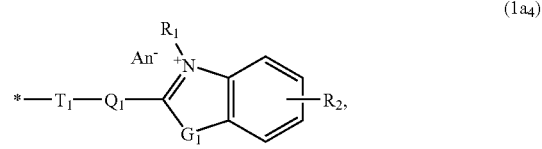

($1a_5$)

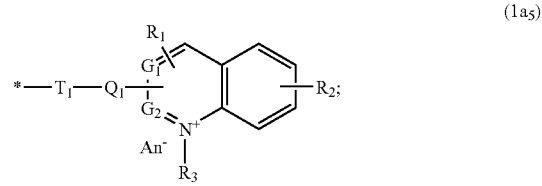

;  ($1a_6$)

($1a_7$)

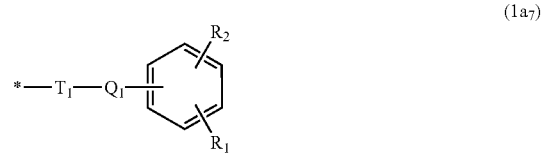

(1b)

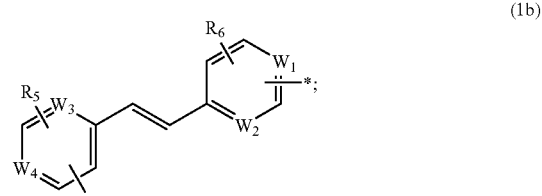

(1c)

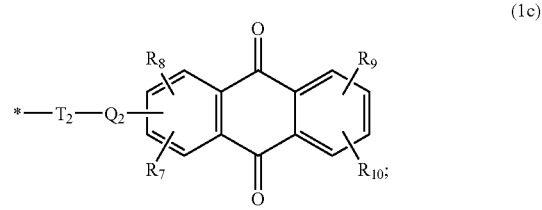

(1d)

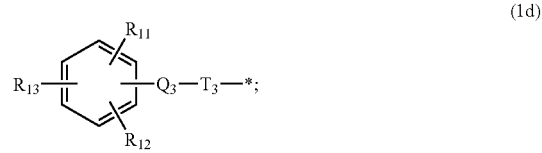

(1e)

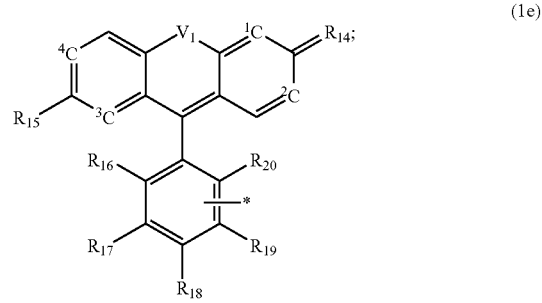

(1f)

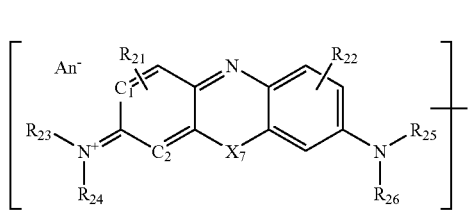

(1g)

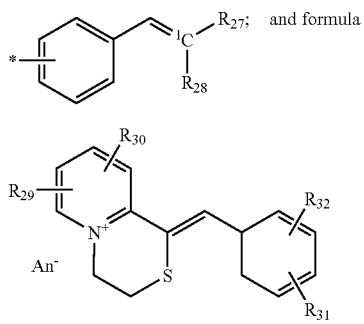

(1h)

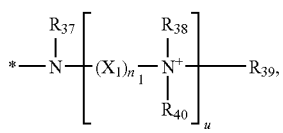

(2)

wherein the mixture comprises at least two compounds of formula (1), and/or at least two compounds of formula (2) and/or at least one compound of formula (1) and at least one compound of formula (2), wherein $R_1$, $R_2$ and $R_3$ independently from each other hydrogen; halogen; $C_1$-$C_{16}$alkyl, which is saturated or unsaturated, linear or branched, substituted or unsubstituted, or interrupted or uninterrupted with heteroatoms; phenyl, which substituted or unsubstituted; a carboxylic acid radical; sulfonic acid radical; hydroxy; nitrile; $C_1$-$C_{16}$alkoxy, (poly)-hydroxy-$C_2$-$C_4$-alkoxy; halogen; $SO_2NR_{33}R_{34}$; $SR_{33}$; $NR_{33}R_{34}$; $OR_{33}$; $SO_2$; $COOR_{33}$; $NR_{33}COR_{34}$; or $CONR_{33}$;

$Q_1$ is a bivalent radical selected from —N=N—; —$CR_d$=N—; —N=$CR_d$—; —$NR_d$—N=$CR_e$—; and —$R_d$C=N—$NR_e$—;

$T_1$ is a bivalent radical of an aromatic or heteroaromatic substituted or unsubstituted compound;

$R_d$ and $R_e$ independently from each other are hydrogen; unsubstituted or substituted $C_1$-$C_{14}$alkyl; $C_2$-$C_{14}$alkenyl; $C_5$-$C_{10}$aryl; $C_1$-$C_{10}$alkyl-$C_5$-$C_{10}$aryl; or $C_5$-$C_{10}$aryl-$C_1$-$C_{10}$alkyl;

$R_{33}$ and $R_{34}$ independently from each other are hydrogen; $C_1$-$C_{12}$alkyl, which may be substituted by one or more $C_1$-$C_5$alkyl, $C_1$-$C_5$-alkoxy, hydroxy or —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$R_4$, $R_5$ and $R_6$ independently from each other are hydrogen; $C_1$-$C_{20}$alkyl or $C_1$-$C_{20}$alkoxy, which may be substituted by one or more $C_1$-$C_5$alkoxy, halogen, —$NH_2$, mono-$C_1$-$C_5$alkylamino, di-$C_1$-$C_5$alkylamino, —$NO_2$ or hydroxy; $C_3$-$C_6$cycloalkyl; —C(O)H; —C(O)—$C_1$-$C_5$alkyl; halogen; $NO_2$; OH; phenyl, which may be substituted by one or more $C_1$-$C_5$alkyl, $C_1$-$C_5$alkoxy, —$NH_2$, mono-$C_1$-$C_5$alkylamino, di-$C_1$-$C_5$alkylamino, —$NO_2$ or hydroxy; or a radical of formula —$NR_{35}R_{36}$;

$W_1$, $W_2$, $W_3$, and $W_4$ independently from each other are —CH— or —N$^+$—; wherein only one of $W_1$, $W_2$, $W_3$ or $W_4$ is —N$^+$—; and the radical *—$(Z_1)_r$—$Y_1$—S-A is bonded to $W_1$ or $W_2$;

$R_{35}$ and $R_{36}$ independently from each other are hydrogen; $C_1$-$C_{12}$alkyl, which may be substituted by one or more $C_1$-$C_5$alkyl, $C_1$-$C_5$-alkoxy, hydroxy or —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$R_7$, $R_8$, $R_9$ and $R_{10}$ independently from each other are hydrogen; $C_1$-$C_{20}$alkyl; $C_1$-$C_{20}$alkoxy; $C_3$-$C_6$cycloalkyl; halogen; $NO_2$; OH; SH; or a radical of formula ($1c_1$)

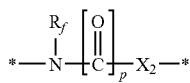

$X_1$ is $C_1$-$C_{18}$alkylene; —(CO)—$C_1$-$C_{18}$alkylene $C_1$-$C_{18}$arylene; $C_6$-$C_{18}$arylene-$C_1$-$C_{12}$alkylene; or —($OCH_2CH_2$)$_{n2}$—O—;

$T_2$ is a radical of formula ($1c_2$);

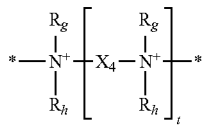

or —O—$(X_3)_s$;

$Q_2$ is a cationic biradical of a saturated, aromatic or heteroaromatic group; or a radical of formula ($1c_3$)

$R_f$, $R_g$ and $R_h$ independently from each other are hydrogen; $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_1$-$C_{10}$alkyl($C_5$-$C_{10}$aryl);

$X_2$, $X_3$ and $X_4$ independently from each other are $C_1$-$C_{18}$alkylene; —(CO)—$C_1$-$C_{18}$alkylene-$C_1$-$C_{18}$arylene; $C_6$-$C_{18}$arylene-$C_1$-$C_{12}$alkylene; or —($OCH_2CH_2$)$_n$—O—;

t is 0; or 1

$R_{37}$ is hydrogen; or $C_1$-$C_{20}$alkyl;

$R_{38}$, $R_{39}$ and $R_{40}$ independently from each other are hydrogen, $C_1$-$C_{20}$alkyl, $C_4$-$C_{12}$cycloalkyl, $C_6$-$C_{13}$aralkyl; phenyl-$C_1$-$C_5$alkyl; or $R_{38}$ and $R_{39}$ together with the linking nitrogen atom form a $C_4$-$C_{12}$-membered heterocyclic ring which may be interrupted by one or more than one —O— or —NH— groups;

$n_1$ is 0 or 1;

p is 0; or 1;

s is 0; or 1;

t is 0; or 1;

u is 0 or 1;

$R_{11}$, $R_{12}$ and $R_{13}$ independently from each other are hydrogen; $C_1$-$C_{20}$alkyl or $C_1$-$C_{20}$alkoxy, which may be substituted by one or more $C_1$-$C_5$alkoxy, halogen, —$NH_2$, mono-$C_1$-$C_5$alkylamino, di-$C_1$-$C_5$alkylamino, —$NO_2$ or hydroxy; $C_3$-$C_6$cycloalkyl; —C(O)H; —C(O)—$C_1$-$C_5$alkyl; —C(O)OH; —C(O)O—$C_1$-$C_5$alkyl; halogen;

NO$_2$; OH; SH; phenyl, which may be substituted by one or more C$_1$-C$_5$alkyl, C$_1$-C$_5$alkoxy, halogen, —NH$_2$, mono-C$_1$-C$_5$alkylamino, di-C$_1$-C$_5$alkylamino, —NO$_2$ or hydroxy; or a radical —NR$_{41}$R$_{42}$;

Q$_3$ is —C(O)—; —C(O)O—; —OCO—; —N(R$_t$)—X$_5$—; —CON(R$_t$)—; —(R$_t$)NC(O)—; —O—; —S—; —S(O)—; or

T$_3$ is the direct bond;

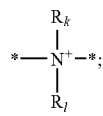

or a cationic biradical of a saturated, aromatic or heteroaromatic group;

R$_t$, R$_k$, R$_l$ independently from each other are C$_1$-C$_{14}$alkyl; C$_2$-C$_{14}$alkenyl; C$_6$-C$_{10}$aryl; C$_6$-C$_{10}$aryl-C$_1$-C$_{10}$alkyl; or C$_1$-C$_{10}$alkyl(C$_5$-C$_{10}$aryl);

R$_{41}$ and R$_{42}$ independently from each other are hydrogen; C$_1$-C$_{12}$alkyl, which may be substituted by one or more C$_1$-C$_5$alkyl, C$_1$-C$_5$-alkoxy, hydroxy or —(CO)—H; —(CO)—C$_1$-C$_5$alkyl; phenyl or phenyl-C$_1$-C$_4$alkyl, wherein the phenyl moiety may be substituted by one or more C$_1$-C$_5$alkyl, C$_1$-C$_5$alkoxy, halogen, —NH$_2$, mono-C$_1$-C$_5$alkylamino, di-C$_1$-C$_5$alkylamino, —NO$_2$, carboxy or hydroxy; or a radical of formula

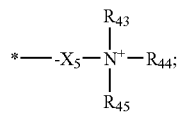

wherein at least one of the radicals R$_{11}$, R$_{12}$ or R$_{13}$ is NO$_2$;

R$_{43}$, R$_{44}$ and R$_{45}$ independently from each other are hydrogen; C$_1$-C$_{14}$alkyl; C$_2$-C$_{14}$alkenyl; C$_6$-C$_{10}$aryl; C$_6$-C$_{10}$aryl-C$_1$-C$_{10}$alkyl; or C$_1$-C$_{10}$alkyl(C$_5$-C$_{10}$aryl);

X$_5$ and X$_6$ independently from each other are the direct bond; C$_1$-C$_{10}$alkylene; C$_5$-C$_{10}$cycloalkylene; C$_5$-C$_{10}$arylene; or C$_5$-C$_{10}$arylene-(C$_1$-C$_{10}$alkylene);

R$_{14}$ is N+R$_{46}$R$_{47}$;

R$_{46}$ and R$_{47}$ independently from each other are hydrogen; C$_1$-C$_{12}$alkyl; or phenyl-C$_1$-C$_4$alkyl; or R$_{46}$ and/or R$_{47}$ are a bivalent C$_3$-C$_6$alkylene radical which is linked to the carbon atoms C$^1$ or C$^2$ in formula (1e) respectively and, together with the linking nitrogen atom form a 6 to 16-membered carbocyclic ring;

R$_{15}$ is NR$_{48}$R$_{49}$; or OR$_{48}$;

R$_{48}$ and R$_{49}$, independently from each other are hydrogen; C$_1$-C$_{12}$alkyl; or phenyl-C$_1$-C$_4$alkyl; or R$_{48}$ and R$_{49}$ are a bivalent C$_3$-C$_6$alkylene radical which is linked to the carbon atoms C$^3$ or C$^4$ in formula (1e) respectively and, together with the linking nitrogen or oxygen atom form a 6 to 16-membered carbocyclic ring; or R$_{48}$ and R$_{49}$ together with the linking nitrogen atom form a 4 to 8 membered carbocyclic ring;

R$_{16}$, R$_{17}$, R$_{18}$, R$_{19}$ and R$_{20}$ independently form each other are hydrogen; C$_1$-C$_{12}$alkyl; halogen; NR$_5$OR$_{51}$; or a radical of formula (1e$_1$)

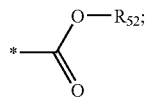

R$_{50}$ and R$_{51}$ independently from each other are hydrogen; C$_1$-C$_{12}$alkyl; phenyl-C$_1$-C$_4$alkyl; or a radical of formula (1e$_2$)

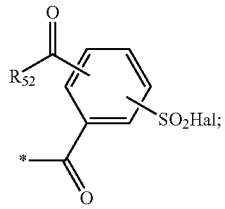

V$_1$ is —O—; or —NR$_{53}$;

R$_{52}$ and R$_{53}$ independently from each other are hydrogen; or C$_1$-C$_5$alkyl;

Hal is a halogen atom; and wherein at least one of R$_{16}$, R$_{17}$, R$_{18}$, R$_{19}$ and R$_{20}$ is hydrogen;

B$_2$ and B$_3$, independently from each other are C$_6$-C$_{10}$aryl; or a 5-7-membered heterocyclic compound, which may be substituted by C$_1$-C$_{12}$alkyl, C$_1$-C$_{12}$alkoxy, phenyl, hydroxy, halogen, sulfonic acid, carboxylate, or by the radical —NR$_{54}$R$_{55}$ or —OR$_{56}$;

B$_4$ is C$_6$-C$_{10}$arylene, or a bivalent radical of a 5-7-membered heterocyclic compound, which may be substituted by C$_1$-C$_{12}$alkyl, C$_1$-C$_{12}$alkoxy, phenyl, hydroxy, halogen, sulfonic acid, carboxylate, or by the radical —NR$_{54}$R$_{55}$ or —OR$_{56}$;

R$_{54}$ R$_{55}$ and R$_{56}$ independently from each other are hydrogen; or C$_1$-C$_{12}$alkyl, which may be substituted by hydroxy or C$_6$-C$_{10}$aryl; or R$_{54}$ and R$_{55}$ together with the linking nitrogen atom form a 5 to 7 membered heterocyclic ring; or R$_{55}$ and R$_{56}$ together with the linking nitrogen atom form a piperidine ring of

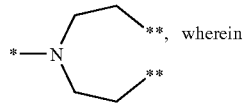

formul (1f$_1$)

the asterix (*) is directed to Z$_1$ or Z$_2$ respectively; and the asterix (**) is directed to the linking nitrogen atom;

R$_{21}$ and R$_{22}$ independently from each other are hydrogen; C$_1$-C$_{20}$alkyl; C$_1$-C$_{20}$alkoxy; C$_3$-C$_6$cycloalkyl; C$_5$-C$_{10}$aryl; anellated aromatic groups; carboxylate; or sulfonate groups;

R$_{23}$, R$_{24}$ R$_{25}$ and R$_{26}$ each independently from each other are hydrogen; unsubstituted or substituted, straight-chain or branched, monocyclic or polycyclic, interrupted or uninterrupted C$_1$-C$_{14}$alkyl, C$_2$-C$_{14}$alkenyl, C$_6$-C$_{10}$aryl, C$_6$-C$_{10}$aryl-C$_1$-C$_{10}$alkyl or C$_5$-C$_{10}$alkyl(C$_5$-C$_{10}$aryl); or R$_{23}$ and R$_{24}$ and/or R$_{25}$ and R$_{26}$ together with the linking nitrogen atom form a 5 to 7 membered carbocyclic ring which may contain one or more than one hetero atom; or $R_{23}$ is linked to $C_1$ together with N+forming a 5-7 membered carbocyclic ring; or $R_{24}$ is linked to $C_2$ together with N+forming a 5-7 membered carbocyclic ring;

$X_7$ is —O—; or —N($R_{24}$)—; or —S—;

$R_{27}$ is hydrogen; or $C_1$-$C_5$alkyl;

$R_{28}$ is a radical of formula ($1g_1$)

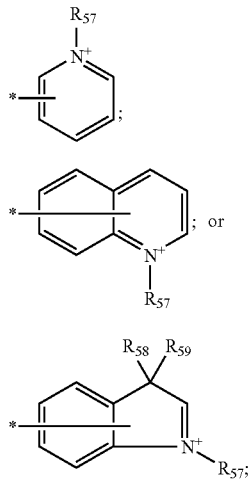

or $R_{27}$ and $R_{28}$ together with the linking carbon atom $^1C$ form a 6 to 10 membered carbocyclic ring which may optionally be a condensated aromatic system and may contain one or more than one hetero atom;

$R_{57}$, $R_{58}$ and $R_{59}$ independently from each other are hydrogen; or $C_1$-$C_5$alkyl;

$R_{29}$, $R_{30}$, $R_{31}$ and $R_{32}$ independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; —$NR_{69}R_{70}$; —$NO_2$; —(CO)H or (CO)—$C_1$-$C_5$alkyl; $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl; —$NR_{69}R_{70}$; —$NO_2$; —(CO)—H; or —(CO)—$C_1$-$C_5$alkyl;

$R_{69}$ and $R_{70}$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; phenyl or phenyl-$C_1$-$C_5$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$Y_1$ and $Y_2$ independently from each other are unsubstituted or substituted, straight-chain or branched, interrupted or uninterrupted $C_1$-$C_{10}$alkylene; $C_5$-$C_{10}$cycloalkylene; $C_5$-$C_{10}$arylene; or —$C_5$-$C_{10}$arylene-($C_1$-$C_{10}$alkylene);

$Z_1$ and $Z_2$ independently from each other are *—($CH_2$)$_q$—C(O)—**; *—($CH_2CH_2$—O)$_w$—**; *—($CH_2$)$_q$—C(O)O—**; *—($CH_2$)$_q$—OCO—**; *—($CH_2$)$_q$—N($R_{60}$)—**;

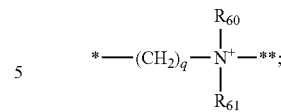

*—($CH_2$)$_q$—CON($R_{60}$)—**; *—($CH_2$)$_q$—($R_{60}$)NC(O)—; —O—; —S—; —S(O)—; —S(O)$_2$—; or a cationic biradical of a substituted or unsubstituted aromatic or heteroaromatic compound of the formula (1a)

(1b)

(1c)

(1d)

(1e)

$G_1$ and $G_2$ independently from each other are N; —O—; —S—; or a radical of $CR_{64}$;

the asterix * indicates the linkage to $D_1$ and/or $D_2$;

the asterix ** indicates the linkage to $Y_1$ and/or $Y_2$ $R_{60}$, $R_{61}$, $R_{62}$, $R_{63}$ and $R_{64}$ independently from each other are hydrogen; $C_1$-$C_{14}$alkyl; $C_2$-$C_{14}$alkenyl; $C_6$-$C_{10}$aryl; $C_5$-$C_{10}$aryl-($C_1$-$C_{10}$alkyl); or —$C_1$-$C_{10}$alkyl($C_5$-$C_{10}$aryl);

$R_{29}$, $R_{30}$, $R_{31}$ and $R_{32}$ independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; —$NR_{65}R_{66}$; —$NO_2$; —(CO)H or (CO)—$C_1$-$C_5$alkyl; $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl; —$NR_{67}R_{68}$; —$NO_2$; —(CO)—H; or —(CO)—$C_1$-$C_5$alkyl;

$R_{65}$, $R_{66}$, $R_{67}$ and $R_{68}$ independently from each other are hydrogen; hydroxy; $C_1$-$C_{12}$alkyl; hydroxy-$C_1$-$C_{12}$alkyl;

—(CO)—H; —(CO)—C$_1$-C$_5$alkyl; phenyl or phenyl-C$_1$-C$_5$alkyl, wherein the phenyl moiety may be substituted by one or more C$_1$-C$_5$alkyl, C$_1$-C$_5$alkoxy, halogen, —NH$_2$, mono-C$_1$-C$_5$alkylamino, di-C$_1$-C$_5$alkylamino, —NO$_2$, carboxy or hydroxy;

q is a number from 0 to 5;

w is a number from one to 5;

r is 0; or 1; and

An is an anion.

C$_1$-C$_{12}$alkyl is for example, methyl, ethyl, propyl, isopropyl, n-butyl, sec-butyl, tert-butyl, n-pentyl, 2-pentyl, 3-pentyl, 2,2'-dimethylpropyl, cyclopentyl, cyclohexyl, n-hexyl, n-octyl, 1,1',3,3'-tetramethylbutyl or 2-ethylhexyl, nonyl, decyl.

C$_1$-C$_{12}$alkylene is for example methylene, ethylene, propylene, isopropylene, n-butylene, sec-butylene, tert-butylene, n-pentylene, 2-pentylene, 3-pentylene or 2,2'-dimethylpropylene, n-hexylene, n-octylene, 1,1',3,3'-tetramethylbutylene, 2-ethylhexylene, nonylene, decylene, undecylene or dodecylene.

Alkylene may be straight-chain, branched, or, from C$_5$alkyl upwards, monocyclic or polycyclic, and may be interrupted by hetero atoms, such as such as O, S, —CO—, N, NH, NR$_{54}$, —OCO—, —CO(OR$_4$)—, —CONR$_4$—, —(R$_5$)NC(O)—; for example C$_1$-C$_{10}$alkylene may be a residue such as: —CH$_2$CH$_2$—O—CH$_2$CH$_2$—O—CH$_2$CH$_2$—, —CH$_2$CH$_2$—O—CH$_2$CH$_2$—, —CH$_2$CH$_2$—O—CH$_2$—, —CH$_2$—O—CH$_2$—, —CH$_2$CH$_2$—CH$_2$CH$_2$—O—CH$_2$—CH$_2$—, —CH$_2$CH$_2$—CH(N(CH$_3$)$_2$)—CH$_2$—CH$_2$—, CH$_2$—NH$_2$—CH$_2$—CH$_2$—, —CH$_2$CH$_2$—NH—CH$_2$CH$_2$—, —CH$_2$CH$_2$—NCH$_3$—CH$_2$CH$_2$—, —CO—CH$_2$—, —CH$_2$CO—, —CH$_2$CH$_2$—NHCO—CH$_2$CH$_2$—, —CH$_2$CH$_2$—CONH—CH$_3$—CH$_2$CH$_2$—, —CH$_2$CH$_2$—NCH$_3$CO—CH$_2$CH$_2$—, —CH$_2$CH$_2$—CONCH$_3$—CH$_3$CH$_2$CH$_2$—, —CH$_2$—NHCO—CH$_2$CH$_2$—, —CH$_2$CH$_2$—NHCO—CH$_2$—, —CH$_2$CH$_2$—CONH—CH$_2$— or —CH$_2$—CONH—CH$_2$CH$_2$—.

C$_5$-C$_{10}$cycloalkylene is for example cyclopentylene, cyclohexylene, cycloheptylene, cyclooctylene, cyclononylene or cyclodecylene.

C$_5$-C$_{10}$arylene is for example phenylene or naphthylene.

Aryl-alkylene is for example C$_5$-C$_{10}$aryl-C$_1$-C$_{10}$alkylene.

Alkyl-arylene is for example C$_1$-C$_{10}$alkyl-C$_5$-C$_{10}$arylene.

Preferred is a dye mixture, wherein in formula (1) Y$_1$ and Y$_2$ are C$_1$-C$_5$alkylene.

Furthermore, a composition is preferred, wherein in formula (1)

Z$_1$ and Z$_2$ independently from each are other —N(R$_{60}$)—;

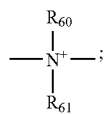

—CON(R$_{60}$)—;—(CH$_2$)$_q$NC(O)—; —O—; or —S—; and

R$_{60}$ R$_{61}$ and q are defined as in formula (1).

Preferred is a composition, wherein D$_1$ is a radical of a cationic aromatic substituted or unsubstituted heterocyclic compound of formulae Preferably, D$_1$ and D$_2$ independently from each other are a radical of formula

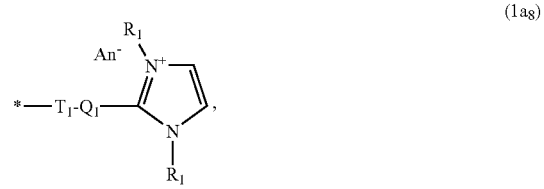

(1a$_8$)

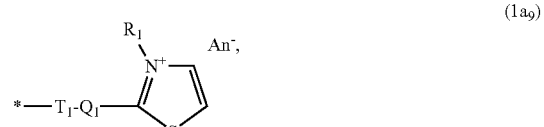

(1a$_9$)

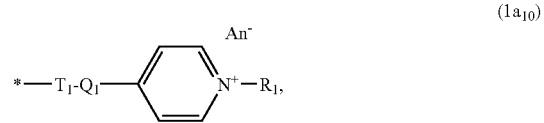

(1a$_{10}$)

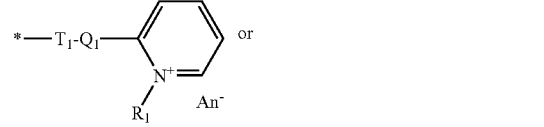

(1a$_{11}$)

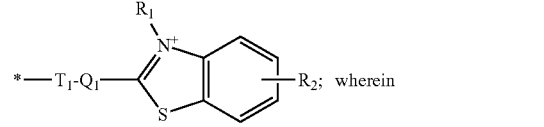

(1a$_{12}$)

R$_2$; wherein

R$_1$, R$_2$, Q$_1$ and T$_1$ independently from each other are defined as in formula (1).

T$_1$ is preferably a bivalent radical of formulae

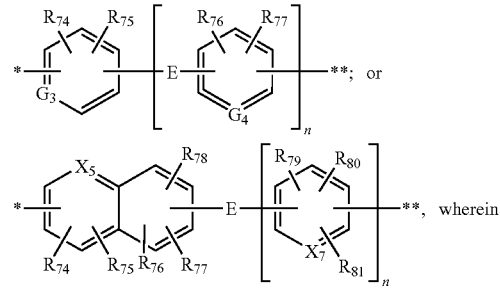

the asterix * indicates the bond to Q$_1$;

the asterix ** indicates the bond to D$_1$; and the heteroaromatic cycles of these radicals may be interrupted by one or more than one —O—, —S—, —(SO$_2$)—, —C$_1$-C$_{10}$alkylene or —(NR$_{82}$)—;

are independently from each other hydrogen; halogen; C$_1$-C$_{14}$alkyl, which is saturated or unsaturated, linear or branched, substituted or unsubstituted, or interrupted or uninterrupted with heteroatoms; a radical of phenyl, which substituted or unsubstituted; a of carboxylic acid radical; sulfonic acid radical; hydroxy; nitrile; C$_1$-C$_{16}$alkoxy, (poly)-hydroxy-C$_2$-C$_4$-alkoxy; halogen; SO$_2$NR$_{33}$R$_{34}$; SR$_{83}$, NR$_{83}$R$_{84}$; OR$_{831}$; SO$_2$; COOR$_{83}$; NR$_{83}$COR$_{84}$; or CONR$_{83}$; and R$_{74}$, R$_{75}$, R$_{76}$, R$_{77}$, R$_{78}$, R$_{79}$, R$_{80}$, R$_{81}$, R$_{82}$ and R$_{83}$ and R$_{84}$ are each independently of the other hydrogen; unsubstituted or substituted C$_1$-C$_{14}$alkyl, C$_2$-C$_{14}$alkenyl, C$_5$-C$_{10}$aryl, C$_5$-C$_{10}$aryl-(C$_1$-C$_{10}$alkyl), or —C$_1$-C$_{10}$alkyl(C$_5$-C$_{10}$aryl).

More preferably, the dyes are selected from the compounds of formula

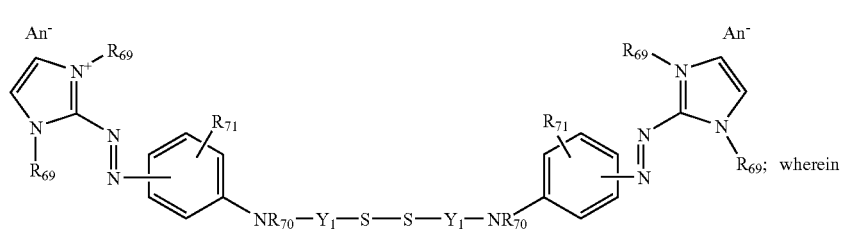
(AZO-01)

$R_{69}$, $R_{70}$, $R_{72}$ and $R_{73}$ independently from each other are hydrogen; unsubstituted or substituted $C_1$-$C_{14}$alkyl; $C_5$-$C_{10}$cycloalkyl; $C_2$-$C_{14}$alkenyl; $C_5$-$C_{10}$aryl-($C_1$-$C_{10}$alkyl); $C_1$-$C_{10}$alkyl-($C_5$-$C_{10}$aryl); $C_5$-$C_{10}$aryl;
$R_{71}$ is hydrogen; or a radical of formula (2a)

An is an anion; and
$Y_1$ is defined as in formula (1).

More preferably, the dyes are selected from the compounds of formula

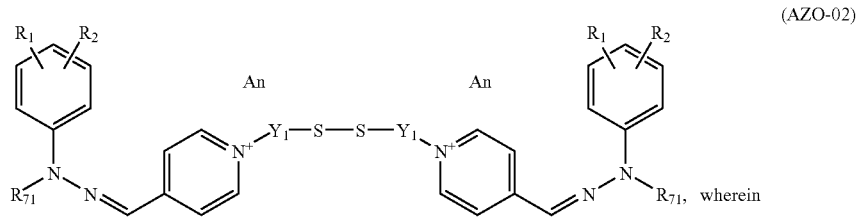
(AZO-02)

More preferably, the dyes are selected from the compounds of formula (AZO-03)

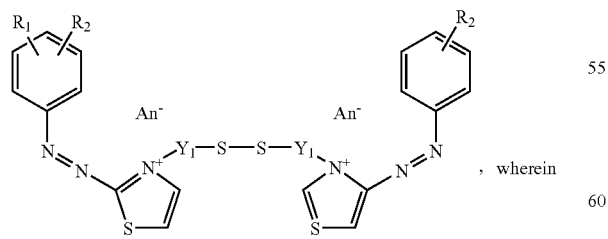

$R_1$ and $R_2$ independently from each other are hydrogen; unsubstituted or substituted $C_1$-$C_{14}$alkyl; $C_5$-$C_{10}$cycloalkyl; $C_2$-$C_{14}$alkenyl; $C_5$-$C_{10}$aryl; $C_1$-$C_{10}$alkyl-($C_5$-$C_{10}$aryl); $C_5$-$C_{10}$aryl-($C_1$-$C_{10}$alkyl).

Examples for dyes of formula (1), wherein $D_1$ and $D_2$ are selected from the radicals of formula $(1a_1)$-$(1a_7)$ are:
AZO-04
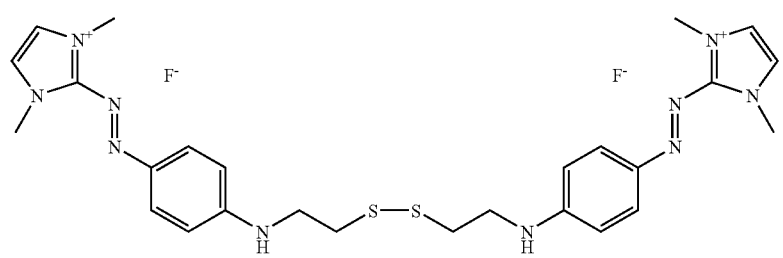
AZO-05
AZO-06
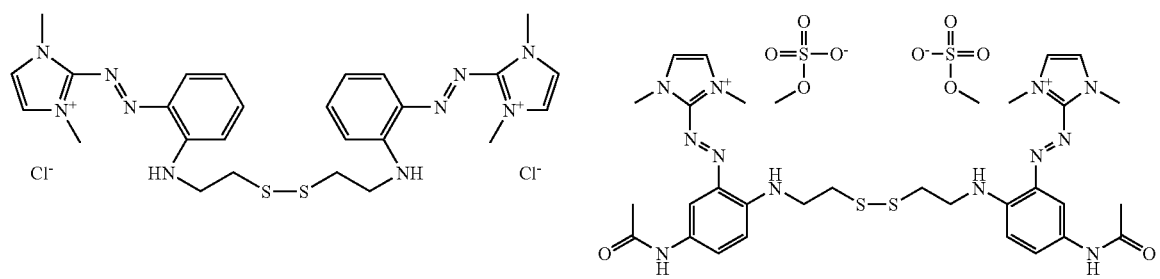
AZO-07
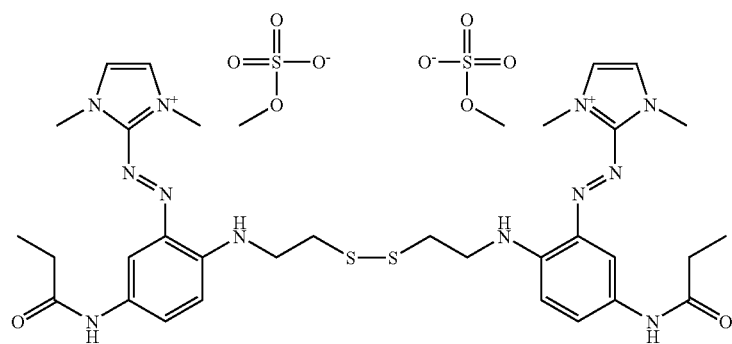
AZO-08
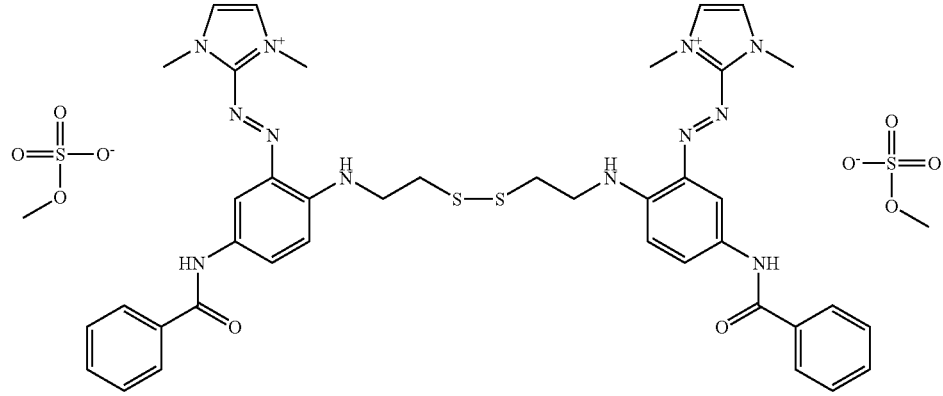

-continued
AZO-09
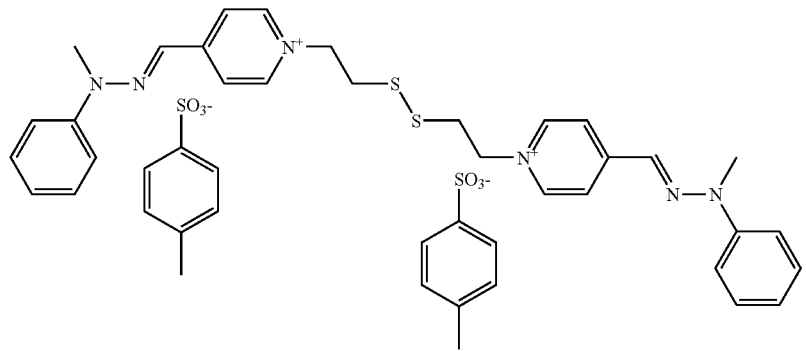
AZO-10
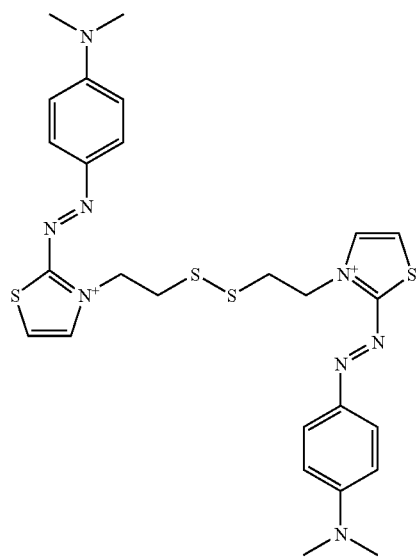
AZO-11
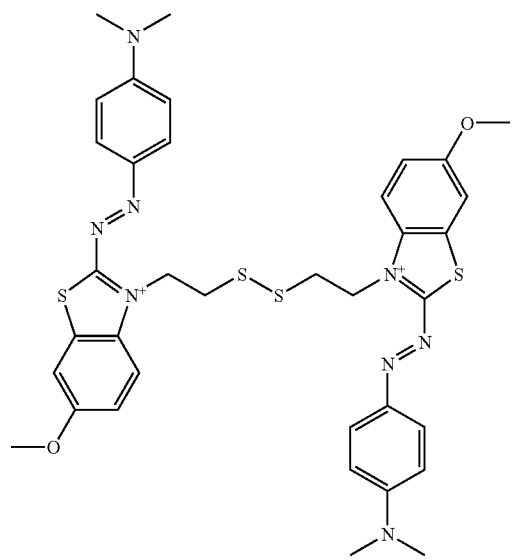
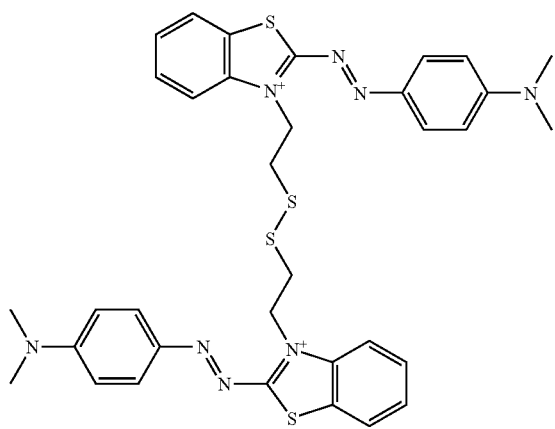
AZO-12
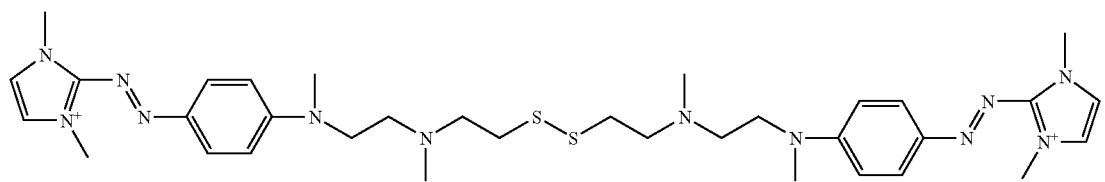
AZO-13

-continued
AZO-14
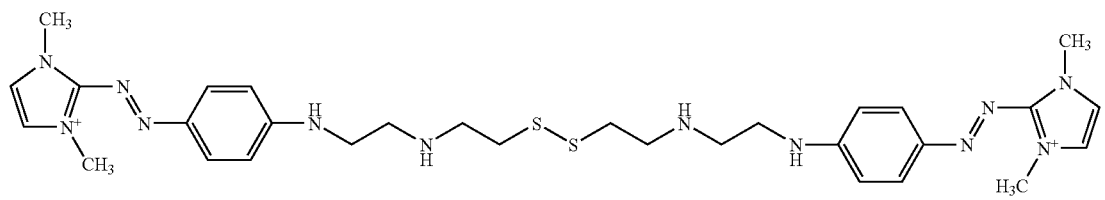
AZO-15
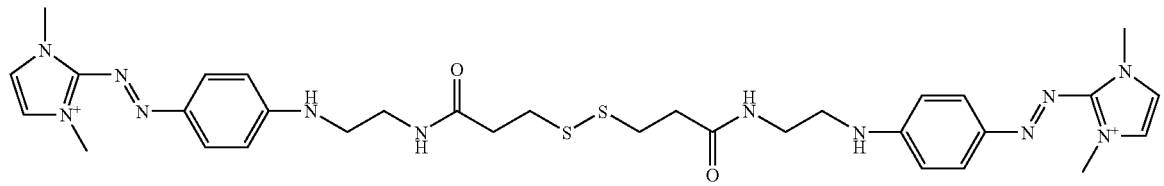
AZO-16
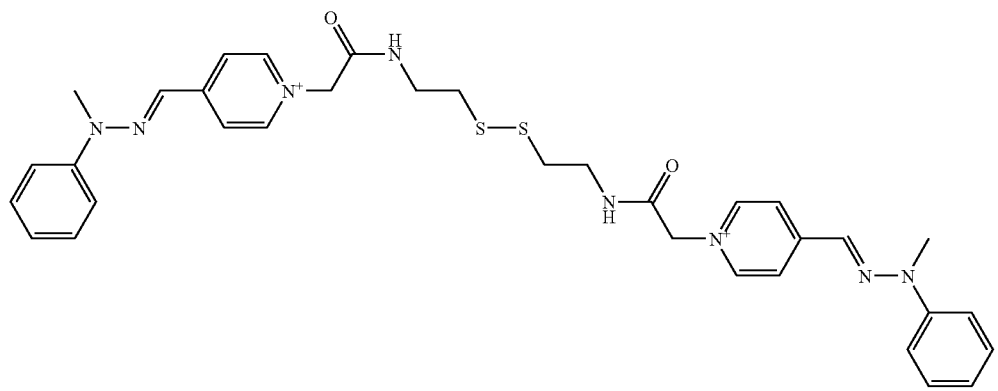
AZO-17
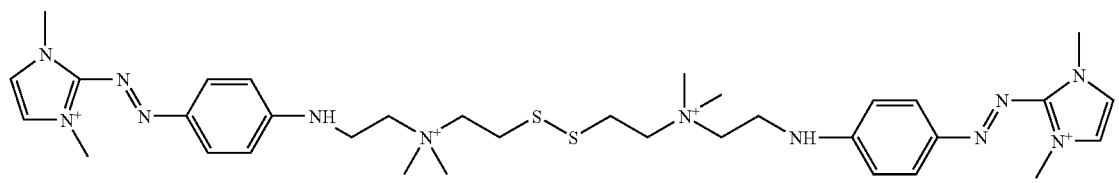
AZO-18
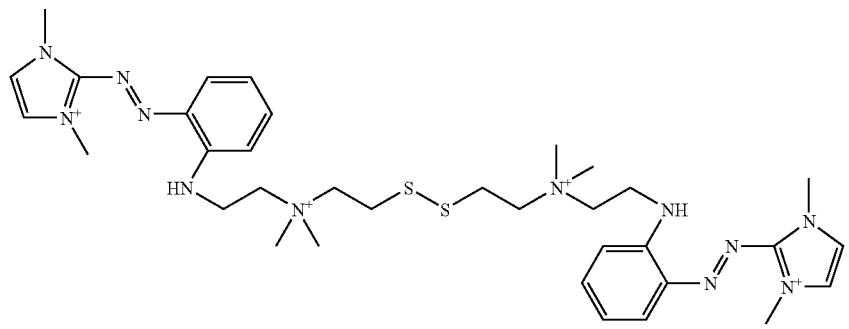

-continued
AZO-19
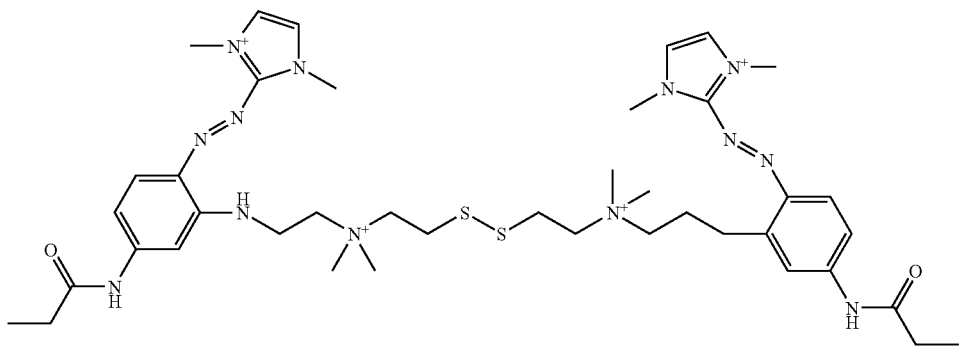
Further preferred dyes are selected from the compounds of formula
(STY-01)
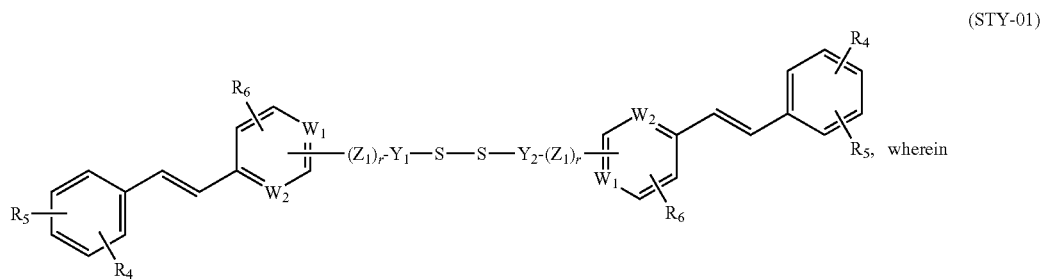
wherein
one of $W_1$ or $W_2$ is —N+— the other is —CH; and
the biradical *—$(Z_1)_r$—$Y_1$—S—S—$Y_2$—$(Z_1)_r$—* is bonded to —N+; and
$R_4$, $R_5$, $R_6$, $Y_1$, $Y_2$, $Z_1$ and r are defined as in formula (1).
Preferred are also dyes of formula
(STY-02)
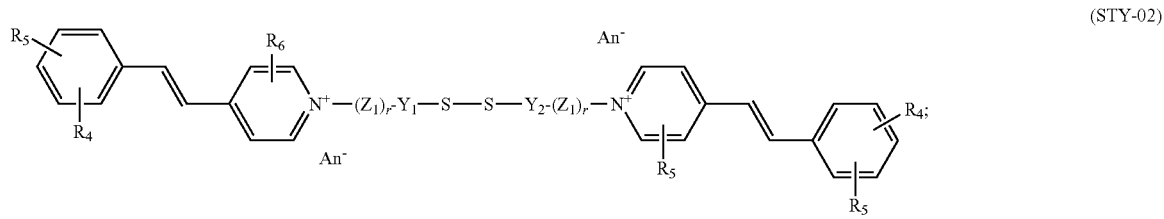
(STY-03)
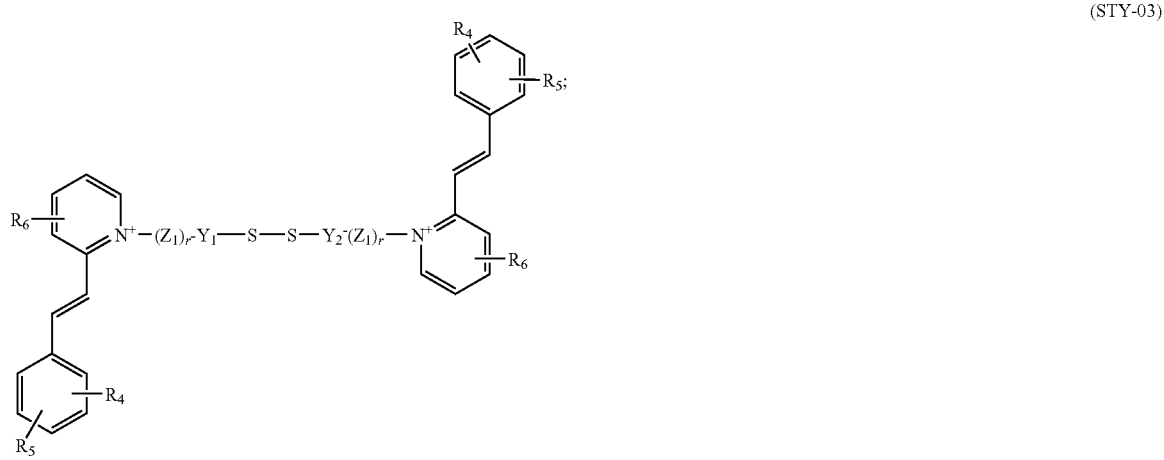

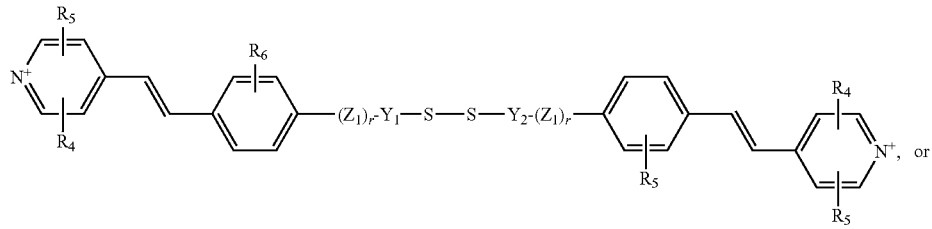
(STY-04)
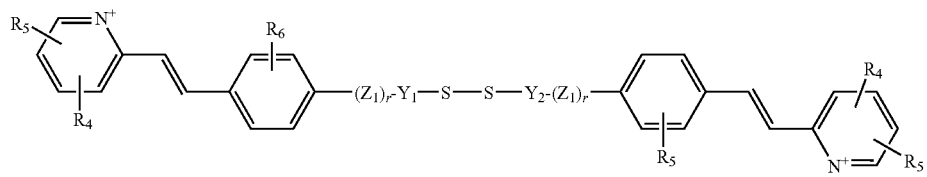
(STY-05)
wherein
$R_4, R_5, R_6, Z_1, Y_1, Y_2$, An and r are defined as in formula (1).
Examples for dyes of formula (1), wherein $D_1$ and $D_2$ are selected from the radicals of formula (1b) are:
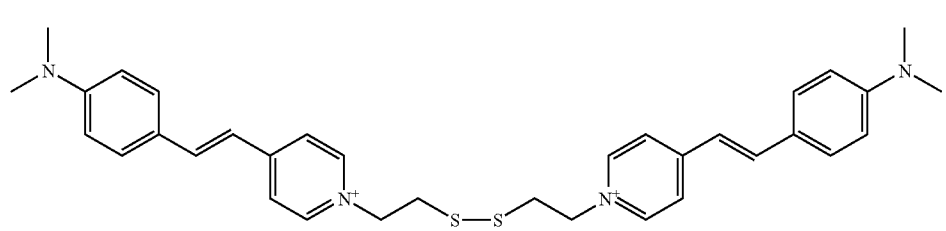
(STY-06)
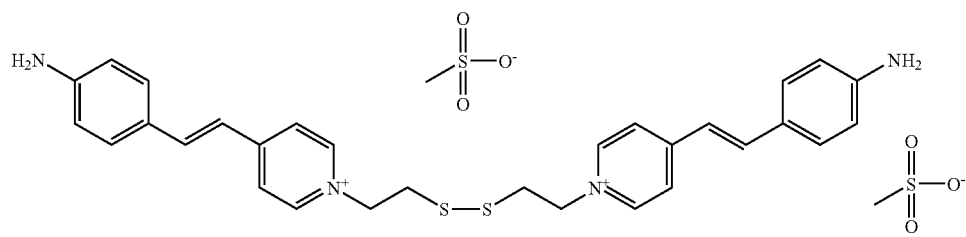
(STY-07)
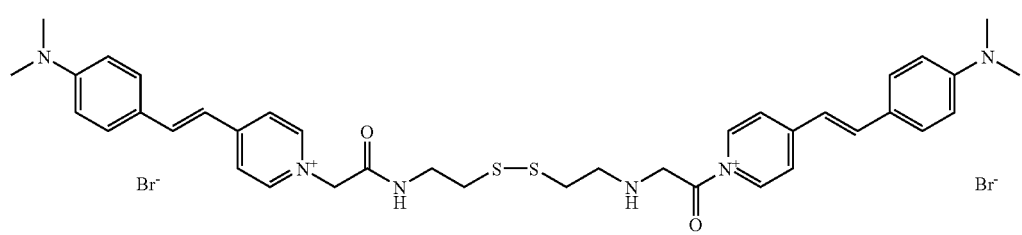
(STY-08)
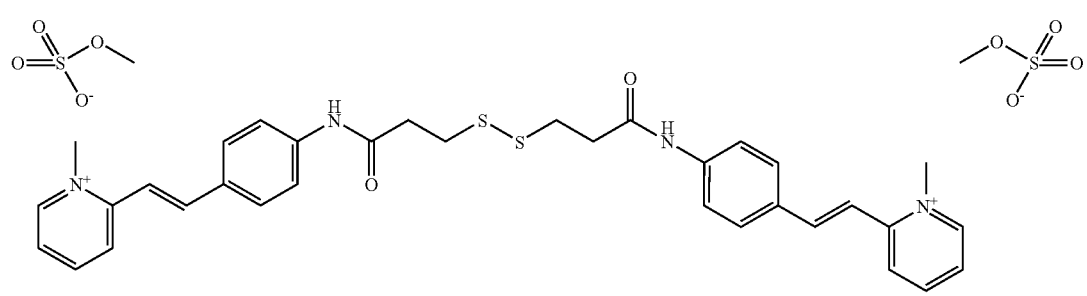
(STY-09)

-continued
(STY-10)
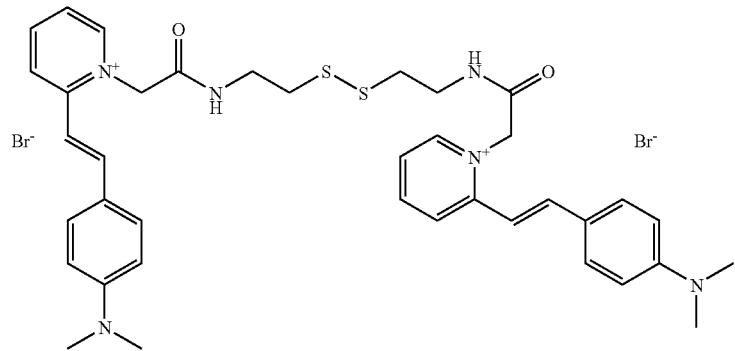
(STY-11)
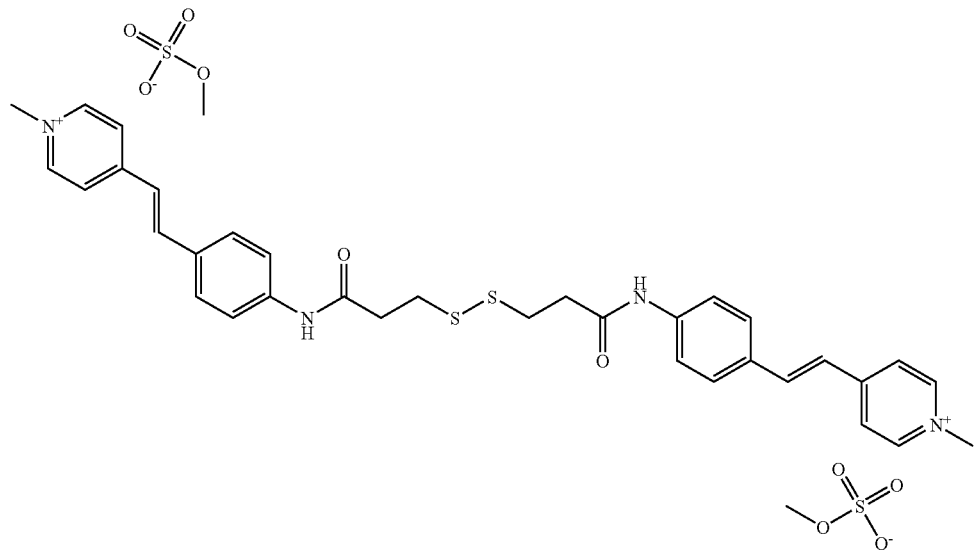
(STY-12)
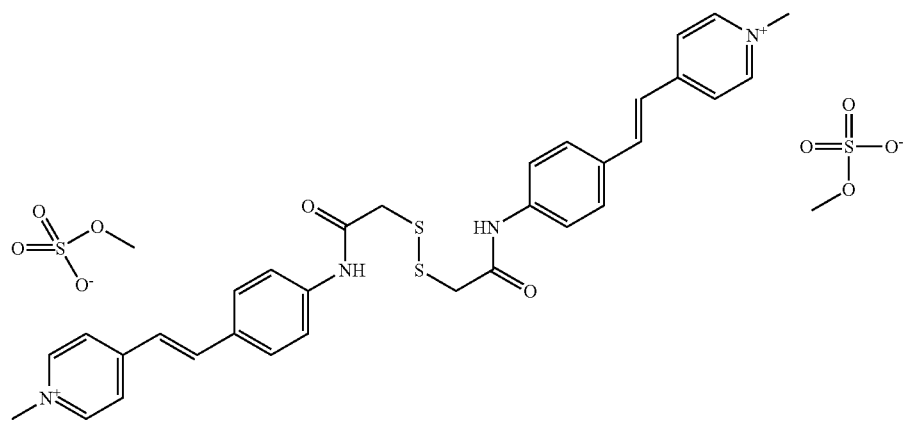
(STY-13)
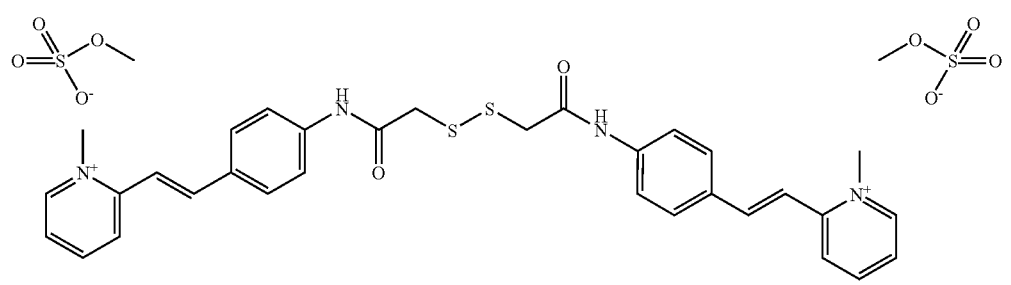

-continued

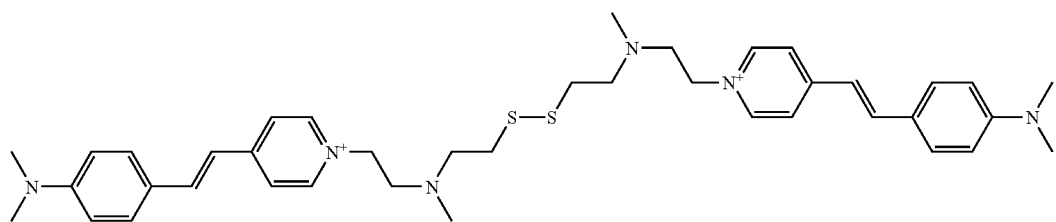
(STY-14)

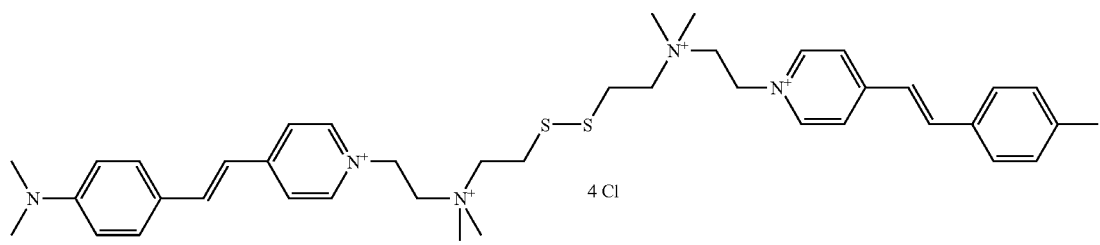
(STY-15)

4 Cl

Preferred are also compositions, wherein the dyes are selected from the compounds of formula

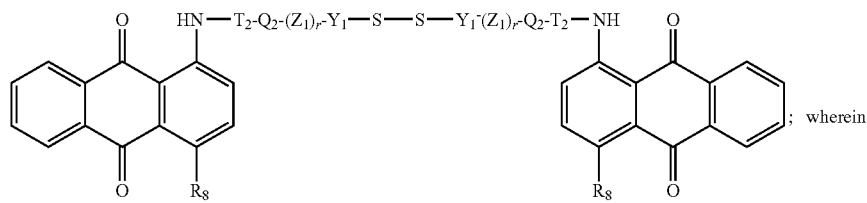
(ANT-01)

; wherein $T_2$ is a radical of formula

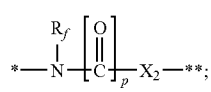

or $-O-(X_2)_s$;

$R_8$ is hydrogen; $C_1$-$C_{20}$alkyl; $NH_2$; or hydroxy; and $R_f$, $Q_2$, $Z_1$, $Y_1$, $X_2$, p and r are defined as in formula (1).

Examples for dyes of formula (1), wherein $D_1$ and $D_2$ are selected from the radicals of formula (1c) are:

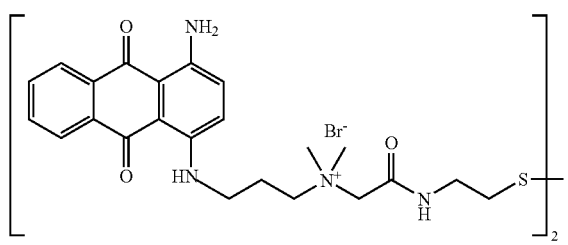
(ANT-02)

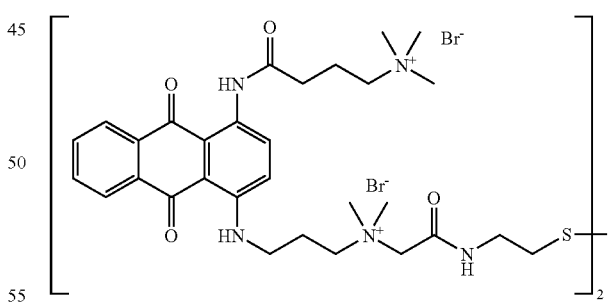
(ANT-03)

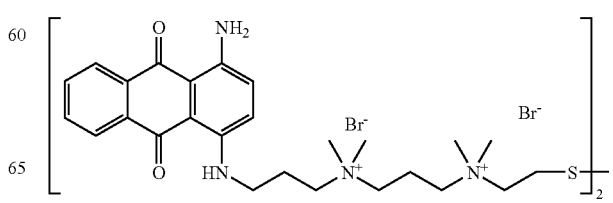
(ANT-04)

-continued (ANT-05)
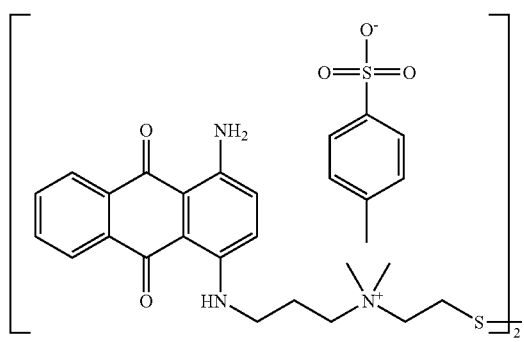

(ANT-06)
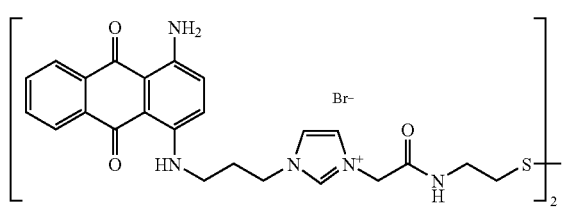

(ANT-07)
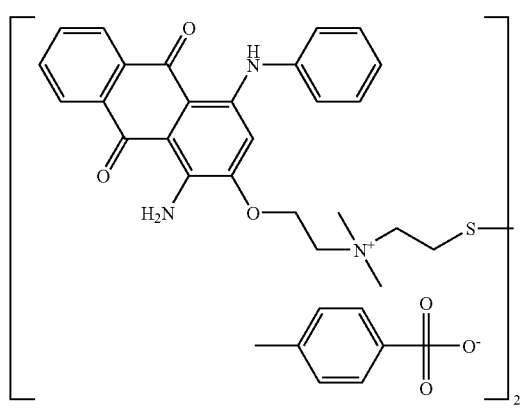

(ANT-08)
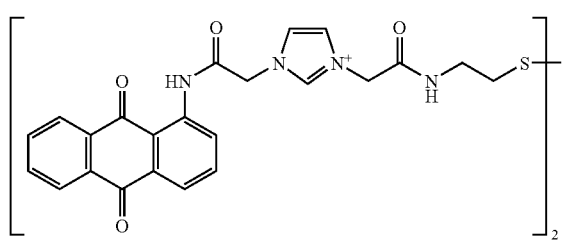

Preferred are also mixtures, wherein the dyes are selected from the compounds of formula (NIT-01)
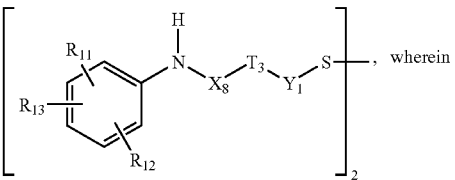, wherein $R_{11}$, $R_{12}$ and $R_{13}$, independently from each other are hydrogen; $C_1$-$C_5$alkyl; —(CO)—; —C(O)H; —C(O)—$C_1$-$C_5$alkyl; —C(O)OH; —C(O)O—$C_1$-$C_5$alkyl; $NO_2$; $NH_2$; or —NH(CO)—$CH_3$;

$Y_1$ is $C_1$-$C_{10}$alkylene; $C_5$-$C_{10}$cycloalkylene; $C_5$-$C_{10}$arylene; or $C_5$-$C_{10}$arylene-($C_1$-$C_{10}$alkylene);

$X_8$ is the direct bond: or $C_1$-$C_5$alkylene;

$T_3$ is the direct bond; or

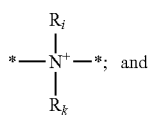; and $R_i$ and $R_k$ each independently from each other are hydrogen; $C_1$-$C_{14}$alkyl; $C_2$-$C_{14}$alkenyl; $C_6$-$C_{10}$aryl; $C_6$-$C_{10}$aryl-$C_1$-$C_{10}$alkyl; or $C_1$-$C_{10}$alkyl($C_5$-$C_{10}$aryl).

Most preferably compounds of formula (NIT-01) are used, wherein $R_{11}$, $R_{12}$ and $R_{13}$ independently from each other are hydrogen; $NO_2$; $NH_2$; carboxy; —C(O)OH; or —NH(CO)—$CH_3$;

$Y_1$ is $C_1$-$C_5$alkylene;

$T_3$ is the direct bond; or

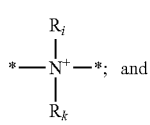; and $R_i$ and $R_k$ each independently from each other are hydrogen; or $C_1$-$C_{14}$alkyl.

The nitro-sulfide dyes (NIT-01) used in the present invention are derived form nitro-dyes, ie. the phenyl moieties

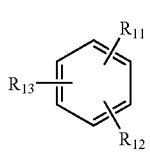

correspond to nitro dyes well known in the literature, for example the following nitro dyes listed in the table below:

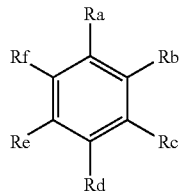

| $R_a$ | $R_b$ | $R_c$ | $R_d$ | $R_e$ | $R_f$ |
|---|---|---|---|---|---|
| —O—CH$_3$ | | —NHCH$_2$CH$_2$OH | | —NO$_2$ | |
| —NH$_2$ | —NHCH$_2$CH$_2$OH | | | —NO$_2$ | |
| —NHCH$_2$CH(OH)CH$_2$OH | NO$_2$ | | —CF$_3$ | | |
| —NHCH$_2$CH$_2$OH | NO$_2$ | | Cl | | |
| —N(CH$_2$CH$_2$OH)$_2$ | —NO$_2$ | —NO$_2$ | —NH$_2$ | | |
| —NHCH$_2$CH(OH)CH$_2$OH | | —NO$_2$ | *—NH—CH$_2$CH(OH)CH$_2$OH | | |
| | *—NH—CH$_2$CH(OH)CH$_2$OH | Cl | —NH$_2$ | | NO$_2$ |
| —NHCH$_2$CH$_2$OH | | NO$_2$ | NH$_2$ | | |
| —NHCH$_2$CH$_2$OH | NO$_2$ | | NH$_2$ | | |
| —NO$_2$ | —NH—C$_6$H$_4$—OH (para) | | | | |
| —NHCH$_2$CH$_2$NH$_2$ | NO$_2$ | | —OCH$_2$CH$_2$OH | | |
| —NHCH$_2$CH$_2$OH | NO$_2$ | | —OCH$_2$CH(OH)OH | | |
| —NHCH$_2$CH$_2$OH | —CH$_3$ | | —NH$_2$ | | NO$_2$ |
| —NH(CH$_2$)$_3$OH | —NO$_2$ | | —N(CH$_2$)$_2$OH | | |
| —NH(CH$_2$)$_2$OH | —NO$_2$ | | —N(CH$_2$CH$_2$OH)$_2$ | | |
| —N(CH$_3$)CH$_2$CH(OH)CH$_2$OH | —NO$_2$ | —NO$_2$ | —NHCH$_3$ | | |
| —NHCH$_2$CH(OH)CH$_2$OH | NO$_2$ | | —N(CH$_2$CH$_3$)(CH$_2$CH$_2$OH) | | |
| —NHCH$_2$CH(OH)CH$_2$OH | NO$_2$ | | —N(CH$_3$)(CH$_2$CH$_2$OH) | | |
| —NH(CH$_2$)$_2$OH | NO$_2$ | | | | |

Examples for dyes of formula (1), wherein $D_1$ and $D_2$ are a radical of formula (1d) are listed below.

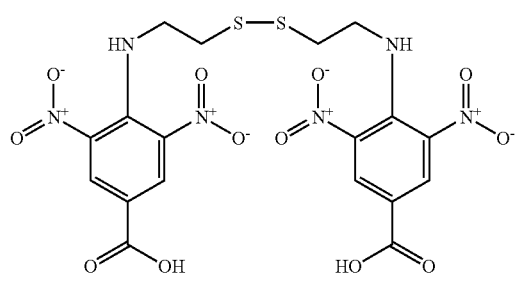
(NIT-02)

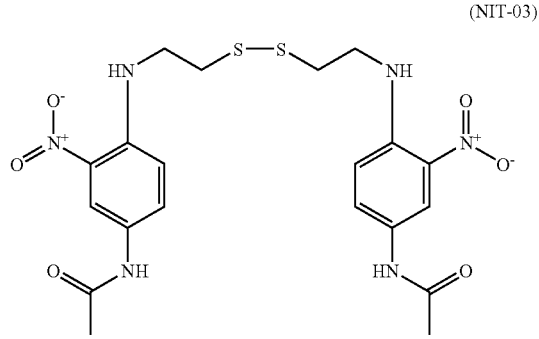
(NIT-03)

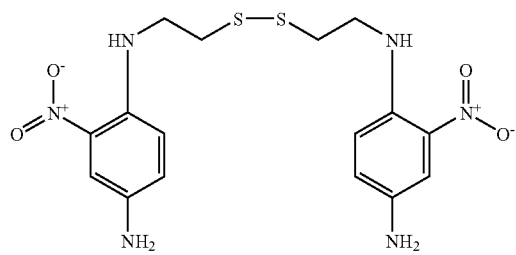
(NIT-04)

(NIT-05)

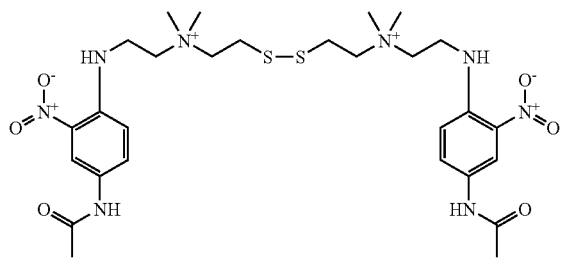

Furthermore, mixtures are preferred wherein the dyes are selected from the compounds of formula (1), wherein
$D_1$ and $D_2$ independently from each other are a radical of formula (1e);
$R_{14}$ is N+$R_{48}R_{49}$;
$R_{48}$ and $R_{49}$ independently from each other are hydrogen; $C_1$-$C_{12}$alkyl; or phenyl-$C_1$-$C_4$alkyl; and
$R_{16}$, $R_{17}$, $R_{18}$, $R_{19}$, $R_{20}$ and $V_1$ are defined as in formula (1); or compounds of formula (1), wherein
$D_1$ and $D_2$ independently from each other are a radical of formula (1e);
$R_{15}$ is NR$_{48}R_{49}$; or OR$_{48}$;
$R_{48}$ and $R_{49}$, independently from each other are hydrogen; $C_1$-$C_{12}$alkyl; or phenyl-$C_1$-$C_4$alkyl; and
$R_{16}$, $R_{17}$, $R_{18}$, $R_{19}$, $R_{20}$ and $V_1$ are defined as in formula (1); or compounds of formula (1), wherein
$D_1$ and $D_2$ independently from each other are a radical of formula (1e);
$R_{14}$ is N+$R_{46}R_{47}$;
$R_{46}$ and/or $R_{47}$ independently from each other are hydrogen; $C_1$-$C_{12}$alkyl; or phenyl-$C_1$-$C_4$alkyl; and
$R_{16}$, $R_{17}$, $R_{18}$, $R_{19}$, $R_{20}$ and $V_1$ are defined as in formula (1); or compounds of formula (1), wherein
$D_1$ and $D_2$ independently from each other are a radical of formula (1e);
$R_{15}$ is NR$_{48}R_{49}$; or OR$_{48}$;
$R_{10}$ and $R_{11}$, independently from each other are hydrogen; $C_1$-$C_{12}$alkyl; or phenyl-$C_1$-$C_4$alkyl; and
$R_{16}$, $R_{17}$, $R_{18}$, $R_{19}$, $R_{20}$ and $V_1$ are defined as in formula (1).

More preferred are mixtures comprising a compound of formula (1), wherein
$D_1$ and $D_2$ independently from each other are a radical of formula

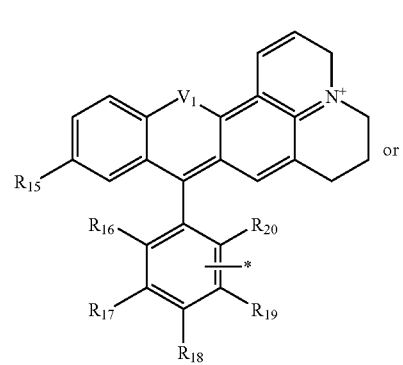
(1e$_1$)

or

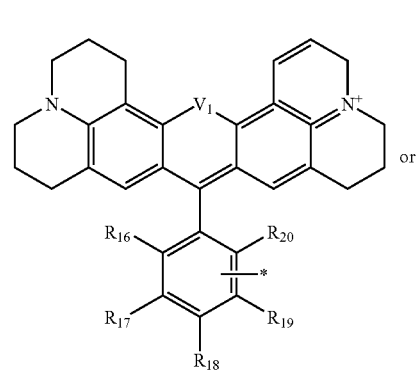
(1e$_2$)

or

-continued
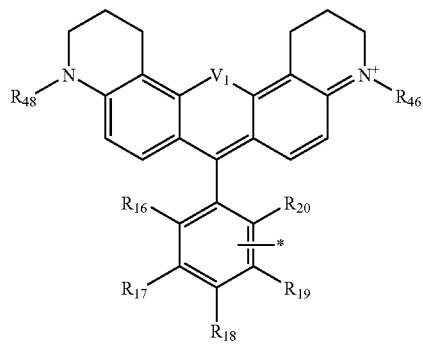
(1e₃)
wherein
$R_{15}, R_{16}, R_{17}, R_{18}, R_{19}, R_{20}, R_{46}$ and $R_{48}$ and $V_1$ are defined as in formula (1).
Most preferred are compounds of formula
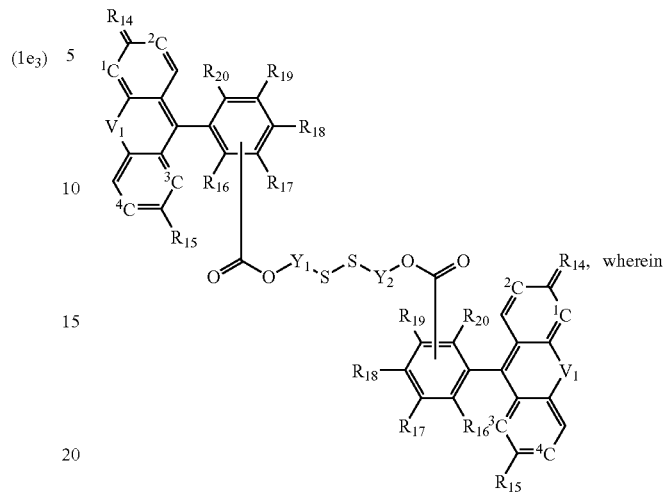
(XAN-01)
wherein
$R_{14}, R_{15}, R_{16}, R_{17}, R_{18}, R_{19}, R_{20}, Y_1, Y_2$ and $V_1$ are defined as in formula (1).
Examples for dyes of formula (1), wherein $D_1$ and $D_2$ are a radical of formula (1e) are listed below.
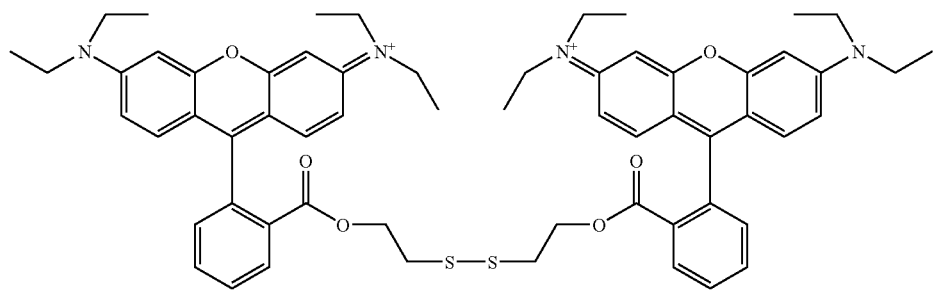
(XAN-02)
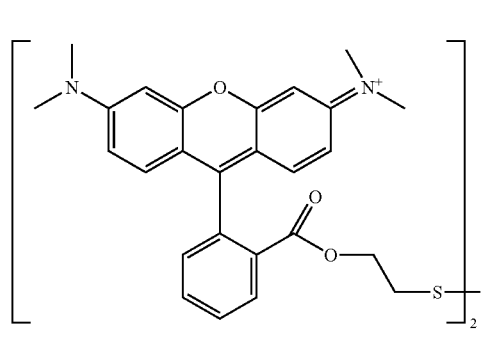
(XAN-03)
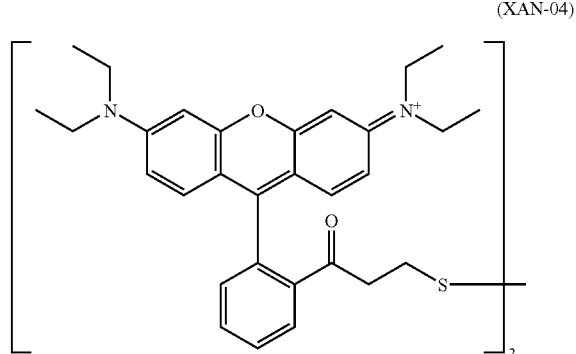
(XAN-04)

-continued
(XAN-05)
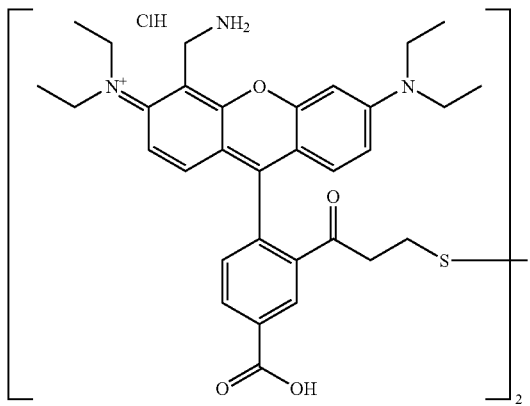
(XAN-06)
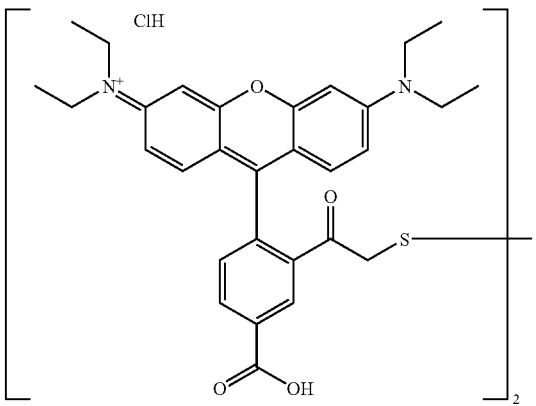
(XAN-07)
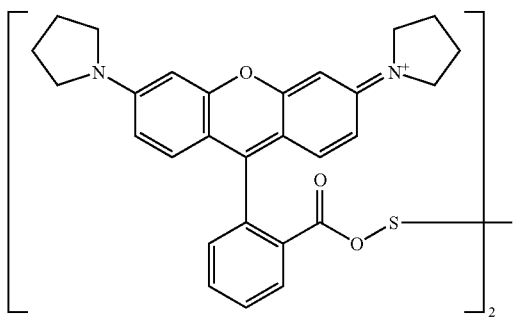
(XAN-08)
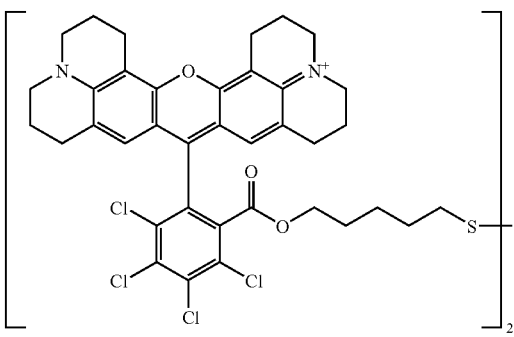
(XAN-09)
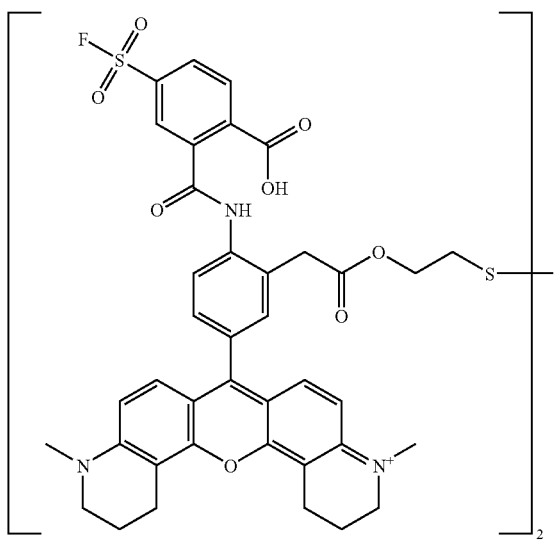
(XAN-10)
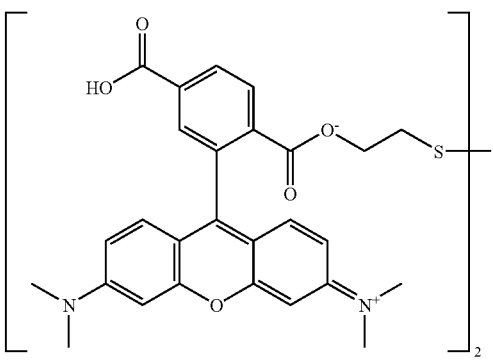

(XAN-10)
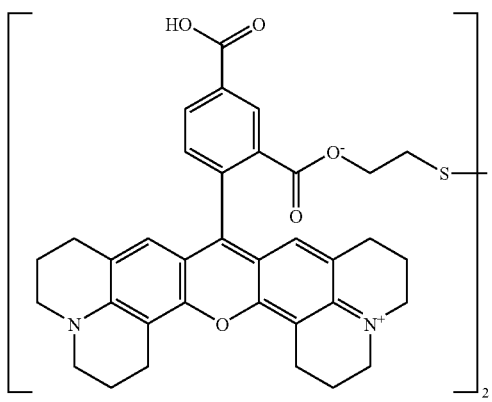
(XAN-11)
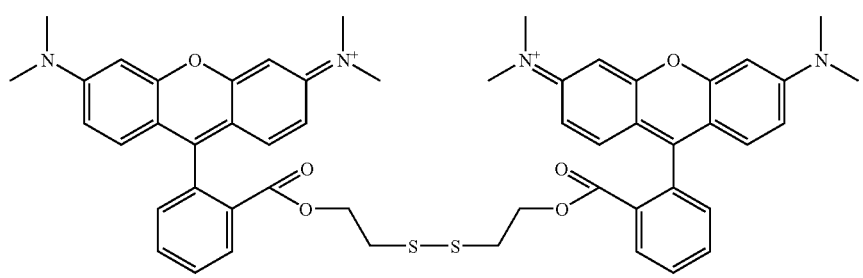
(XAN-12)
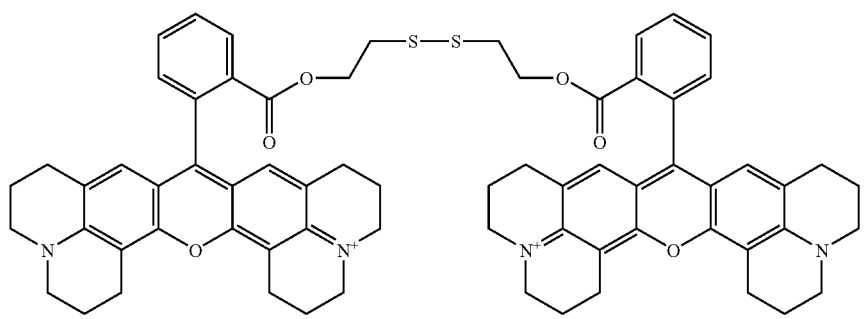
(XAN-14)
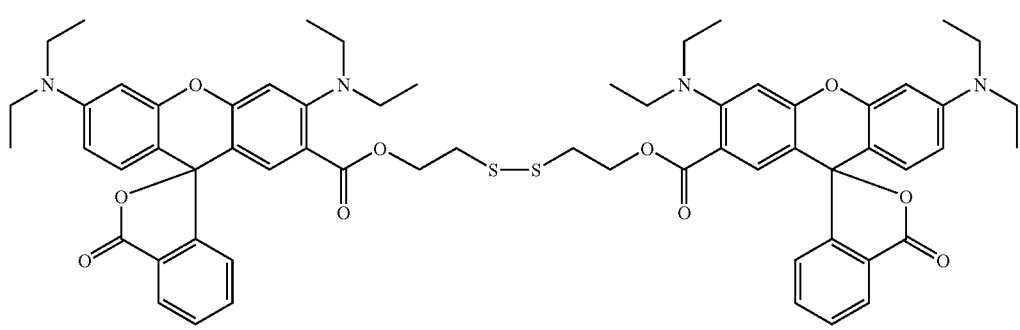

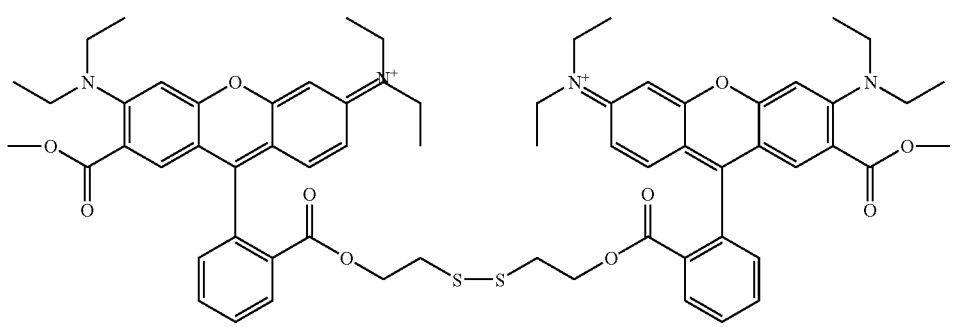

(XAN-15)

Furthermore, mixtures are preferred which comprise a dye of formula

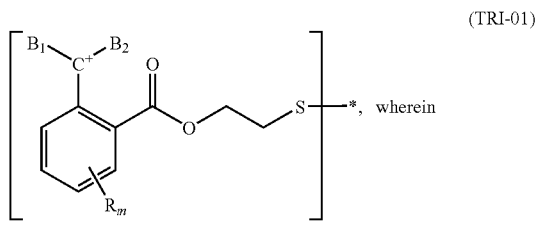

(TRI-01)

$R_m$ is $C_1$-$C_{12}$alkyl, $C_1$-$C_{12}$alkoxy, phenyl, hydroxy, halogen, sulfonic acid, carboxylate, or the radical —$NR_n$, $R_o$ or —$OR_n$; and $R_n$, $R_o$, $B_1$ and $B_2$ are defined as in formula (1).

Examples for dyes of formula (1), wherein $D_1$ and $D_2$ are a radical of formula (1f) are listed below.

Furthermore, mixtures are preferred which comprise a dye of formula (1), wherein $D_1$ and $D_2$ independently from each other are a radical of formula (1g), wherein $R_{23}$ and $R_{24}$ and $R_{25}$ and $R_{26}$ together with the linking nitrogen atom form a piperidine ring of

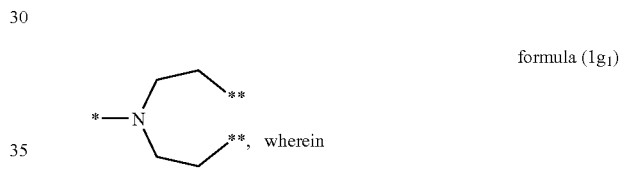

formula (1g$_1$)

the asterix (*) is directed to $Z_1$ or $Z_2$ respectively; and the asterices (**) are directed to the linking nitrogen atom of $R_{23}$/$R_{24}$ or $R_{25}$/$R_{26}$ respectively.

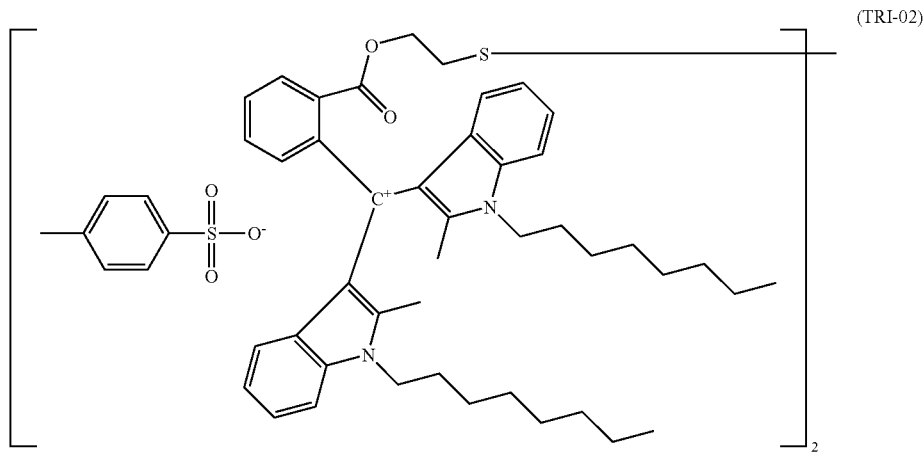

(TRI-02)

Examples for dyes of formula (1), wherein $D_1$ and $D_2$ are a radical of formula (1g) are listed below are:

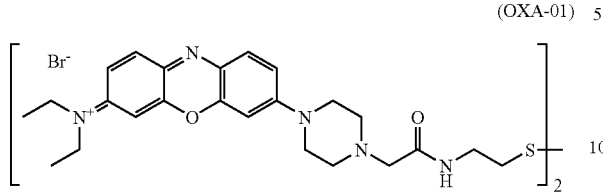
(OXA-01)

Furthermore, mixtures are preferred, which comprise a dye of formula

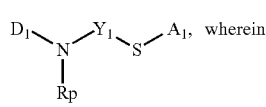
(PRO-01)

$R_p$ is hydrogen; $C_1$-$C_{12}$alkyl; or phenyl-$C_1$-$C_4$alkyl;
$Y_1$ is $C_1$-$C_{12}$alkylene; $C_2$-$C_{12}$alkenylene; $C_5$-$C_{10}$cycloalkylene; $C_5$-$C_{10}$arylene; or $C_5$-$C_{10}$arylene-$C_1$-$C_{10}$alkylene;
$D_1$ is the residue of an organic dye which corresponds to the formula

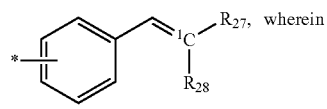
(1h)

$R_{27}$ is hydrogen; or $C_1$-$C_5$alkyl;
$R_{28}$ is a radical of formula (1h$_1$)

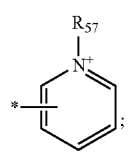
(1h$_1$)

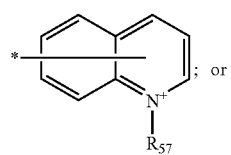
(1h$_2$)

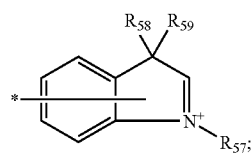
(1h$_3$)

or $R_{27}$ and $R_{28}$ together with the linking carbon atom $^1C$ form a 6 to 10 membered carbocyclic ring which may optionally be a condensated aromatic system and may contain one or more than one hetero atom; and
$R_{57}$, $R_{58}$ and $R_{59}$ independently form each other are hydrogen, or $C_1$-$C_5$alkyl;

$A_1$ is H; or a thio ester group of formula

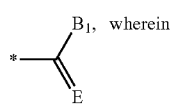
(1b)

E is O; S; or N—$R_a$;
$B_1$ is —$OR_b$; —$NR_bR_c$; or —$SR_b$; and
$R_a$, $R_b$ and $R_c$, independently from each other are hydrogen; $C_1$-$C_{12}$alkyl; $C_6$-$C_{12}$aryl; or $C_6$-$C_{12}$aryl-$C_1$-$C_{12}$alkyl.
Preferred are compounds of formula

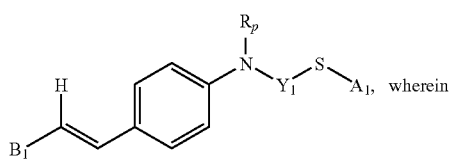
(PRO-02)

$A_1$, $Y_1$, $R_p$ and $B_1$ are defined as in formula (PRO-01).
Preferred are dyes of formula (PRO-01), wherein
$D_1$ is selected from the radicals of formulae (1h$_3$)

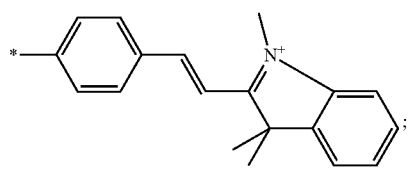

(1h$_4$)

(1h$_5$)

(1h$_6$)

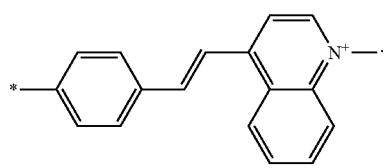
(1h$_7$)

Examples of compounds of the present invention are represented in the Table below:

Exemplified compounds of the present invention

General formula:

$$R_3-CH=CH-C_6H_4-N(R_1)-X-S-Z$$

(with H on the vinyl carbon bearing the phenyl side)

| Compound of formula | $R_3$ | $R_1$ | X | Z |
|---|---|---|---|---|
| (PRO-03) | 1-methylpyridinium-4-yl (*—pyridinium N$^+$—CH$_3$) | H<br>CH$_3$<br>C$_2$H$_5$ | —CH$_2$—CH$_2$— | —(CO)H<br>—(CO)CH$_3$<br>—(CO)C$_6$H$_5$ |
| (PRO-04) | 1-methylpyridinium-2-yl | CH$_3$ | —CH$_2$—CH$_2$— | —(CO)H<br>—(CO)CH$_3$ |
| (PRO-05) | 1-methylquinolinium-4-yl | CH$_3$ | —CH$_2$—CH$_2$— | —(CO)H<br>—(CO)CH$_3$ |
| (PRO-06) | 1-methylquinolinium-2-yl | CH$_3$ | —CH$_2$—CH$_2$— | —(CO)H<br>—(CO)CH$_3$ |
| (PRO-07) | 1,3,3-trimethyl-3H-indolium-2-yl | CH$_3$ | —CH$_2$—CH$_2$— | —(CO)H<br>—(CO)CH$_3$ |
| (PRO-08) | pyridinium-2-yl with —S—CH$_2$—CH$_2$— bridge to N$^+$ (* and ** with $^1$C) | CH$_3$ | —CH$_2$—CH$_2$— | —(CO)H<br>—(CO)CH$_3$ |
| (PRO-09) | 1-methylpyridinium-4-yl | CH$_3$ | —CH$_2$—CH$_2$— | —(CS)H<br>—(CS)CH$_3$ |
| (PRO-10) | 1-methylpyridinium-2-yl | CH$_3$ | —CH$_2$—CH$_2$— | —(CS)H<br>—(CS)CH$_3$ |

-continued

Exemplified compounds of the present invention

[Structure: styryl-aryl-N(R1)-X-S-Z with H and R3 on vinyl]

| Compound of formula | R3 | R1 | X | Z |
|---|---|---|---|---|
| (PRO-11) | 4-(1-methylquinolinium-4-yl) | CH₃ | —CH₂—CH₂— | —(CS)H<br>—(CS)CH₃ |
| (PRO-12) | 1-methylquinolinium-2-yl | CH₃ | —CH₂—CH₂— | —(CS)H<br>—(CS)CH₃ |
| (PRO-13) | 1,3,3-trimethyl-3H-indolium-2-yl | CH₃ | —CH₂—CH₂— | —(CS)H<br>—(CS)CH₃ |
| (PRO-14) | [cyclic: S–CH₂–CH₂–N⁺(pyridinium)-, connected to ¹C] | CH₃ | —CH₂—CH₂— | —(CS)H<br>—(CS)CH₃ |
| (PRO-15) | 1-methylpyridinium-4-yl | CH₃ | —CH₂—CH₂— | —(CO)N(CH₃)₂ |
| (PRO-16) | 1-methylpyridinium-2-yl | CH₃ | —CH₂—CH₂— | —(CO)N(CH₃)₂ |
| (PRO-17) | 1-methylquinolinium-4-yl | CH₃ | —CH₂—CH₂— | —(CO)N(CH₃)₂ |
| (PRO-18) | 1-methylquinolinium-2-yl | CH₃ | —CH₂—CH₂— | —(CO)N(CH₃)₂ |

-continued

Exemplified compounds of the present invention

[Structure: styryl-aniline with R₁ on N, connected via X–S–Z; R₃ on vinyl]

| Compound of formula | R₃ | R₁ | X | Z |
|---|---|---|---|---|
| (PRO-19) | [1,3,3-trimethyl-3H-indol-1-ium-2-yl] | CH₃ | —CH₂—CH₂— | —(CO)N(CH₃)₂ |
| (PRO-20) | [2-(pyridinium-2-yl)ethylthio-methyl, cyclic via ¹C] | CH₃ | —CH₂—CH₂— | —(CO)N(CH₃)₂ |
| (PRO-21) | [1-methylpyridinium-4-yl] | CH₃ | —CH₂—CH₂— | —(CS)N(CH₃)₂ |
| (PRO-22) | [1-methylpyridinium-2-yl] | CH₃ | —CH₂—CH₂— | —(CS)N(CH₃)₂ |
| (PRO-23) | [1-methylquinolinium-4-yl] | CH₃ | —CH₂—CH₂— | —(CS)N(CH₃)₂ |
| (PRO-24) | [1-methylquinolinium-2-yl] | CH₃ | —CH₂—CH₂— | —(CS)N(CH₃)₂ |
| (PRO-25) | [1,3,3-trimethyl-3H-indol-1-ium-2-yl] | CH₃ | —CH₂—CH₂— | —(CS)N(CH₃)₂ |
| (PRO-26) | [2-(pyridinium-2-yl)ethylthio-methyl, cyclic via ¹C] | CH₃ | —CH₂—CH₂— | —(CS)N(CH₃)₂ |
| (PRO-27) | [1-methylpyridinium-4-yl] | CH₃ | —CH₂—CH₂— | —(CO)N(CH₃)₂ |

-continued

Exemplified compounds of the present invention (structure: R3-CH=CH-C6H4-N(R1)-X-S-Z, with H on the CH adjacent to ring)

| Compound of formula | R$_3$ | R$_1$ | X | Z |
|---|---|---|---|---|
| (PRO-28) | 1-methyl-pyridinium-2-yl | CH$_3$ | —CH$_2$—CH$_2$— | —(CO)N(CH$_3$)$_2$ |
| (PRO-29) | 1-methyl-quinolinium-4-yl | CH$_3$ | —CH$_2$—CH$_2$— | —(CO)N(CH$_3$)$_2$ |
| (PRO-30) | 1-methyl-quinolinium-2-yl | CH$_3$ | —CH$_2$—CH$_2$— | —(CO)N(CH$_3$)$_2$ |
| (PRO-31) | 1,3,3-trimethyl-3H-indolium-2-yl | CH$_3$ | —CH$_2$—CH$_2$— | —(CO)N(CH$_3$)$_2$ |
| (PRO-32) | (cyclic S-CH$_2$CH$_2$-N$^+$-pyridin-2-yl linkage to $^1$C) | CH$_3$ | —CH$_2$—CH$_2$— | —(CO)N(CH$_3$)$_2$ |
| (PRO-33) | 1-methyl-pyridinium-4-yl | CH$_3$ | —CH$_2$—CH$_2$— | —C(=NH)NH$_2$ |
| (PRO-34) | 1-methyl-pyridinium-2-yl | CH$_3$ | —CH$_2$—CH$_2$— | —C(=N—CH$_3$)N(CH$_3$)$_2$ |
| (PRO-35) | 1-methyl-quinolinium-4-yl | CH$_3$ | —CH$_2$—CH$_2$— | —C(=N—CH$_3$)N(CH$_3$)$_2$ |

-continued

Exemplified compounds of the present invention

$$\text{R}_3\text{-CH=CH-C}_6\text{H}_4\text{-N(R}_1\text{)-X-S-Z}$$

| Compound of formula | R₃ | R₁ | X | Z |
|---|---|---|---|---|
| (PRO-36) | 1-methyl-2-quinolinium (attached at 2-position) | CH₃ | —CH₂—CH₂— | *—C(=N—CH₃)—N(CH₃)₂ |
| (PRO-37) | 1,3,3-trimethyl-3H-indolium (attached at 2-position) | CH₃ | —CH₂—CH₂— | *—C(=N—CH₃)—N(CH₃)₂ |
| (PRO-38) | *—S—CH₂—CH₂—N⁺(pyridinium-2-yl) (¹C marked) | CH₃ | —CH₂—CH₂— | *—C(=N—CH₃)—N(CH₃)₂ |
| (PRO-39) | 1-methylpyridinium-4-yl | CH₃ | —CH₂—CH₂— | *—C≡N |
| (PRO-40) | 1-methylpyridinium-2-yl | CH₃ | —CH₂—CH₂— | *—C≡N |
| (PRO-41) | 1-methylquinolinium-4-yl | CH₃ | —CH₂—CH₂— | *—C≡N |
| (PRO-42) | 1-methylquinolinium-2-yl | CH₃ | —CH₂—CH₂— | *—C≡N |
| (PRO-43) | 1,3,3-trimethyl-3H-indolium-2-yl | CH₃ | —CH₂—CH₂— | *—C≡N |

-continued

Exemplified compounds of the present invention

[Structure: R3-CH=CH-C6H4-N(R1)-X-S-Z]

| Compound of formula | R3 | R1 | X | Z |
|---|---|---|---|---|
| (PRO-44) | [2-(pyridinium-1-yl)ethylthiomethyl, with *C and **C arrows to ¹C] | CH₃ | —CH₂—CH₂— | *—C≡N |
| (PRO-45) | [4-(1-methylpyridinium-4-yl)] | CH₃ | —CH₂—CH₂— | —(CO)O—C₂H₅ |
| (PRO-46) | [1-methylpyridinium-2-yl] | CH₃ | —CH₂—CH₂— | —(CO)O—CH₃ |
| (PRO-47) | [1-methylquinolinium-4-yl] | CH₃ | —CH₂—CH₂— | —(CO)O—CH₃ |
| (PRO-48) | [1-methylquinolinium-2-yl] | CH₃ | —CH₂—CH₂— | —(CO)O—CH₃ |
| (PRO-49) | [1,3,3-trimethyl-3H-indolium-2-yl] | CH₃ | —CH₂—CH₂— | —(CO)O—CH₃ |
| (PRO-50) | [2-(pyridinium-1-yl)ethylthiomethyl, with *C and **C arrows to ¹C] | CH₃ | —CH₂—CH₂— | —(CO)O—CH₃ |
| (PRO-51) | [4-(1-methylpyridinium-4-yl)] | CH₃ | —CH₂—CH₂— | —(CS)O—CH₃ |
| (PRO-52) | [1-methylpyridinium-2-yl] | CH₃ | —CH₂—CH₂— | —(CS)O—CH₃ |

-continued

Exemplified compounds of the present invention

[Structure: R3-CH=CH-C6H4-N(R1)-X-S-Z, with H on the CH bonded to phenyl]

| Compound of formula | R3 | R1 | X | Z |
|---|---|---|---|---|
| (PRO-53) | 4-(1-methylquinolinium-4-yl) | CH3 | —CH2—CH2— | —(CS)O—CH3 |
| (PRO-54) | 1-methylquinolinium-2-yl | CH3 | —CH2—CH2— | —(CS)O—CH3 |
| (PRO-55) | 1,3,3-trimethyl-3H-indolium-2-yl | CH3 | —CH2—CH2— | —(CS)O—CH3 |
| (PRO-56) | [S-CH2-CH2-N+(pyridinium-2-yl), with * and ** positions indicated, ¹C label] | CH3 | —CH2—CH2— | —(CS)O—CH3 |
| (PRO-57) | 1-methylpyridinium-4-yl | CH3 | —CH2—CH2— | —(CS)S—C2H5 |
| (PRO-58) | 1-methylpyridinium-2-yl | CH3 | —CH2—CH2— | —(CS)S—CH3 |
| (PRO-59) | 1-methylquinolinium-4-yl | CH3 | —CH2—CH2— | —(CS)S—CH3 |
| (PRO-60) | 1-methylquinolinium-2-yl | CH3 | —CH2—CH2— | —(CS)S—CH3 |

-continued

Exemplified compounds of the present invention

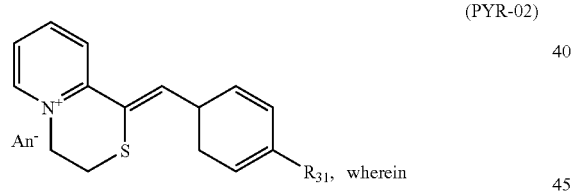

| Compound of formula | $R_3$ | $R_1$ | X | Z |
|---|---|---|---|---|
| (PRO-61) | (indolinium group) | $CH_3$ | $-CH_2-CH_2-$ | $-(CS)S-CH_3$ |
| (PRO-62) | (pyridinium-S group) | $CH_3$ | $-CH_2-CH_2-$ | $-(CS)S-CH_3$ |

Furthermore, mixtures are preferred which comprise a dye of formula (2), wherein
$R_{30}$, $R_{31}$ and $R_{32}$ are hydrogen; or $C_1$-$C_{12}$alkyl; and
$R_{32}$ is defined as formula (2).

Preferred are dyes of formula (PYR-02)

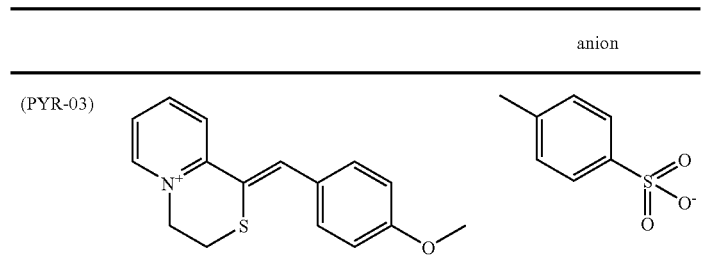

$R_{31}$, wherein $R_{31}$ is hydrogen; $C_1$-$C_5$-alkoxy; halogen; or $-NR_{69}R_{70}$, wherein
$R_{69}$ and $R_{70}$, independently from each other are hydrogen; $C_1$-$C_{12}$alkyl; $-(CO)-H$; or $-(CO)-C_1$-$C_5$alkyl; and
An is an anion.

Examples of these dyes are listed in the Table below:

| | | anion |
|---|---|---|
| (PYR-03) | (pyridinium-S-phenyl-OCH3 structure) | (tosylate structure) |

-continued

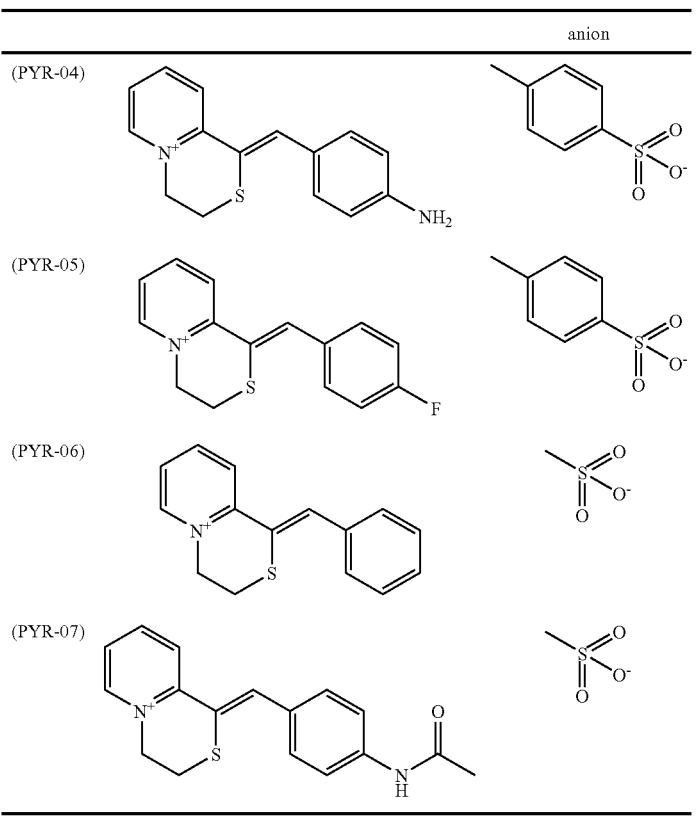

All compounds of the present invention mentioned above can exist as hydrates or solvates.

The mixture of dyes according to the invention are suitable for dyeing organic materials, such as keratin-containing fibers, wool, leather, silk, cellulose or polyamides, cotton or nylon, and preferably human hair. The dyeings obtained are distinguished by their depth of shade and their good fastness properties for example to washing, fastness to light, shampooing and rubbing. The stabilities, in particular the storage stability of the dyes and the dyes in formulations according to the invention are excellent.

Generally, hair dyeing agents on a synthetic base may be classified into three groups:
temporary dyeing agents
semipermanent dyeing agents, and
permanent dyeing agents.

The multiplicity of shades of the dyes can be increased by combination with other dyes.

Therefore the mixture of dyes of the present invention may be combined with dyes of the same or other classes of dyes, especially with direct dyes, oxidation dyes; dye precursor combinations of a coupler compound as well as a diazotized compound, or a capped diazotized compound; and/or cationic reactive dyes.

Direct dyes are of natural origin or may be prepared synthetically. They are uncharged, cationic or anionic, such as acid dyes.

The mixture of dyes may be used in combination with at least one single direct dye different from the dyes of formula (1) and (2).

Direct dyes do not require any addition of an oxidizing agent to develop their dyeing effect. Accordingly the dyeing results are less permanent than those obtained with permanent dyeing compositions. Direct dyes are therefore preferably used for semipermanent hair dyeings.

Examples of direct dyes are described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, and in "Europäisches Inventar der Kosmetikrohstoffe", 1996, published by The European Commission, obtainable in diskette form from the Bundesverband der deutschen Industrie-und Handelsunternehmen für Arzneimittel, Reformwaren und Körperpflegemittel e.V., Mannheim.

More preferred direct dyes which are useful for the combination with the mixture of dyes of the present invention, especially for semi permanent dyeing, are: 2-amino-3-nitrophenol, 2-amino-4-hydroxyethylamino-anisole sulfate, 2-amino-6-chloro-4-nitrophenol, 2-chloro-5-nitro-N-hydroxyethylene-p-phenylendiamine, 2-hydroxyethyl-picramic acid, 2,6-diamino-3-((pyridine-3-yl)-azo)pyridine, 2-nitro-5-glyceryl-methylaniline, 3-methylamino-4-nitrophenoxyethanol, 4-amino-2-nitrodiphenyleneamine-2'-carboxilic acid, 6-nitro-1,2,3,4,-tetrahydroquinoxaline, 4-N-ethyl-1,4-bis(2'-hydroxyethylamino-2-nitrobenzene hydrochloride, 1-methyl-3-nitro-4-(2'-hydroxyethyl)-aminobenzene, 3-nitro-p-hydroxyethyl-aminophenol, 4-amino-3-nitrophenol, 4-hydroxypropylamine-3-nitrophenol, hydroxyanthrylaminopropylmethyl morpohlino methosulfate, 4-nitrophenyl-aminoethylurea, 6-nitro-p-toluidine, Acid Blue 62, Acid Blue 9, Acid Red 35, Acid Red 87 (Eosin), Acid Violet 43, Acid Yellow 1, Basic Blue 3, Basic Blue 6, Basic Blue 7, Basic Blue 9, Basic Blue 12, Basic Blue 26, Basic Blue 99, Basic Brown 16, Basic Brown 17, Basic Red 2, Basic Red 22, Basic Red 76, Basic Violet 14, Basic Yellow 57, Basic Yellow 9, Disperse Blue 3, Disperse Orange 3, Disperse Red 17, Disperse Violet 1, Disperse Violet 4, Disperse Black 9, Fast Green FCF, HC Blue 2, HC Blue 7, HC Blue 8, HC Blue 12, HC Orange 1, HC Orange 2, HC Red 1, HC Red 10-11, HC Red 13, HC Red 16, HC Red 3, HC Red BN, HC Red 7, HC Violet 1, HC Violet 2, HC Yellow 2, HC Yellow 5, HC Yellow 5, HC Yellow 6, HC Yellow 7, HC Yellow 9, HC Yellow 12, HC Red 8, hydroxyethyl-2-nitro-p-toluidine, N,N-Bis-(2-Hydroxyethyl)-2-nitro-p-phenylendiamine, HC Violet BS, Picramic Acid, Solvent Green 7.

Furthermore, mixture of dyes of the present invention may be combined with at least one cationic azo dye, for example the compounds disclosed in GB-A-2 319 776 as well as the oxazine dyes described in DE-A-299 12 327 and mixtures thereof with the other direct dyes mentioned therein, and even more preferred with cationic dyes such as Basic Yellow 87, Basic Orange 31 or Basic Red 51, or with cationic dyes as described in WO 01/66646, especially example 4, or with cationic dyes as described in WO 02/31056, especially example 6 (compound of formula 106); or the cationic dye of formula (3) as described in EP-A-714,954, or with a yellow cationic dye of formula

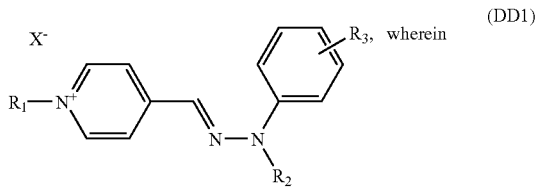

(DD1)

$R_1$ and $R_2$ are each independently of the other a $C_1$-$C_8$alkyl; or an unsubstituted or substituted benzyl;

$R_3$ is hydrogen; $C_1$-$C_8$alkyl; $C_1$-$C_8$alkoxy; cyanide; or halide; preferably hydrogen; and $X^-$ is an anion; and preferably a compound of formula (DD1), wherein $R_1$ is methyl; $R_2$ is benzyl; $R_3$ is hydrogen; and $X^-$ is an anion; or wherein $R_1$ is benzyl; $R_2$ is benzyl; $R_3$ is hydrogen; and $X^-$ is an anion; or wherein $R_1$ is benzyl; $R_2$ is methyl; $R_3$ is hydrogen; and $X^-$ is an anion.

Furthermore, cationic nitroaniline and anthraquinone dyes are useful for a combination with mixture of dyes of the present invention, for example the dyes as described in the following patent specifications: U.S. Pat. No. 5,298,029, especially in col 2, l. 33 to col 5, l. 38; U.S. Pat. No. 5,360, 930, especially in col 2, l. 38 to col 5, l. 49; U.S. Pat. No. 5,169,403, especially in col 2, l. 30 to col 5, l. 38; U.S. Pat. No. 5,256,823, especially in col 4, l. 23 to col 5, l. 15; U.S. Pat. No. 5,135,543, especially in col 4, l. 24 to col 5, l. 16; EP-A-818 193, especially on p. 2, l. 40 to p. 3, l. 26; U.S. Pat. No. 5,486,629, especially in col 2, l. 34 to col 5, l. 29; and EP-A-758 547, especially on p. 7, l. 48 to p. 8, l. 19.

The mixture of dyes of the present invention may also be combined with acid dyes, for example the dyes which are known from the international names (Color index), or trade names.

Preferred acid dyes which are useful for the combination with the mixture of dyes of the present invention are described in U.S. Pat. No. 6,248,314. They include Red Color No. 120, Yellow Color No. 4, Yellow Color No. 5, Red Color No. 201, Red Color No. 227, Orange Color No. 205, Brown Color No. 201, Red Color No. 502, Red Color No. 503, Red Color No. 504, Red Color No. 506, Orange Color No. 402, Yellow Color No. 402, Yellow Color No. 406, Yellow Color No. 407, Red Color No. 213, Red Color No. 214, Red Color No. 3, Red Color No. 104, Red Color No. 105(1), Red Color No. 106, Green Color No. 2, Green Color No. 3, Orange Color No. 207, Yellow Color No. 202(1), Yellow Color No. 202(2), Blue Color No. 202, Blue Color No. 203, Blue Color No. 205, Blue Color No. 2, Yellow Color No. 203, Blue Color No. 201, Green Color No. 201, Blue Color NO. 1, Red Color No. 230(1), Red Color No. 231, Red Color No. 232, Green Color No. 204, Green Color No. 205, Red Color No. 401, Yellow Color No. 403(1), Green Color No. 401, Green Color No. 402, Black Color No. 401 and Purple Color No. 401, especially Black Color No. 401, Purple Color 401, Orange Color No. 205.

These acid dyes may be used either as single component or in any combination thereof.

Hair dye compositions comprising an acid dye are known. They are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 253 and 254.

Hair dye compositions which comprise an acid dye have a pH of 2-6, preferably 2-5, more preferably 2.5-4.0.

The mixture of dyes of the present invention may also readily be used in combination with acid dyes and/or adjuvants, for example acid dyes and an alkylene carbonate, as described in U.S. Pat. No. 6,248,314, especially in examples 1 and 2;

acid hair dye compositions comprising various kinds of organic solvents represented by benzyl alcohol as a penetrant solvent have good penetrability into hair, as described in Japanese Patent Application Laid-Open Nos. 210023/1986 and 101841/1995;

acid hair dye compositions with a water-soluble polymer or the like to prevent the drooping of the hair dye composition, as described for example in Japanese Patent Application Laid-Open Nos. 87450/1998, 255540/1997 and 245348/1996;

acid hair dye compositions with a water-soluble polymer of aromatic alcohols, lower alkylene carbonates, or the like as described in Japanese Patent Application Laid-Open No. 53970/1998 and Japanese Patent Invention No. 23911/1973.

The mixture of dyes of the present invention may also be combined with uncharged dyes, for example selected from the group of the nitroanilines, nitrophenylenediamines, nitroaminophenols, anthraquinones, indophenols, phenazines, phenothiazines, bispyrazolons, bispyrazol aza derivatives and methines.

Furthermore, the mixture of dyes of the present invention may also be used in combination with oxidation dye systems.

Oxidation dyes, which, in the initial state, are not dyes but dye precursors are classified according to their chemical properties into developer and coupler compounds.

Suitable oxidation dyes are described for example in

DE 19 959 479, especially in col 2, l. 6 to col 3, l. 11;

"Dermatology", edited by Ch. Culnan, H. Maibach, Verlag Marcel Dekker Inc., New York, Basle, 1986, Vol. 7, Ch. Zviak, The Science of Hair Care, chapter 8, on p. 264-267 (oxidation dyes);

Preferred developer compounds are for example primary aromatic amines, which are substituted in the para- or ortho-position with a substituted or unsubstituted hydroxy- or amino residue, or diaminopyridine derivatives, heterocyclic hydrazones, 4-aminopyrazol derivatives, 2,4,5,6-tetraminopyrimidine derivatives, or unsaturated aldehydes as described in DE 19 717 224, especially on p. 2, l. 50 to l. 66 and on p. 3 l. 8 to l. 12, or cationic developer compounds as described in WO 00/43367, especially on p., 2 l. 27 to p. 8, l. 24, in particular on p. 9, l. 22 to p. 11, l. 6.

Furthermore, developer compounds in their physiological compatible acid addition salt form, such as hydrochloride or sulfate can be used. Developer compounds, which have aromatic OH radicals are also suitable in their salt form together with a base, such as alkali metal-phenolates.

Preferred developer compounds are disclosed in DE 19959479, p. 2, l. 8-29.

More preferred developer compounds are p-phenylendiamine, p-toluoylendiamine, p-, m- o-aminophenol, N,N-bis-(2-hydroxyethyl)-p-phenylenediamine sulfate, 2-amino-4-hydroxy-ethylaminoanisole sulfate, hydroxyethyl-3,4-methylenedioxyaniline, 1-(2'-hydroxyethyl)-2,5-diaminobenzene, 2,6-dimethoxy-3,5-diamino-pyridine, hydroxypropyl-bis-(N-hydroxyethyl-p-phenylenediamine) hydrochloride, hydroxyethyl-p-phenylenediamine sulfate, 4-amino-3-methylphenol, 4-methylaminophenol sulfate, 2-aminomethyl-4-aminophenol, 4,5-diamino-1-(2-hydroxyethyl)-1H-pyrazol, 4-amino-m-cresol, 6-amino-m-cresol, 5-amino-6-chloro-cresol, 2,4,5,6-tetraminopyrimidine, 2-hydroxy-4,5,6-triaminopyrimidine or 4-hydroxy-2,5,6-triaminopyrimidine sulfate.

Preferred coupler compounds are m-phenylendiamine derivatives, naphthol, resorcine and resorcine derivatives, pyrazolone and m-aminophenol derivatives, and most preferably the coupler compounds disclosed in DE 19959479, p. 1, l. 33 to p. 3, l. 11.

The mixture of dyes of the present invention may also be used together with unsaturated aldehydes as disclosed in DE 19 717 224 (p. 2, l. 50 to l. 66 and on p. 3, l. 8 to l. 12) which may be used as direct dyes or, alternatively together with oxidation dye precursors.

Further preferred for a combination with the mixture of dyes of the present invention are the following oxidation dye precursors:

the developer/-coupler combination 2,4,5,6-tetraminopyrimidine and 2-methylresorcine for assessing of red shades;

p-toluenediamine and 4-amino-2-hydroxytoluene for assessing of blue-violet shades;

p-toluenediamine and 2-amino-4-hydroxyethylaminoanisole for assessing of blue shades;

p-toluenediamine and 2,4-diamino-phenoxyethanol for assessing of blue shades;

methyl-4-aminophenol and 4-amino-2-hydroxytoluene for assessing of orange shades;

p-toluenediamine and resorcine for assessing of brown-green shades;

p-toluenediamine and 1-naphthol for assessing of blue-violet shades, or p-toluenediamine and 2-methylresorcine for assessing of brown-gold shades.

Furthermore, autooxidizable compounds may be used in combination with the mixture of dyes according to the present invention.

Autooxidizable compounds are aromatic compounds with more than two substituents in the aomatic ring, which have a very low redox potential and will therefore be oxidized when ex-posed to the air. The dyeings obtained with these compounds are very stable and resistant to shampoo.

Autooxidizable compounds are for example benzene, indol, or indoline, especially 5,6-dihydro-xyindol or 5,6-dihydroxyindoline derivatives as described in WO 99/20234, especially on p. 26, l. 10 to p. 28, l. 15, or in WO 00/28957 on p. 2, third paragraph.

Preferred autooxidizable benzene derivatives are 1,2,4-trihydroxybenzene, 1-methyl-2,4,5-trihydroxybenzene, 2,4-diamino-6-methylphenol, 2-amino-4-methylaminophenol, 2,5-diamino-4-methyl-phenol, 2,6-diamino-4-diethylaminophenol, 2,6-diamino-1,4-dihydroxybenzene, and the salts of these compounds, which are accessible with acid.

Preferred autooxidizable indol derivatives are 5,6-dihydroxyindole, 2-methyl-5,6-dihydroxyindole, 3-methyl-5,6-dihydroxyindole, 1-methyl-5,6-dihydroxyindole, 2,3-dimethyl-5,6-dihydroxyindole, 5-methoxy-6-dihydroxyindole, 5-acetoxy-6-hydroxyindole, 5,6-diacetoxyindol, acid of 5,6-dihydroxyindole-2-carbon acid, and the salts of these compounds, which are accessible with acid.

The mixture of dyes of the present invention may also be used in combination with naturally occurring dyes, such as henna red, henna neutral, henna black, chamomile blossom, sandalwood, black tea, Rhamnus frangula bark, sage, campeche wood, madder root, catechu, sedre and alkanet root. Such dyeings are described, for example, in EP-A-404 868, especially on p. 3, l. 55 to p. 4, l. 9.

Furthermore, the mixture of dyes of the present invention may also be used in combination with capped dia-zotised compounds.

Suitable diazotised compounds are for example the compounds of formulae (1)-(4) in WO 2004/019897 (bridging pages 1 and 2) and the corresponding water soluble coupling components (I)-(IV) as disclosed in the same reference.

Further preferred dyes or dye combinations which are useful for the combination with mixture of dyes of the present invention are described in (DC-01): WO 95/01772, wherein mixtures of at least two cationic dyes are disclosed, especially p. 2, l. 7 to p. 4, l. 1, preferably p. 4, l. 35 to p. 8, l. 21; formulations p. 11, last §-p. 28, l. 19;

(DC-02): U.S. Pat. No. 6,843,256, wherein cationic dyes are disclosed, especially the compounds of formulae (1), (2), (3) and (4) (col. 1, l. 27-col. 3, l. 20, and preferably the compounds as prepared in the examples 1 to 4 (col. 10, l. 42 to col. 13, l. 37; formulations col. 13, l. 38 to col. 15, l. 8;

(DC-03): EP 970 685, wherein direct dyes are described, especially p. 2, l. 44 to p. 9, l. 56 and preferably p. 9, l. 58 to p. 48, l. 12; processes for dyeing of keratin-containing fibers especially p. 50, l. 15 to 43; formulations p. 50, l. 46 to p. 51, l. 40;

(DC-04): DE-A-19 713 698, wherein direct dyes are described, especially p. 2, l. 61 to p. 3, l. 43; formulations p. 5, l. 26 to 60;

(DC-05): U.S. Pat. No. 6,368,360, wherein directed dyes (col. 4, l. 1 to col. 6, l. 31) and oxidizing agents (col. 6, l. 37-39) are disclosed; formulations col. 7, l. 47 to col. 9, l. 4;

(DC-06): EP 1 166 752, wherein cationic dyes (p. 3, l. 22-p. 4, l. 15) and anionic UV-absorbers (p. 4, l. 27-30) are disclosed; formulations p. 7, l. 50-p. 9, l. 56;

(DC-07): EP 998,908, wherein oxidation dyeings comprising a cationic direct dye and pyrazolo-[1,5-a]-pyrimidines (p. 2, l. 48-p. 4, l. 1) are disclosed; dyeing formulations p. 47, l. 25 to p. 50, l. 29;

(DC-08): FR-2788432, wherein combinations of cationic dyes with Arianors are disclosed, especially p. 53, l. 1 to p. 63, l. 23, more especially p. 51 to 52, most especially Basic Brown 17, Basic brown 16, Basic Red 76 and Basic Red 118, and/or at least one Basic Yellow 57, and/or at least one Basic Blue 99; or combinations of arianoren and/or oxidative dyes, especially p. 2, l. 16 to p. 3, l. 16; dyeing formulations on p. 53, l. 1 to p. 63, l. 23;

(DC-09): DE-A-19 713 698, wherein the combinations of direct dyes and permanent-wave fixing comprising an oxidation agent, an oxidation dye and a direct dye are disclosed; especially p. 4, l. 65 to p. 5, l. 59;

(DC-10): EP 850 638, wherein developer compounds and oxidizing agents are disclosed; especially p. 2, l. 27 to p. 7, l. 46 and preferably p. 7, l. 20 to p. 9, l. 26; dyeing formulations p. 2, l. 3-12 and l. 30 to p. 14, and p. 28, l. 35-p. 30, l. 20; preferably p. 30, l. 25-p. 32, l. 30;

(DC-11): U.S. Pat. No. 6,190,421 wherein extemporaneous mixtures of a composition (A) containing one or more oxidation dye precursors and optionally one or more couplers, of a composition (B), in powder form, containing one or more direct dyes (col. 5,1,40-col. 7, l. 14), optionally dispersed in an organic pulverulent excipient and/or a mineral pulverulent excipient, and a composition (C) containing one or more oxidizing agents are disclosed; formulations col. 8, l. 60-col. 9, l. 56;

(DC-12): U.S. Pat. No. 6,228,129, wherein a ready-to-use composition comprising at least one oxidation base, at least one cationic direct dye and at least one enzyme of the 2-electron oxidoreductase type in the presence of at least one donor for the said enzyme are disclosed; especially col. 8, l. 17-col. 13, l. 65; dyeing formulations in col. 2, l. 16 to col. 25, l. 55, a multi-compartment dyeing device is described in col. 26, l. 13-24;

(DC-13): WO 99/20235, wherein compositions of at least one cationic dye and at least one nitrated benzene dye with cationic direct dyes and nitro benzene direct dyes are described; on p. 2, l. 1 to p. 7, l. 9, and p. 39, l. 1 to p. 40, l. 11, preferably p. 8, l. 12 to p. 25 l. 6, p. 26, l. 7 to p. 30, l. 15; p. 1, l. 25 to p. 8, l. 5, p. 30, l. 17 to p. 34 l. 25, p. 8, l. 12 to p. 25 l. 6, p. 35, l. 21 to 27, especially on p. 36, l. 1 to p. 37;

(DC-14): WO 99/20234, wherein compositions comprising at least one direct cationic dye and at least one autooxidisable dye, especially benzene, indol and indoline derivatives are described, preferably direct dyes on p. 2, l. 19 to p. 26, l. 4, and autooxidisable dyes as disclosed especially on p. 26, l. 10 to p. 28, l. 15; dyeing formulations especially on p. 34, l. to p. 35, li 18;

(DC-15): EP 850 636, wherein oxidation dyeing compositions comprising at least one direct dye and at least one meta-aminophenol derivative as coupler component and at least one developer compound and an oxidizing agent are disclosed, especially p. 5, l. 41 to p. 7, l. 52, dyeing formulations p. 19, l. 50-p. 22, l. 12;

(DC-16): EP-A-850 637, wherein oxidation dyeing compositions comprising at least one oxidation base selected from para-phenylenediamines and bis(phenyl)alkylenediamines, and the acid-addition salts thereof, at least one coupler selected from meta-diphenols, and the acid-addition salts thereof, at least one cationic direct dye, and at least one oxidizing agent are disclosed, especially p. 6, l. 50 to p. 8, l. 44 are disclosed; dyeing formulations p. 21, l. 30-p. 22, l. 57;

(DC-17): WO 99/48856, wherein oxidation dyeing compositions comprising cationic couplers are disclosed, especially p. 9, l. 16-p. 13, l. 8, and p. 11, l. 20-p. 12, l. 13; dyeing formulations p. 36, l. 7-p. 39, l. 24;

(DC-18): DE 197 172 24, wherein dyeing agents comprising unsaturated aldehydes and coupler compounds and primary and secondary amino group compounds, nitrogen-containing heterocyclic compounds, amino acids, oligopeptides, aromatic hydroxy compounds, and/or at least one CH-active compound are disclosed p. 3, l. 42-p. 5, l. 25; dyeing formulations p. 8, l. 25-p. 9, l. 61.

In the dye combinations disclosed in the references (DC-01-DC-18) above, the mixture of dyes of the present invention may be added to the dye combinations or dyeing formulations or may be replaced with the mixture of dyes of the present invention.

The present invention also relates to formulations, which are used for the dyeing of organic materials, preferably keratin-containing fibers, and most preferably human hair, comprising mixture of dyes of the present invention.

The formulations comprise at least 2 dyes as defined in formula (1) and (2). According to the desired color results the mixtures may comprise 3, 4, 5 or more than 5 dyes of formula (1) and/or (2).

Preferably the mixture of dyes of the present invention are incorporated into the composition for treating organic material, preferably for dyeing in amounts of 0.001-5% b.w. (hereinafter indicated merely by "%"), particularly 0.005-4%, more particularly 0.2-3%, based on the total weight of the composition.

The formulations may be applied on the keratin-containing fiber, preferably the human hair in different technical forms.

Technical forms of formulations are for example a solution, especially a thickened aqueous or aqueous alcoholic solution, a cream, foam, shampoo, powder, gel, or emulsion.

Customary the dyeing compositions are applied to the keratin-containing fiber in an amount of 50 to 100 g.

Preferred forms of formulations are ready-to-use compositions or multi-compartment dyeing devices or 'kits' or any of the multi-compartment packaging systems with compartments as described for example in U.S. Pat. No. 6,190,421, col 2, l. 16 to 31.

The pH value of the ready-to-use dyeing compositions is usually from 2 to 11, preferably from 5 to 10.

Preferably the dyeing compositions, which are not stable to reduction, are prepared with oxidizing agent free compositions just before the dyeing process.

One preferred embodiment of the present invention relates to the formulation of dyes, wherein the mixture of dyes of the present invention are in powder form.

Powder formulations are preferably used if stability and/or solubility problems as for example described in DE 197 13 698, p. 2, l. 26 to 54 and p. 3, l. 51 to p. 4, l. 25, and p. 4, l. 41 to p. 5 l. 59.

Suitable cosmetic hair-care formulations are hair-treatment preparations, e.g. hair-washing preparations in the form of shampoos and conditioners, hair-care preparations, e.g. pre-treatment preparations or leave-on products such as sprays, creams, gels, lotions, mousses and oils, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colorants, preparations containing self-oxidizing dyes, or natural hair colorants, such as henna or chamomile.

For use on human hair, the dyeing compositions of the present invention can usually be incorporated into an aqueous cosmetic carrier. Suitable aqueous cosmetic carriers include, for example W/O, O/W, O/W/O, W/O/W or PIT emulsions and all kinds of microemulsions, creams, sprays, emulsions, gels, powders and also surfactant-containing foaming solutions, e.g. shampoos or other preparations, that are suitable for use on keratin-containing fibers. Such forms of use are described in detail in Research Disclosure 42448 (August 1999). If necessary, it is also possible to incorporate the dyeing compositions into anhydrous carriers, as described, for example, in U.S. Pat. No. 3,369,970, especially col 1, l. 70 to col 3, l. 55. The dyeing compositions according to the invention are also excellently suitable for the dyeing method described in DE-A-3 829 870 using a dyeing comb or a dyeing brush.

The constituents of the aqueous carrier are present in the dyeing compositions of the present invention in the customary amounts, for example emulsifiers may be present in the dyeing compositions in concentrations from 0.5 to 30% b.w. and thickeners in concentrations from 0.1 to 25% b.w. of the total dyeing composition.

Further carriers for dyeing compositions are for example described in "Dermatology", edited by Ch. Culnan, H. Maibach, Verlag Marcel Dekker Inc., New York, Basle, 1986, Vol. 7, Ch. Zviak, The Science of Hair Care, chapter 7, p. 248-250, especially on p. 243, l. 1 to p. 244, l. 12.

A shampoo has, for example, the following composition:
0.01 to 5% b.w. of mixture of dyes of the present invention;
8% b.w of disodium PEG-5 laurylcitrate Sulfosuccinate, Sodium Laureth Sulfate;
20% b.w. of sodium cocoamphoacetate;
0.5% b.w. of methoxy PEG/PPG-7/3 aminopropyl dimethicone;
0.3% b.w. of hydroxypropyl guar hydroxypropyltrimonium chloride;
2.5% b.w. of PEG-200 hydrogenated glyceryl palmate; PEG-7 glyceryl cocoate;
0.5% b.w. of PEG-150 distearate;
2.2% b.w of citric acid;
perfume, preservatives; and
water ad 100%.

The mixture of dyes of the present invention may be stored in a liquid to paste-like preparation (aqueous or non-aqueous) or in the form of a dry powder.

When the dyes and adjuvants are stored together in a liquid preparation, the preparation should be substantially anhydrous in order to reduce reaction of the compounds.

The dyeing compositions according to the invention may comprise any active ingredients, additives or adjuvants known for such preparations, like surfactants, solvents, bases, acids, perfumes, polymeric adjuvants, thickeners and light stabilisers.

The following adjuvants are preferably used in the hair dyeing compositions of the present invention:

non-ionic polymers, for example vinylpyrrolidone/vinyl acrylate copolymers, polyvinyl-pyrrolidone and vinylpyrrolidone/vinyl acetate copolymers and polysiloxanes;

cationic polymers, such as quaternised cellulose ethers, polysiloxanes having quaternary groups, dimethyldiallylammonium chloride polymers, copolymers of dimethyldiallyl-ammonium chloride and acrylic acid, as available commercially under the name Merquat® 280 and the use thereof in hair dyeing as described, for example, in DE-A-4 421 031, especially p. 2, l. 20 to 49, or EP-A-953 334;

acrylamide/dimethyldiallylammonium chloride copolymers, diethyl-sulfate-quaternised dimethylaminoethyl methacrylate/vinylpyrrolidone copolymers, vinylpyrrolidone/-imidazolinium methochloride copolymers;

quaternised polyvinyl alcohol:

zwitterionic and amphoteric polymers, such as acrylamido-propyltrimethylammonium chloride/acrylate copolymers and octylacrylamide/methyl methacrylate/tert-butylaminoethyl methacrylate/2-hydroxypropyl methacrylate copolymers;

anionic polymers, such as, for example, polyacrylic acids, crosslinked polyacrylic acids, vinyl acetate/crotonic acid copolymers, vinylpyrrolidone/vinyl acrylate copolymers, vinyl acetate/butyl maleate/isobornyl acrylate copolymers, methyl vinyl ether/maleic an hydride copolymers and acrylic acid/ethyl acrylate/N-tert-butyl acrylamide terpolymers;

thickeners, such as agar, guar gum, alginates, xanthan gum, gum arabic, karaya gum, locust bean flour, linseed gums, dextrans, cellulose derivatives, e.g. methyl cellulose, hydroxyalkyl cellulose and carboxymethyl cellulose, starch fractions and derivatives, such amylose, amylopectin and dextrins, clays, e.g. bentonite or fully synthetic hydrocolloids such as, for example, polyvinyl alcohol;

structuring agents, such as glucose and maleic acid;

hair-conditioning compounds, such as phospholipids, for example soya lecithin, egg lecithin, cephalins, silicone oils, and conditioning compounds, such as those described in DE-A-19 729 080, especially p. 2, l. 20 to 49, EP-A-834 303, especially p. 2, l. 18-p. 3, l. 2, or EP-A-312 343, especially p. 2, l. 59-p. 3, l. 11;

protein hydrolysates, especially elastin, collagen, keratin, milk protein, soya protein and wheat protein hydrolysates, condensation products thereof with fatty acids and also quaternised protein hydrolysates;

perfume oils, dimethyl isosorbitol and cyclodextrins, solubilisers, such as ethanol, isopropanol, ethylene glycol, propylene glycol, glycerol and diethylene glycol, anti-dandruff active ingredients, such as piroctones, olamines and zinc Omadine, substances for adjusting the pH value;

panthenol, pantothenic acid, allantoin, pyrrolidinecarboxylic acids and salts thereof, plant extracts and vitamins;

cholesterol;

light stabilisers and UV absorbers as listed in Table below:

TABLE 1

UV absorbers which may be use in the dyeing compositions of the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one | 36861-47-9 |
| 2 | 1,7,7-trimethyl-3-(phenylmethylene)bicyclo[2.2.1]heptan-2-one | 15087-24-8 |
| 3 | (2-Hydroxy-4-methoxyphenyl)(4-methylphenyl)methanone | 1641-17-4 |
| 4 | 2,4-dihydroxybenzophenone | 131-56-6 |

TABLE 1-continued

UV absorbers which may be use in the dyeing compositions of the present invention

| No. | Chemical Name | CAS No. |
|---|---|---|
| 5 | 2,2',4,4'-tetrahydroxybenzophenone | 131-55-5 |
| 6 | 2-Hydroxy-4-methoxy benzophenone; | 131-57-7 |
| 7 | 2,2'-dihydroxy-4,4'-dimethoxybenzophenone | 131-54-4 |
| 8 | 2,2'-Dihydroxy-4-methoxybenzophenone | 131-53-3 |
| 9 | 1-[4-(1,1-dimethylethyl)phenyl]-3-(4-methoxyphenyl)propane-1,3-dione | 70356-09-1 |
| 10 | 3,3,5-Trimethyl cyclohexyl-2-hydroxy benzoate | 118-56-9 |
| 11 | Isopentyl p-methoxycinnamate | 71617-10-2 |
| 12 | Menthyl-o-aminobenzoate | 134-09-8 |
| 13 | Menthyl salicylate | 89-46-3 |
| 14 | 2-Ethylhexyl 2-cyano,3,3-diphenylacrylate | 6197-30-4 |
| 15 | 2-ethylhexyl 4-(dimethylamino)benzoate | 21245-02-3 |
| 16 | 2-ethylhexyl 4-methoxycinnamate | 5466-77-3 |
| 17 | 2-ethylhexyl salicylate | 118-60-5 |
| 18 | Benzoic acid, 4,4',4"-(1,3,5-triazine-2,4,6-triyltriimino)tris-tris(2-ethylhexyl)ester; 2,4,6-Trianilino-(p-carbo-2'-ethylhexyl-1'-oxi)-1,3,5-triazine | 88122-99-0 |
| 19 | Benzoic acid, 4-amino-, ethyl ester, polymer with oxirane | 113010-52-9 |
| 20 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 21 | Triethanolamine salicylate | 2174-16-5 |
| 22 | 2,2'-Methylene-bis-[6-(2H-benzotriazol-2-yl)-4-(1,1,3,3-tetramethyl-butyl)-phenol] | 103597-45-1 |
| 23 | 2,4-bis{[4-(2-ethylhexyloxy)-2-hydroxy]-phenyl}-6-(4-methoxy-phenyl)-(1,3,5)-triazine (Tinosorb S) | 187393-00-6 |
| 24 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethylhexyl)-ester | 154702-15-5 |
| 25 | Phenol, 2-(2H-benzotriazol-2-yl)-4-methyl-6-[2-methyl-3-[1,3,3,3-tetramethyl-1-[(trimethylsilyl)oxy]disiloxanyl]propyl]- | 155633-54-8 |
| 26 | Dimethicodiethylbezalmalonate | 207574-74-1 |
| 27 | Benzoic acid, 2-[4-(diethylamino)-2-hydroxybenzoyl]-, hexyl ester | 302776-68-7 |
| 28 | 1,3,5-Triazine, 2,4,6-tris(4-methoxyphenyl)- | 7753-12-0 |
| 29 | 1,3,5-Triazine, 2,4,6-tris[4-[(2-ethylhexyl)oxy]phenyl]- | 208114-14-1 |
| 30 | 2-Propenoic acid, 3-(1H-imidazol-4-yl)- | 104-98-3 |
| 31 | Benzoic acid, 2-hydroxy-, [4-(1-methylethyl)phenyl]methyl ester | 94134-93-7 |
| 32 | 1,2,3-Propanetriol, 1-(4-aminobenzoate) | 136-44-7 |
| 33 | Benzeneacetic acid, 3,4-dimethoxy-α-oxo- | 4732-70-1 |
| 34 | 2-Propenoic acid, 2-cyano-3,3-diphenyl-, ethyl ester | 5232-99-5 |
| 35 | Anthralinic acid, p-menth-3-yl ester | 134-09-8 |
| 36 | 1,3,5-Triazine-2,4,6-triamine, N,N'-bis[4-[5-(1,1-dimethylpropyl)-2-benzoxazolyl]phenyl]-N"-(2-ethylhexyl)- or Uvasorb K2A | 288254-16-0 |
| 37 | 2-Hydroxy-4-methoxy benzophenone-5-sulfonic acid | 4065-45-6 |
| 38 | Alpha-(2-oxoborn-3-ylidene)toluene-4-sulphonic acid and its salts | 56039-58-8 |
| 39 | Methyl N,N,N-trimethyl-4-[(4,7,7-trimethyl-3-oxobicyclo[2,2,1]hept-2-ylidene)methyl]anilinium sulphate; | 52793-97-2 |
| 40 | 4-aminobenzoic acid | 150-13-0 |
| 41 | 2-phenyl-1H-benzimidazole-5-sulphonic acid | 27503-81-7 |
| 42 | 3,3'-(1,4-phenylenedimethylene)bis[7,7-dimethyl-2-oxo-bicyclo-[2.2.1]heptane-1-methanesulfonic acid] | 90457-82-2 |
| 43 | 1H-Benzimidazole-4,6-disulfonic acid, 2,2'-(1,4-phenylene)bis-, disodium salt | 180898-37-7 |
| 44 | Benzenesulfonic acid, 3-(2H-benzotriazol-2-yl)-4-hydroxy-5-(1-methylpropyl)-, monosodium salt | 92484-48-5 |
| 45 | 1-Dodecanaminium, N-[3-[[4-(dimethylamino)benzoyl]amino]propyl]-N,N-dimethyl-, salt with 4-methylbenzenesulfonic acid (1:1) | 156679-41-3 |
| 46 | 1-Propanaminium, N,N,N-trimethyl-3-[(1-oxo-3-phenyl-2-propenyl)-amino]-, chloride | 177190-98-6 |
| 47 | 1H-Benzimidazole-4,6-disulfonic acid, 2,2'-(1,4-phenylene)bis- | 170864-82-1 |
| 48 | 1-Propanaminium, 3-[[3-[3-(2H-benzotriazol-2-yl)-5-(1,1-dimethyl-ethyl)-4-hydroxyphenyl]-1-oxopropyl]amino]-N,N-diethyl-N-methyl-, methyl sulfate (salt) | 340964-15-0 |
| 49 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |

The use of UV absorbers can effectively protect natural and dyed hair from the damaging rays of the sun and increase the wash fastness of dyed hair.

Furthermore, the following UV absorbers or combinations may be used in the dyeing compositions according to the invention:

cationic benzotriazole UV absorbers as for example described in WO 01/36396 especially on p. 1, l. 20 to p. 2, l. 24, and preferred on p. 3 to 5, and on p. 26 to 37;

cationic benzotriazole UV in combination with antioxidants as described in WO 01/36396, especially on p. 11, l. 14 to p. 18;

UV absorbers in combination with antioxidants as described in U.S. Pat. No. 5,922,310, especially in col 2, I. 1 to 3;

UV absorbers in combination with antioxidants as described in U.S. Pat. No. 4,786,493, especially in col 1, 42 to col 2, I. 7, and preferred in col 3, 43 to col 5, I. 20;

combination of UV absorbers as described in U.S. Pat. No. 5,830,441, especially in col 4, I. 53 to 56;

combination of UV absorbers as described in WO 01/36396, especially on p. 11, I. 9 to 13; or triazine derivatives as described in WO 98/22447, especially on p. 1, I. 23 to p. 2, I. 4, and preferred on p. 2, I. 11 to p. 3, I. 15 and most preferred on p. 6 to 7, and 12 to 16.

Suitable cosmetic preparations may usually contain 0.05 to 40% b.w., preferably 0.1 to 20% b.w., based on the total weight of the composition, of one or more UV absorbers;

consistency regulators, such as sugar esters, polyol esters or polyol alkyl ethers;

fats and waxes, such as spermaceti, beeswax, montan wax, paraffins, fatty alcohols and fatty acid esters;

fatty alkanolamides;

polyethylene glycols and polypropylene glycols having a molecular weight from 150 to 50 000, for example such as those described in EP-A-801 942, especially p. 3, I. 44 to 55, complexing agents, such as EDTA, NTA and phosphonic acids, swelling and penetration substances, such as polyols and polyol ethers, as listed extensively, for example, in EP-A-962 219, especially p. 27, I. 18 to 38, for example glycerol, propylene glycol, propylene glycol monoethyl ether, butyl glycol, benzyl alcohol, carbonates, hydrogen carbonates, guanidines, ureas and also primary, secondary and tertiary phosphates, imidazoles, tannins, pyrrole;

opacifiers, such as latex;

pearlising agents, such as ethylene glycol mono- and di-stearate;

propellants, such as propane-butane mixtures, $N_2O$, dimethyl ether, $CO_2$ and air;

antioxidants; preferably the phenolic antioxidants and hindered nitroxyl compounds disclosed in ip.com (IPCOM # 000033153D);

sugar-containing polymers, as described in EP-A-970 687;

quaternary ammonium salts, as described in WO 00/10517;

Bacteria inhibiting agents, like preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% b.w., based on the solids content of the preparations;

The dyeing compositions according to the present invention generally comprise at least one surfactant.

Suitable surfactants are zwitterionic or ampholytic, or more preferably anionic, non-ionic and/or cationic surfactants.

Suitable anionic surfactants in the dyeing compositions according to the present invention include all anionic surface-active substances that are suitable for use on the human body. Such substances are characterised by an anionic group that imparts water solubility, for example a carboxylate, sulfate, sulfonate or phosphate group, and a lipophilic alkyl group having approximately 10 to 22 carbon atoms. In addition, glycol or polyglycol ether groups, ester, ether and amide groups and also hydroxy groups may be present in the molecule. The following are examples of suitable anionic surfactants, each in the form of sodium, potassium or ammonium salts or mono-, di- or tri-alkanolammonium salts having 2 or 3 carbon atoms in the alkanol group:

linear fatty acids having 10 to 22 carbon atoms (soaps), ether carboxylic acids of formula $R-O-(CH_2-CH_2-O)_x-CH_2-COOH$, in which R is a linear alkyl group having 10 to 22 carbon atoms and x=0 or from 1 to 16, acyl sarcosides having 10 to 18 carbon atoms in the acyl group, acyl taurides having 10 to 18 carbon atoms in the acyl group, acyl isothionates having 10 to 18 carbon atoms in the acyl group, sulfosuccinic mono- and di-alkyl esters having 8 to 18 carbon atoms in the alkyl group and sulfosuccinic monoalkylpolyoxyethyl esters having 8 to 18 carbon atoms in the alkyl group and from 1 to 6 oxyethyl groups, linear alkane sulfonates having 12 to 18 carbon atoms, linear α-olefin sulfonates having 12 to 18 carbon atoms, α-sulfo fatty acid methyl esters of fatty acids having 12 to 18 carbon atoms, alkyl sulfates and alkyl polyglycol ether sulfates of formula $R'-O(CH_2-CH_2-O)_{x'}-SO_3H$, in which R' is a preferably linear alkyl group having 10 to 18 carbon atoms and x'=0 or from 1 to 12, mixtures of surface-active hydroxysulfonates according to DE-A-3 725 030;

sulfated hydroxyalkylpolyethylene and/or hydroxyalkylenepropylene glycol ethers according to DE-A-3 723 354, especially p. 4, I. 42 to 62, sulfonates of unsaturated fatty acids having 12 to 24 carbon atoms and 1 to 6 double bonds according to DE-A-3 926 344, especially p. 2, I. 36 to 54, esters of tartaric acid and citric acid with alcohols which are addition products of approximately from 2 to 15 molecules of ethylene oxide and/or propylene oxide with fatty alcohols having from 8 to 22 carbon atoms, or anionic surfactants, as described in WO 00/10518, especially p. 45, I. 11 to p. 48, I. 3.

Preferred anionic surfactants are alkyl sulfates, alkyl polyglycol ether sulfates and ether carboxylic acids having 10 to 18 carbon atoms in the alkyl group and up to 12 glycol ether groups in the molecule, and also especially salts of saturated and especially unsaturated $C_8$-$C_{22}$-carboxylic acids, such as oleic acid, stearic acid, isostearic acid and palmitic acid.

Surface-active compounds that carry at least one quaternary ammonium group and at least one —COO⁻ or —SO₃⁻ group in the molecule are terminated zwitterionic surfactants. Preference is given the so-called betaines, such as the N-alkylN,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazoline having from 8 to 18 carbon atoms in the alkyl or acyl group and also cocoacylaminoethylhydroxyethylcarboxymethyl glycinate. A preferred zwitterionic surfactant is the fatty acid amide derivative known by the CTFA name cocoamidopropyl betaine.

Ampholytic surfactants are surface-active compounds that, in addition to a $C_8$-$C_{18}$-alkyl or -acyl group and contain at least one free amino group and at least one —COOH or —SO₃H group in the molecule and are capable of forming internal salts. Examples of suitable ampholytic surfactants include N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids, each having approximately from 8 to 18 carbon atoms in the alkyl group. Ampholytic surfactants to which special preference is given are N-cocoalkylaminopropionate, cocoacylaminoethylaminopropionate and $C_{12}$-$C_{18}$acylsarcosine.

Suitable non-ionic surfactants are described in WO 00/10519, especially p. 45, l. 11 to p. 50, l. 12. Non-ionic surfactants contain as hydrophilic group, for example, a polyol group, a poly-alkylene glycol ether group or a combination of polyol and polyglycol ether groups. Such compounds are, for example:
- addition products of 2 to 30 mol of ethylene oxide and/or 0 to 5 mol of propylene oxide with linear fatty alcohols having 8 to 22 carbon atoms, with fatty acids having 12 to 22 carbon atoms and with alkylphenols having 8 to 15 carbon atoms in the alkyl group,
- $C_{12}$-$C_{22}$ fatty acid mono- and di-esters of addition products of 1 to 30 mol of ethylene oxide with glycerol,
- $C_8$-$C_{22}$alkyl-mono- and -oligo-glycosides and ethoxylated analogues thereof,
- addition products of 5 to 60 mol of ethylene oxide with castor oil and hydrogenated castor oil,
- addition products of ethylene oxide with sorbitan fatty acid esters,
- addition products of ethylene oxide with fatty acid alkanolamides.

The surfactants which are addition products of ethylene and/or propylene oxide with fatty alcohols or derivatives of such addition products may either be products having a "normal" homologue distribution or products having a restricted homologue distribution. "Normal" homologue distribution are mixtures of homologues obtained in the reaction of fatty alcohol and alkylene oxide using alkali metals, alkali metal hydroxides or alkali metal alcoholates as catalysts. Restricted homologue distributions, on the other hand, are obtained when, for example, hydrotalcites, alkali metal salts of ether carboxylic acids, alkali metal oxides, hydroxides or alcoholates are used as catalysts.

The use of products having restricted homologue distribution may be preferred.

Examples of cationic surfactants that can be used in the dyeing compositions according to the invention are especially quaternary ammonium compounds. Preference is given to ammonium halides, such as alkyltrimethylammonium chlorides, dialkyldimethylammonium chlorides and trialkylmethylammonium chlorides, for example cetyltrimethylammonium chloride, stearyltrimethylammonium chloride, distearyldimethyl-lammonium chloride, lauryldimethylammonium chloride, lauryldimethylbenzylammonium chloride and tricetylmethylammonium chloride. Further cationic surfactants that can be used in accordance with the invention are quaternised protein hydrolysates.

Also suitable are cationic silicone oils, such as, for example, the commercially available pro-ducts Q2-7224 (manufacturer: Dow Corning; a stabilised trimethylsilylamodimethicone), Dow Corning 929 emulsion (comprising a hydroxylamino-modified silicone, which is also referred to as amodimethicone), SM-2059 (manufacturer: General Electric), SLM-55067 (manufacturer: Wacker) and also Abil®-Quat 3270 and 3272 (manufacturer: Th. Goldschmidt; diquaternary polydimethylsiloxanes, quaternium-80), or silicones, as described in WO 00/12057, especially p. 45, l. 9 to p. 55, l. 2.

Alkylamidoamines, especially fatty acid amidoamines, such as the stearylamidopropyl-dimethylamine obtainable under the name Tego Amid® 18 are also preferred as surfactants in the present dyeing compositions. They are distinguished not only by a good conditioning action but also especially by their good biodegradability.

Quaternary ester compounds, so-called "esterquats", such as the methyl hydroxyalkyl-dialkoyloxyalkylammonium methosulfates marketed under the trademark Stepantex®, are also very readily biodegradable.

An example of a quaternary sugar derivative that can be used as cationic surfactant is the commercial product Glucquat®100, according to CTFA nomenclature a "lauryl methyl gluceth-10 hydroxypropyl dimonium chloride".

The alkyl-group-containing compounds used as surfactants may be single substances, but the use of natural raw materials of vegetable or animal origin is generally preferred in the preparation of such substances, with the result that the substance mixtures obtained have different alkyl chain lengths according to the particular starting material used.

The mixture of dyes of the present invention are suitable for the dyeing of organic material, preferably keratin-containing fibers.

A further preferred embodiment of the present invention relates to a method of treating keratin-containing fibers with the mixture of dyes of the present invention.

The process comprises
(a) contacting the keratin fiber with a mixture of dyes of the present invention,
(b) leaving the fibers to stand, and
(c) then rinsing the fiber.

The process for dyeing is for example described in WO 01/66646 on page 15, line 32 to page 16, line 2.

A further preferred method comprises treating the hair in the presence of a reduction agent.

Preferred reduction agents are for example thioglycol acid or salts thereof, gycerine monothioglycolat, cystein, 2-mercaptopropionic acid, 2-mercaptoethylamine, thiolactic acid, thioglycerine, sodium sulfite, dithionithe, ammonium sulfite, sodium bisulfite, sodium metabisulfite, hydroquinone, phosphines, borhydride, cyanoborohydride, triacetoxy borohydride, trimethoxy borohydride salts (sodium, lithium, potassium, calcium quaternary salts).

Furthermore, the present invention relates to a process, comprising treating the hair with
(a) optionally a reduction agent,
(b) a mixture of dyes of the present invention s defined above, and
(c) with an oxidizing agent.

The step (a) may be of short duration from 0.1 sec to 30 minutes, for example from 0.1 seconds to 10 minutes with a reducing agent mentioned above.

The application of the dye mixture on the hair may be carried out at temperatures ranging from 15° to 100° C. Generally the application is carried out at room temperature.

The sequence of the reaction steps is generally not important, the reduction agent can be applied first or in a final step.

Usually, the oxidizing agent is applied together with an acid or a base.

The acid is for example citric acid, phosphoric acid or tartrate acid.

The base is for example sodium hydroxide, ammonia or monoethanolamine.

The mixture of dyes of the present invention are suitable for all-over dyeing of the hair, that is to say when dyeing the hair on a first occasion, and also for re-dyeing subsequently, or dyeing of locks or parts of the hair.

The mixture of dyes of the present invention is applied on the hair for example by massage with the hand, a comb, a brush, or a bottle, or a bottle, which is combined with a comb or a nozzle.

Further preferred is a process for dyeing keratin-containing fibers which comprises treating the keratin-containing fiber with mixture of dyes of the present invention, a base and an oxidizing agent.

The oxidation dyeing process usually involves lightening, that is to say that it involves applying to the keratin-containing fibers, at basic pH, a mixture of bases and aqueous hydrogen peroxide solution, leaving the applied mixture to stand on the hair and then rinsing the hair. It allows, particularly in the case of hair dyeing, the melanin to be lightened and the hair to be dyed.

Lightening the melanin has the advantageous effect of creating a unified dyeing in the case of grey hair, and, in the case of naturally pigmented hair, of bringing out the color, that is to say of making it more visible.

In general, the oxidizing agent containing composition is left on the fiber for 0.1 seconds to 15 minutes, in particular for 0.1 seconds to 5 minutes at 15 to 45° C., usually in amounts of 30 to 200 g.

Oxidizing agents are for example persulfate or diluted hydrogen peroxide solutions, hydrogen peroxide emulsions or hydrogen peroxide gels, alkaline earth metal peroxides, organic per-oxides, such as urea peroxides, melamine peroxides. Alkalimetalbromate fixations or enzymes are also appropriate if a shading powder on the basis of semi-permanent, direct hair dyes is used.

Further preferred oxidizing agents are oxidizing agents to achieve lightened coloration, as described in WO 97/20545, especially p. 9, l. 5 to 9, oxidizing agents in the form of permanent-wave fixing solution, as described in DE-A-19 713 698, especially p. 4, l. 52 to 55, and l. 60 and 61 or EP-A-1062940, especially p. 6, l. 41 to 47 (and in the equivalent WO 99/40895).

Most preferred oxidizing agent is hydrogen peroxide, preferably used in a concentration from about 2 to 30%, more preferably about 3 to 20% by, and most preferably from 6 to 12% b.w. the corresponding composition.

The oxidizing agents may be present in the dyeing compositions according to the invention preferably in an amount from 0.01% to 6%, especially from 0.01% to 1%, based on the total dyeing composition.

In general, the dyeing with an oxidative agent is carried out in the presence of a base, for example ammonia, alkali metal carbonates, earth metal (potassium or lithium) carbonates, alkanol amines, such as mono-, di- or triethanolamine, alkali metal (sodium) hydroxides, earth metal hydroxides or compounds of the formula

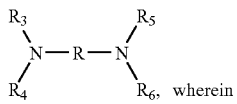

wherein

R is a propylene residue, which may be substituted with OH or $C_1$-$C_4$alkyl, $R_3$, $R_4$, $R_5$ and $R_6$ are independently or dependently from each other hydrogen, $C_1$-$C_4$alkyl or hydroxy-($C_1$-$C_4$)alkyl.

The pH-value of the oxidizing agent containing composition is usually about 2 to 7, and in particular about 2 to 5.

One preferred method of applying formulations comprising the mixture of dyes of the present invention on the keratin-containing fiber, preferably the hair is by using a multi-compartment dyeing device or "kit" or any other multi-compartment packaging system, as described for example in WO 97/20545 on p. 4, l. 19 to l. 27.

The first compartment contains for example the mixture of dyes of the present invention and optionally further direct dyes and a basifying agent, and in the second compartment an oxidizing agent; or in the first compartment the mixture of dyes of the present invention and optionally further direct dyes, in the second compartment a basifiying agent and in the third compartment an oxidizing agent.

A further preferred embodiment of the present invention relates to a method of dyeing hair with oxidative dyes, which comprises (a) mixing at least one dye of formula (1) and optionally at least one coupler compound and at least one developer compound, and an oxidizing agent, which optionally contains at least one further dye, and (b) contacting the keratin-containing fibers with the mixture as prepared in step (a).

The pH-value of the oxidizing agent free composition is usually from 3 to 11, and in particular from 5 to 10, and most particular about 9 to 10.

Preferably, a ready-to-use composition is prepared according to a first preferred embodiment by a process which comprises a preliminary step which involves separately storing, on the one hand, a composition (A) comprising, in a medium which is suitable for dyeing, at least one developer compound, especially selected from para-phenylenediamines and bis(phenyl)-alkylenediamines, and the acid-addition salts thereof, at least one coupler, especially selected from meta-phenylenediamines and the acid-addition salts thereof, and the mixture of dyes of the present invention, on the other hand, a composition (B) containing, in a medium which is suitable for dyeing, at least one oxidizing agent and mixing (A) and (B) together immediately before applying this mixture to the keratin-containing fibers.

According to a second preferred embodiment for the preparation of the ready-to-use dye composition, the process includes a preliminary step which involves separately storing, on the one hand, a composition (A) comprising, in a medium which is suitable for dyeing, at least one developer compound, especially selected from para-phenylenediamines and bis-(phenyl)alkylenediamines, and the acid-addition salts thereof, at least one coupler compound, especially selected from meta-phenylenediamines and the acid-addition salts thereof; on the other hand, a composition (A') comprising, in a medium which is suitable for dyeing, at least one dye of formula (1), and, finally, a composition (B) containing, in a medium which is suitable for dyeing, at least one oxidizing agent as defined above, and mixing them together at the time of use immediately before applying this mixture to the keratin-containing fibers.

The composition (A') used according to this second embodiment may optionally be in powder form, the mixture of dyes of the present invention constituting, in this case, all of the composition (A') or optionally being dispersed in an organic and/or inorganic pulverulent excipient.

When present in the composition A', the organic excipient may be of synthetic or natural origin and is selected in particular from crosslinked and non-crosslinked synthetic polymers, polysaccharides such as celluloses and modified or unmodified starches, as well as natural products such as sawdust and plant gums (guar gum, carob gum, xanthan gum, etc.).

When present in the composition (A'), the inorganic excipient may contain metal oxides such as titanium oxides, aluminium oxides, kaolin, talc, silicates, mica and silicas.

A very suitable excipient in the dyeing compositions according to the invention is sawdust.

The powdered composition (A') may also contain binders or coating products in an amount which preferably does not exceed approximately 3% b.w. relative to the total weight of composition (A'). These binders are preferably selected from oils and liquid fatty substances of inorganic, synthetic, animal or plant origin.

Furthermore, the present invention relates to a process of dyeing of keratin-containing fibers with the mixture of dyes of the present invention and autooxidable compounds and optionally further dyes.

Furthermore, the present invention relates to a process for dyeing keratin-containing fibers with the mixture of dyes of the present invention and capped diazotised compounds, which comprises, (a) treating the keratin-containing fibers under alkaline conditions with at least one capped diazotised compound and a coupler compound, and optionally a developer compound ad optionally an oxidizing agent, and optionally in the presence of a further dye, and optionally with the mixture of dyes of the present invention; and (b) adjusting the pH in the range of 6 to 2 by treatment with an acid, optionally in the presence of a further dye, and optionally with the mixture of dyes of the present invention with the proviso that at least in one step (a) or (b) the mixture of dyes of the present invention is present.

The capped diazotised compound and coupler compound and optionally the oxidizing agent and developer compound can be applied in any desired order successively, or simultaneously.

Preferably, the capped diazotised compound and the coupler compound are applied simultaneously, in a single composition.

"Alkaline conditions" denotes a pH in the range from 8 to 10, preferably 9-10, especially 9.5-10, which are achieved by the addition of bases, for example sodium carbonate, ammonia or sodium hydroxide.

The bases may be added to the hair, to the dye precursors, the capped diazotised compound and/or the water-soluble coupling component, or to the dyeing compositions comprising the dye precursors.

Acids are for example tartaric acid or citric acid, a citric acid gel, a suitable buffer solution with optionally an acid dye.

The ratio of the amount of alkaline dyeing composition applied in the first stage to that of acid dyeing composition applied in the second stage is preferably about from 1:3 to 3:1, especially about 1:1.

Furthermore, the present invention relates to a process for dyeing keratin-containing fibers with the mixture of dyes of the present invention and at least one acid dye.

The following Examples serve to illustrate the processes for dyeing without limiting the processes thereto. Unless specified otherwise, parts and percentages relate to weight. The amounts of dye specified are relative to the material being coloured.

EXAMPLES

A. Preparation Examples

Example AZO-01

12.4 g 4-fluoroaniline are added to a stirred solution of 25 ml water and 25 ml of 32% hydrochloric acid at 295 K. The reaction mixture is cooled to 273 K and 19 ml of a 36% sodium nitrite solution are dropped at such a rate that the temperature of the mixture is maintained in the range of 273 to 276 K. After the addition of the sodium nitrite solution the mixture is stirred for one hour. If no excess of nitrite is detected during one hour (detection by using a potassium iodide paper) further sodium nitrite solution is added. The remaining excess of nitrite is reduced with sulfamic acid. The obtained diazo solution is dropped to a 273 K cold solution of 7.4 g imidazole in 30 ml water, whereby the pH of the solution is maintained in the range of pH 10 to 11 by adding 36% of a sodium hydroxide solution. After completing the diazo addition the obtained suspension is warmed up to 295 K, the pH is adjusted to 10.5 with 36% sodium hydroxide solution. After stirring for one hour at this pH and temperature the suspension is filtered off and washed twice with 50 ml water to obtain 55 g of a humid product, which is suspended in 200 ml water and 3 weight equivalents dimethyl sulfate and sodium hydroxide are simultaneously added for maintaining the pH at 10-10.3 and the temperature at 298-303K.

The reaction is allowed to stand for one more hour to finish the hydrolysis of excess of dimethyl sulfate.

100 g sodium chloride and 50 g potassium chloride are added at 273K and allowed to stand for 16 hours. The product is separated by filtration and washed with a cold solution of sodium/potassium chloride. About 20 g of the compound of formula

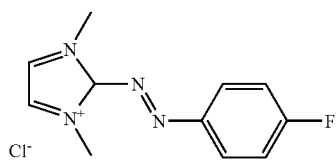

(AZO-101a)

are obtained 6.9 g of cisteamine dihydrochloride are added at 293 K under nitrogen atmosphere to 20 g of the compound of formula (101a) in 120 g isopropanol and 24 g triethylamine. The temperature is raised to 333 K and the reaction mixture is stirred at this temperature during 25 hours. The reaction mass is stirred for 4 hours while the temperature is decreased to 295 K. The reaction mass is filtered off and the filter residue washed with 45 ml of isopropanol and again filtered. 300 ml water are added to the humid filter residue and the mixture is stirred for 3 hours at 353 K. Then the temperature is decreased to 295 K and the mixture filtered off. The filter residue is washed with 100 ml water, filtered and dried in vacuum to obtain 16 g of compound of formula (101).

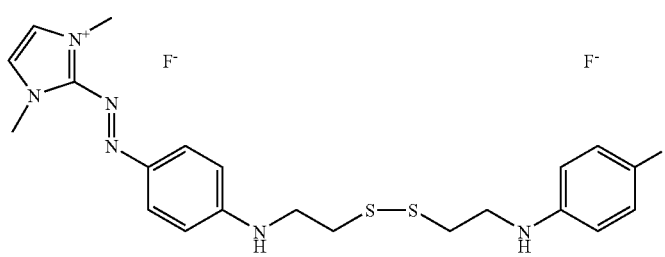

(AZO-101)

$^1$H-NMR Data in deuterated methanol (128 scans)/360 MHz:

| | | | | |
|---|---|---|---|---|
| 7.924 | d | 7.3 | 3.95 | phenylen |
| 7.5109 | s | | 3.82 | imidazol |
| 6.857 | d | 7.8 | 3.96 | phenylen |
| 4.038 | s | | 12.06 | dimethyl |
| 3.595 | t | | 3.982 | methylen |
| 2.925 | t | | 4.00 | methylen |

Example AZO-02

(AZO-102)

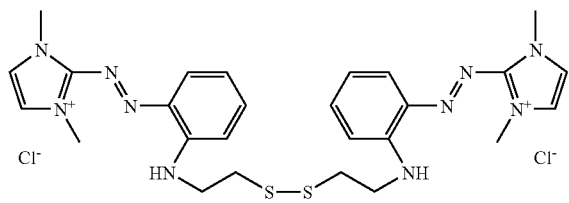

12.4 g 2-fluoroaniline are added to a stirred solution of 25 ml water and 25 ml of 32% hydrochloric acid at 295 K. The reaction mixture is cooled to 273 K and 19 ml 36% sodium nitrite solution are dropped at such a rate that the temperature of the mixture is maintained in the range of 273 to 276 K. After the addition of the sodium nitrite solution the mixture is stirred for one hour. If no excess of nitrite is detected during one hour (detection by using a potassium iodide/starch paper) further amounts of sodium nitrite solution are added. Then the remaining excess of nitrite is destroyed with sulfamic acid. The obtained diazo solution is dropped to a 273 K cold solution of 7.4 g imidazole in 30 ml water, whereby the pH of the solution is maintained in the range of pH 10 to 11 by adding 36% sodium hydroxide solution. After completing the diazo addition the obtained suspension is warmed up to 295 K and the pH is adjusted to 10.5 with 36% sodium hydroxide solution. After stirring for one hour at this pH and temperature the suspension is filtered off and then washed twice with 50 ml water to obtain 55 g of the humid product, which is suspended in 500 ml water. 0.3 mol dimethyl sulfate and sodium hydroxide are simultaneously added for maintaining the pH in the range of 10-10.3 and the temperature at 298-303K. The reaction mixture is hold for one hour. Then the water is evaporated.

About 40 g humid solid, which gives 27 g of dried product of the formula (AZO-102a)

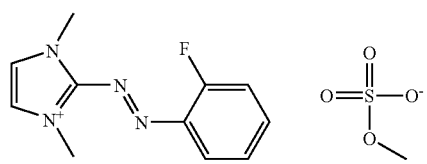

is obtained

The product is characterized by $^1$H-NMR Data in deuterated methanol (128 scans)/360 MHz:

| | | | |
|---|---|---|---|
| 8.002 ddd | J = 7.6; J = 7.5; j = 1.4 | 1.029 | |
| 7.893 s | | 2.00 | imidazol |
| 7.812 m | J = 8.6, J = 6.7, J = 1.4 | 0.99 | |
| 7.505 ddd | J = 8.6 | 1.06 | |
| 7.436 t | | 0.949 | |
| 4.211 s | | 5.78 | dimethyl of imidazol |
| 3.69 s | | 4.01 | methy of monomethylsulfate |

11 g cisteamin chlorohydrate are added to 27 g of compound of formula (102a) in 20 g triethylamine and 120 g isopropanol under nitrogen atmosphere at 293 K. The temperature is raised to 333 K. The reaction mixture is stirred for 28 hours at this temperature. Then the reaction mass is stirred for 4 hours while the temperature is decreased to 295 K. The reaction mass is filtered off and the filter residue washed with 45 ml isopropanol and dried in vacuum to obtain 17.6 g of product f formula (102).

The product is characterized by $^1$H-NMR Data in deuterated methanol (128 scans)/360 MHz:

| | | | |
|---|---|---|---|
| 7.78 dd | J = 8.6; J = 1.4 | 2.07 | |
| 7.620 s | | 4.00 | imidazol |
| 7.498 m | J = 8.6; J = 6.7 J = 1.4 | 1.968 | |
| 7.083 d | J = 8.6 | 1.875 | |
| 6.831 m | | 1.938 | |
| 4.057 s | | 12.08 | dimethyl of dmidazol |
| 3.846 t | 6 | 3.75 | methylene |
| 3.69 s | | 4.01 | methy of monomethylsulfate |
| 3.109 t | 6 | 3.95 | methylene |

Example AZO-03

(AZO-103)

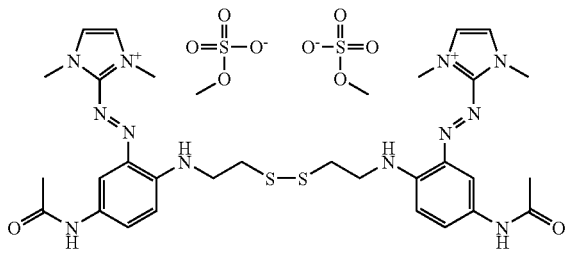

100 g 4-fluoro-3-nitroaniline are added to a stirred mass of 80 g methanol and heated to 333 K. 0.1 ml sulfuric acid and 90 ml of acetic anhydride are added during 15 minutes. Heating and boiling are continued for 15 minutes. Then the reaction mixture is cooled slowly to 273 K with stirring. At the final temperature stirring is continued for 30 minutes, then the suspension is filtered off, washed with cold methanol, dried in the vacuum dryer getting 114 g acetyl derivative which is worked up further. The acetyl derivative is solved in 520 ml ethanol and continuously added to 130 g iron in 35 ml concentrated hydrochloric acid and 220 ml water at 363K during 1 hour. The temperature drops to 353 K. The reaction mixture is stirred for further 3 hours. The hot mass is separated through filtration the residue washed with 100 ml ethanol. The filtrate and wash solution are cooled to 380 K with mixing, when crystallization of the product takes place. The product is separated by filtration, washed with cold ethanol and dried in a vacuum dryer.

The dried material is dissolved in 132 ml water and 110 ml of 32% hydrochloric acid at 295 K. The reaction mixture is cooled to 273 K and 86.4 g 36% sodium nitrite solution are dropped at such a rate that the temperature of the mixture is maintained in the range of 273 to 276 K. The mixture is further stirred for one hour. If no excess of nitrite is detected during one hour (detection by using a potassium iodide/starch paper) further amounts of sodium nitrite solution are added. After this one hour the remaining excess of nitrite is destroyed with sulfamic acid. Then the obtained diazo solution is dropped to a 273 K cold solution of 33.4 g imidazole in 130 ml water, whereby the pH of the solution is maintained in the range of pH 10 to 11 by adding 36% of a sodium hydroxide solution. After completing the diazo addition, the obtained suspension is warmed up to 295 K and the pH is adjusted to 10.5 with 36% sodium hydroxide solution. After stirring for one hour at this pH and temperature the suspension is filtered off and then washed twice with 100 ml water to obtain 200 g of the humid product. The filtercake from the previous step is suspended in water and 3 weight equivalents dimethylsulfate and sodium hydroxide are simultaneously added for maintaining the pH in the range of 10-10.3 and the temperature at 300 K. Then the reaction mixture is hold for one more hour to finish the hydrolysis of excess of dimethylsulfate. Then the suspension is separated by filtration. About 240 g of a humid solid which gives 140 g dried product of formula (AZO-103a)

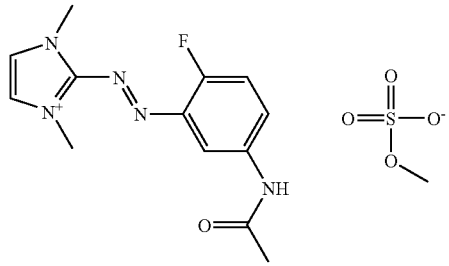

Is obtained.

38.8 g of the product of formula (103a) are added to a stirred mixture of 10.6 g of cisteamin chlorhydrate in 15 g triethylamine and 70 g acetonitrile under nitrogen atmosphere at 293 K. The temperature is maintained at 273 K. The reaction mixture is stirred for 20 hours at this temperature. The reaction mass is filtered off and the filter residue washed with 45 ml of acetonitrile and dried in vacuum to obtain 42 g of product of formula (103).

The product is characterized by $^1$H-NMR Data in deuterated methanol (128 scans)/360 MHz:

| 8.11 | d, J = 1.7 | 2.00 | orto |
|------|-----------|------|------|
| 7.6 | d, d, J = 8.6; J = 1.4 | 6.06 | para |
| 7.57 | s | | imidazol |
| 7.00 | d, J = 9.5 | 2.04 | meta |
| 4.03 | s | 12.22 | methyl |
| 3.860 | t | 3.89 | methylene |
| 3.69 | s | 6.44 | methylsulfate |
| 3.1o9 | t | 4.28 | methylene |
| 2.14 | s | 6.22 | acetyl |

Example AZO-04

(104)

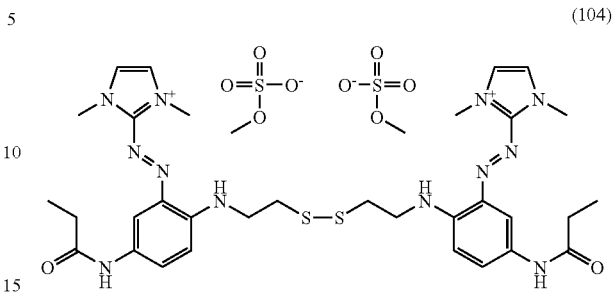

100 g 4-fluoro-3-nitro-aniline is added to a stirred mass of 80 g methanol, heated to 333 K, 0.1 ml sulfuric acid added, and then 90 ml of propionic anhydride during 15 minutes. Then heating and boiling is continued for 15 minutes. Then the reaction mixture is cooled slowly to 273 K with stirring. At the final temperature stirring is continued for 30 minutes, then the suspension is filtered, washed with cold methanol, dried in the vacuum dryer getting 114 g acetyl derivative which is worked up further. Then, the acetyl derivative is solved in 520 ml ethanol and continuously added to 130 g iron in 35 ml concentrated chlorhidric acid and 220 ml water at 363K during 1 hour. The temperature drops to 353 K. The reaction mixture is stirred for further 3 hours. The hot mass is separated through filtration, the residue washed with 100 ml ethanol. The filtrate and wash solution is cooled to 380 K with mixing, when crystallization of the product takes place. The product is separated by filtration, washed with cold ethanol and dried in a vacuum dryer.

The dried material is dissolved in 132 ml water and 110 ml of 32% hydrochloric acid at 295 K. Then the reaction mixture is cooled to 273 K and 86.4 g 36% sodium nitrite solution is dropped at such a rate that the temperature of the mixture is maintained in the range of 273 to 276 K. After the addition of the sodium nitrite solution, the mixture is stirred for one hour. If no excess of nitrite is detected during one hour (detection by using a potassium iodide/starch paper), further amounts of sodium nitrite solution is added. After this one hour the remaining excess of nitrite is destroyed with sulfamic acid. Then, the obtained diazo solution is dropped to a 273 K cold solution of 33.4 g imidazole in 130 ml water, whereby the pH of the solution is maintained in the range of pH 10 to 11 by adding 36% sodium hydroxide solution. After completing the diazo addition, the obtained suspension is warmed up to 295 K, the pH is adjusted to 10.5 with 36% sodium hydroxide solution. After one hour stirring at this pH and temperature, the suspension is filtrated and then washed twice with 100 ml water to obtain 200 g of the humid product Then, the filtercake from the previous step is suspended in water and 3 weight equivalents dimethylsulphate and sodium hydroxide simultaneously added for maintaining the pH in the range of 10-10.3 and the temperature at 300 K. Then, the reaction mixture is hold for one more hour, to finish the hydrolysis of excess of dimethylsulphate. Then, the suspension is separated by filtration. About 240 g humid solid, which gives 140 g dried product of formula

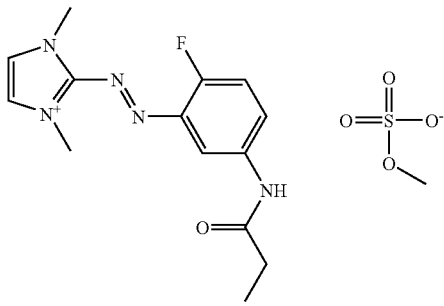

(AZO-104a)

Characterization by ¹H-NMR Data in deuterated methanol (128 scans)/360 MHz

|  |  |  | Residue of compound (104) |
|---|---|---|---|
| 8.11 | d, J = 1.7 | 2.00 | ortho coupling |
| 7.6 overlaid | d, d, J = 8.6; J = 1.4 | 6.06 | para coupling |
| 7.57 | s |  | imidazol |
| 7.00 | d, j = 9.5 | 2.04 | meta coupling |
| 4.03 | s | 12.22 | methyl |
| 3.860 | t | 3.89 | methylene |
| 3.69 | s | 6.44 | methylsulfate |
| 3.1o9 | t | 4.28 | methylene |
| 2.14 | q | 4.22 | propionyl |
| 1.20 | t | 6.27 | propionyl |

Example AZO-05

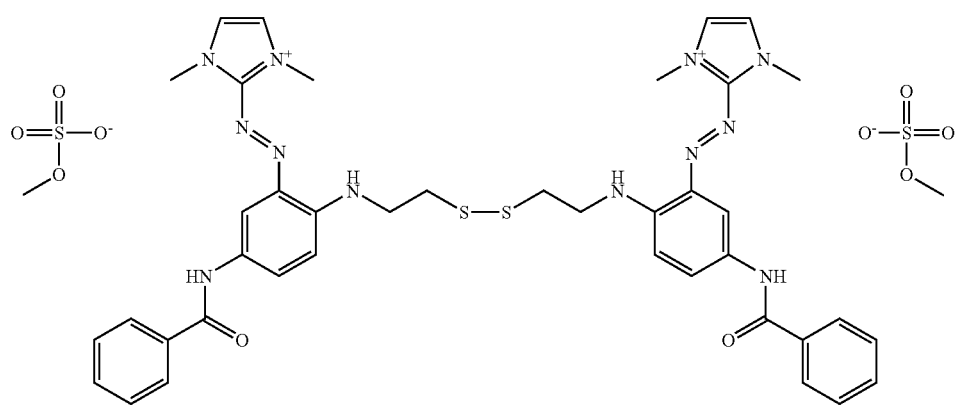

(AZO-105)

|  |  |  | Residue of compound |
|---|---|---|---|
| 8.415 | d, J = 2.7; 6.6 | 0.95 | ortho coupling |
| 7.889 | s | 2.00 | imidazol |
| 7.820 | d, d, d; | 0.98 | para coupling |
| 7.468 | d, d J = 9.5: 9.5 | 1.04 | meta coupling |
| 4.203 | s | 6.22 | methyl |
| 3.69 | s | 3.00 | methylsulfat |
| 2.175 | q | 2.22 | propionyl |
| 1.20 | t | 3.28 | propionyl |

38.8 g of the product of formula (104a) are added under nitrogen atmosphere at 293 K to a stirred mixture of 10.6 g of cisteamin chlorohydrate in 15 g triethylamine and 70 g acetonitrile. The temperature is maintained at 273 K. The reaction mixture is stirred for 20 hours at this temperature. The reaction mass is filtered off and the filter residue is washed with 45 ml of acetonitrile and dried in vacuum to obtain 32.6 g of product of formula (104).

Characterization by ¹H-NMR Data in deuterated methanol (128 scans)/360 MHz 100 g 4-fluoro-3-nitro-aniline are added to a stirred mass of 80 g methanol and heated to 333 K. 0.1 ml sulfuric acid and 90 ml of benzoyl chloride are added during 15 minutes. Heating and boiling is continued for 15 minutes. The reaction mixture is cooled slowly to 273 K with stirring and continued for 30 minutes. The suspension is filtered off, washed with cold methanol, dried in the vacuum dryer getting 114 g acetyl derivative which is worked up further. The acetyl derivative is dissolved in 520 ml ethanol and continuously added to 130 g iron in 35 ml concentrated chlorhidric acid and 220 ml water at 363K during 1 hour. The temperature drops to 353 K. The reaction mixture is stirred for further 3 hours. The hot mass is separated through filtration, the residue washed with 100 ml ethanol. The filtrate and wash solution are cooled to 380 K with mixing when crystallization of the product takes place. The product is separated by filtration, washed with cold ethanol and dried in a vacuum dryer. The dried material is dissolved in 132 ml water and 110 ml of 32% hydrochloric acid at 295 K. Then the reaction mixture is cooled to 273 K and 86.4 g of a 36% sodium nitrite solution are dropped at such a rate that the temperature of the mixture is maintained in the range of 273 to 276 K. After the addition of the sodium nitrite solution the mixture is stirred for one hour. If no excess of nitrite is detected during one hour (detection by using a potassium iodide/starch paper) further amounts of sodium nitrite solution are added. The remaining excess of nitrite is destroyed with sulfamic acid. Then the obtained diazo solution is dropped to a 273 K cold solution of 33.4 g imidazole in 130 ml water, whereby the pH of the solution is maintained in the range of pH 10 to 11 by adding 36% of a sodium hydroxide solution. After completion of the diazo addition the obtained suspension is warmed up to 295 K, the pH adjusted to 10.5 with 36% sodium hydroxide solution. After stirring for one hour at this pH and temperature the suspension is filtered off and then washed twice with 100 ml water to obtain 200 g of the humid product Then the filtercake from the previous step is suspended in water and 3 weight equivalents dimethylsulfate and sodium hydroxide simultaneously added for maintaining the pH in the range of 10-10.3 and the temperature at 300 K. Then the reaction mixture is hold for one more hour to finish the hydrolysis of excess of dimethylsulfate. Then, the suspension is separated by filtration.

About 240 g of a humid solid, which gives 140 g dry product of the following formula (AZO-105a)

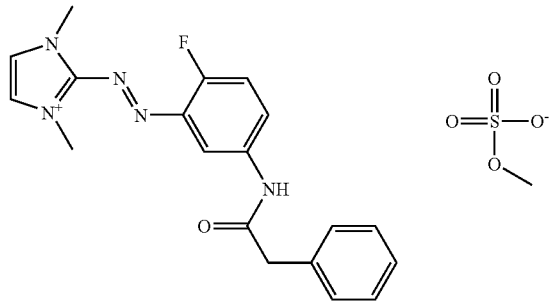

is obtained

Characterization by $^1$H-NMR Data in deuterated methanol (128 scans)/360 MHz

|       |              |       | Residue of compound |
|-------|--------------|-------|---------------------|
| 8.415 | D, j = 2.7; 6.6 | 0.95  | ortho coupling      |
| 7.889 | s            | 2.00  | Imidazol            |
| 7.820 | d, d, d;     | 0.98  | para coupling       |
| 7.468 | D, d j = 9.5: 9.5 | 1.04 | meta coupling    |
| 4.203 | s            | 6.22  | methyl              |
| 3.69  | s            | 3.oo  | methylsulfat        |

48 g of the compound of formula (105a) are added to a stirred mixture of 11.6 g of cisteamin chlorohydrate in 15 g triethylamine and 70 g acetonitrile under nitrogen atmosphere at 293 K. Then the temperature is maintained at 273 K. The reaction mixture is stirred for 20 hours at this temperature. The reaction mass is filtered off and the filter residue is washed with 45 ml acetonitrile and dried in vacuum to obtain 42.6 g of the compound of formula (105).

Characterization by $^1$H-NMR Data in deuterated methanol (128 scans)/360 MHz:

|             |                  |       | Residue of compound |
|-------------|------------------|-------|---------------------|
| 8.11        | d, j = 1.7       | 2.00  | ortho coupling      |
| 7.6 overlaid | d, d, J = 8.6; j = 1.4 | 6.06 | para coupling |
| 7.57        | S                |       | Imidazol coupling   |
| 7.00        | d, j = 9.5       | 2.04  | meta coupling       |
| 4.03        | s                | 12.22 | methyl              |
| 3.860       | t                | 3.89  | methylene           |
| 3.69        | s                | 6.44  | methylsulfat        |
| 3.1o9       | t                | 4.28  | methylene           |

Example AZO-06

(AZO-106)

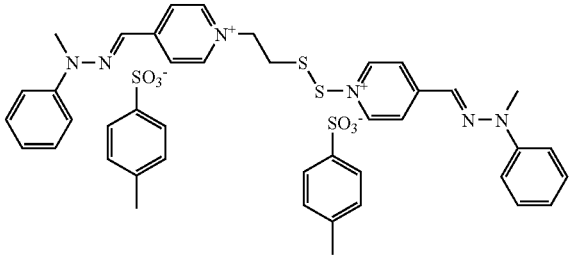

1. Formation of the Hydrazone: 14 g sulfuric acid are added to 42 g of water and cooled to 293K. 24 g of N-methyl-phenyl hydrazine (100%) are added with stirring. 24.5 g of 4-pyridine-aldehyde are dropped in during 15 minutes and stirring is continued for 1 hour. The pH is raised to 2.2 by adding a solution of 36% sodium hydroxide in water. 2.7 g sodium chloride are added at the 333K. Stirring is continued at this temperature for one hour. The slurry is separated by filtration; the filter cake is dried at 343K in vacuum to yield 42 g of an orange powder.

2. Alkylating agent: A mixture of 15.4 g of 2.2-dithiodiethanol in 100 ml chloroform and 24.1 g pyridine are cooled with stirring at 273K and then 41.0 g of tosyl chloride are added in small amounts, maintaining the temperature.

After completion of the addition the mixture is left over night in the refrigerator. The reaction mixture is mixed with a water/hydrochloric acid/ice slurry. The phases are separated, washed with water and dried. The obtained solution of toluenesulfonate diester is used in the 3. step.

3. Alkylation: The foregoing hydrazone is dissolved by stirring with the equivalent amount of diester solution. Temperature is raised to 334K which is maintained during the following 48 hours. Crystals separated in the slurry are filtered off. The product is washed with 50 ml chloroform and dried in vacuum to obtain 59 g of an orange solid product. The product is recrystallized twice from methanol.

Characterization by $^1$H-NMR data in deuterated methanol (32 scans)/360 MHz:

|       |   |      |       | Residues of the compound |
|-------|---|------|-------|--------------------------|
| 8.632 | d | 6.8  | 4.00  | pyridinyl                |
| 8.070 | d | 6.7  | 3.98  | pyridinyl                |
| 7.701 | d | 7.0  | 3.74  | tosylate                 |
| 7.648 | s |      | 2.04  | hydrazon                 |
| 7.528 | d | 6.1  | 3.967 | phenyl                   |
| 7.410 | t | 6.1  | 4.025 | phenyl                   |
| 7.195 | t | 6.6  | 3.846 | tosylate                 |
| 7.148 | t | 6.4  | 2.05  | phenyl                   |
| 4.78  | t | 6.77 | 4.00  | ethylene                 |
| 3.625 | s |      | 6.05  | mehydrazon               |
| 3.385 | t | 6.55 | 4.087 | ethylene                 |
| 2.326 | s |      | 5.90  | tosylate                 |

Example AZO-07

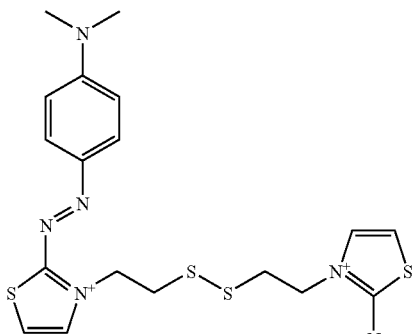
(AZO-107)

Characterization by ¹H-NMR Data in deuterated methanol (128 scans)/360 MHz:

| | | | | Residues of the compound |
|---|---|---|---|---|
| 8.095 | d | J = 8.6; | 2.07 | |
| 7.867 | d | J = 4.2 | 2.00 | thiazol |
| 7.696 | d | overlaid | 6 | phenylene |
| 7.470 | d | J = 4.3 | 1.968 | thiazol |
| 7.217 | d | J = 8.6 | 4.00 | tosyl |
| 7.083 | d | J = 8.6 | 3.97 | phenylene |
| 4.856 | t | 5.6 | 4.08 | methylene |
| 3.419 | s | | 12 | methyl |
| 3.139 | t | 5.6 | 4.01 | methylen |
| 2.309 | s | | 6.00 | Methyl |

Example AZO-08

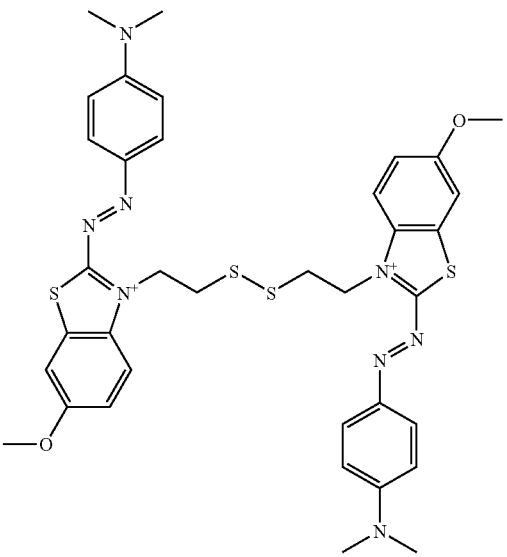
(AZO-108)

1. Monoazo: 50.0 of g 2-amino-thiazol are added to a stirred solution of 135 ml 60% sulfuric acid at 293-310 K. Then, the reaction mixture is cooled to 273 K and 81 ml of a 40% nitrosylsulfuric acid are dropped at such a rate that the temperature of the mixture is maintained in the range of 273 to 276 K by cooling. After the addition the mixture is stirred for four hours. The solution is dropped to a well-stirred water ice mixture (400 g) containing 2.5 g amidosulfuric acid. To the obtained diazo solution (at 273 K ice added if need) 60.5 g dimethylaniline are dropped. Then the pH of the solution is raised to the range of 5 to 6 by adding 36% sodium hydroxide solution. After one hour stirring at this pH and temperature the suspension is filtered off and then washed twice with 50 ml water to obtain 155 g of the humid product. After drying 100 monoazo dye is obtained.
2. Alkylating agent: A mixture of 15.4 g of 2,2-dithiodiethanol in 100 ml chloroform and 24.1 g pyridine are cooled with stirring to 273 K and then 41.0 g of tosyl chloride are added in small amounts maintaining the temperature.

After completion of the addition the mixture is left over night in the refrigerator. The reaction mixture is mixed with a water/hydrochloric acid/ice slurry, the phases are separated, washed with water and dried. The obtained solution of toluenesulfonate diester is used in the following step 3. Alkylation: The foregoing monoazo is dissolved by stirring into the diester solution. Temperature is raised to 333K. The temperature is maintained at 333K during the following 60 hours. Crystals separated in the slurry are filtered off. The product is washed with 50 ml of chloroform and dried in vacuum to obtain 59 g of a dark violet solid product.

The product is recrystallized twice from methanol.

Monoazo Synthesis 90.0 g 2-amino-6-methoxy-benzothiazol are added to a stirred solution of 135 ml 60% sulfuric acid at 293 K. The reaction mixture is cooled to 273 K and 81 ml of a 40% nitrosylsulfuric acid are dropped at such a rate that the temperature of the mixture is maintained in the range of 273 to 276 K with cooling and stirred for four hours. The solution is dropped to a well-stirred water ice mixture (400 g) containing 2.5 g amidosulfuric acid. 60.5 g dimethylaniline are dropped to the obtained diazo solution (at 273 K ice added if need). The pH of the solution is adjusted between 5 and 6 by adding 36% sodium hydroxide solution. After stirring for one hour at this pH and temperature the suspension is filtered off and washed twice with 50 ml water to obtain 255 g of the humid product. After drying 151 monoazo dye is obtained.

2. Alkylating agent: A mixture of 21.4 g of 2,2-dithiodiethanol in 100 ml chloroform and 24.1 g pyridine are cooled with stirring to 273K and then 41.0 g of mesyl anhydride are added in small amounts under constant temperature.

After completion of the addition the mixture is left over night in the refrigerator to finish the reaction. The reaction mixture is mixed with a water/hydrochloric acid/ice slurry, the phases are separated, washed with water and dried. The obtained solution of methanesulfonate diester is used in the following step 3. Alkylation: Two equivalents of the foregoing monoazo are dissolved by stirring into the diester solution. Temperature was raised to 334K. The temperature was maintained at 334K during the following 80 hours. Crystals separated in the slurry are filtered off. The product is washed with 50 ml of chloroform and dried in vacuum to obtain 80 g of a dark violet solid product. The product is recrystallized twice from methanol.

Characterization by $^1$H-NMR in deuterated methanol (128 scans)/360 MHz:

|  |  |  |  | Residues of compound |
|---|---|---|---|---|
| 7.924 | d | 7.3 | 3.95 | phenylene |
| 7.5109 | s |  | 3.82 | imidazol |
| 6.857 | d | 7.8 | 3.96 | phenylene |
| 4.038 | s |  | 12.06 | dimethyl |
| 3.595 | t |  | 3.982 | methylene |
| 2.925 | t |  | 4.00 | methylene |

Example AZO-09

(AZO-109)

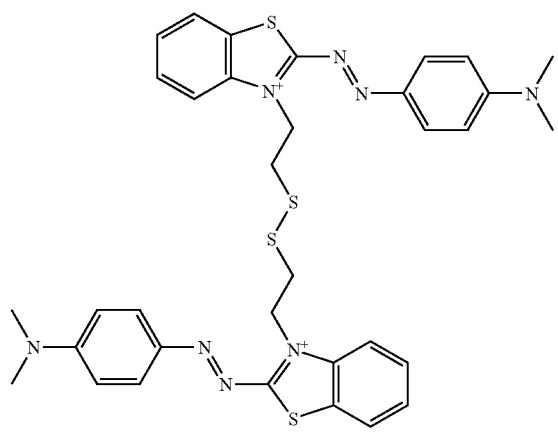

Same preparation process as described in example A8, but with the difference that 2-amino-benzothiazol instead of 2-amino-6-methoxy-benzothiazol is used.

Example AZO-10

(AZO-110)

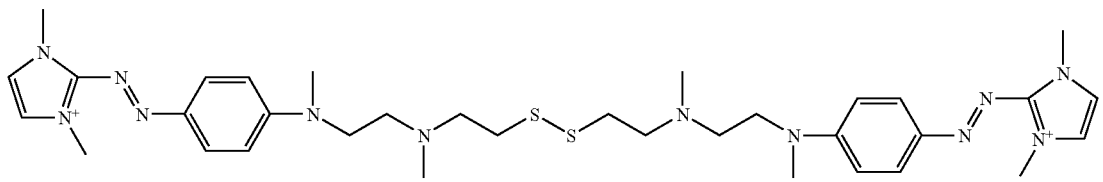

19.9 g of N,N'-dimethyl-ethylendiamine are added with stirring to 120 g acetonitrile and compound of the formula of formula (101a) at 293 K under nitrogen atmosphere.

The temperature is raised to 333 K while the viscosity of the reaction mixture decreases. The reaction mixture is stirred at this temperature during 25 hours. Then the reaction mass is stirred for 4 hours while the temperature is decreased to 295 K. The reaction mass is filtered off and the filter residue is washed with 45 ml of acetonitrile. Then the material is dried in vacuum to obtain 16 g of product.

2. Alkylating agent: A mixture of 15.4 g of 2.2-dithiodiethanol in 100 ml chloroform and 24.1 g pyridine are cooled with stirring to 273K and then 41.0 g of tosyl chloride are added in small amounts under constant temperature.

After completion of the addition the mixture is left over night in the refrigerator. The reaction mixture is mixed with a water/hydrochloric acid/ice slurry, the phases are separated, washed with water and dried. The obtained solution of methane-benzene-sulfonate diester is used in the following step.

3. Alkylation: Stirring into the diester solution in chloroform dissolves two equivalents of the foregoing monoazo. Temperature is raised to 333K. The temperature is maintained at 333K during the following 20 hours. Crystals separated in the slurry are filtrated. The product is washed with 50 ml of chloroform and dried in vacuum to obtain 80 g of a dark solid product. The product is recrystallized twice from methanol.

|  |  |  |  | Residue of compound |
|---|---|---|---|---|
| 7.924 | d | 7.3 | 3.95 | phenylen |
| 7.5109 | s |  | 3.82 | imidazol |
| 6.857 | d | 7.8 | 3.96 | phenylen |
| 4.038 | s |  | 12.06 | dimethyl |
| 3.595 | t |  | 3.982 | methylen |
| 2.925 | t |  | 4.00 | methylen |

Example AZO-11

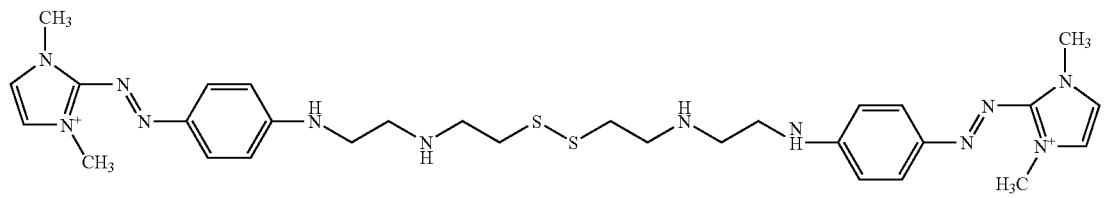

(AZO-111)

Same preparation process as described in example A10, but with the difference that ethylendiamine is used instead of N,N'-dimethyl-ethylendiamine.

Example AZO-12

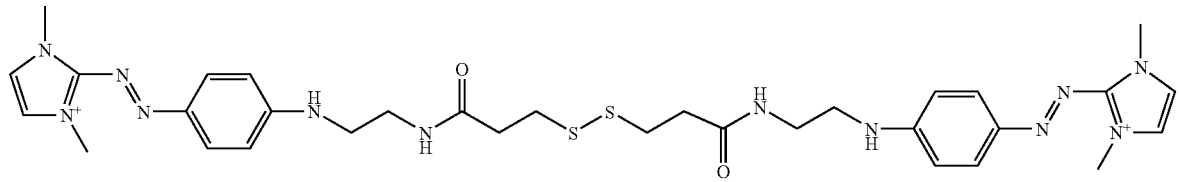

(AZO-112)

1. 16.9 g of ethylenediamine are added to the compound of the formula (101a) (prepared in Example A1) and 120 g isopropanol at 293 K under nitrogen atmosphere under stirring. The temperature is raised to 333 K while the viscosity of the reaction mixture decreases. The reaction mixture is stirred at this temperature during 25 hours. Then the reaction mass is stirred for 4 hours while the temperature is decreased to 295 K. The reaction mass is filtered off and the filter residue is washed with 45 ml of isopropanol. Then the filter residue is dried in vacuum to obtain 16 g of the product.
2. Acylating agent: A mixture of 15.4 g of 2,2-dithiodipropionic acid and then 41.0 g of thionyl chloride is warmed to 333 K for 2 hours under constant temperature.
   After completion of the addition the mixture is distilled under vacuum
3. Alkylation: Two equivalents of the foregoing monoazo are dissolved by stirring into the acid chloride solution in chloroform. The temperature is raised to 333K and maintained during the following 48 hours. Crystals separated in the slurry are filtrated. The product is washed with 50 ml of chloroform and dried in vacuum to obtain 80 g of a dark redish solid product which is re-crystallized twice from methanol.

$^1$H-NMR Data in deuterated methanol (128 scans)/360 MHz

| | | | | Residues of compound |
|---|---|---|---|---|
| 7.924 | d | 7.3 | 3.95 | phenylen |
| 7.5109 | s | | 3.82 | imidazol |
| 6.857 | d | 7.8 | 3.96 | phenylen |
| 4.038 | s | | 12.06 | dimethyl |
| 3.595 | t | | 3.982 | methylen |
| 2.925 | t | | 4.00 | methylen |

Example AZO-13

(AZO-113)

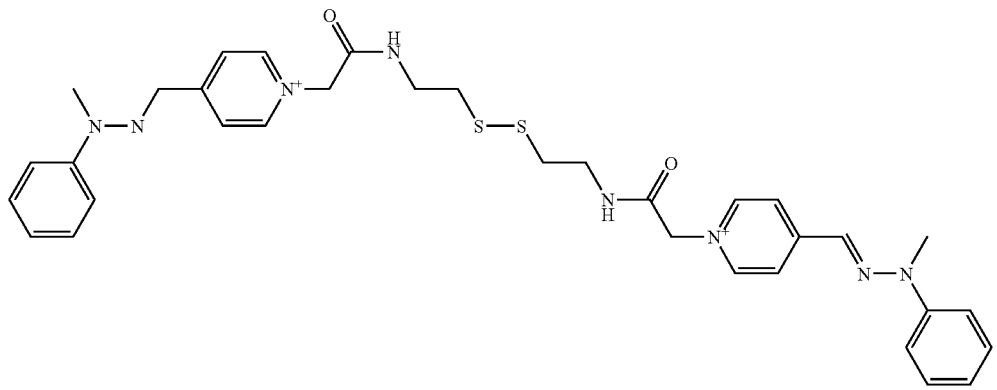

1. Formation of the Hydrazone: 14 g sulfuric acid are added to 42 g of water and cooled to 293K. 25 g of N-methyl-phenyl hydrazine (100%) are added with stirring. 24.0 g of 4-pyridine-aldehyde are dropped in during 15 minutes and stirring is continued for 1 hour. The pH is raised to 2.2 by adding a solution of 36% sodium hydroxide in water. 2.7 g sodium chloride are added at a temperature of 333K and stirred for one more hour at this temperature. The slurry is separated by filtration, the filter cake dried at 343K in vacuum to yield 43 g of an orange powder.
2. Alkylating agent: A solution of 22.5 g of cisteamine dichlorohydrate in water and 31.4 g bromoacetic chloride are cooled with stirring to 273K and then the pH is kept constant by adding NaOH solution in small amounts under constant temperature.

After completion of the addition the mixture is left over night in the refrigerator. The mixture has two phases, which are separated, washed with water and dried.
3. Alkylation: The foregoing hydrazone is dissolved in methanol by stirring with the dibromide solution. The temperature is raised to 60° C. and maintained at 60° C. during the following 24 hours. The crystals separated in the slurry are filtrated. The product is washed with 50 ml of methanol and dried in vacuum to obtain 49 g of an orange solid product. The product is recrystallized twice from methanol.

Characterization by $^1$H-NMR data in deuterated methanol (32 scans)/360 MHz:

1. 9.9 g of N,N-dimethyl-ethylendiamine are added to 120 g acetonitrile and to the compound of the formula (101a) (prepared in example A1) at 293 K under nitrogen atmosphere with stirring. The temperature is raised to 333 K while the viscosity of the reaction mixture decreases. The reaction mixture is stirred at this temperature during 25 hours.

The reaction mass is stirred for 4 hours while the temperature is decreased to 295 K. The reaction mass is filtered off and the filter residue washed with 45 ml of acetonitrile. Then the material is dried in vacuum to obtain 16 g of product.
2. Alkylating agent: A mixture of 15.4 g of 2.2-dithiodiethanol in 100 ml chloroform and 24.1 g pyridine is cooled with stirring to 273K and then 41.0 g of tosyl chloride are added in small amounts under constant temperature. After completion of the addition the mixture is left over night in the refrigerator. The reaction mixture is mixed with a water/chlorhidric acid/ice slurry, the phases are separated, washed with water and dried. The obtained solution of methane-benzene-sulfonate diester is used in the following step
3. Alkylation: Stirring into the diester solution in chloroform dissolves two equivalents of the foregoing monoazo. The temperature is raised to 333K and maintained at 333K during the following 20 hours. Crystals separated in the slurry are filtrated. The product is washed with 50 ml of chloroform and dried in vacuum to obtain 80 g of a dark solid product, which is recrystallized twice from methanol.

|  |  |  |  | Residues of the compound |
|---|---|---|---|---|
| 8.442 | d | 6.8 | 4.00 | pyridinyl |
| 8.007 | d | 6.7 | 3.935 | pyridinyl |
| 7.517 | s |  | 2.04 | hydrazon |
| 7.4 | m |  | 8.08 | phenyl |
| 7.162 | t | 6.4 | 1.982 | phenyl |
| 5.235 | s |  | 3.648 | ethylene |
| 3.625 | t | 6.75 | 3.05 | ethylene |
| 3.489 | s |  | 6.23 | methyl |
| 2.947 | t | 6.55 | 4.087 | ethylene |

Example AZO-14

|  |  |  |  | Residue of compound |
|---|---|---|---|---|
| 7.966 | d | 7.3 | 3.95 | phenylene |
| 7.718 | d | 8 | 4.04 | tosylate |
| 7.564 | s |  | 3.82 | imidazol |
| 7.226 | d | 8 | 4.05 | tosylate |
| 6.927 | d | 7.8 | 3.96 | phenylene |
| 4.050 | s |  | 12.06 | dimethyl |
| 3.90 | m |  | 4.1 | methylene |
| 3.76 | m |  | 4. | methylene |
| 3.595 | t |  | 3.982 | methylene |
| 3.31 | s |  | 12 | methyl |
| 2.925 | t |  | 4.00 | methylene |
| 2.32 | s |  |  | methyl |

(AZO-114)

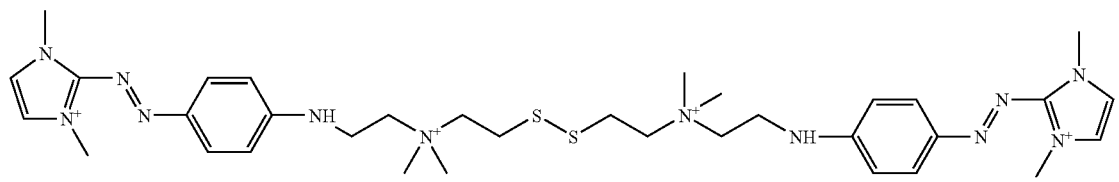

Example AZO-15

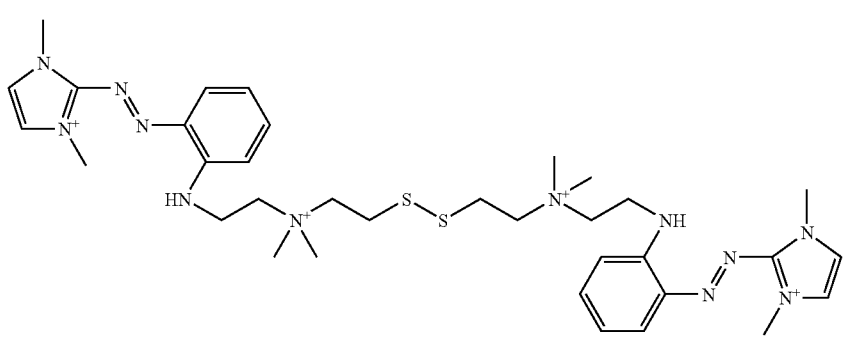
(AZO-115)

The compound of formula (102a) (prepared in example 2) is reacted with N,N-dimethyl-ethyl-lenediamine according to the procedure as described in Example A14. The same alkylating agent is used to give the compound of formula (115).

Example AZO-16

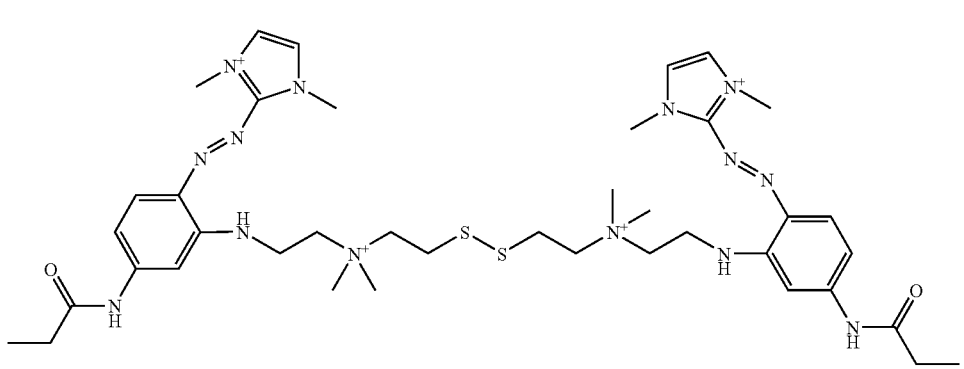
(AZO-116)

The compound of formula (104a) (prepared in example A 4) is reacted with N,N-dimethyl-ethylendiamine according to the method as described in Example A14.

The same alkylating agent is used and the compound of formula (116) is obtained.

Example AZO-17

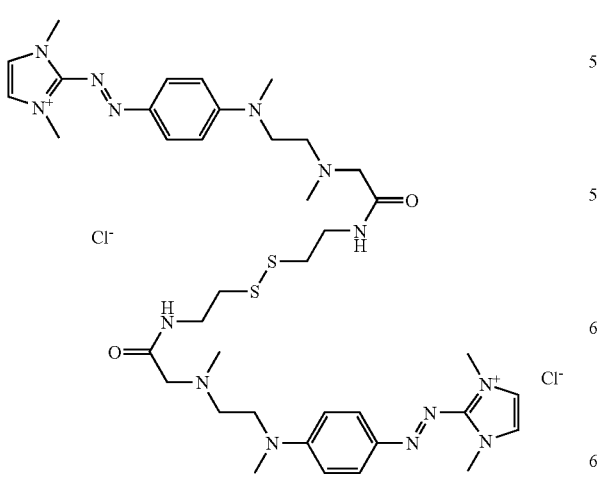
(AZO-117)

Step 1:

19.9 g of N,N'-dimethyl-ethylendiamine is added at 293 K, under nitrogen atmosphere, with stirring to 120 g isopropanol and the foregoing compound of the formula (AZO-101a).

Then the temperature is raised to 333 K, and viscosity of the reaction mixture decreases. The reaction mixture is stirred at this temperature during 25 hours. Then, the reaction mass is stirred for 4 hours, while the temperature is decreased to 295 K. The reaction mass is filtered and the filter residue is washed with 45 ml of isopropanol. Then the material is dried in vacuum to obtain 16 g of the product:

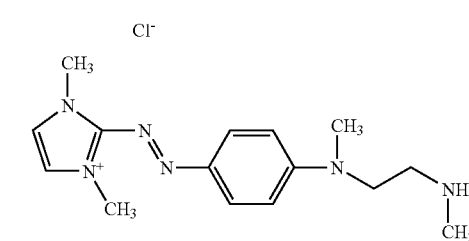
(AZO-117a)

2. Alkylating agent

A solution of 22.5 g of cysteamine dichlorohydrate in water and 31.4 g Bromoacetic chloride were cooled with stirring to 273K and then pH was hold through NaOH solution added in small amounts, maintaining the temperature.

After completion of the addition the mixture was left over night in the refrigerator. The mixture has two phases, which are separated, washed with water and dried. The compound is used in the following step (AZO-117b)

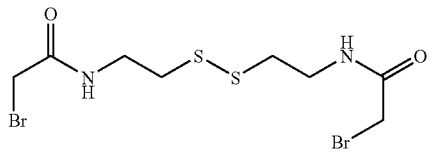

3. Alkylation 4.0 g of Magnesiumoxide is added at 293 K with well-stirring to 100 ml methanol and the foregoing compound of the formula (117a). Then the temperature is raised to 323 K and the reaction mixture is stirred at this temperature for half an hour. After been slowly cooled at room temperature, the reaction mass is filtrated. 14.0 g of the alkylating agent (117b) and 4.0 g of Magnesiumoxide are added at 293 K to the well-stirred foregoing filtrate. A catalytic amount of potassium iodide is added to the reaction mixture. The temperature is then raised to 313 K and the reaction mixture is stirred at this temperature for five days. The reaction mass is then diluted with 100 ml methanol and filtrated. The filtrate is evaporated to dryness and finally the material is dried in vacuum to obtain 57.5 g of the product (AZO-117).

MS (ES$^+$): m/z 403 (M$^{2+}$).

Example AZO-18

(AZO-118)

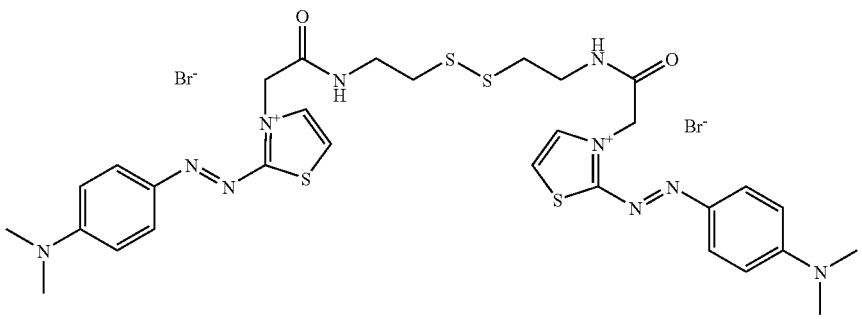

1. Monoazo 50.0 g of 2-amino-thiazol are added to a stirred solution of 135 ml 60% sulfuric acid at 293-310K. Then the reaction mixture is cooled to 273K and 81 ml of a 40% nitrosylsulfuric acid are dropped at such a rate that the temperature of the mixture is maintained in the range of 273 to 276K by cooling. After the addition the mixture is stirred for four hours. The solution is dropped to a well-stirred water ice mixture (400 g) containing 2.5 g amidosulfuric acid. To the obtained diazo solution (at 273K ice added if need) 60.5 g dimethylaniline are dropped. Then the pH of the solution is raised to the range of 5 to 6 by adding 36% sodium hydroxide solution. After stirring one hour at this pH and temperature the suspension is filtered off and then washed twice with 50 ml water to obtain 155 g of the humid product.

After drying 10 g monoazo dye of formula (118a) is obtained.

(AZO-118a)

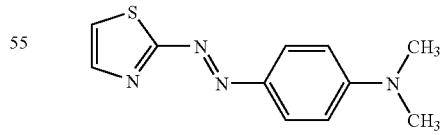

2. Alkylation 14.7 g of the monoazo dye of formula (118a), 9.9 g of the alkylating agent of formula (AZO-117b) and 0.1 g KI are stirred for 20 h in 100 ml tetramethylurea at 100° C. After extraction of the crude product with tetrahydrofurane the final product is obtained after crystallization from Methanol/Acetone (7:3).

Yield after vacuum-drying: 20.5 g of the dye of formula (AZO-118).

Example AZO-19

(AZO-119)

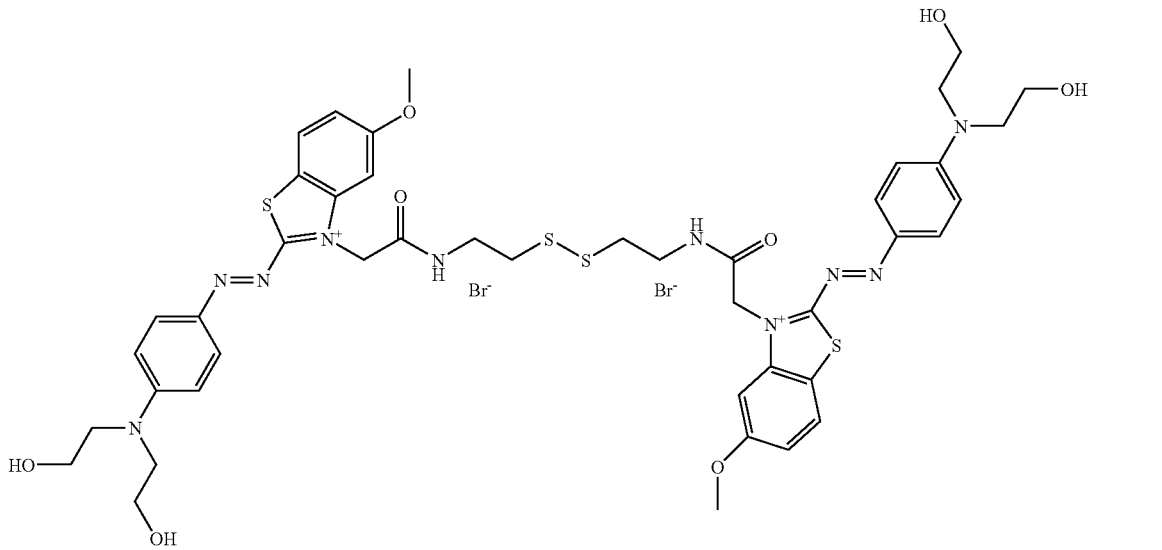

1. Monoazo 184 g of 2-amino-6-methoxy-benzothiazol are added to a well-stirred solution of 270 ml 60% sulfuric acid at 293-310 K. Then the reaction mixture is cooled to 266K and 174 ml of a 40% nitrosylsulfuric acid are added at such a rate that the temperature of the mixture is maintained in the range of 266 to 268 K by cooling. After the addition the mixture is stirred for 4 h at 268K. The solution is poured into to a well-stirred water ice mixture (600 g) containing 5 g amido-sulfuric acid (at 273K ice added if need). To the obtained diazo solution (at 273K ice added if need) 196.5 g of melting N-phenyldiethanolamine are dropped. After the addition the mixture is stirred for 2 h. Then the pH of the solution is raised to 7 by adding 36% sodium hydroxide solution (the temperature of the mixture is maintained under 313K by addition of ice). After 1 h stirring at this pH the suspension is filtered off and then washed with water to obtain 1322 g of the humid product. After drying 505 g monoazo dye of the formula (119a) are obtained.

(AZO-119a)

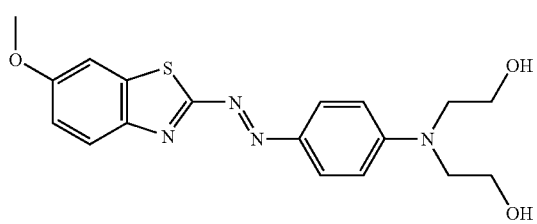

2. Alkylation 39.1 g of the monoazo dye of the formula (119a) and 13.8 g of the alkylating agent (117b) and 0.1 g KI are stirred for 20 h in 100 ml tetramethylurea at 100° C. The work-up is carried out by extraction of the crude product with tetrahydrofurane.

After vacuum-drying 32 g of the dye of the formula (AZO-119) are obtained.

Example AZO-20

(AZO-120)

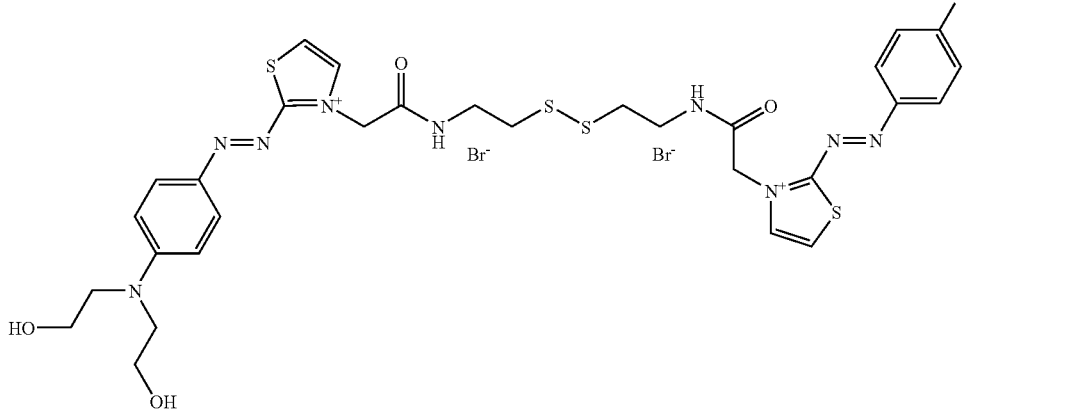

1. Monoazo 10 g of 2-amino-thiazol are added to a well-stirred solution of 270 ml 60% sulfuric acid at 293-310K. Then the reaction mixture is cooled to 273K and 146 ml of a 40% nitrosylsulfuric acid are added at such a rate that the temperature of the mixture is maintained in the range of 273 to 276K by cooling. After the addition the mixture is stirred for four hours. The solution is poured into to a well-stirred water ice mixture (700 g) containing 5 g amidosulfuric acid (at 273K ice added if need). To the obtained diazo solution (In the range 273-278 K ice added if need) 180 g of melting N-Phenyldiethanolamine is dropped. After the addition the mixture is stirred for one hour. Then the pH of the solution is raised to the range of 5 by adding 36% sodium hydroxide solution (The temperature of the mixture is maintained under 303K by addition of ice). After two hours stirring at this pH the suspension is filtered off and then washed with water to obtain 439 g of the humid product. After drying 243 g monoazo dye of formula (120a) are obtained.

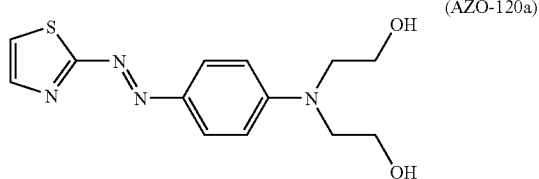

(AZO-120a)

2. Alkylation 26.6 g of the monoazo of formula (120a), 15.8 g of the alkylating agent (117b) and 0.1 g KI are stirred in 160 ml tetramethylurea for 20 h at 100° C. The solvent is distilled off under reduced pressure and the residue is extracted with tetrahydrofurane (5×500 ml) and vacuum-dried. 21 g of the dye of formula (120) are obtained as a deep blue powder.

Example STY-01

Preparation of the Compound of Formula

1. Alkylating Agent

A mixture of 15.4 g of 2,2-dithiodiethanol in 100 ml chloroform and 24.1 g pyridine are cooled with stirring to 0° C. and then 41.0 g of tosyl chloride are added in small amounts, maintaining the temperature at 0° C. by cooling externally.

After completion of the addition the mixture is left over night in the refrigerator to complete the reaction. The reaction mixture is mixed with a water/hydrochloric acid and ice slurry, the phases are separated, washed with water and dried.

The solution of toluenesulfonate diester is used as starting compound in the $2^{nd}$ reaction step.

2. Alkylation

The alkylation agent obtained in the $1^{st}$ reaction step is delivered from the solvent, dissolved in two equivalent amounts (18.8 g) of 4-methyl-pyridine. The temperature is raised to 70° C. and maintained at 60° C. during the following 12 hours.

3. Condensation

To the reaction mixture of the foregoing step 50 ml of isopropanol are added. Then the equivalent amount (30.0 g) of dimethylamino-benzaldehyde and a catalytic amount (3.6 g) of piperidine are added and the reaction mixture is stirred for 24 hours at 70° C.

The reaction product is precipitated by cooling, then separated by filtration and dried in vacuum to obtain 45 g of a reddish orange solid product.

The product is recrystallized twice from methanol.

The product is characterized by the following data:

The HPLC-MS gives a main component of a dication of the mass 568

1H-NMR data in deuterated chloroform (128 scans)/360 MHz:

| | | | | |
|---|---|---|---|---|
| 9.62 | s | | .03 | Benzal (trace) |
| 8.528 | d | 6.7 | 3.98 | Py |
| 7.92 | d | 6.7 | 4.02 | Py |
| 7.781 | d | 16.6 | 2.03 | vinyl |
| 7.715 | d | 7.0 | 4.070 | tosilate |
| 7.58 | d | 6.1 | 4.04 | Phe |
| 7.476 | d | 6.8 | 4.02 | tosilate |
| 7.210 | d | 6.5 | 4.025 | Phe |
| 7.04 | d | 16.9 | 2.02 | vinyl |
| 6.76 | d | 6.4 | 4.05 | Phe |
| 4.71 | t | 6 | 4.00 | ethylene |
| 3.36 | t | 6 | 4.05 | etylene |
| 3.057 | s | | 12.087 | Dimethyl(amine) |
| 2.326 | s | | 5.90 | Me-tosilate |

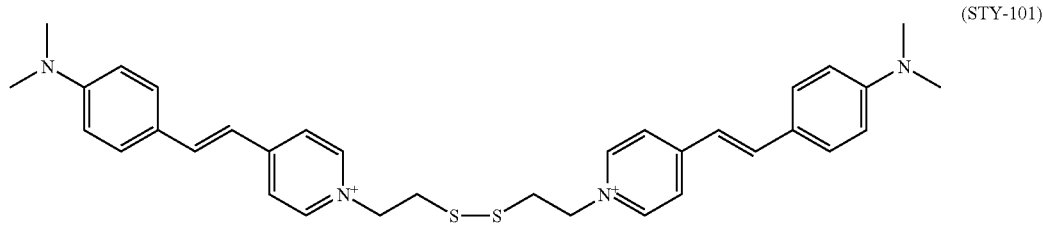

(STY-101)

Example STY-02

Preparation of the Compound of Formula

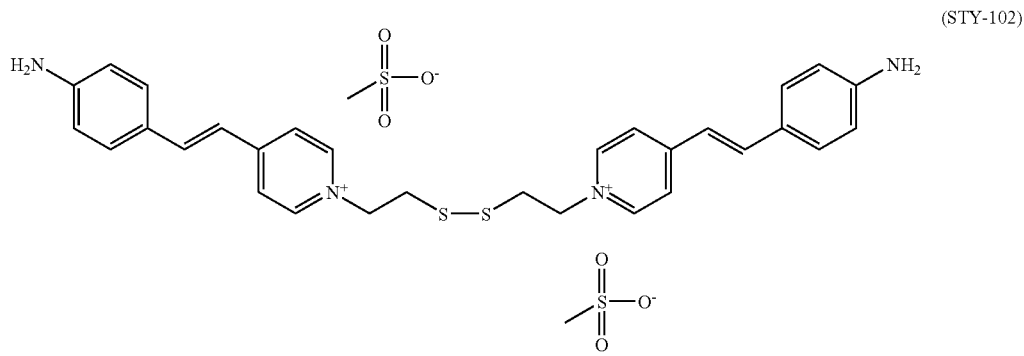
(STY-102)

1. Alkylating Agent

A mixture of 15.4 g 2,2-dithiodiethanol in 100 ml chloroform and 24.1 g pyridine are cooled with stirring to 0° C. and then 22.0 g of mesyl chloride are added in small amounts, maintaining the temperature by external cooling.

After completion of the addition the mixture is left over night in the refrigerator to complete the reaction.

The reaction mixture is mixed with a water/hydrochloric acid and ice slurry, the phases are separated, washed with water and dried.

The solution of methanesulfonate diester is used as starting compound in the $2^{nd}$ reaction step.

2. Alkylation

Two equivalents (18.8 g) of 4-methyl-pyridine are dissolved in the foregoing alkylation agent together with a solvent. The temperature is raised to reflux and maintained at 70° C. during the following 12 hours.

3. Condensation

The equivalent amount (24.0 g) of amino-benzaldehyde and a catalytic amount (3.6 g) of piperidine are added to the reaction mixture obtained in the $2^{nd}$ reaction step and the reaction mixture is stirred for 24 hours at 70° C.

The reaction product is precipitated by cooling, then separated by filtration and dried in vacuum to obtain 42 g of an orange solid product.

The product is recrystallized twice from methanol.

The product is characterized by the following data:

The HPLC-MS gave a main component of a dication of the mass 512

1H-NMR data in deuterated chloroform (128 scans)/360 MHz:

| | | | | |
|---|---|---|---|---|
| 8.56 | d | 6.7 | 3.98 | Py |
| 8.38 | d | 6.7 | 4.02 | Py |
| 7.78 | d | 16.6 | 2.03 | vinyl |
| 7.51 | d | 6.1 | 4.04 | Phe |
| 7.28 | d | 6.5 | 4.025 | Phe |
| 7.06 | d | 16.9 | 2.02 | vinyl |
| 4.88 | t | 6 | 4.00 | ethylene |
| 3.14 | t | 6 | 4.05 | ethylene |
| 2.706 | s | | 5.90 | Mesylate |

Example STY-03

Preparation of the Compound of Formula

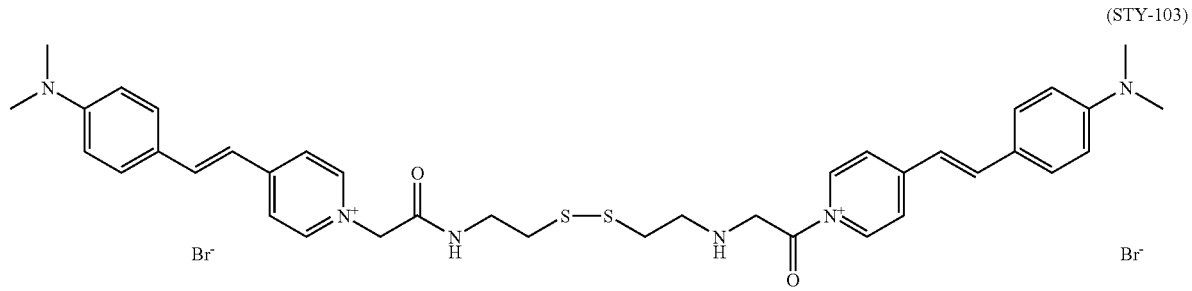
(STY-103)

1. Alkylating Agent

A mixture of 25.4 g of cisteamine as dichlorohydrate in 100 ml water is cooled with stirring to 0° C. and 41.0 g of bromoacetic acid bromide are added in small amounts, maintaining the temperature at 0° C. by external cooling. The pH is adjusted with sodium hydroxide to 8.0.

After completion of the addition the mixture is left for one hour with agitation to complete the reaction.

The reaction mixture is separated by filtration, the solid washed with water and dried.

The alkylating agent used as starting compound in the $2^{nd}$ reaction step.

2. Alkylation

The alkylation agent obtained in the $1^{st}$ reaction step is added to 50 ml isopropanol and dissolved in two equivalent amounts (18.8 g) of 4-methyl-pyridine. The temperature is raised to 80° C. and maintained during the following 10 hours.

3. Condensation 20 ml of isopropanol are added to the reaction mixture obtained in the $2^{nd}$ reaction step. Then the equivalent amount (30.0 g) of dimethylamino benzaldehyde and a catalytic amount (3.6 g) of piperidine are added and the reaction mixture is stirred for 24 hours at 80° C.

The reaction product is precipitated by cooling, then separated by filtration and dried in vacuum to obtain 59 g of an orange solid product.

The product is recrystallized twice from isopropanol.
The product is characterized by the following data:
The HPLC-MS gives a main component of a dication of the mass 682
1H-NMR data in deuterated chloroform (128 scans)/360 MHz:

| Compound (103) | 8.528 | d | 6.7 | 3.98 | Py |
|---|---|---|---|---|---|
| | 7.92 | d | 6.7 | 4.02 | Py |
| | 7.781 | d | 16.6 | 2.03 | vinyl |
| | 7.58 | d | 6.1 | 4.04 | Phe |
| | 7.210 | d | 6.5 | 4.025 | Phe |
| | 7.04 | d | 16.9 | 2.02 | vinyl |
| | 5.28 | s | | 4.04 | methylene |
| | 3.65 | t | 6 | 4.00 | ethylene |
| | 3.157 | s | | 12.087 | Dimethyl(amine) |
| | 2.94 | t | 6 | 3.95 | ethylene |

Example STY-04

Preparation of the Compound of Formula

2. Alkylation

The dimethylsulfate as alkylation agent is used without solvent and mixed with two equivalent amounts (18.8 g) 2-methyl-pyridine. The temperature is raised to 80° C. and maintained during the following 2 hours.

3. Condensation 50 ml of isopropanol are added to the reaction mixture of the foregoing step. The equivalent amount (24.0 g) of aminobenzaldehyde and a catalytic amount (3.6 g) of piperidine are added and the reaction mixture is stirred for 16 hours at 70° C.

The reaction product is precipitated by cooling, then separated by filtration and dried in vacuum to obtain 49 g of an orange solid product.

The product is recrystallized twice from water.

4. Acylation

A mixture of 49 g of the fstyrene compound obtained in the $3^{rd}$ reaction step and 200 ml water are cooled with stirring to 0° C. and then 41.0 g of the acid chloride obtained in reaction step 1 dissolved in tetrahydrofurane are added in small amounts, maintaining the temperature by external cooling. The pH is adjusted to 6.0 by addition of sodium hydroxide.

After completion of the addition the mixture is left for one hour with agitation to complete the reaction. The reaction mixture is separated by filtration, the solid washed with water and dried.

The product may be used as such for dyeing applications.

The product is characterized by the following data:
1H-NMR data in deuterated chloroform (128 scans)/360 MHz:

| 8.74 | d | 6.7 | 1.98 | Py |
|---|---|---|---|---|
| 8.41 | d | 6.7 | 4.02 | Py |
| 7.701 | m | | 12.070 | überlagert |
| 7.45 | d | 16.9 | 2.02 | vinyl |
| 4.390 | s | | 4.00 | methyl |

(STY-104)

1. Acylating Agent

A mixture of 21.4 g 2,2-dithiodipropionic acid in 100 ml chloroform and 24.0 g thionyl chloride are added in small amounts, maintaining the temperature by external cooling.

After completion of the addition the mixture is heated to remove the formed gases and the reaction was finished. The solvent is removed by distillation under low pressure and the acid chloride used as starting compound in the $2^{nd}$ reaction step.

-continued

| 3.686 | s | | 5.89 | Methyl-sulfate |
|---|---|---|---|---|
| 3.09 | t | 6 | 4.05 | ethylene |
| 2.86 | t | 6 | 3.87 | ethylene |

Example STY-05

Preparation of the Compound of Formula

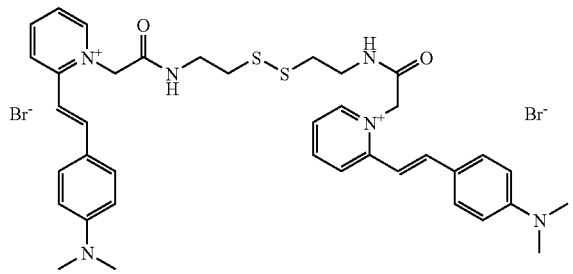

(STY-105)

1. Alkylating Agent

A mixture of 25.4 g of 2,2-dithiodiethylamine (cisteamine) as dichlorohydrate and 100 ml water is cooled with stirring to 0° C. and then 41.0 g of bromo acetic acid bromide are added in small amounts, maintaining the temperature by cooling externally. The pH is adjusted to 8.0 by addition of sodium hydroxide.

After completion of the addition the mixture is left for one hour with agitation to complete the reaction.

The reaction mixture is separated by filtration, the solid washed with water and dried.

The alkylating agent is used as starting compound in the $2^{nd}$ reaction step.

2. Alkylation

The alkylation agent obtained in the $1^{st}$ reaction step is delivered from the solvent and dissolved in two equivalents (18.8 g) 2-methyl-pyridine. The temperature is raised to 80° C. and maintained at 60° C. during the following 16 hours.

3. Condensation 50 ml of isopropanol are added to the reaction mixture obtained in the $2^{nd}$ reaction step. The equivalent amount (30.0 g) of dimethylamino benzaldehyde and a catalytic amount (3.6 g) of piperidine are added and the reaction mixture is stirred for 24 hours at 70° C.

The reaction product is precipitated by cooling, then separated by filtration and dried in vacuum to obtain 57 g of an orange solid product.

The product is recrystallized twice from methanol.
The product is characterized by the following data:
The HPLC-MS gave a main component of a dication of the mass 682.
1H-NMR data in deuterated chloroform (128 scans)/360 MHz:

| | | | | |
|---|---|---|---|---|
| 8.6478 | d | 6.7 | 1.98 | Py |
| 8.360 | d | 6.7 | 2.02 | Py |
| 8.287 | t | 6.5 | 1.96 | Py |
| 7.838 | d | 16.6 | 2.03 | vinyl |
| 7.675 | d | 6.1 | 4.04 | Phe |
| 7.670 | t | 6.5 | 2.025 | Py |
| 7.210 | d | 16.9 | 2.02 | vinyl |
| 6.792 | d | 6.4 | 4.05 | Phe |
| 5.3 | s | | 4.01 | methylene |
| 4.71 | t | 6 | 4.00 | ethylene |
| 3.36 | t | 6 | 4.05 | etylene |
| 3.075 | s | | 12.087 | Dimethyl(amine) |

Example STY-06

Preparation of the Compound of Formula

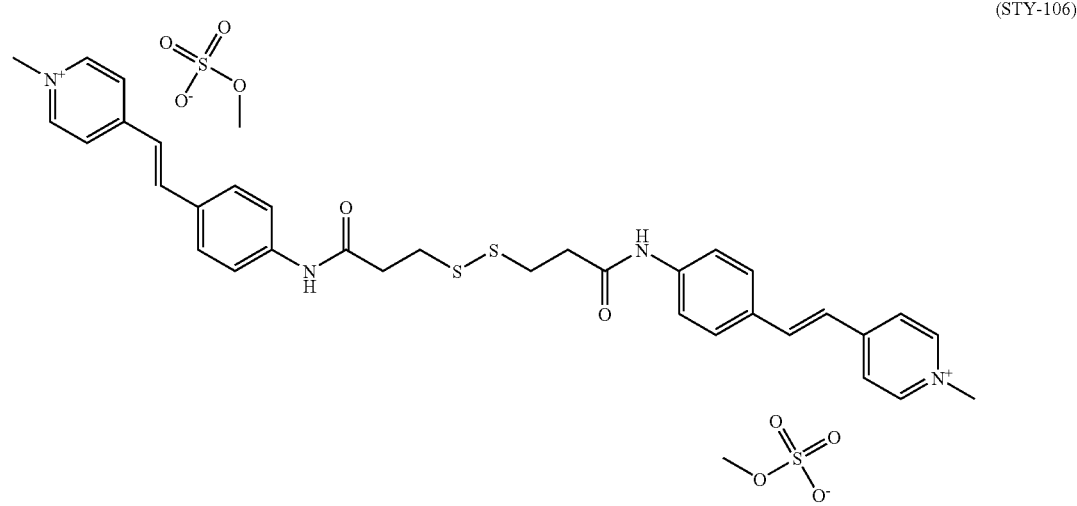

(STY-106)

1. Acylating Agent 24.0 g of thionyl chloride are added to a mixture of 21.4 g of 2,2-dithiodipropionic acid in 100 ml chloroform in small amounts, maintaining the temperature by external cooling.

After completion of the addition the mixture is heated to remove the formed gases and the reaction is completed within one hour.

The solvent is removed by distillation under low pressure.
The acid chloride used as starting compound in the 2nd step 2. Alkylation The dimethylsulfate as alkylation agent is used without solvent, with two equivalent amounts (18.8 g) of 4-methyl-pyridine. The temperature is raised to 80° C. and maintained at 80° C. during the following 2 hours.

3. Condensation 50 ml of isopropanol are added to the reaction mixture obtained in the 2$^{nd}$ reaction step. Then the equivalent amount (24.0 g) of aminobenzaldehyde and a catalytic amount (3.6 g) of piperidine are added and the reaction mixture is stirred for 12 hours at 70° C.

The reaction product is precipitated by cooling, then separated by filtration and dried in vacuum to obtain 55 g of an orange solid product.

The product is recrystallized twice from water.

4. Acylation

A mixture of 55 g of the styrene compound obtained in the 3$^{rd}$ reaction step and 200 ml water is cooled with stirring to 0° C. and then 45.0 g of the acid chloride obtained in the 1$^{st}$ reaction step, dissolved in tetrahydrofurane, are added in small amounts, maintaining the temperature at 0° C. by external cooling. The pH is adjusted to 7.0 by addition of sodium hydroxide.

After completion of the addition the mixture is left for one hour with agitation to complete the reaction.

The reaction mixture is separated by filtration; the solid washed with water and dried, The product may be used as such for dyeing applications.

The product is characterized by the following data:

1H-NMR data in deuterated chloroform (128 scans)/360 MHz:

| 8.66 | d | 6.7 | 3.98 | Py |
|---|---|---|---|---|
| 8.10 | d | 6.7 | 4.02 | Py |
| 7.95 | d | 16.6 | 2.03 | vinyl |
| 7.68 | m | | 8.04 | overlaid |
| 7.210 | d | 6.5 | 4.025 | Phe |
| 7.28 | d | 16.9 | 2.02 | vinyl |
| 4.298 | s | | 6.00 | methyl |
| 3.69 | s | | 5.75 | Methyl-sulfate |
| 3.09 | t | 6 | 4.087 | ethylene |
| 2.85 | t | 6 | 3.90 | ethylene |

Example STY-07

Preparation of the Compound of Formula

1. Acylating Agent

A mixture of 18.4 g 2,2-dithioglycolic acid in 100 ml chloroform and then 24.0 g of thionyl chloride are added in small amounts, maintaining the temperature by external cooling. After completion of the addition the mixture is heated to remove the formed gases and the reaction is completed within one hour.

The solvent is removed by distillation under low pressure and the acid chloride is used as such in the 4$^{th}$ reaction step.

2. Alkylation

The dimethylsulfate as alkylation agent is used without solvent with two equivalents (18.8 g) 4-methyl-pyridine. The temperature is raised to 70° C. and maintained at 80° C. during the following 2 hours.

3. Condensation 50 ml of isopropanol are added to the reaction mixture obtained in the 2$^{nd}$ reaction step. The equivalent amount (24.0 g) of amino-benzaldehyde and a catalytic amount (3.6 g) of piperidine are added and the reaction mixture is stirred for 24 hours at 70° C.

The reaction product is precipitated by cooling, then separated by filtration and dried in vacuum to obtain 49 g of an orange solid product.

The product is recrystallized twice from water.

4. Acylation

A mixture of 49 g of the styrene compound obtained in the 3$^{rd}$ reaction step in 200 ml water are cooled with stirring to 0° C. and then 35.0 g of the acid chloride obtained in the 1$^{st}$ reaction step, diluted with 30 ml tetrahydrofurane are added in small amounts, maintaining the temperature at 0° C. by external cooling. The pH is adjusted to 6.0 by addition of sodium hydroxide.

After completion of the addition the mixture is left for one hour with agitation to complete the reaction. The reaction mixture is separated by filtration, the solid washed with water and dried. The product may be used as such for dyeing applications.

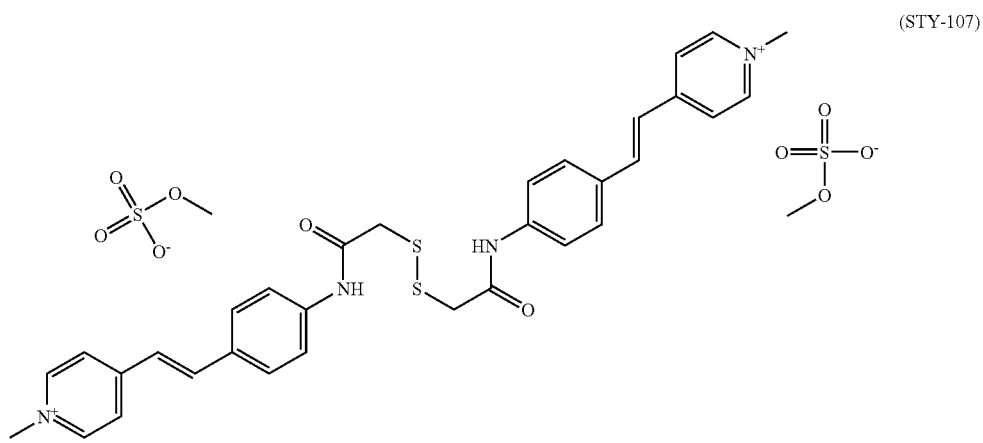

(STY-107)

The product is characterized by the following data:
1H-NMR data in deuterated chloroform (128 scans)/360 MHz

| | | | | |
|---|---|---|---|---|
| 9.62 | s | | .03 | ba |
| 8.528 | d | 6.7 | 3.98 | Py |
| 7.92 | d | 6.7 | 4.02 | Py |
| 7.781 | d | 16.6 | 2.03 | vinyl |
| 7.701 | d | 7.0 | 4.070 | tosilate |
| 7.58 | d | 6.1 | 4.04 | Phe |
| 7.210 | d | 6.5 | 4.025 | Phe |
| 7.04 | d | 16.9 | 2.02 | vinyl |
| 6.76 | d | 6.4 | 4.05 | Phe |
| 4.91 | t | 6 | 4.00 | methylene |
| 3.057 | s | | 12.087 | Dimethyl(amine) |

Example STY-08

Preparation of the Compound of Formula

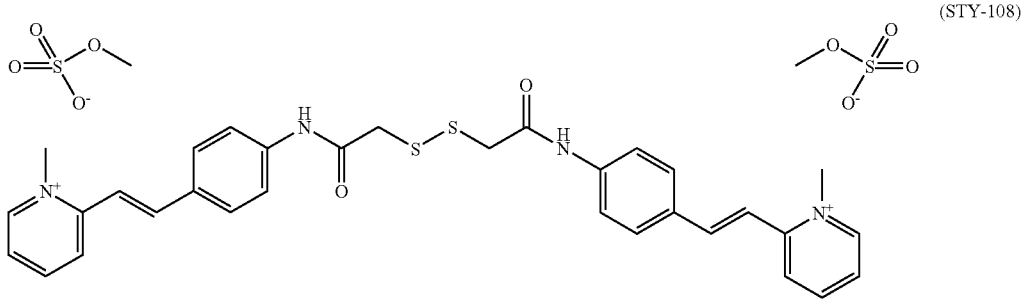
(STY-108)

1. Acylating Agent

A mixture of 18.4 g 2,2-dithioglycolic acid in 100 ml chloroform and 24.0 g thionyl chloride are added in small amounts, maintaining the temperature at 20° C. by external cooling.

After completion of the addition the mixture is heated to remove the formed gases and to complete the reaction.

The solvent is removed by distillation under low pressure and the acid chloride is used as such in the following step 2. Alkylation The dimethylsulfate as alkylation agent is used without solvent, dissolved in two equivalent amounts (18.8 g) of 2-methylpyridine. The temperature is raised to 70° C. and maintained at 80° C. during the following 2 hours.

3. Condensation 50 ml of isopropanol are added to the reaction mixture obtained in the $2^{nd}$ reaction step. The equivalent amount (24.0 g) amino-benzaldehyde and a catalytic amount (3.6 g) of piperidine are added and the reaction mixture is stirred for 24 hours at 70° C.

The reaction product is precipitated by cooling, then separated by filtration and dried in vacuum to obtain 49 g of an orange solid product.

The product is recrystallized twice from isopropanol.

4. Acylation

A mixture of 49 g of the styrene compound obtained in the $3^{rd}$ reaction step and 200 ml water are cooled with stirring to 0° C. and then 41.0 g of acid chloride obtained in the 1st reaction step are added in small amounts, maintaining the temperature at by 0° C. external cooling. The pH is adjusted to 6.0 by sodium hydroxide addition After completion of the addition the mixture is left for one hour with agitation to complete the reaction.

The reaction mixture is separated by filtration, the solid washed with water and dried.

The product may be used for dyeing applications.

The product is characterized by the following data:
1H-NMR data in deuterated chloroform (128 scans)/360 MHz:

| | | | | |
|---|---|---|---|---|
| 8.6478 | d | 6.7 | 1.98 | Py |
| 8.360 | d | 6.7 | 2.02 | Py |
| 8.287 | t | 6.5 | 1.96 | Py |
| 7.838 | d | 16.6 | 2.03 | vinyl |
| 7.675 | d | 6.1 | 4.04 | Phe |
| 7.670 | t | 6.5 | 2.025 | Py |
| 7.210 | d | 16.9 | 2.02 | vinyl |
| 6.792 | d | 6.4 | 4.05 | Phe |
| 5.3 | s | | 4.01 | methylene |
| 3.075 | s | | 12.087 | Dimethyl(amine) |

Example STY-09

Preparation of the Compound of Formula

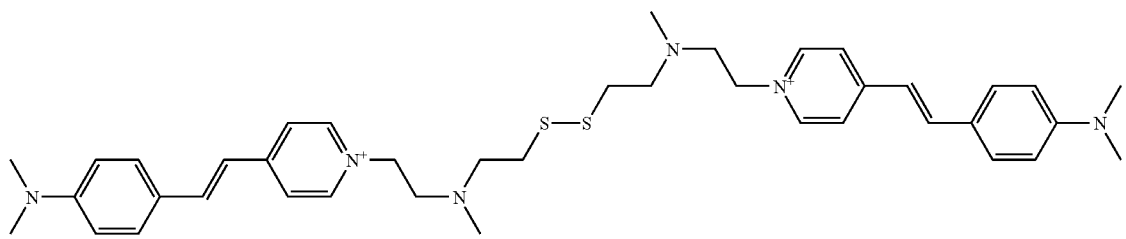

(STY-109)

1. Alkylating Agent

A mixture of 21.5 g 2-hydroxyethyl-methylamine are neutralized with hydrochloric acid and evaporated to dryness. The salt is suspended in chloroform and cooled under stirring to 0° C. and then 41.0 g of thionyl chloride are added in small amounts, maintaining the temperature at by 0° C. external cooling.

After completion of the addition the reaction is completed by heating to reflux and degassing the mixture.

The solution is evaporated to dryness, the 2-chloroethyl-methylamine is used as chlorohydrate in the $2^{nd}$ reaction step.

2. Alkylation

The alkylation agent obtained in the $1^{st}$ reaction step is dissolved in n-butanol and two equivalent amounts (16.8 g) 4-methyl-pyridine are added. The temperature is raised to 120° C. and maintained during the following 6 hours. Than the temperature is lowered to 70° C.

3. Condensation

The equivalent amount (30.0 g) of dimethylaminobenzaldehyde and a catalytic amount (3.6 g) of piperidine are added to the reaction mixture obtained in the $2^{nd}$ reaction step and the reaction mixture is stirred for 24 hours at 70° C.

The reaction product is precipitated by cooling, then separated by filtration and dried in vacuum to obtain 50 g of an orange solid product.

The structure of the compound of formula (STY-109a)

is confirmed by $^1$H-NMR data in deuterated chloroform (128 scans)/360 MHz:

| 8.585 | d | 6.7 | 1.98 | Py |
| 7.975 | d | 6.7 | 2.02 | Py |

-continued

| 7.846 | d | 16.6 | 1.03 | vinyl |
| 7.620 | d | 6.1 | 2.04 | Phe |
| 7.089 | d | 16.9 | 1.02 | vinyl |
| 6.798 | d | 6.4 | 2.05 | Phe |
| 4.574 | t | 6 | 2.00 | ethylene |
| 3.207 | t | 6 | 2.05 | etylene |
| 3.073 | s | | 6.087 | Dimethyl(amine) |
| 2.436 | s | | 3.00 | Methyl-amin |

4. Alkylating Agent

A mixture of 15.4 g of 2,2-dithiodiethanol in 100 ml chloroform and 24.1 g pyridine are cooled with stirring to 0° C. and then 22.0 g of mesyl chloride are added in small amounts, maintaining the temperature at 0° C. by external cooling.

After completion of the addition the mixture is left over night in the refrigerator to complete the reaction.

The reaction mixture is mixed with a water/hydrochloric acid and ice slurry, the phases are separated, washed with water and dried.

The solution of methanesulfonate diester is used as such in the $5^{th}$ reaction step.

5. Alkylation

Two equivalents (18.8 g) of the intermediate dye molecule obtained in the $3^{rd}$ reaction step are dissolved in alkylation agent obtained in the $4^{th}$ reaction step with a solvent. The temperature is raised to reflux and maintained at 70° C. during the following 12 hours.

The reaction mixture is cooled to ambient temperature with agitation and separated through filtration.

The solid is washed with chloroform and dried.

The product is characterized by the following data:
1H-NMR data in deuterated chloroform (128 scans)/360 MHz

| 8.606 | d | 6.7 | 3.98 | Py |
| 7.920 | d | 6.7 | 4.02 | Py |
| 7.781 | d | 16.6 | 2.03 | vinyl |
| 7.696 | d | 7.0 | 4.070 | tosilate |
| 7.598 | d | 6.1 | 4.04 | Phe |
| 7.212 | d | 6.5 | 4.025 | Phe |
| 7.040 | d | 16.9 | 2.02 | vinyl |
| 6.772 | d | 6.4 | 4.05 | Phe |
| 4.815 | t | 6 | 4.00 | ethylene |
| 3.792 | t | 6 | 3.8 | ethylene |
| 3.659 | t | 6 | 4.05 | etylene |

-continued

| | | | | |
|---|---|---|---|---|
| 3.059 | s | | 12.087 | Dimethyl(amine) |
| 2.928 | t | 6 | 3.9 | ethylene |
| 2.783 | s | | 5.4 | Methyl-amin |
| 2.326 | s | | 5.90 | Me-tosilate |

Example STY-10

Preparation of the Compound of Formula

1. Alkylation

The alkylation agent 2-chloroethyl-N,N-dimethylamine is dissolved in n-butanol and equivalent amounts (18.028 g) of 4-methyl-pyridine are added. The temperature is raised to 120° C. and maintained at 120° C. during the following 6 hours. Than the temperature is lowered to 70° C.,

2. Condensation

The equivalent amount (30.0 g) of dimethylamino-benzaldehyde and a catalytic amount (3.6 g) of piperidine are added to the reaction mixture obtained in the 1$^{st}$ reaction step and the reaction mixture is stirred for 24 hours at 70° C.

The reaction product is precipitated by cooling, then separated by filtration and dried in vacuum to obtain 50 g of an orange solid product.

The structure corresponding to formula

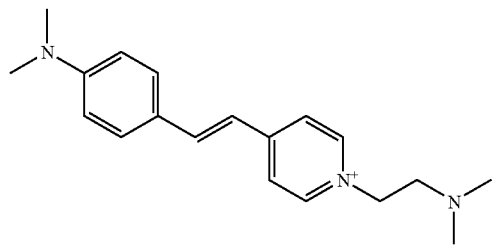

(STY-110a)

is confirmed by $^1$H-NMR data in deuterated chloroform (128 scans)/360 MHz:

| | | | | |
|---|---|---|---|---|
| 8.623 | d | 6.7 | 1.98 | Py |
| 7.992 | d | 6.7 | 2.02 | Py |
| 7.819 | d | 16.6 | 1.03 | vinyl |
| 7.528 | d | 6.1 | 2.06 | Phe |
| 7.082 | d | 16.9 | 1.02 | vinyl |

-continued

| | | | | |
|---|---|---|---|---|
| 6.742 | d | 6.4 | 2.05 | Phe |
| 4.774 | t | 6 | 2.00 | ethylene |
| 3.157 | t | 6 | 2.05 | etylene |
| 3.073 | s | | 6.087 | Dimethyl(amine) |
| 2.590 | | | 6.09 | Dimethyl-am |

3. Alkylating Agent

A mixture of 15.4 g of 2,2-dithiodiethanol in 100 ml chloroform and 24.1 g pyridine are cooled with stirring to 0° C.

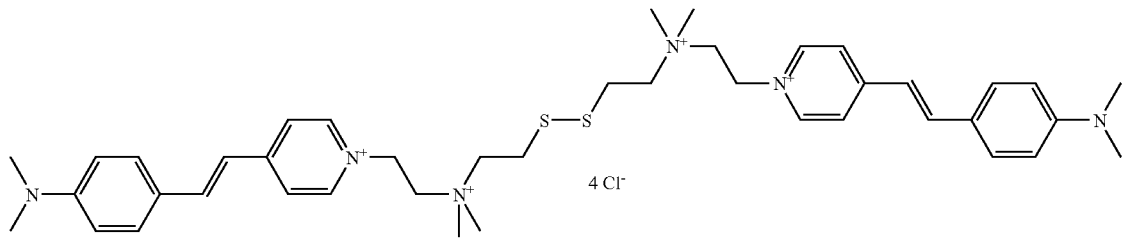

(STY-110)

and then 41.0 g of tosyl chloride are added in small amounts, maintaining the temperature at 0° C. by cooling externally.

After completion of the addition the mixture is left over night in the refrigerator to complete the reaction.

The reaction mixture is mixed with a water/chlorhidric acid and ice slurry, the phases are separated, washed with water and dried.

The solution of toluenesulfonate diester is used as starting compound in the 4$^{th}$ reaction step.

4. Alkylation

Two equivalents (56 g) of the intermediate dye molecule are dissolved in the foregoing alkylation agent obtained in the 4$^{th}$ reaction step with solvent. The temperature is raised to reflux and maintained at 70° C. during the following 12 hours.

The reaction mixture is cooled to ambient temperature with agitation and separated through filtration.

The solid is washed with chloroform and dried.

The product is characterized by the following data:

1H-NMR data in deuterated chloroform (128 scans)/360 MHz:

| | | | | |
|---|---|---|---|---|
| 9.62 | s | | .03 | ba |
| 8.628 | d | 6.7 | 4.00 | Py |
| 7.969 | d | 6.7 | 4.04 | Py |
| 7.781 | d | 16.6 | 2.03 | vinyl |
| 7.701 | d | 7.0 | 4.070 | tosilate |
| 7.58 | d | 6.1 | 4.04 | Phe |
| 7.239 | d | 6.5 | 4.025 | Phe |
| 7.067 | d | 16.9 | 2.02 | vinyl |
| 6.813 | d | 6.4 | 4.05 | Phe |
| 4.867 | t | 6 | 4.00 | ethylene |
| 3.718 | t | 6 | 4.05 | ethylene |
| 3.36 | t | 6 | 3.89 | ethylene |
| 3.057 | s | | 12.087 | Dimethyl(amine) |
| 2.959 | s | | 12.12 | dimethyl |
| 2.346 | s | | 6.070 | Me-tosilate |

Example ANT-01

2.95 g of 1-(3-dimethylaminopropyl)amino-4-amino-anthraquinone (RN 65274-31-9) and 1.80 g of bis(2-(2-bromoacetamido)ethyl)-disulfide (RN 697755-79-6) are dissolved in 20 ml DMF and stirred for 5 h at 40° C. The dark blue solution is than dropped slowly into 500 ml acetone under vigorous stirring. The precipitate is filtered off, washed with 100 ml acetone and dried in a vacuum oven at 50° C. to yield 4.06 g of the compound of formula

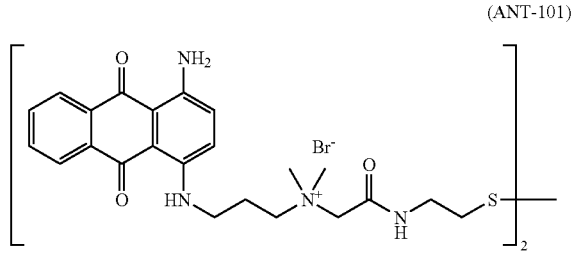

(ANT-101)

MS (ES+):m/z 440 ($M^{2+}$). UV/VIS [nm] (water): $\lambda_1$=567, $\lambda_2$=616.

Example ANT-02

2.06 g of the compound of formula (101) are dissolved in 30 ml NMP and 530 µl 4-bromo-butyryl chloride are added under stirring. After 40 min 10 ml of a 4.2 M solution of trimethyl-amine in ethanol are added and the reaction mixture is stirred at 80° C. for 17 h. Then 10 ml of acetone are added and the resulting precipitate is separated by filtration, washed with acetone and dried to give 1.40 g of the compound of formula

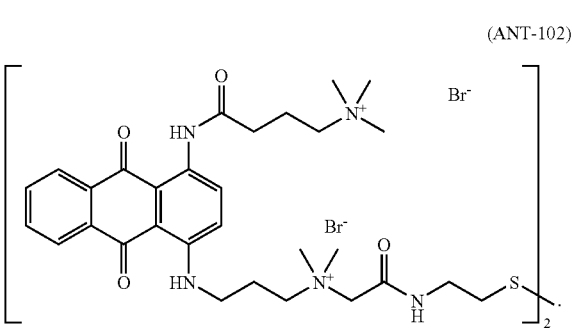

(ANT-102)

UV/VIS [nm] (water): $\lambda_{max}$564.

Example ANT-03

Step 1: A solution of 19.39 g 1,3-dibromopropane in 10 ml of chloroform is stirred at room temperature and a solution of 0.50 g N,N'-tetramethylcystamine (RN 1072-11-3) in 10 ml of chloroform is added over a period of 8 h. After additional stirring for 2 days the resulting white precipitate is filtered off, washed with chloroform and dried under vacuum.

Step 2: The white solid prepared in step 1 is added to a solution of 1.06 g of 1-(3-dimethyl-aminopropyl)amino-4-amino-anthraquinone (RN 65274-31-9) in 10 ml DMF. The solution is stirred for 3 days at 40° C. After that time the reaction mixture is poured into 200 ml of acetone and the resulting precipitate is collected by filtration. Than the crude product is refluxed for 40 min in 120 ml of acetone. The suspension is filtered off and the collected solid is dried under vacuum at 60° C.

Yield: 1.64 g of the compound of formula

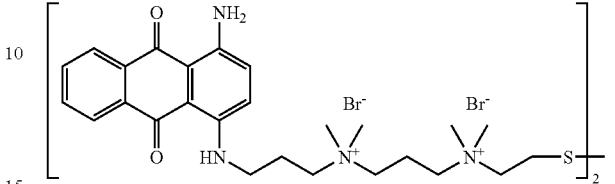

(ANT-103)

$^{13}C$ NMR (DMSO-$d_6$) [ppm]: δ 181.68, 181.23, 146.66, 146.58, 134.46, 134.17, 132.80, 132.70, 130.12, 126.13, 126.05, 124.12, 108.76, 108.43, 62.93, 61.93, 60.05, 60.00, 51.19, 51.00, 39.66, 30.86, 23.34, 17.36.

Example ANT-04

5.00 g of 1-(3-dimethylaminopropyl)amino-4-amino-anthraquinone (RN 65274-31-9) and 3.58 g of the bis(toluolsulfonate) of (2-hydroxyethyl)-disulfide (RN 69981-39-1; prepared as described in Delacroix et al., Bull. Soc. Chim. France (1978), (9-10, Pt. 2), 481-4) are dissolved in 15 ml NMP and stirred at 80° C. for 72 h. Then the reaction mixture is poured into 150 ml of acetone and the precipitate is separated from the supernatant liquid. The residue is refluxed for 1 h in 60 ml acetone collected by filtration and dried under high vacuum to obtain 3.55 g of the compound of formula

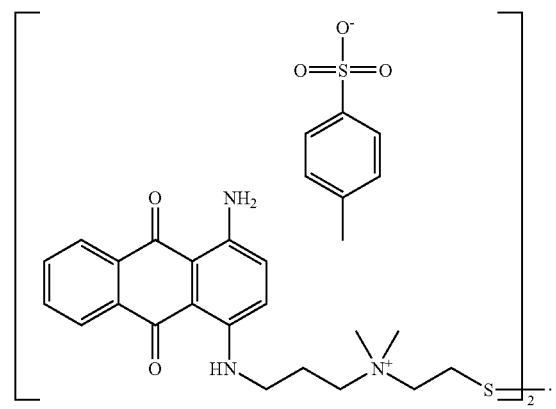

(ANT-104)

MS (ES+):m/z 383 ($M^{2+}$). UV/VIS [nm] (water): $\lambda_1$=567, $\lambda_2$=615.

Example ANT-05

Step 1: To a solution of 61.32 g 1-(3-aminopropyl)-imidazole, 5.92 g lithium hydroxide and 1.48 g Cu(I) CI in 150 ml water, 100 g of sodium 1-amino-4-bromoanthraquinone-2-sulfonate (RN 6258-06-6) are added over a period of 15 min. The reaction mixture is stirred for 30 min at 65° C. and then for 1 h at 85° C. After the resulting blue solution had cooled down to room temperature 75 ml concentrated hydrochloric acid are added. The resulting precipitate is filtered off, suspended in 200 ml acetone and stirred for 1 h. After filtration the crude product is suspended in 500 ml water and dissolved by addition of 19.98 g of a 4 molar sodium hydroxide solution. Then 18 g of sodium chloride are added and the resulting precipitated is filtered off and dried to yield 44.23 g of the compound of formula (ANT-105a)

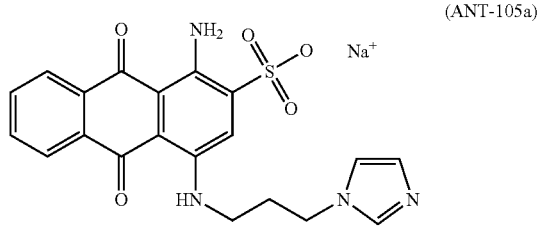

MS (ES−):m/z 425 (M⁻). UV/VIS [nm] (water): $\lambda_1$=591, $\lambda_2$=633.

Step 2: To a suspension of 30.78 g of the compound of formula (105a) in 300 ml of water 34 ml sodium hydroxide solution (30%) are added. The mixture is heated to 80° C. and a solution of 16.31 g glucose in 90 ml water is added dropwise over a period of 40 min. After 30 min the suspension is cooled to room temperature and filtered. The press cake is stirred in 450 ml 4 molar sodium hydroxide solution, filtered off and washed with water. The residue is dried in a vacuum oven at 50° C. to yield 19.69 g of the compound of formula (ANT-105b)

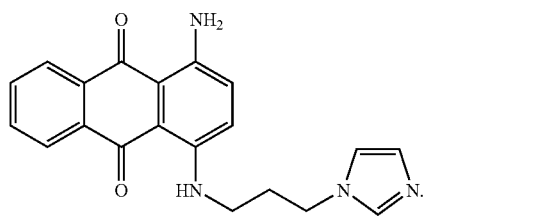

MS (ES⁺): m/z 347 (M+1). UV/VIS [nm] (water/acetonitrile 1:1): $\lambda_1$ 569, $\lambda_2$ 612.

Step 3: 1.28 g of the compound of formula (105b) and 0.73 g of bis(2-(2-bromoacetamido)-ethyl)-disulfide (RN 697755-79-6) are dissolved in 20 ml DMF and stirred for 3 days at 40° C. The dark blue solution is than dropped slowly into 500 ml acetone under vigorous stirring. The precipitate is filtered off, washed with 100 ml acetone and dried in a vacuum oven at 50° C. to yield 0.935 g of the compound of formula (ANT-105)

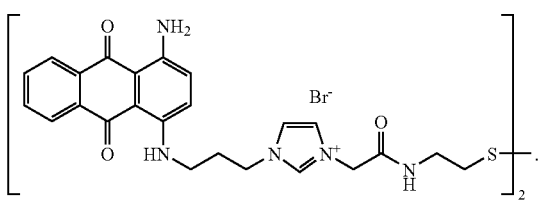

MS (ES⁺): m/z 463 (M²⁺). UV/VIS [nm] (water/acetonitrile 1:1): $\lambda_1$ 571, $\lambda_2$ 609.

Example ANT-06

Step 1: A mixture of 5.00 g of C.I. Acid Blue 25 (RN 6408-78-2), 7.93 g potassium hydroxide and 20 ml of N,N-dimethyl-ethanolamine is stirred at room temperature for 2 h. Then the reaction mixture is poured into 200 ml of water and the resulting precipitate is collected by filtration. The solid is stirred in 200 ml of water for 30 min, then filtered off and dried under vacuum at 60° C. to obtain 1.69 g of the compound of formula (ANT-106a)

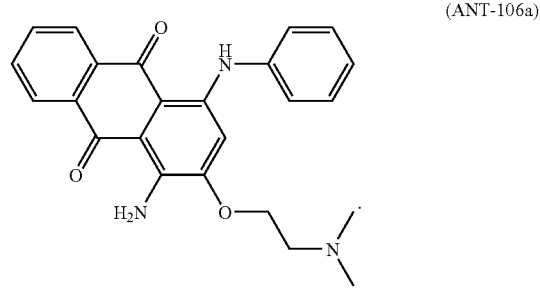

MS (ES+): m/z 402 (M+1). UV/VIS [nm] (water/acetonitrile 1:1): $\lambda_1$=554, $\lambda_2$=591.

Step 2: 0.50 g of the compound of formula (106a) and 0.29 g of the bis(toluolsulfonate) of (2-hydroxyethyl)-disulfide (RN 69981-39-1) are dissolved in 3 ml of NMP and stirred at 40° C. for 72 h. Then the mixture is stirred for additional 72 h at 50° C. Then the reaction mixture is dropped into 200 ml of tert-butyl-methyl-ether. The precipitate is separated by filtration, dissolved again in 3 ml of NMP and precipitated by dropping the solution into 50 ml tert-butyl-methyl-ether. After filtration the product is dried under vacuum to obtain 0.32 g of the compound of formula (106)

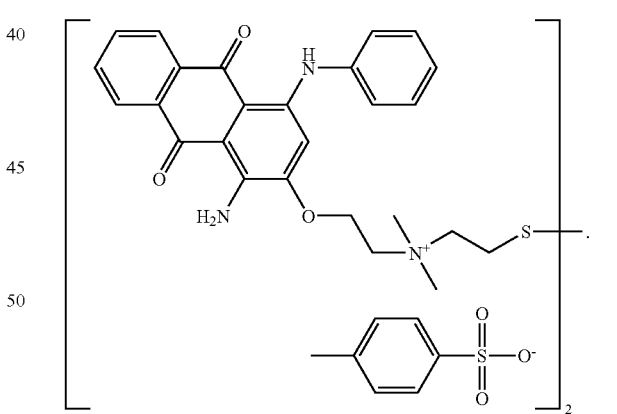

MS (ES+): m/z 461 (M²⁺). UV/VIS [nm] (water/acetonitrile 1:1): $\lambda_1$ 556, $\lambda_2$ 593.

Example ANT-07

Step 1: 1.43 g of 1-(2-chloroacetamido)-anthraquinone (RN 20149-91-1) and 6.46 g imidazole are mixed in 10 ml o-dichlorobenzene and stirred at 110° C. for 1 h. The reaction mixture is cooled to room temperature and poured into 1 L water under stirring. The precipitate is filtered, washed with water and dried under vacuum at 60° C. to yield 1.30 g of the compound of formula (ANT-107a)

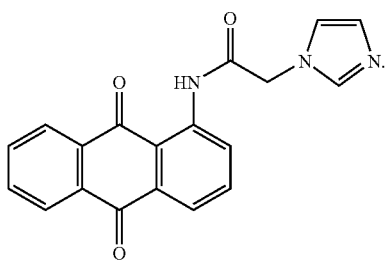

MS (ES+): m/z 332 (M+1). UV/VIS [nm] (water/acetonitrile 1:1): λ$_{max}$ 394.

Step 2: 1.28 g of the compound of formula (107a) and 0.726 g of bis(2-(2-bromoacetamido)-ethyl)-disulfide (RN 697755-79-6) are mixed in 5 ml dimethylformamide and stirred at 60° C. for 24 h. The reaction mixture is poured into 150 ml acetone under stirring. The precipitate is filtered and washed twice with 100 ml acetone. The filter cake is dried under vacuum at 50° C. to yield 1.72 g of the compound of formula (ANT-107)

MS (ES+): m/z 448 (M$^{2+}$). UV/VIS [nm] (water): λ$_{max}$=395.

Example NIT-01

Preparation of the Compound of Formula (NIT-101)

2.0 g (8.1 mmol) of 4-chloro-3,5-dinitro benzoic acid are brought in 6 ml acetone. 0.092 g (8.1 mmol) of cysteamine hydrochloride dissolved in 10 ml H$_2$O is added to the resulting solution. The pH value of this mixture is adjusted to 9 with 10 N sodium hydroxide. The reaction solution is stirred at room temperature under nitrogen atmosphere. The pH value is controlled in distinct intervals by addition of 10 N sodium hydroxide and adjusted to 9.

After reaction time of 6 h the mixture is acidified with 2 N HCl and the precipitate is filtered off. The filter cake is washed with HCl (10 N) and than with destined water.

The solid is recrystallized from water/acetone.

1.5 g of a yellow-orange solid are obtained.

Mp: 253-255° C.

Example NIT-02

Preparation of the Compound of Formula (NIT-102)

5.66 g (25.2 mmol) cystamine dihydrochloride are furnished in 40 ml dimethylsulfoxide. 8.46 g (100.8 mmol) sodium hydrogen carbonate are added stepwise.

Then 10.0 g (50.4 mmol) 4-fluoro-3-nitrophenylacetamide, dissolved in 100 ml dimethylsulfoxide are added dropwise at 45° C.

The reaction mixture is stirred for 7 h at 80° C. and cooled down to room temperature. The reaction mixture is placed on a water/ice mixture and adjusted to pH 3 by addition of conc. HCl.

The resultant precipitate is filtered off, washed with water for several times and dried in vacuo. 12.4 g (97%) of a red dye are obtained.

Mp: 199-201° C.

Example NIT-03

Preparation of the Compound of Formula (NIT-103)

5.00 g (9.8 mmol) of di 2-[4-acetamino-2-nitrophenyl] ethyl disulfide are furnished in 50 ml of 20% hydrochloric acid.

The obtained suspension is refluxed for 4 h, whereupon the color of the reaction mixture changes from red to orange.

Then the heterogenic reaction mixture is cooled down to room temperature and the pH is adjusted to 4 with 20% NaOH.

The precipitate is filtered off and washed with 10% sodium hydrogen carbonate solution and then neutral with water.

3.5 g (84%) of a violet dye are obtained.

Mp.: 193-195° C.

Example NIT-04

Preparation of the Compound of Formula

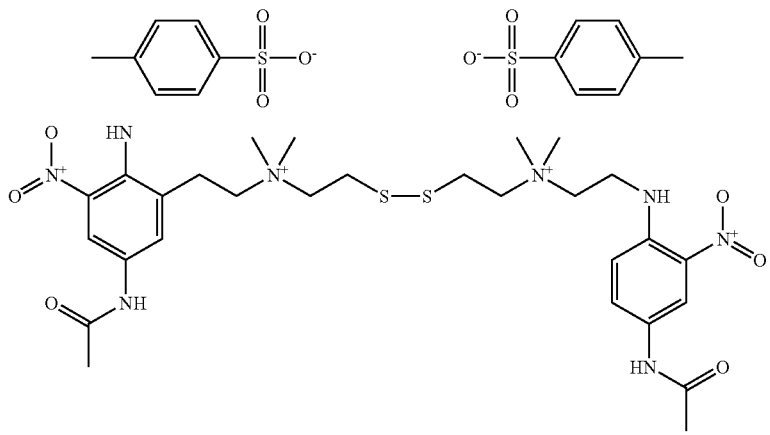

(NIT-104)

a. 20 g of 4-fluoro-3-nitrophenylacetamide, 8.48 g of potassium carbonate and 9.07 g of N,N-dimethyl-ethylenediamine are dissolved in 50 ml dimethyl sulfoxide. The reaction mixture is stirred for 3 days at 80° C. and then cooled to room temperature. The resulting suspension is poured into 300 ml of ice and filtered. The collected solid is dried in vacuo over night at 60° C. to yield 23.79 g of a red powder.

MS (ES−): m/z 265 (M−1). UV/VIS [nm] (water): $\lambda_{max}$ 458

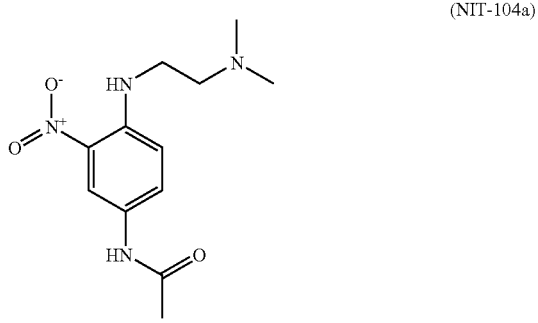

(NIT-104a)

b. 34 g of the compound of formula (104a) and 30 g of the bis(toluolsulfonate) of (2-hydroxy-ethyl)-disulfide (RN 69981-39-1; prepared as described in Delacroix et al., Bull. Soc. Chim. France (1978), (9-10, Pt. 2), 481-4) are suspended in 80 ml of NMP and stirred for 3 days at 45° C. Then 1 l tert.-butyl methyl ether are added slowly to the reaction mixture and the resulting precipitate is collected by filtration. Then the crude product is redissolved in 200 ml ethanol and precipitated again by addition of 150 ml of tert.-butyl methyl ether. The solid is collected by filtration and dried in vacuo to yield 22.6 g of an orange powder which corresponds to the compound of formula (104).

MS (ES+): m/z 326 ($M^{2+}$), UV/VIS [nm] (water): $\lambda_{max}$ 466.

Example XAN-01

Preparation of the Compound of Formula

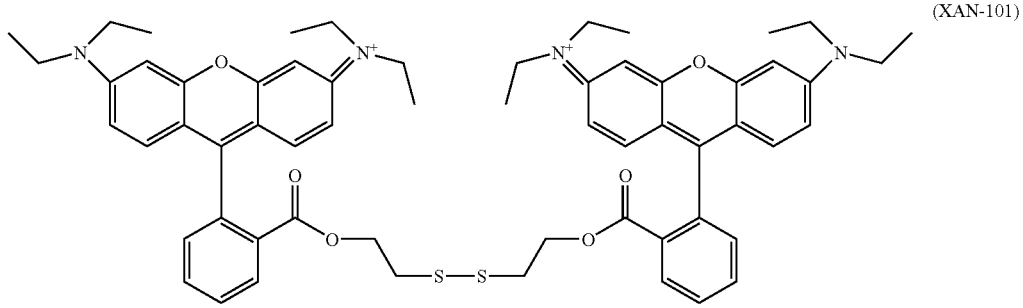

(XAN-101)

(a₁) Condensation 300 ml of chloroform are added to the reaction vessel.

10.5 g rhodamine B are introduced with mixing.

The equivalent amount (1.54 g) of 2,2-dithiodiethanol, 12.0 g dicyclohexylcarbodiimide and a catalytical amount (7.6 g) of pyrrolidinopyridine are added.

The reaction mixture is stirred for 24 h at 293° C.

The reaction product is separated by washing with 100 ml of a 3% hydrochloric acid solution then with 100 ml water with 3% salt.

The solution is evaporated to dryness in vacuum to obtain 12 g of a reddish blue solid product.

The product is characterized by ¹H-NMR data in deuterated methanol (128 scans)/360 MHz:

| 8.350 | d | 6.7 | 1.98 | phe |
| 7.831 | d überlagert | 6.7 | 2.02 | Phe |
| 7.831 | d überlagert | 6.6 | 2.03 | phe |
| 7.425 | d | 6.1 | 2.04 | phe |
| 7.153 | d | 8.8 | 4.02 | xanten |
| 7.102 | d | 9.1 | 4.05 | xanten |
| 6.984 | s |  | 4.0 | xanten |
| 4.21 | t | 6 | 4.00 | Ethylen |
| 3.70 | t | 7 | 16.10 | ethyl |
| 2.57 | t | 6 | 4.08 | Ethylen |
| 1.319 | t | 7 | 24.3 | Ethyl |

Examples XAN-02-XAN-10

The following compounds (XAN-102-XAN-110) can be prepared according to the method described in Example XAN-01:

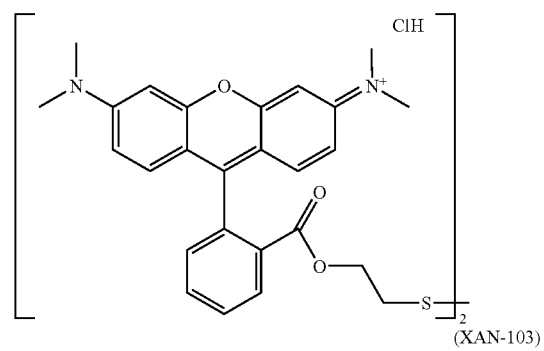
(XAN-102)

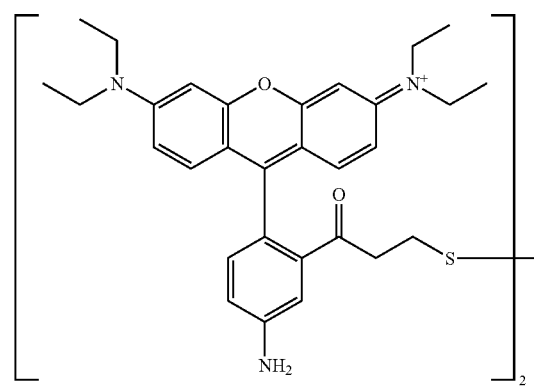
(XAN-103)

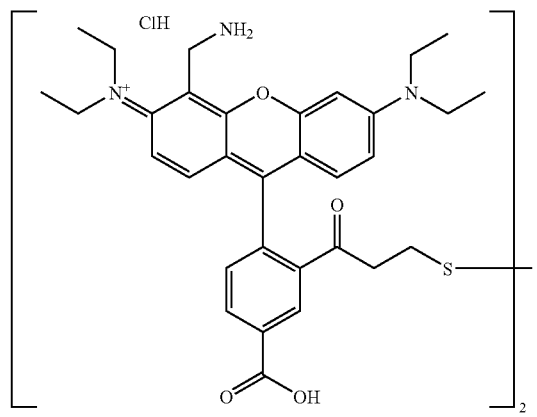
(XAN-104)

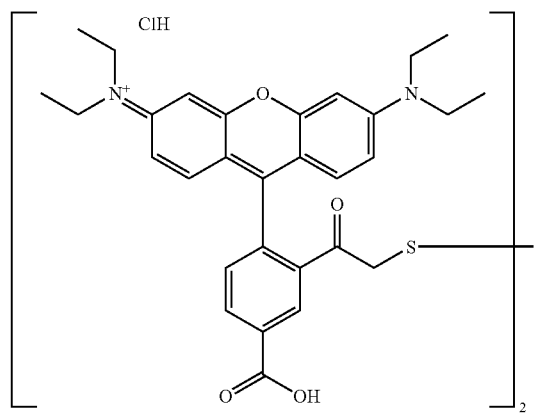
(XAN-105)

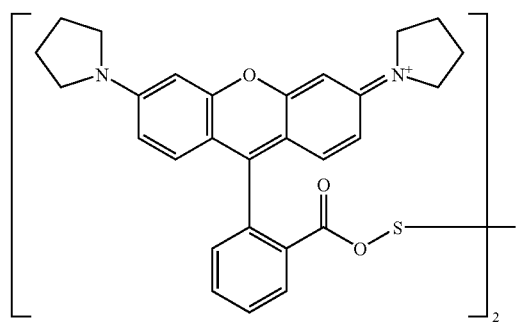
(XAN-106)

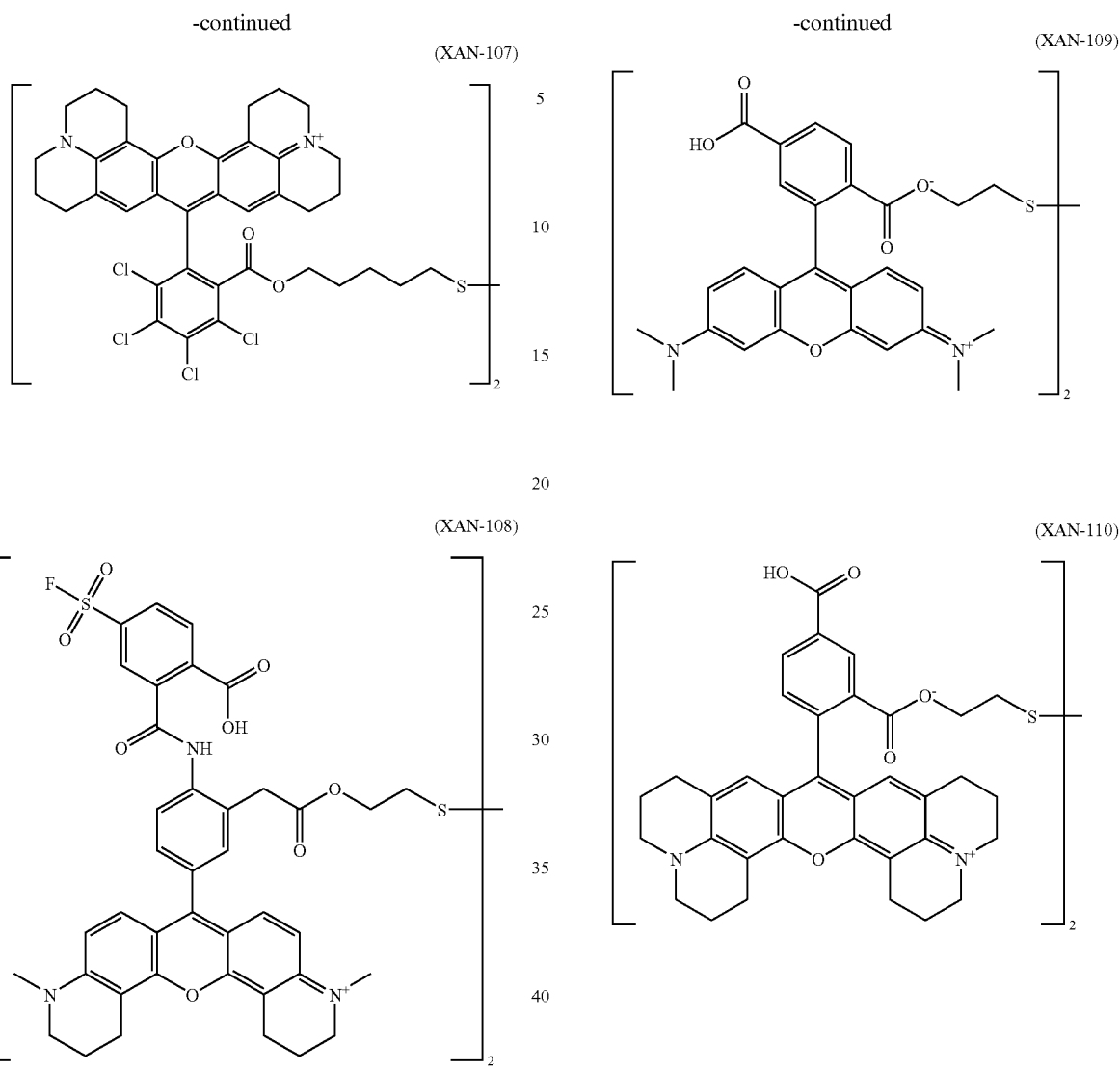
Example XAN-11
Preparation of the Compound of Formula
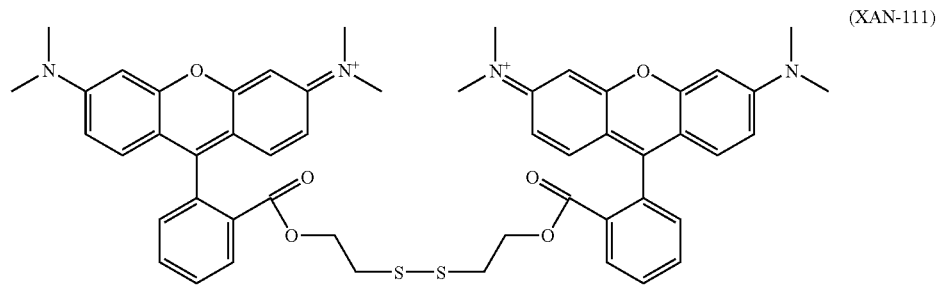

(a) Condensation 300 ml chloroform are added to the reaction vessel.

10.5 g raw material are introduced with mixing, the equivalent amount (1.54 g) of 2,2-dithiodiethanol, 12.0 g dicyclohexylcarbodiimide and a catalytical amount (7.6 g) of pyrrolidinopyridine are added.

The reaction mixture is stirred for 24 h at 293° C.

The reaction product is separated by washing with 100 ml of a 3% hydrochloric acid solution, then with 100 ml water with 3% salt.

The solution is evaporated to dryness in vacuum to obtain 12 g of a reddish blue solid product.

The product is characterized by ¹H-NMR data in deuterated methanol (128 scans)/360 MHz

| 7.970 | d | 9.7 | 1.98 | phe |
|---|---|---|---|---|
| 7.571 | d (overlaid) | 9.5 | 2.02 | phe |
| 7.571 | d (overlaid) | 9.6 | 2.03 | phe |
| 7.436 | d | 2.6 | 2.04 | xanthene |
| 7.215 | d | 6.8 | 4.02 | xanthene |
| 7.102 | d | 6.5 | 2.025 | phe |
| 6.528 | s | | 4.05 | xanten |
| 4.19 | t | 7 | 4.00 | ethylene |
| 3.29 | t | 7 | 16.10 | methyle |
| 2.57 | t | 7 | 4.08 | ethylene |

Example XAN-12

Preparation of the Compound of Formula 300 ml chloroform are added to the reaction vessel.

10.5 g rhodamine G are introduced with mixing, the equivalent amount (1.54 g) 2,2-dithiodiethanol, 12.0 g dicyclohexylcarbodiimide and a catalytical amount (7.6 g) pyrrolidinopyridine are added and the reaction mixture is stirred for 24 h at 293° C.

The reaction product is separated by washing with 100 ml of a 3% hydrochloric acid solution, then with 100 ml water with 3% salt.

The solution is evaporated to dryness in vacuum to obtain 12 g of a reddish blue solid product.

The product is characterized by ¹H-NMR data in deuterated chloroform (128 scans)/360 MHz

| 8.350 | d | 6.7 | 1.98 | phe |
|---|---|---|---|---|
| 7.831 | d overlaid | 6.7 | 2.02 | phe |
| 7.831 | d overlaid | 6.6 | 2.03 | phe |
| 7.425 | d | 6.1 | 2.04 | phe |
| 7.153 | d | 8.8 | 4.02 | xanthene |
| 7.102 | d | 9.5 | 4.025 | xanthene |
| 6.984 | s | | 4.05 | xanthene |
| 4.21 | t | 6 | 4.00 | ethylene |
| 3.70 | t | 7 | 16.10 | ethylene |
| 2.57 | t | 6 | 4.08 | ethylene |
| 2.319 | t | 7 | 16.3 | ethylene |

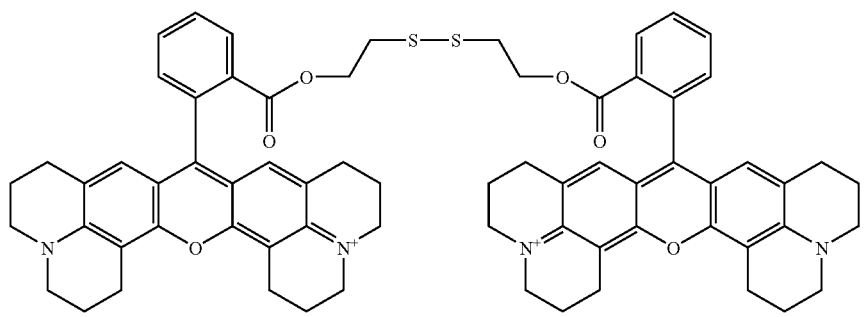

(XAN-112)

Example XAN-13

Preparation of the Compound of Formula

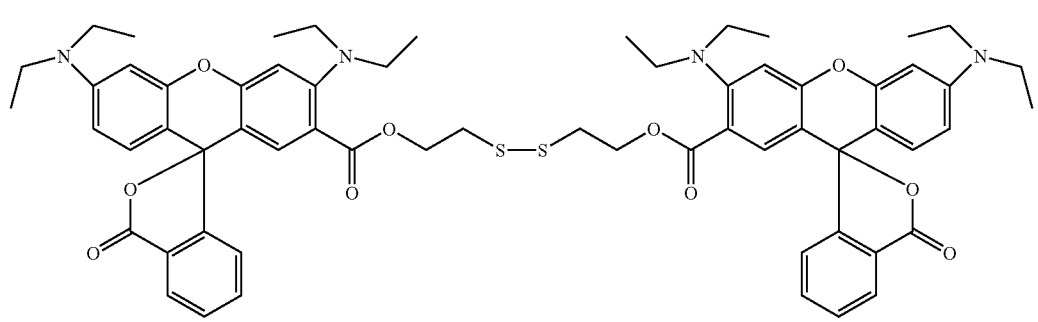

(XAN-113)

(a) Alkylating Agent

A mixture of 15.4 g 2,2-dithiodiethanol in 100 ml chloroform and 241 g pyridine are cooled with stirring to 0° C.

22.0 g mesyl chloride are added in small amounts, maintaining the temperature by cooling externally.

After completion of the addition the mixture is left over night in the refrigerator to finish the reaction.

The reaction mixture is mixed with a water/hydrochloric acid and ice slurry, the phases are separated, washed with water and dried.

The solution of methanesulfonate diester used for reaction step (b).

(b) Alkylation

The reaction mixture of 250 g water and 103 g of the xanthene precursor obtained in reaction step (a) is adjusted to pH 9.2 with sodium carbonate.

80 ml toluene and the equivalent amount (32.0 g) of diester and a catalytical amount (0.6 g) of tetrabutyl-ammonium bromide are added and the reaction mixture is stirred for 6 hours at 300 K.

The reaction product is heated to 350 K, the lower water phase is separated, the upper toluene phase washed, then 160 ml water are added and toluene distillated.

The precipitate is separated by filtration and dried in vacuum to obtain 90 g of an orange solid product.

The product is characterized by $^1$H-NMR data in deuterated chloroform (128 scans)/360 MHz

| 7.970 | d | 6.7 | 1.98 | phe |
| 7.571 | d overlaid | 6.5 | 2.02 | phe |
| 7.571 | d overlaid | 6.6 | 2.03 | phe |
| 7.436 | d | 2.6 | 2.04 | xanthene |
| 7.215 | d | 8.8 | 4.02 | xanthene |
| 7.102 | d | 9.5 | 2.025 | phe |
| 6.528 | s |   | 4.05 | xanthene |
| 4.19 | t | 7 | 4.00 | ethylene |
| 3.29 | t | 7 | 16.10 | ethyl |
| 2.57 | t | 7 | 4.08 | ethylene |
| 1.319 | t | 7 | 24.3 | ethyl |

Example XAN-14

Preparation of the Compound of Formula (a) Condensation 300 ml chloroform are added to the reaction vessel.

10.5 g Pergascript Orange are introduced with mixing, the equivalent amount (1.54 g) 2,2-dithiodiethanol and 12.0 g dicyclohexylcarbodiimide and a catalytical amount (7.6 g) of pyrrolidinopyridine are added and the reaction mixture is stirred for 24 h at 293° C.

The reaction product is separated by washing with 100 ml of a 3% hydrochloric acid solution, then with 100 ml water with 3% salt.

The solution is evaporated to dryness in vacuum to obtain 12 g of a reddish blue solid product.

The product is characterized by $^1$H-NMR data in deuterated chloroform (128 scans)/360 MHz

| 7.970 | d |  | 9.7 | 1.98 | phe |
| 7.571 | d overlaid |  | 9.5 | 2.02 | phe |
| 7.571 | d overlaid |  | 9.6 | 2.03 | phe |
| 7.436 | d |  | 2.6 | 2.04 | xanthene |
| 7.215 | d |  | 6.8 | 4.02 | xanthene |
| 7.102 | d |  | 6.5 | 2.025 | phe |
| 6.528 | s |  |  | 4.05 | xanthene |
| 4.19 | t |  | 7 | 4.00 | ethylene |
| 3.29 | t |  | 7 | 16.10 | ethyl |
| 2.57 | t |  | 7 | 4.08 | ethylene |
| 1.319 | t |  | 7 | 24.3 | ethyl |

Example ARY-01

A solution of 10.00 g Pergascript I-6B (RN 50292-95-0), 1.259 g dithiodiethanol and 3.95 g of toluene sulfonic acid monohydrate in 100 ml chloroform is refluxed for 4 days with a water separator.

After that time no separation of water is observed any more.

The solvent is removed in vacuo and the crude product was purified by column chromatography (silica, toluene/acetone gradient).

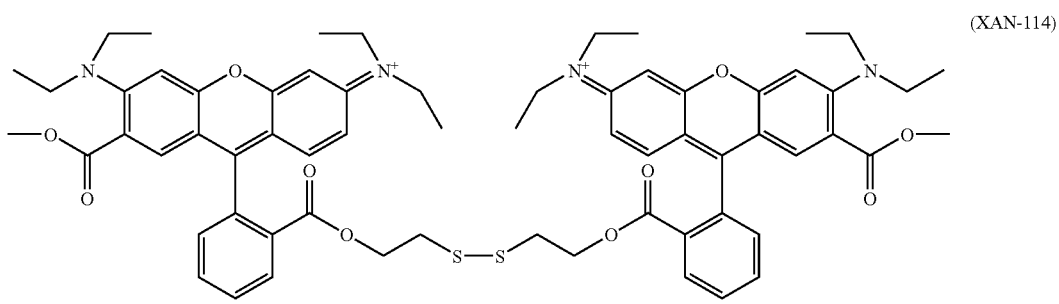

(XAN-114)

Yield: 1.78 g of the compound of formula

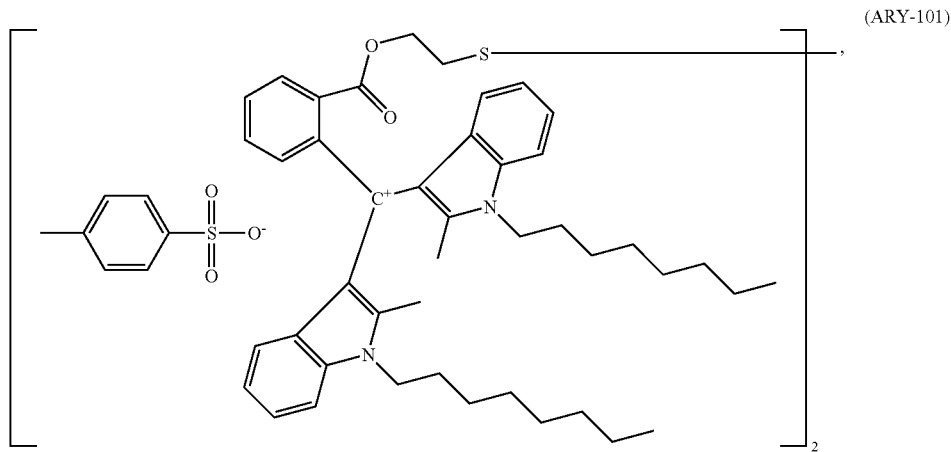

(ARY-101)

MS (ES+): m/z=677 ($M^{2+}$); UV/VIS: $\lambda_{max}$=531 nm.

Example OXA-01

Procedure (a)

Step 1: 6.34 g of 1-(3-methoxyphenyl)-piperazine dihydrochloride are suspended in 4 ml and cooled to 0-5° C.

8.58 g of a sodium methylate solution in methanol (1 mol methylate in 179.6 g solution) are added dropwise to this suspension, maintaining the temperature at 0-5C.

After completion of the addition the mixture is was stirred for 30 min at room temperature. Finally the solvent is removed by evaporation and the remaining brown oil is dissolved in 40 ml dimethyl formamide.

6.58 g bis(2-(2-bromoacetamide) ethyl disulfide (RN 697755-79-6) and 4.66 g potassium carbonate are added to this solution and the reaction mixture is stirred for 5 days at 40° C. Then the reaction mass is poured into 50 ml diethyl ether.

The product precipitates as an oil, which is dissolved in 100 ml dichloromethane and washed with a $NaHCO_3$ solution.

The organic phase is dried over sodium sulphate and filtered.

Then the solvent is evaporated and the remaining oil is purified by column chromatography (acetone, silica) to obtain 0.64 g of compound of formula MS (ES+): m/z 617 (M+1).

Step 2: 0.88 g HBr (33%) are added drop wise to a suspension of 0.5 g of the compound of formula (1o1a) in 2 g dimethyl formamide and 2.5 g water at 0-5° C.

After completion of the addition the yellow solution is warmed up to room temperature and 0.32 g of an aqueous sodium nitrite solution (46 w. %) is added slowly.

The reaction mixture is stirred at room temperature until the test on nitrite is negative (potassium iodide/starch paper).

The dark reaction mixture was used for reaction step 3.

Step 3: 0.27 g 3-diethylaminophenol are dissolved in 3 g dimethyl formamide and after addition of a few drops of HBr (33%) the solution is heated to 70° C.

At this temperature the dark reaction mixture obtained in the nitrosation step is added via a dropping funnel over a period of 1 h.

The resulting blue solution is stirred for an additional hour, then cooled to room temperature and poured into 200 ml of acetone.

The precipitate is collected by filtration and dried in vacuo to obtain 0.43 g of the compound of (OXA-101)

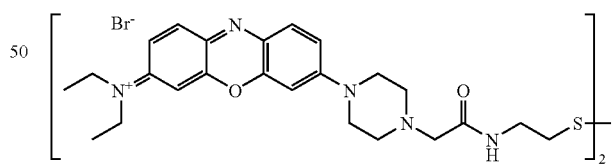

(OXA-101a)

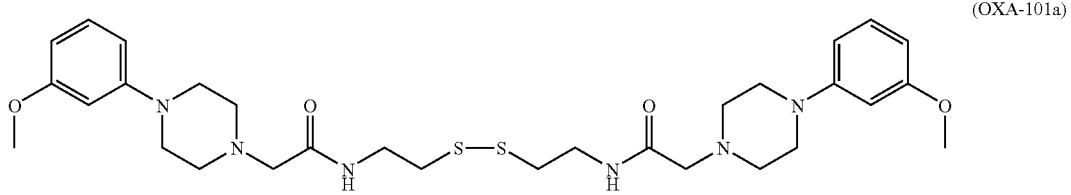

as a dark blue powder, which can be used for the dyeing of hair.

MS (ES+): m/z 453 ($M^{2+}$); UV/VIS (water): $\lambda_{max1}$ 642 nm, $\lambda_{max2}$ 588 nm.

Example OXA-02

Procedure (b)

Step 1: A solution of 7.58 g of 3-diethylamino-anisole in 37 g dimethyl formamide and 45 g water is cooled to 0° C. Then 19.5 g HBr (33%) are added via a dropping funnel over a period of 1 h, during which time the temperature is rising to 15° C.

Then 7.04 g of an aqueous sodium nitrite solution (46% b.w.) is added dropwise over a period of 30 min.

The reaction mixture is stirred at room temperature until the test on nitrite is negative (potassium iodide/starch paper).

The resulting dark solution is used for step 2.

Step 2: A solution of 6.68 g 1-(3-hydroxyphenyl)piperazine and 9 g HBr (33%) in 10 g dimethyl formamide is heated to 70° C.

At this temperature the dark solution obtained in step 1 s added via a dropping funnel over a period of 2.5 h.

The resulting blue solution ios stirred for an additional hour, then cooled to room temperature and poured into 300 ml of acetone.

The precipitate is collected by filtration and stirred in 100 ml of refluxing acetone two times before it is filtered off and dried in vacuo to obtain 6.97 g of the compound of formula (OXA-102a)

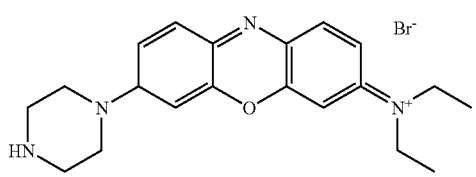

as a dark blue powder, which is used for step 3.

MS (ES+): m/z 337 ($M^+$−1); UV/VIS (water): $\lambda_{max1}$ 634 nm, $\lambda_{max2}$ 590 nm.

Step 3: A solution of 0.5 g of the compound of formula (102a), 0.24 g of bis(2-(2-bromo-acetamide)ethyl)-disulfide (RN 697755-79-6) and 0.08 g of potassium carbonate in 50 ml methanol is stirred at 40° C. for 12 h.

After that time the solvent is removed by evaporation, the remaining solid is dissolved in 5 ml dimethyl formamide and this solution is dropped into 20 ml of acetone.

The resulting precipitate is collected by filtration and dried to obtain 0.23 g of the compound of formula (OXA-101) as a dark blue powder, which can be used for the dyeing of hair.

MS (ES+): m/z 453 ($M^{2+}$); UV/VIS (water): $\lambda_{max1}$ 642 nm, $\lambda_{max2}$ 588 nm.

Preparation of the Compound of Formula (PRO-101a)

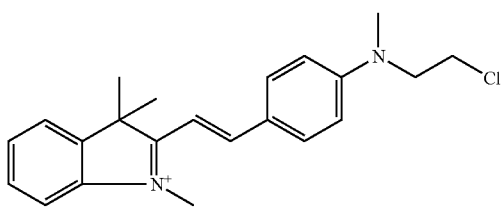

(a) Condensation 35.7 g 1,3,3 trimethyl-2-methylene-indoline are added to 60 g acetic acid.

The equivalent amount (35.0 g) of 2-chloroethyl-methylamino-benzaldehyde is added and the reaction mixture stirred for 6 h at 30-40° C.

The reaction product is precipitated by cooling, diluted with 375 ml water and salted out with 40 g sodium chloride, then separated by filtration and dried in vacuum to obtain 65 g of a reddish violet solid product.

The product is recrystallized twice from methanol.

The product is characterized by $^1$H-NMR data in deuterated chloroform (128 scans)/360 MHz:

| 9.65 | s | | .03 | benzal (trace) |
|---|---|---|---|---|
| 8.328 | d | 6.7 | 1.00 | vinyl |
| 7.973 | d | 6.7 | 2.01 | phe |
| 7.669 | d | 16.6 | 2.03 | ind |
| 7.58 | m | 6.1 | 1.04 | ind |
| 7.52 | m | 6.5 | 1.025 | ind |
| 7.04 | d | 16.9 | 1.01 | vinyl |
| 6.976 | d | 6.4 | 2.00 | phe |
| 4.016 | s | | 3.00 | methyl |
| 3.949 | t | 6 | 2.03 | ethylene |
| 3.821 | t | 6 | 2.05 | ethylene |
| 3.257 | s | | 3.087 | methyl(amine) |
| 1.8326 | s | | 6.04 | di me-ind | is obtained.

(b) Alkylation

One equivalent (10.0 g) sodium thiosulfate is dissolved in 30 g of the alkylating dye (101c) with 75 ml ethanol as solvent.

The temperature is raised to reflux and maintained at 80° C. during the following 4 hours.

The product of formula (PRO-101 b)

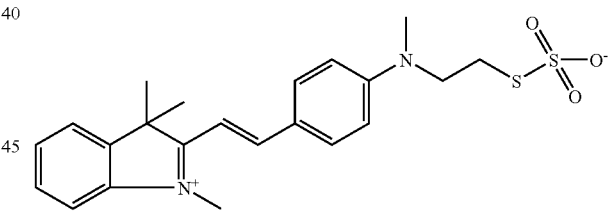

is obtained.

The product is characterized by $^1$H-NMR data in deuterated chloroform (128 scans)/360 MHz

| 8.328 | d | 6.7 | 1.00 | vinyl |
|---|---|---|---|---|
| 7.973 | d | 6.7 | 2.01 | phe |
| 7.669 | d | 16.6 | 2.03 | ind |
| 7.58 | m | 6.1 | 1.04 | ind |
| 7.52 | m | 6.5 | 1.025 | ind |
| 7.04 | d | 16.9 | 1.01 | vinyl |
| 6.976 | d | 6.4 | 2.00 | phe |
| 4.016 | s | | 3.00 | methyl |
| 3.949 | t | 6 | 2.03 | ethylene |
| 3.821 | t | 6 | 2.05 | ethylene |
| 3.257 | s | | 3.087 | methyl(amine) |
| 1.8326 | s | | 6.04 | di me-ind |

137

(c) Hydrolysis

One equivalent (4.0 g) sodium hydroxide is dissolved with absolute ethanol as solvent in the compound (101b) as obtained in step (b).

The temperature is maintained at 80° C. during the following 4 hours.

The product is crystallized by cooling to room temperature under mixing, than separated by filtration, washed and dried in vacuum dryer.

The compound of formula (PRO-110d)

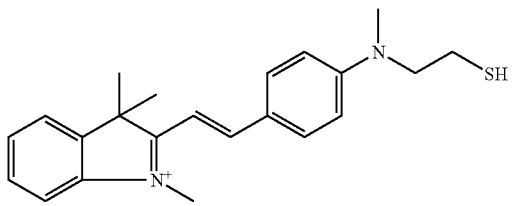

is obtained.

The product is characterized by ¹H-NMR data in deuterated chloroform (128 scans)/360 MHz

| 8.82 | d | 6.7 | 1.00 | vinyl |
| 7.932 | d | 6.7 | 2.01 | phe |
| 7.645 | d | 16.6 | 2.03 | ind |
| 7.58 | m | 6.1 | 1.04 | ind |
| 7.49 | m | 6.5 | 1.025 | ind |
| 7.215 | d | 16.9 | 1.01 | vinyl |
| 7.043 | d | 6.4 | 2.00 | phe |
| 3.978 | s | | 3.00 | methyl |
| 3.949 | t | 6 | 2.03 | ethylene |
| 3.280 | t | 6 | 2.05 | ethylene |
| 3.224 | s | | 3.087 | methyl(amine) |
| 1.810 | s | | 6.04 | di me-ind |

Example PRO-02

Preparation of the Compound of Formula

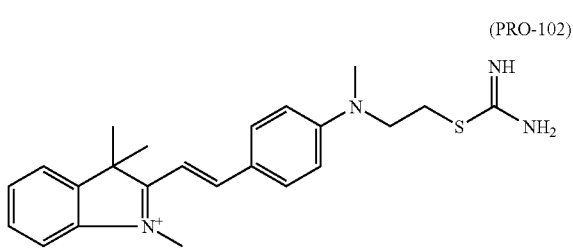
(PRO-102)

(a) Alkylation

One equivalent (6.0 g) of thiourea is dissolved with absolute ethanol as solvent in 30 g of the alkylating dye of formula (101a).

The temperature is raised to reflux and maintained at 80° C. during the following 48 hours. The product is crystallized by cooling to room temperature under mixing, than separated by filtration, washed and dried in vacuum dryer.

138

The product is characterized by ¹H-NMR data in deuterated chloroform (128 scans)/360 MHz

| 8.335 | d | 6.7 | 1.00 | vinyl |
| 7.997 | d | 6.7 | 2.01 | Phe |
| 7.669 | d | 16.6 | 2.03 | Ind |
| 7.58 | m | 6.1 | 1.04 | Ind |
| 7.532 | m | 6.5 | 1.025 | ind |
| 7.32 | d | 16.9 | 1.01 | vinyl |
| 6.996 | d | 6.4 | 2.00 | Phe |
| 4.016 | s | | 3.00 | methyl |
| 3.952 | t | 6 | 2.03 | ethylene |
| 3.548 | t | 6 | 2.05 | ethylene |
| 3.235 | s | | 3.087 | methyl(amine) |
| 1.826 | s | | 6.04 | Di Me-ind |

Example PRO-03

Preparation of the Compound of Formula

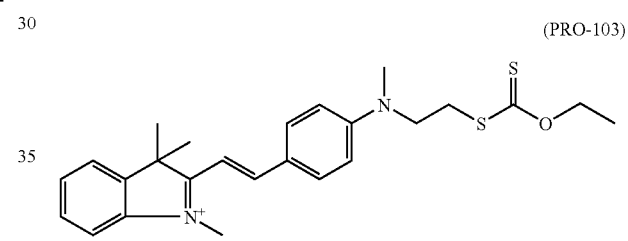
(PRO-103)

One equivalent (14.0 g) of ethyl xantogenate is dissolved with absolute ethanol as solvent in the alkylating dye of formula (101a).

The temperature is raised to reflux and maintained at 80° C. during the following 8 hours.

The product is crystallized by cooling to room temperature under mixing, than separated by filtration, washed and dried in vacuum dryer.

The product is characterized by ¹H-NMR data in deuterated chloroform (128 scans)/360 MHz

| 8.328 | d | 6.7 | 1.00 | vinyl |
| 7.990 | d | 6.7 | 2.03 | phe |
| 7.690 | d | 16.6 | 2.00 | ind |
| 7.58 | m | 6.1 | 1.04 | ind |
| 7.54 | m | 6.5 | 1.025 | ind |
| 7.420 | d | 16.9 | 1.03 | vinyl |
| 7.00 | d | 6.4 | 2.00 | phe |
| 4.016 | s | | 3.00 | methyl |
| 3.950 | t | 6 | 2.03 | ethylene |
| 3.504 | t | 6 | 2.05 | ethylene |
| 3.257 | s | | 3.087 | methyl(amine) |
| 1.822 | s | | 6.04 | di me-ind |

Example PRO-04

Preparation of the Compound of Formula

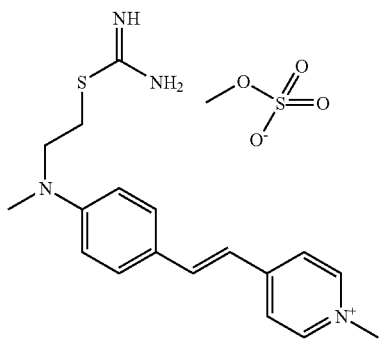

(PRO-104)

(a) Alkylation 68.8 g 4-methyl-pyridine are dissolved in 80 ml absolute ethanol as solvent.

The temperature is raised to 333 K.

94 g dimethylsulfate are introduced into that mixture within one hour.

The temperature is maintained at 333 K during the following 1.5 hours.

(b) Condensation

The equivalent amount (150.0 g) 2-chloroethyl-methylamino-benzaldehyde, 250 ml ethanol and a catalytical amount (9.6 g) of piperidine are added to the reaction mixture obtained in step (a) and the reaction mixture stirred for 8 hours at, The reaction product is precipitated by cooling, then separated by filtration and dried in vacuum to obtain 240 g of an orange solid product.

The product is recrystallized twice from methanol.

The product of formula (PRO-104a)

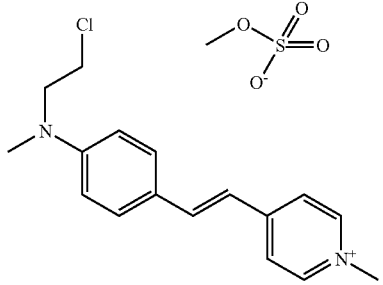

is obtained.

The product is characterized by $^1$H-NMR data in deuterated chloroform (128 scans)/360 MHz

| | | | | |
|---|---|---|---|---|
| 8.522 | d | 6.7 | 1.98 | py |
| 7.983 | d | 6.7 | 2.02 | py |
| 7.828 | d | 16.6 | 1.03 | vinyl |
| 7.632 | d | 6.1 | 2.04 | phe |
| 7.112 | d | 16.9 | 1.00 | vinyl |
| 6.835 | d | 7.5 | 2.025 | phe |

-continued

| | | | | |
|---|---|---|---|---|
| 4.234 | s | | 3.03 | methyl |
| 3.818 | t | 6 | 2.00 | ethylene |
| 3.748 | t | 6 | 2.05 | ethylene |
| 3.696 | s | | 2.59 | mms |
| 3.131 | s | | 2.98 | me at the N |

(c):

One equivalent (6.0 g) thiourea is dissolved with 75 ml absolute ethanol as solvent in 20 g alkylating dye of formula (PRO-104a).

The temperature is raised to reflux and maintained at 80° C. during the following 48 hours. The product is crystallized by cooling to room temperature under mixing, than separated by filtration, washed and dried in the vacuum dryer.

The product is characterized by $^1$H-NMR data in deuterated chloroform (128 scans)/360 MHz

| | | | | |
|---|---|---|---|---|
| 8.522 | d | 6.7 | 2.00 | py |
| 8.012 | d | 6.7 | 2.02 | py |
| 7.848 | d | 16.6 | 1.03 | vinyl |
| 7.662 | d | 6.1 | 2.04 | phe |
| 7.152 | d | 16.9 | 1.00 | vinyl |
| 6.875 | d | 7.5 | 2.025 | phe |
| 4.248 | s | | 3.03 | methyl |
| 3.831 | t | 6 | 2.00 | ethylene |
| 3.696 | s | | | mms |
| 3.480 | t | 6 | 2.09 | ethylene |
| 3.115 | s | | 2.98 | me am N |

Example 5

Preparation of the Compound of Formula (PRO-105)

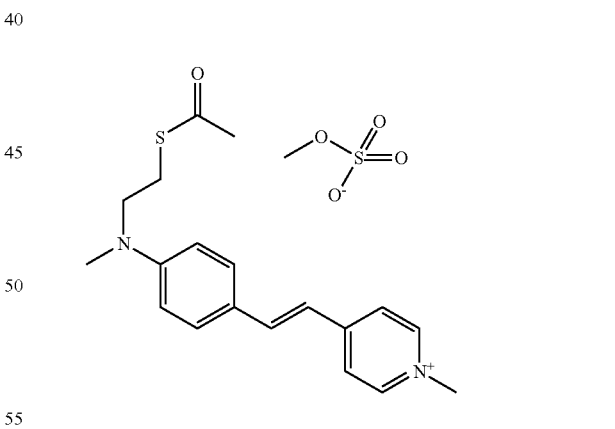

One equivalent (8.0 g) of potassium thioacetate is dissolved with absolute ethanol as solvent to 20 g of the alkylating dye of formula (PRO-104a).

The temperature is raised to reflux and maintained at 80° C. during the following 4 hours.

The product is crystallized by cooling to room temperature under mixing, than separated by filtration, washed and dried in the vacuum dryer.

The product is characterized by $^1$H-NMR data in deuterated chloroform (128 scans)/360 MHz

| | | | | |
|---|---|---|---|---|
| 8.516 | d | 6.7 | 2.00 | py |
| 7.968 | d | 6.7 | 2.03 | py |
| 7.811 | d | 16.6 | 0.99 | vinyl |
| 7.620 | d | 6.1 | 2.01 | phe |
| 7.085 | d | 16.9 | 1.00 | vinyl |
| 6.889 | d | 7.5 | 2.03 | phe |
| 4.223 | s | | 3.03 | methyl |
| 3.696 | s | | 2.59 | mms |
| 3.581 | t | 6 | 1.80 | ethylene |
| 3.104 | s | | 2.98 | me am n |
| 3.084 | t | 6 | 1.90 | ethylene |
| 2.358 | s | | 2.78 | acetat |

Example 6

Preparation of the Compound of Formula (PRO-106)

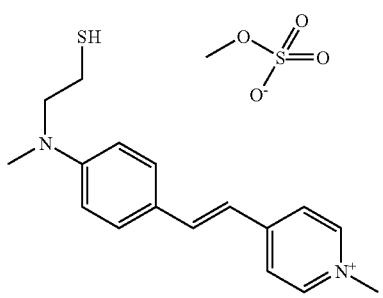

One equivalent (6.0 g) thiourea is dissolved in absolute ethanol the compound of formula (PRO-104a).

The temperature is raised to reflux and maintained at 80° C. during the following 48 hours. The obtained product is dissolved in one equivalent (4.0 g) of sodium hydroxide with absolute ethanol.

The temperature is maintained at 80° C. during the following 4 hours.

The product is crystallized by cooling to room temperature under mixing, than separated by filtration, washed and dried in the vacuum dryer.

The product is characterized by ¹H-NMR data in deuterated chloroform (128 scans)/360 MHz

| | | | | |
|---|---|---|---|---|
| 8.518 | d | 6.7 | 1.95 | py |
| 7.977 | d | 6.7 | 2.02 | py |
| 7.830 | d | 16.6 | 1.03 | vinyl |
| 7.624 | d | 6.1 | 2.04 | phe |
| 7.110 | d | 16.9 | 1.00 | vinyl |
| 6.828 | d | 7.5 | 2.025 | phe |
| 4.233 | s | | 3.03 | methyl |
| 3.696 | s | | 2.59 | mms |
| 3.637 | t | 6 | 2.1 | ethylene |
| 3.131 | s | | 2.98 | me am n |
| 2.728 | t | 6 | 2.0 | ethylene |

Example PRO-07

Preparation of the Compound of Formula (PRO-107)

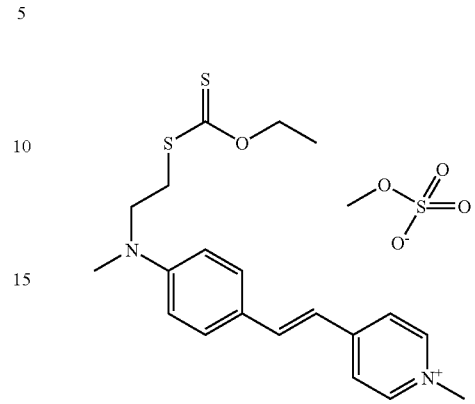

One equivalent (14.0 g) of ethyl xanthogenate is dissolved with 75 ml absolute ethanol in 20 g of the compound of formula (PRO-104a).

The temperature is raised to reflux and maintained at 80° C. during the following 18 hours. The product is crystallized by cooling to room temperature under mixing, than separated by filtration, washed and dried in the vacuum dryer.

The product is characterized by ¹H-NMR data in deuterated chloroform (128 scans)/360 MHz

| | | | | |
|---|---|---|---|---|
| 8.493 | d | 6.7 | 1.98 | py |
| 7.929 | d | 6.7 | 2.02 | py |
| 7.772 | d | 16.6 | 1.03 | vinyl |
| 7.607 | d | 6.1 | 2.04 | phe |
| 7.033 | d | 16.9 | 1.00 | vinyl |
| 6.812 | d | 7.5 | 2.025 | phe |
| 4.2294 | s | | 3.03 | methyl |
| 3.818 | | 6 | | |
| 3.111 | s | | 2.98 | me am n |
| 3.638 | t | 7 | 2.05 | ethylene |
| 2.75 | t | 7 | 2.00 | ethylene |

Example PRO-8

Preparation of the Compound of Formula (PRO-108)

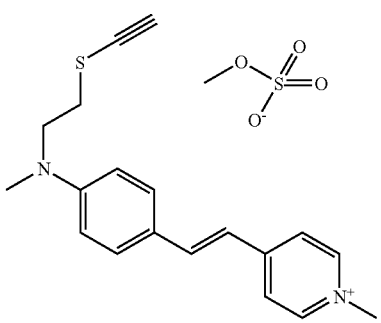

One equivalent (9.0 g) of potassium thiocyanate is dissolved with 100 ml absolute ethanol in 20 g of the compound of formula (PRO-104a).

The temperature is raised to reflux and maintained at 80° C. during the following 36 hours. The product is crystallized by cooling to room temperature under mixing, then separated by filtration, washed and dried in the vacuum dryer.

The product is characterized by $^1$H-NMR data in deuterated chloroform (128 scans)/360 MHz

| | | | | |
|---|---|---|---|---|
| 8.538 | d | 6.7 | 1.99 | py |
| 7.994 | d | 6.7 | 2.05 | py |
| 7.823 | d | 16.6 | 1.03 | vinyl |
| 7.645 | d | 6.1 | 2.04 | phe |
| 7.119 | d | 16.9 | 1.03 | vinyl |
| 6.873 | d | 7.5 | 2.02 | phe |
| 4.2420 | s | | 3.03 | methyl |
| 3.882 | t | 6 | 1.87 | ethylene |
| 3.700 | s | | 3.00 | mms |
| 3.28 | T | 7 | 2.09 | ethylene |
| 3.137 | s | | 2.98 | me am n |

Example PRO-9

Preparation of the Compound of Formula (PRO-109)

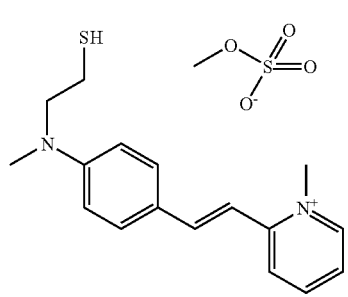

(a) Alkylation 2-methyl-pyridine (68.8 g) are dissolved in 80 ml absolute ethanol.

The temperature is raised to 333 K.

94 g dimethylsulfate are introduced in this mixture within one hour.

The temperature is maintained at 333 K during the following 3 h.

(b) Condensation the equivalent amount (150 g) 2-chloroethyl-methylamino-benzaldehyde, 250 ml ethanol and a catalytical amount (9.6 g) piperidine are added to the reaction mixture obtained in step (a) and is stirred for 18 hours at 343 K.

The reaction product is precipitated by cooling, then separated by filtration and dried in vacuum to obtain 220 g of an orange solid product of formula

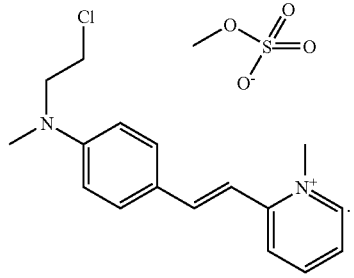

(PRO-109a)

The product is recrystallized twice from methanol.

The product is characterized by $^1$H-NMR data in deuterated chloroform (128 scans)/360 MHz

| | | | | |
|---|---|---|---|---|
| 8.720 | d | 6.7 | 1.00 | py |
| 8.408 | d | 6.7 | 1.02 | py |
| 8.319 | t | 7 | 0.98 | py |
| 7.834 | d | 16.6 | 1.03 | vinyl |
| 7.679 | t | 7 | 1.02 | py |
| 7.576 | d | 7.1 | 2.04 | phe |
| 7.157 | d | 16.9 | 1.00 | vinyl |
| 6.645 | d | 7.5 | 2.025 | phe |
| 4.268 | s | | 3.03 | methyl |
| 3.818 | t | 6 | 2.00 | ethylene |
| 3.748 | t | 6 | 2.05 | ethylene |
| 3.696 | s | | 2.59 | mms |
| 3.152 | s | | 2.98 | me am n |

(c):

One equivalent (6.0 g) of thiourea is dissolved in the compound of formula (107a) with absolute ethanol.

The temperature is raised to reflux and maintained at 80° C. during the following 48 hours.

(d) Hydrolysis

One equivalent (4.0 g) sodium hydroxide is dissolved to the substance obtained in step (c) with absolute ethanol.

The temperature is maintained at 80° C. during the following 4 hours.

The product is crystallized by cooling to room temperature under mixing, than separated by filtration, washed and dried in the vacuum dryer.

The product is characterized by $^1$H-NMR data in deuterated chloroform (128 scans)/360 MHz

| | | | | |
|---|---|---|---|---|
| 8.720 | d | 6.7 | 1.00 | py |
| 8.408 | d | 6.7 | 1.02 | py |
| 8.319 | t | 7 | 0.98 | py |
| 7.834 | d | 16.6 | 1.03 | vinyl |
| 7.679 | t | 7 | 1.02 | py |
| 7.576 | d | 7.1 | 2.04 | phe |
| 7.157 | d | 16.9 | 1.00 | vinyl |
| 6.645 | d | 7.5 | 2.025 | phe |
| 4.268 | s | | 3.03 | methyl |
| 3.849 | t | 6 | 2.00 | ethylene |
| 3.696 | s | | 2.59 | mms |
| 3.280 | t | 6 | 2.11 | ethylene |
| 3.152 | s | | 2.98 | me am n |

Example PRO-10

Preparation of the Compound of Formula

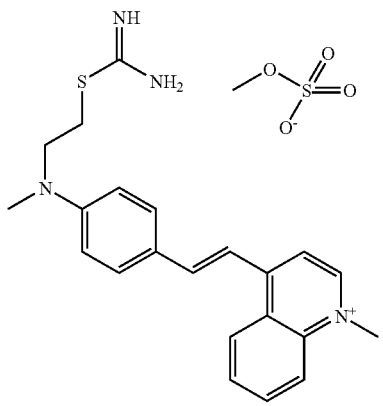
(PRO-110)

(a) Alkylation 250 g of 4-methyl-quinoline are dissolved in 80 ml absolute ethanol.

The temperature was raised to 333 K.

94 g dimethylsulfate are introduced into this mixture within one hour.

The temperature is maintained at 333 K during the following 2.5 hours.

(b) Condensation

The equivalent amount (1500 g) of 2-chloroethyl-methylamino-benzaldehyde, 250 ml ethanol and a catalytical amount (9.6 g) of piperidine are added to the reaction mixture obtained in step (a) and the reaction mixture stirred for 8 hours.

The reaction product is precipitated by cooling, then separated by filtration and dried in vacuum to obtain 340 g of an orange solid product of formula

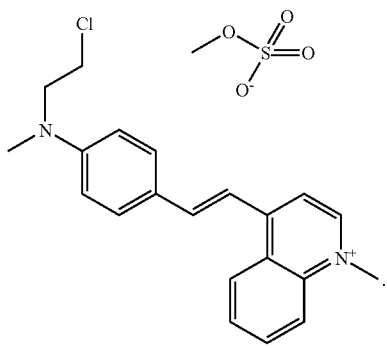
(PRO-110a)

The product is recrystallized twice from methanol.

The product is characterized by $^1$H-NMR data in deuterated chloroform (128 scans)/360 MHz and shows a complex spectra. Through HPLC/MS the identity was proofed, obtaining a single peak with the mass of 337/339 dalton.

(c)

One equivalent (6.0 g) thiourea is dissolved in 30 g of the compound of formula (108a) with absolute ethanol.

The temperature is raised to reflux and maintained at 80° C. during the following 48 hours.

The product is crystallized by cooling to room temperature under mixing, than separated by filtration, washed and dried in vacuum dryer.

The product is characterized by $^1$H-NMR data in deuterated chloroform (128 scans)/360 MHz Through HPLC/MS the identity was proofed, obtaining a single peak with the mass of 377 dalton

Example PRO-11

Preparation of the Compound of Formula

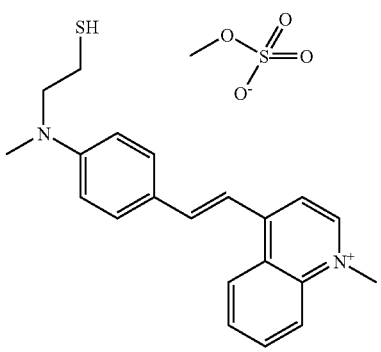
(PRO-111)

(a)

One equivalent (6.0 g) of thiourea is dissolved in 30 g of the compound of formula (PRO-110a) with absolute. ethanol.

The temperature is raised to reflux and maintained at 80° C. during the following 48 hours.

(b) Hydrolysis

One equivalent (4.0 g) sodium hydroxide is dissolved in the substance obtained in step (a) with absolute ethanol.

The temperature is maintained at 80° C. during the following 4 hours.

The product is crystallized by cooling to room temperature under mixing, than separated by filtration, washed and dried in the vacuum dryer.

Through HPLC/MS the identity was proofed, obtaining a single peak with the mass of 333 dalton

Example PRO-12

Preparation of the Compound of Formula

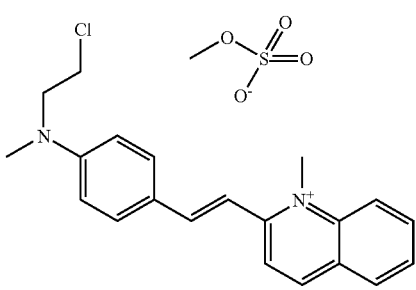
(PRO-112)

(a) Alkylation 250 g 2-methyl-quinoline are dissolved in 80 ml absolute ethanol.

The temperature is raised to 333 K.

94 g dimethylsulfate are introduced within one hour into that mixture.

The temperature is maintained at 333 K during the following 2.5 hours.

(b) Condensation

The equivalent amount (150.0 g) of 2-chloroethyl-methylamino-benzaldehyde, 250 ml ethanol and a catalytical amount (9.6 g) of piperidine are added to the reaction mixture obtained in step (a) and the reaction mixture stirred for 8 hours.

The reaction product is precipitated by cooling, then separated by filtration and dried in vacuum to obtain 340 g of an orange solid product of formula compound of formula (PRO-110).

The product is recrystallized twice from methanol.

The product is characterized by $^1$H-NMR data in deuterated chloroform (128 scans)/360 MHz Showing a complex spectrum. Through HPLC/MS the identity was proofed, obtaining a single peak with the mass of 337/339 dalton Example PRO-13

Preparation of the Compound of Formula (PRO-113)

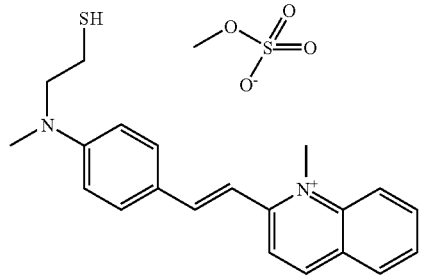

One equivalent (6.0 g) thiourea is dissolved in 30 g of the compound of formula (PRO-112a) with absolute.

The temperature is raised to reflux and maintained at 80° C. during the following 48 hours. The product is crystallized by cooling to room temperature under mixing, than separated by filtration, washed and dried in vacuum dryer.

Through HPLC/MS the identity was proofed, obtaining a single peak with the mass of 334 dalton Example PRO-14

Preparation of the Compound of Formula (PRO-114)

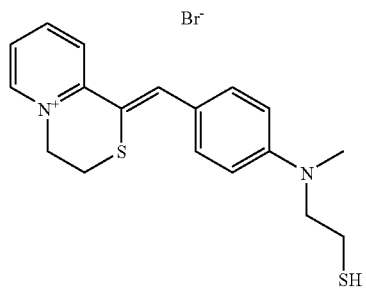

(a) Alkylating Agent

A mixture of 15.4 g 2,2-dithiodiethanol in 100 ml chloroform and 24.1 g pyridine are cooled with stirring to 0° C. and then 41.0 g of tosyl chloride are added in small amounts, maintaining the temperature.

After completion of the addition the mixture is left over night in the refrigerator and the reaction is finished.

The reaction mixture is mixed with a water/hydrochloric acid and ice slurry, the phases are separated, washed with water and dried.

The solution of toluenesulfonate diester is used for step (b).

(b) Alkylation

The alkylation agent obtained in step (a) is freed from the solvent and dissolved in two equivalent amounts of 2-methyl-pyridine.

The temperature is raised to 60° C. and maintained at 60° C. during the following 24 hours.

(c) Condensation 50 ml dimethyl-formamide are added to the reaction mixture obtained in step (b).

The equivalent amount of 2-chloroethyl-methylamino-benzaldehyde and a catalytical amount of piperidine are added and the reaction mixture is stirred for 40 hours at 80° C.

The reaction product is precipitated by cooling, then separated by filtration and dried in vacuum to obtain 39 g of an orange solid product.

The product is recrystallized twice from isopropanol.

The product is characterized by $^1$H-NMR data in deuterated chloroform (128 scans)/360 MHz

| | | | | |
|---|---|---|---|---|
| 9.62 | d | 6.8 | 1.00 | py |
| 828 | t | 6.7 | 0.98 | py |
| 7.92 | d | 6.7 | 1.02 | py |
| 7.81 | t | 6.6 | 1.03 | py |
| 7.701 | d | 7.0 | 1.97 | tosilate |
| 7.58 | d | 6.1 | 1.967 | phe |
| 7.180 | s | | 1.025 | vinyl |
| 7.11 | d | 6.9 | 1.846 | tosilate |
| 6.71 | d | 6.4 | 2.05 | phe |
| 5.10 | m | | 2.00 | ethylene |
| 3.56 | m | | 2.05 | ethylene |
| 3.818 | t | 6 | 2.05 | ethylene |
| 3.748 | t | 6 | 1.96 | ethylene |
| 3.04 | s | | 3.08 | methyl(amine) |
| 2.326 | s | | 2.97 | me-tosilate |

(d)

One equivalent (5.0 g) of thiourea is dissolved in 20 g of the foregoing alkylating dye with 75 ml absolute ethanol.

The temperature is raised to reflux and maintained at 80° C. during the following 48 hours.

(e) Hydrolysis

One equivalent (4.0 g) of sodium hydroxide is dissolved with absolute ethanol as solvent in the substance of step (d).

The temperature is maintained at 80° C. during the following 4 hours.

The product is crystallized by cooling to room temperature under mixing, than separated by filtration, washed and dried in the vacuum dryer.

The product is characterized by $^1$H-NMR data in deuterated chloroform (128 scans)/360 MHz

| | | | | |
|---|---|---|---|---|
| 9.62 | d | 6.8 | 1.00 | py |
| 828 | t | 6.7 | 0.98 | py |

-continued

| | | | | |
|---|---|---|---|---|
| 7.92 | d | 6.7 | 1.02 | py |
| 7.81 | t | 6.6 | 1.03 | py |
| 7.701 | d | 7.0 | 1.97 | tosilate |
| 7.58 | d | 6.1 | 1.967 | phe |
| 7.180 | s | | 1.025 | vinyl |
| 7.11 | d | 6.9 | 1.846 | tosilate |
| 6.71 | d | 6.4 | 2.05 | phe |
| 5.10 | m | | 2.00 | ethylene |
| 3.56 | m | | 2.05 | ethylene |
| 3.949 | t | 6 | 2.05 | ethylene |
| 3.280 | t | 6 | 1.96 | ethylene |
| 3.04 | s | | 3.08 | methyl(amine) |
| 2.326 | s | | 2.97 | me-tosilate |

Example PYR-01

Preparation of the Compound of Formula

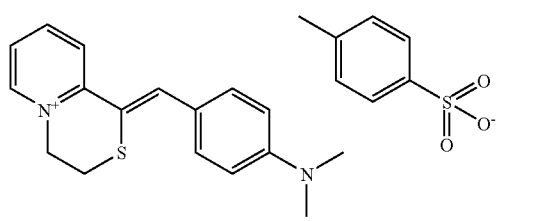

(PYR-101)

a. Alkylating Agent

A mixture of 15.4 g of 2,2-dithiodiethanol in 100 ml chloroform and 24.1 g pyridine are cooled with stirring to 0° C.

41.0 g of tosyl chloride are added in small amounts, maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of toluenesulfonate diester is used as starting compound in step b.

b. Alkylation

The alkylation agent obtained in step a. is delivered from the solvent and dissolved in two equivalent amounts of 2-methyl-pyridine. The temperature is raised to 60° C. and maintained at 60° C. during the following 24 hours.

c. Condensation 50 ml of dimethyl-formamide are added to the reaction mixture obtained in step b.

The equivalent amount of dimethylamino-benzaldehyde and a catalytical amount of piperidine are added and the reaction mixture is stirred for 40 hours at 80° C.

The reaction product is precipitated by cooling, separated by filtration and dried in vacuum to obtain 39 g of an orange solid product.

The product is recrystallized twice from isopropanol.

The product is characterized by the following data:

The HPLC-MS gives a main component of a monocation of the mass 283.

1H-NMR data in deuterated chloroform (128 scans)/360 MHz:

| | | | | | |
|---|---|---|---|---|---|
| Compound (101 | 9.62 | d | 6.8 | 1.00 | Py |
| 828 | t | 6.7 | 0.98 | Py | |
| | 7.92 | d | 6.7 | 1.02 | Py |
| | 7.81 | t | 6.6 | 1.03 | Py |
| | 7.701 | d | 7.0 | 1.97 | tosilate |
| | 7.58 | d | 6.1 | 1.967 | Phe |
| | 7.180 | s | | 1.025 | vinyl |
| | 7.11 | d | 6.9 | 1.846 | tosilate |
| | 6.71 | d | 6.4 | 2.05 | Phe |
| | 5.10 | m | | 2.00 | ethylene |
| | 3.56 | m | | 2.05 | ethylene |
| | 3.04 | s | | 6.08 | Dimethyl(amine) |
| | 2.326 | s | | 2.97 | Me-tosylate |

Example PYR-02

Preparation of the Compound of Formula

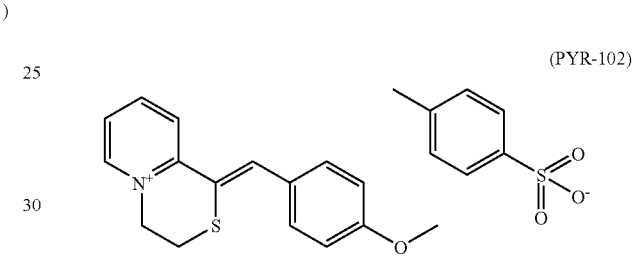

(PYR-102)

a. Alkylating Agent

A mixture of 15.4 g of 2,2-dithiodiethanol in 100 ml chloroform and 24.1 g pyridine are cooled with stirring to 0° C. and then 41.0 g of tosyl chloride are added in small amounts, maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of toluenesulfonate diester is used as starting compound in the step b.

b. Alkylation

The alkylation agent obtained in step a. is delivered from the solvent and dissolved in two equivalent amounts of 2-methyl-pyridine.

The temperature is raised to 60° C. and maintained during the following 24 hours.

c. Condensation 50 ml of isopropanol are added to the reaction mixture obtained in step b.

The equivalent amount of anisaldehyde and a catalytical amount of anhydrous sodium acetate are added and the reaction mixture is stirred for 40 hours at 80° C.

The reaction product is precipitated by cooling, separated by filtration and dried in vacuum to obtain 29 g of a yellowish solid product.

The product is recrystallized twice from isopropanol.

The product is characterized by the following data:

The HPLC-MS gives a main component of a monocation of the mass 270.

1H-NMR data in deuterated methanol 128 scans)/360 MHz:

| Compound (102) | 8.828 | d | 6.8 | 1.00 | Py |
|---|---|---|---|---|---|
| | 8.557 | t | 6.7 | 0.98 | Py |
| | 8.400 | d | 6.7 | 1.02 | Py |
| | 8.319 | t | 6.6 | 1.03 | Py |
| | 7.861 | d | 6.9 | 2.0 | Phe |
| | 7.705 | d | 7.0 | 1.97 | tosylate |
| | 7.50 | s | | 1.025 | vinyl |
| | 7.243 | d | 6.9 | 1.846 | tosilate |
| | 7.085 | d | 6.4 | 2.05 | Phe |
| | 4.86 | m | | 2.00 | ethylene |
| | 3.904 | s | | 3.00 | methyl |
| | 3.53 | m | | 2.05 | ethylene |
| | 2.36 | s | | 5.90 | tosylate |

Example PYR-03

Preparation of the Compound of Formula

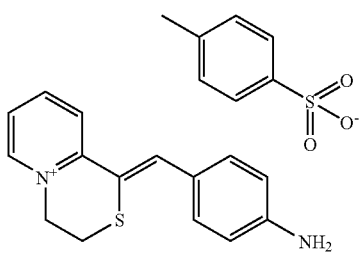

(PYR-103)

a. Alkylating Agent

A mixture of 15.4 g of 2,2-dithiodiethanol in 100 ml ethylene and 24.1 g pyridine are cooled with stirring to 0° C. and then 41.0 g of tosyl chloride are added in small amounts maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of toluenesulfonate diester is used as starting compound in step b.

b. Alkylation

The alkylation agent obtained in step a. is delivered from the solvent and dissolved in two equivalent amounts of 2-methyl-pyridine.

The temperature is raised to 70° C. and maintained during the following 24 hours.

c. Condensation 50 ml of tolurnr are added to the reaction mixture obtained in step b.

The equivalent amounts of amino-benzaldehyde and a catalytical amount of piperidine are added and the reaction mixture is stirred for 30 hours at 80° C.

The reaction product is precipitated by cooling, separated by filtration and dried in vacuum to obtain 41 g of an orange solid product.

The product is recrystallized twice from isopropanol.

The product is characterized by the following data:
The HPLC-MS gives a main component of a monocation of the mass 255.
1H-NMR data in deuterated chloroform (128 scans)/360 MHz.

| Compound (103) | 8.708 | d | 6.8 | 0.98 | Py |
|---|---|---|---|---|---|
| | 8.461 | t | 6.7 | 1.00 | Py |
| | 8.257 | d | 6.7 | 1.00 | Py |
| | 7.833 | t | 6.6 | 1.03 | Py |
| | 7.711 | d | 6.9 | 2.0 | Phe |
| | 7.705 | d | 7.0 | 1.97 | tosylate |
| | 7.445 | s | | 1.025 | vinyl |
| | 7.219 | d | 6.9 | 1.846 | tosylate |
| | 6.814 | d | 6.4 | 2.05 | Phe |
| | 4.828 | m | | 2.00 | ethylene |
| | 3.53 | m | | 2.05 | ethylene |
| | 2.36 | s | | 6.10 | tosylate |

Example PYR-04

Preparation of the Compound of Formula

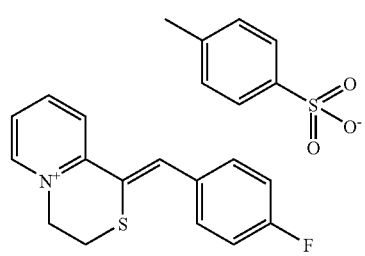

(PYR-104)

a. Alkylating Agent

A mixture of 15.4 g of 2,2-dithiodiethanol in 100 ml chloroform and 24.1 g pyridine are cooled with stirring to 0° C.

41.0 g of tosyl chloride are added in small amounts maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of toluenesulfonate diester is used as starting compound in step b.

b. Alkylation

The alkylation agent obtained in step a. is delivered from the solvent dissolved in two equivalent amounts of 2-methyl-pyridine.

The temperature is raised to 60° C. and maintained during the following 24 hours.

c. Condensation 50 ml of isopropanol are added to the reaction mixture obtained in step b.

The equivalent amounts of 4-fluoro-benzaldehyde and a catalytical amount of piperidine are added and the reaction mixture is stirred for 30 hours at 70° C.

The reaction product is precipitated by cooling, separated by filtration and dried in vacuum to obtain 35 g of a yellow solid product.

The product is recrystallized from isopropanol.

The product is characterized by the following data:
The HPLC-MS gives a main component of a monocation of the mass 258.
1H-NMR data in deuterated methanol (128 scans)/360 MHz:

| | | | | |
|---|---|---|---|---|
| 8.904 | d | 6.8 | 1.00 | Py |
| 8.608 | t | 6.7 | 0.98 | Py |
| 8.360 | d | 6.7 | 1.02 | Py |
| 7.96 | t | 6.6 | 1.03 | Py |
| 7.781 | t | 8 | 2.0 | Phe |
| 7.718 | d | 7.0 | 1.97 | tosylate |
| 7.548 | s | | 1.025 | vinyl |
| 7.317 | t | 8 | 1.967 | Phe |
| 7.11 | d | 6.9 | 2.046 | tosilate |
| 4.911 | m | | 2.00 | ethylene |
| 3.557 | m | | 2.05 | ethylene |
| 2.363 | s | | 2.98 | tosilate |

Example PYR-05

Preparation of the Compound of Formula

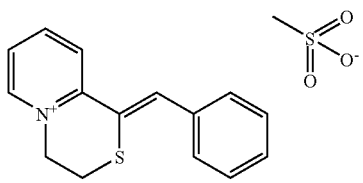

(PYR-105)

a. Alkylating Agent

A mixture of 15.4 g of 2,2-dithiodiethanol in 100 ml chloroform and 24.1 g pyridine are cooled with stirring to 0° C. and then 31.0 g of mesyl chloride are added in small amounts, maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of methanesulfonate diester is used as starting compound in the step b.

b. Alkylation

The alkylation agent obtained in step a. is freed from the solvent and dissolved in two equivalent amounts of 2-methylpyridine.

The temperature is raised to 60° C. and maintained during the following 24 hours.

c. Condensation 50 ml of dimethyl-formamide are added to the reaction mixture obtained in step b.

The equivalent amount of benzaldehyde and a catalytical amount of piperidine are added and the reaction mixture is stirred for 40 hours at 80° C.

The reaction product is precipitated by cooling, separated by filtration and dried in vacuum to obtain 33 g of a yellow solid product.

The product is recrystallized twice from isopropanol.
The product is characterized by the following data:
The HPLC-MS gave a main component of a monocation of the mass 240.

1H-NMR data in deuterated Methanol (128 scans)/360 MHz:

| | | | | |
|---|---|---|---|---|
| 8.802 | d | 6.8 | 0.98 | Py |
| 8.521 | t | 6.7 | 1.00 | Py |
| 8.30 | d | 6.7 | 1.00 | Py |
| 7.910 | t | 6.6 | 1.03 | Py |
| 7.751 | d | 6.9 | 2.02 | Phe |
| 7.705 | d | 7.0 | 1.97 | tosilate |
| 7.495 | s | | 1.02 | vinyl |
| 7.219 | d | 6.9 | 1.86 | tosilate |
| 7.03 | t | 6.4 | 2.05 | Phe |
| 6.814 | t | 6.5 | 1.02 | Phe |
| 4.878 | m | | 2.00 | ethylene |
| 3.54 | m | | 2.05 | ethylene |
| 2.363 | s | | 2.90 | tosilate |

Example PYR-06

Preparation of the Compound of Formula

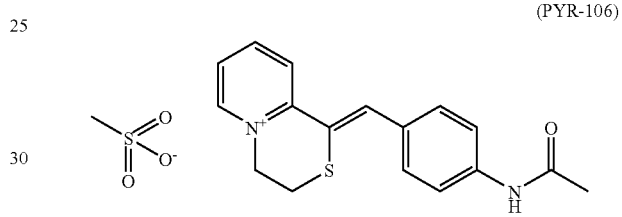

(PYR-106)

a. Alkylating Agent

A mixture of 15.4 g of 2,2-dithiodiethanol in 100 ml chloroform and 24.1 g pyridine are cooled with stirring to 0° C. and then 31.0 g of mesyl chloride are added in small amounts, maintaining the temperature.

After completion of the addition the mixture is left over night in the refrigerator to finish the reaction.

The reaction mixture is mixed with a mixture of water/hydrochloric acid and ice slurry, the phases are separated, washed with water and dried.

The solution of methanesulfonate diester is used as starting compound in step b.

b. Alkylation

The alkylation agent obtained in step b. is delivered from the solvent dissolved in two equivalent amounts of 2-methylpyridine. The temperature is raised to 60° C. and maintained during the following 24 hours.

c. Condensation 50 ml of dimethyl-formamide are added to the reaction mixture obtained in step b.

The equivalent amount of acetylamino-benzaldehyde and a catalytical amount of piperidine are added and the reaction mixture is stirred for 40 hours at 80° C.

The reaction product is precipitated by cooling, separated by filtration and dried in vacuum to obtain 44 g of a brown solid product.

The product is recrystallized twice from isopropanol.
The product is characterized by the following data:
The HPLC-MS gave a main component of a monocation of the mass 297.

1H-NMR data in deuterated methanol (128 scans)/360 MHz:

| | | | | |
|---|---|---|---|---|
| 8.718 | d | 6.8 | 0.99 | Py |
| 8.561 | t | 6.7 | 1.00 | Py |
| 8.357 | d | 6.7 | 1.00 | Py |
| 7.883 | t | 6.6 | 1.03 | Py |
| 7.761 | d | 6.9 | 2.03 | Phe |
| 7.495 | s | | 1.02 | vinyl |
| 6.914 | d | 6.4 | 2.05 | Phe |
| 4.848 | m | | 2.02 | ethylene |
| 3.53 | m | | 2.05 | ethylene |
| 2.724 | s | | 2.90 | mesilate |
| 2.140 | s | | 3.12 | acetyl |

B—Application Examples

Sulfide dyes, which can be combined are shown in Table EX-1, but are not limited to these examples.

TABLE EX-1 sulfide dyes USEFUL FOR HAIR DYEING MIXTURES

| Comp. Of formula | Structure | Color |
|---|---|---|
| (101) | 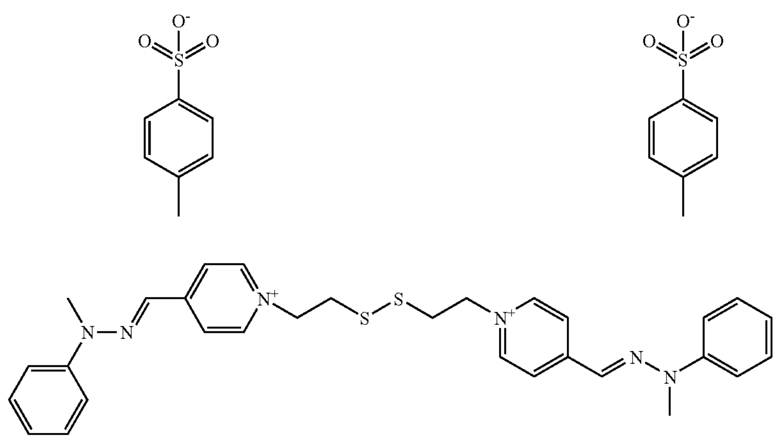 | yellow |
| (102) | 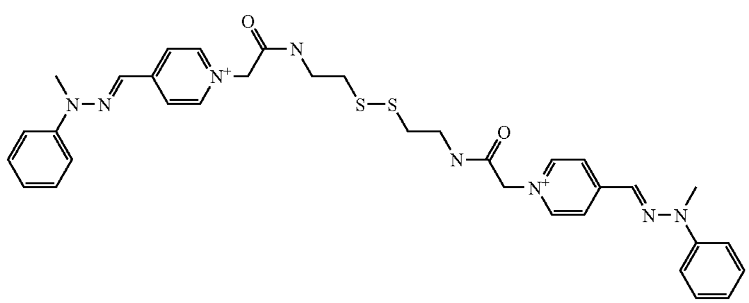 | yellow |
| (103) | 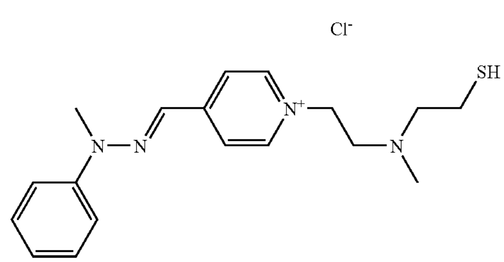 | yellow |

TABLE EX-1-continued
sulfide dyes USEFUL FOR HAIR DYEING MIXTURES
| Comp. Of formula | Structure | Color |
|---|---|---|
| (104) | 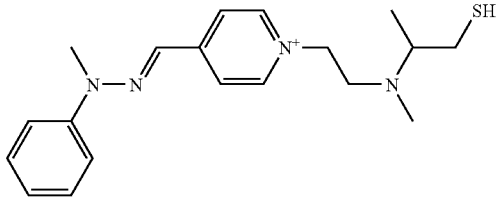 | yellow |
| (105) | 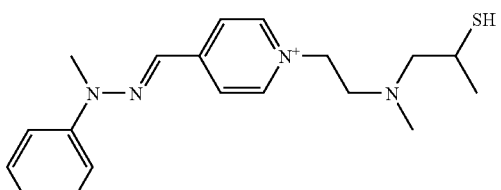 | yellow |
| (106) | 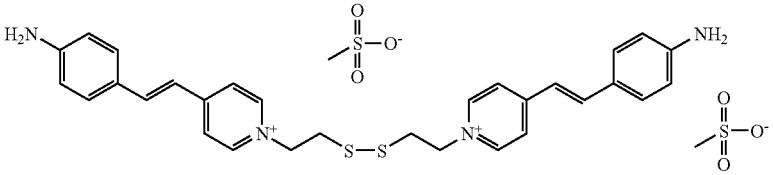 | yellow |
| (107) | 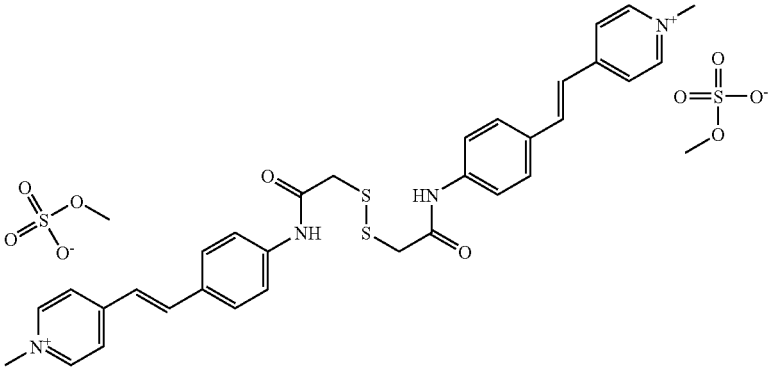 | yellow |

TABLE EX-1-continued sulfide dyes USEFUL FOR HAIR DYEING MIXTURES

| Comp. Of formula | Structure | Color |
|---|---|---|
| (108) | 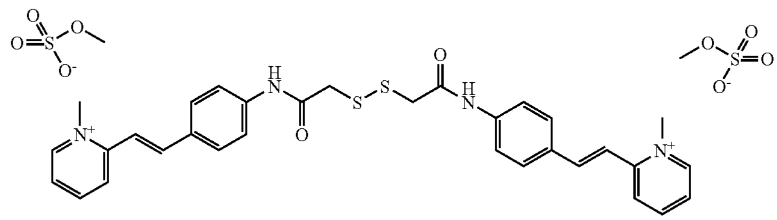 | yellow |
| (109) | 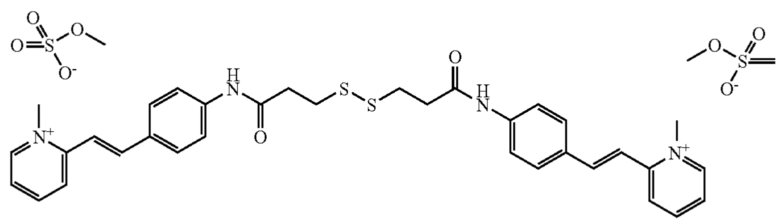 | yellow |
| (110) | 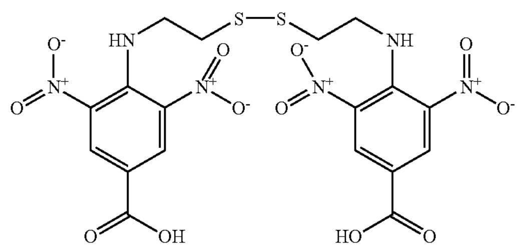 | yellow |
| (111) | 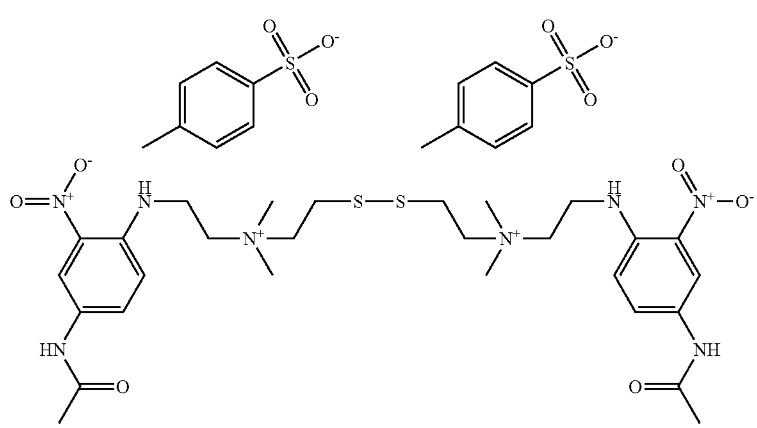 | yellow |
| (112) | 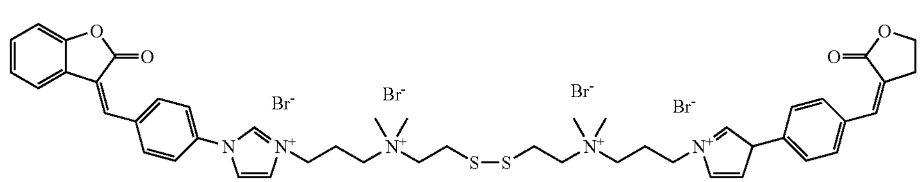 | yellow |
| (113) | 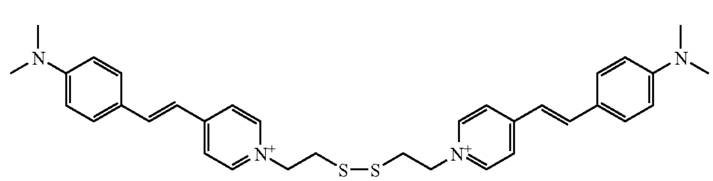 | orange |

TABLE EX-1-continued sulfide dyes USEFUL FOR HAIR DYEING MIXTURES

| Comp. Of formula | Structure | Color |
|---|---|---|
| (114) | 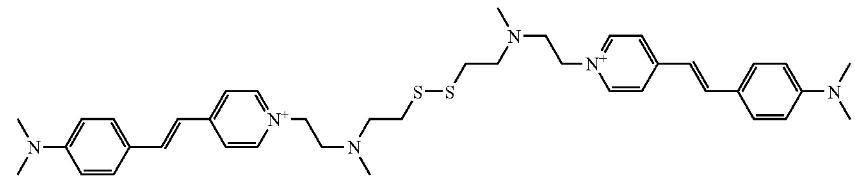 | orange |
| (115) | 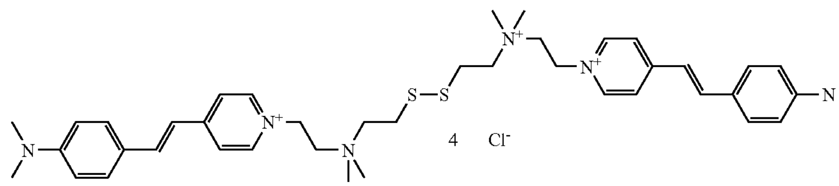 | orange |
| (116) | 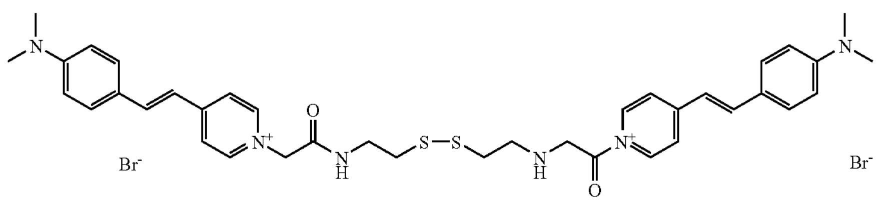 | orange |
| (117) | 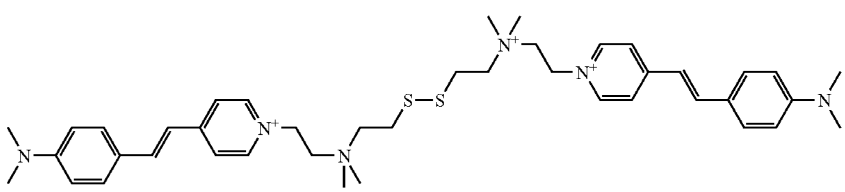 | orange |
| (118) | 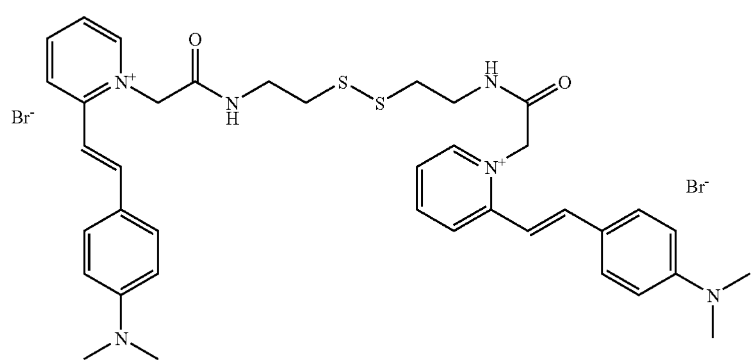 | orange |
| (119) | 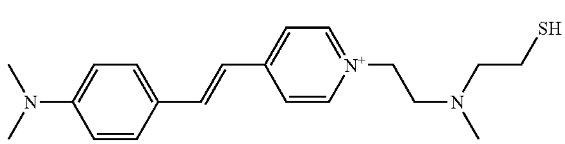 | orange |
| (120) | 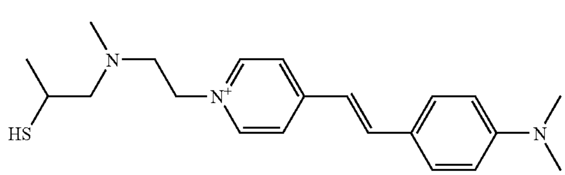 | orange |

TABLE EX-1-continued sulfide dyes USEFUL FOR HAIR DYEING MIXTURES

| Comp. Of formula | Structure | Color |
|---|---|---|
| (121) | 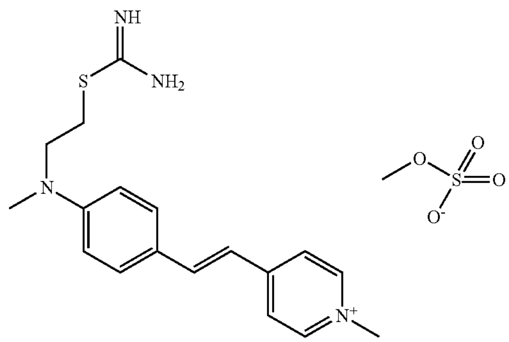 | orange |
| (122) | 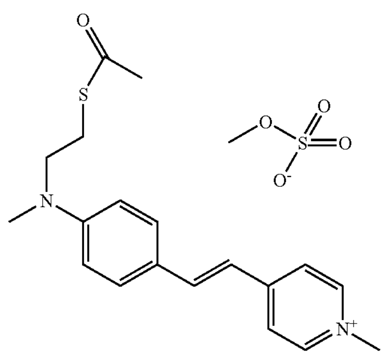 | orange |
| (123) | 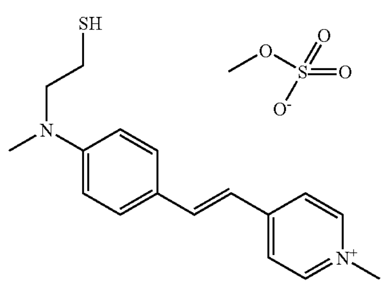 | orange |
| (124) | 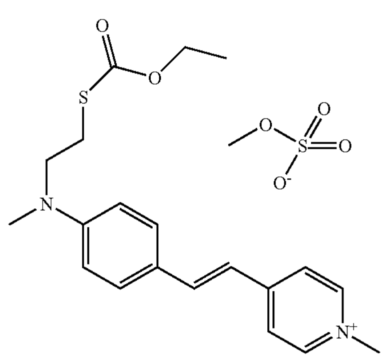 | orange |

TABLE EX-1-continued sulfide dyes USEFUL FOR HAIR DYEING MIXTURES

| Comp. Of formula | Structure | Color |
|---|---|---|
| (125) | 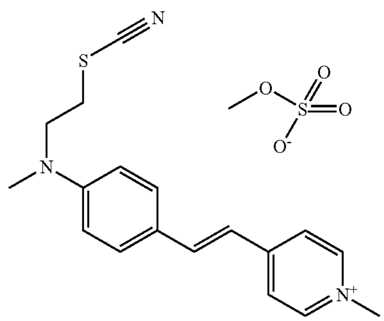 | orange |
| (126) | 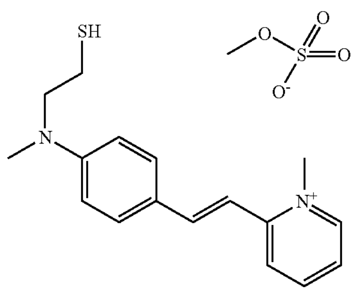 | orange |
| (127) | 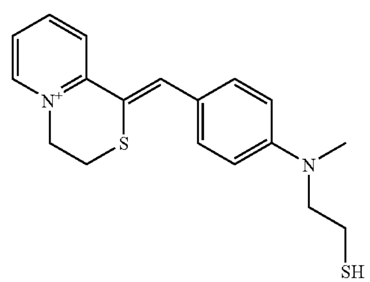 | orange |
| (128) | 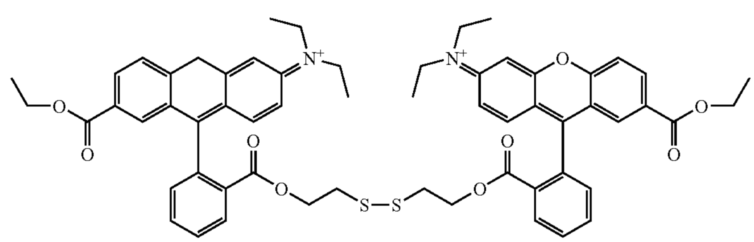 | orange |
| (129) | 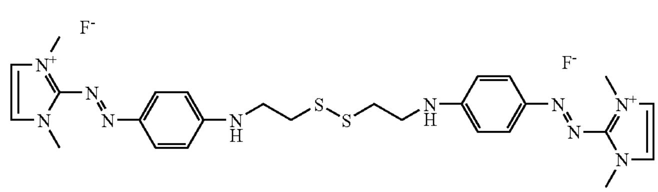 | red |
| (130) | 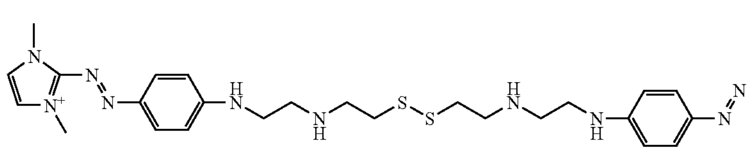 | red |

TABLE EX-1-continued sulfide dyes USEFUL FOR HAIR DYEING MIXTURES

| Comp. Of formula | Structure | Color |
|---|---|---|
| (131) | 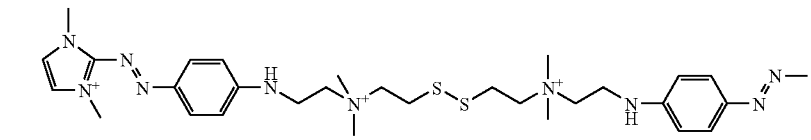 | red |
| (132) | 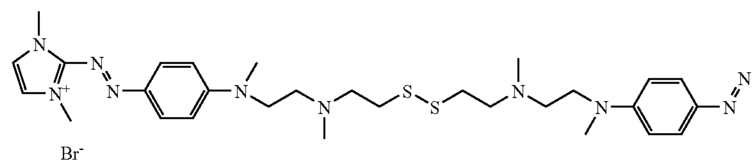 | red |
| (133) | 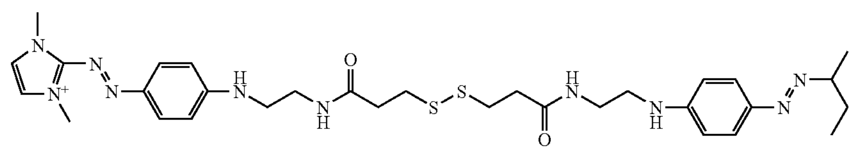 | red |
| (134) | 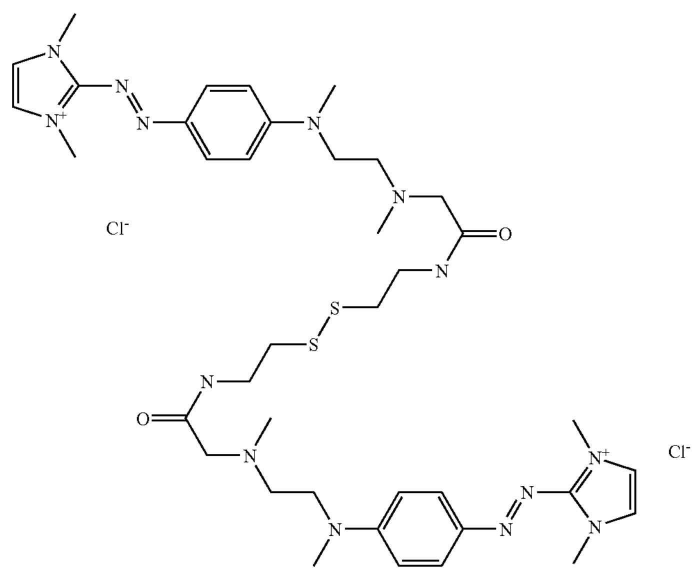 | red |
| (135) | 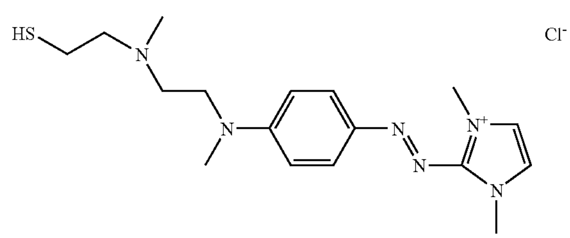 | red |
| (136) | 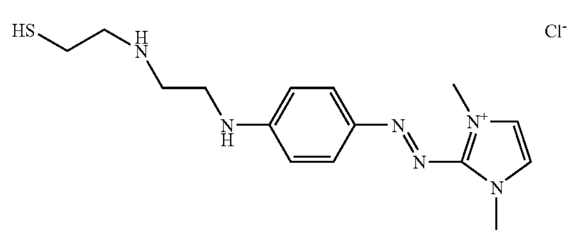 | red |

TABLE EX-1-continued sulfide dyes USEFUL FOR HAIR DYEING MIXTURES

| Comp. Of formula | Structure | Color |
|---|---|---|
| (137) | 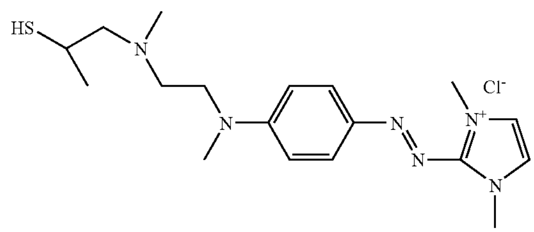 | red |
| (138) | 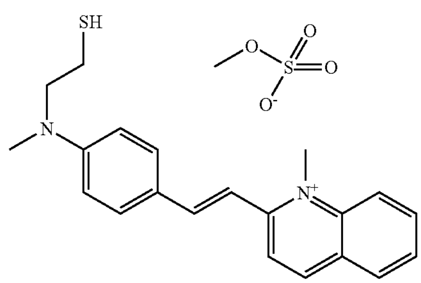 | red |
| (139) | 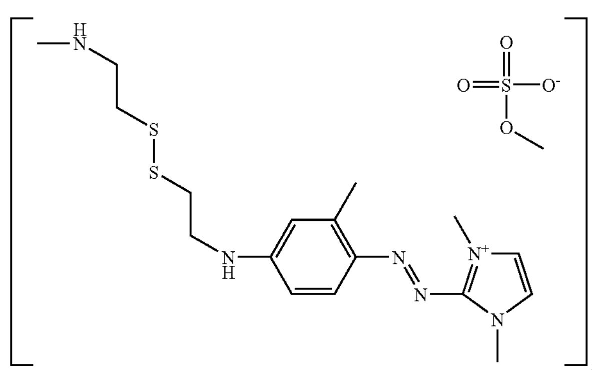 | red |

TABLE EX-1-continued sulfide dyes USEFUL FOR HAIR DYEING MIXTURES

| Comp. Of formula | Structure | Color |
|---|---|---|
| (140) | 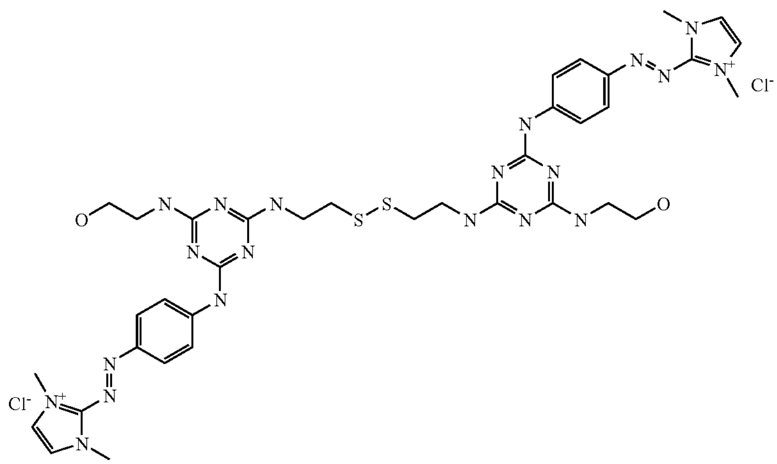 | red |
| (141) | 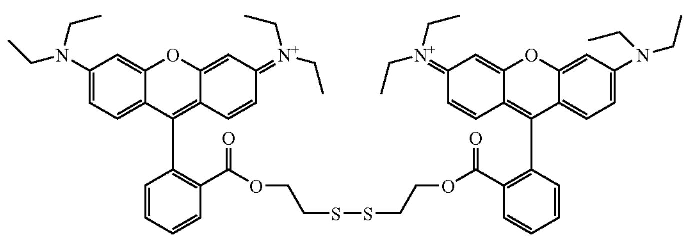 | pink |
| (142) | 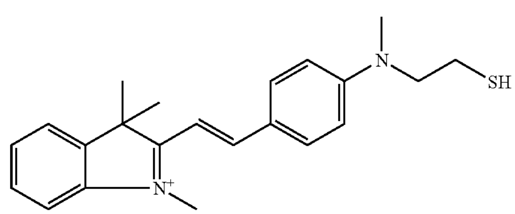 | pink |
| (143) | 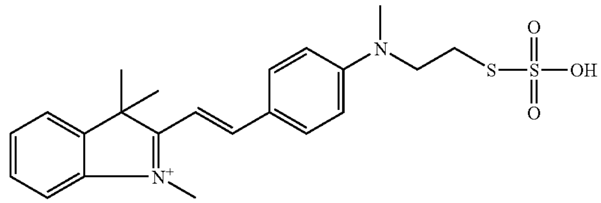 | pink |
| (144) | 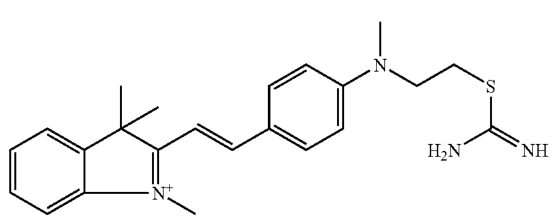 | pink |

TABLE EX-1-continued
sulfide dyes USEFUL FOR HAIR DYEING MIXTURES
| Comp. Of formula | Structure | Color |
|---|---|---|
| (145) | 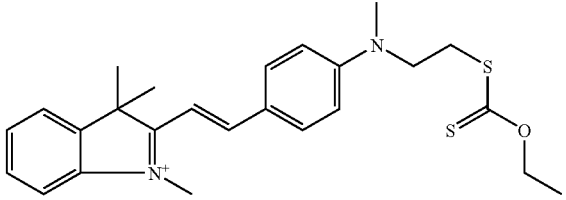 | pink |
| (146) | 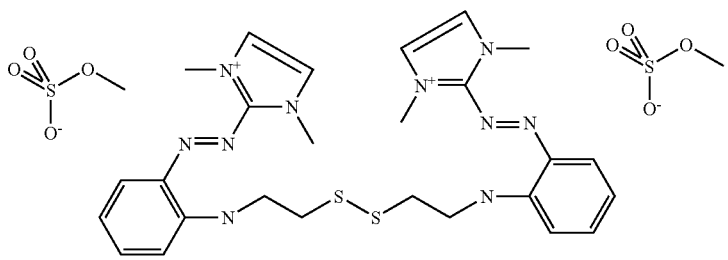 | violet |
| (147) | 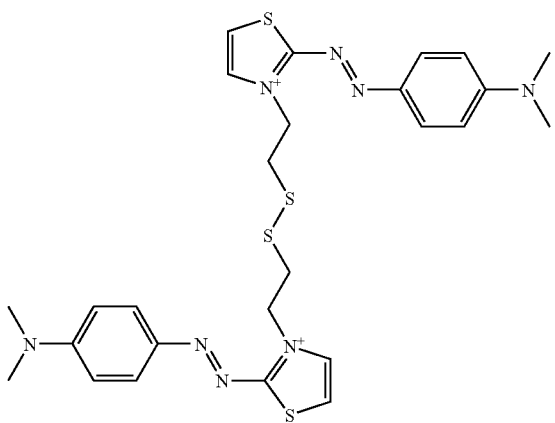 | violet |
| (148) | 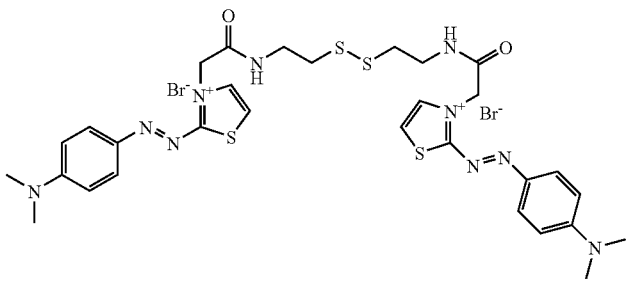 | violet |

TABLE EX-1-continued sulfide dyes USEFUL FOR HAIR DYEING MIXTURES

| Comp. Of formula | Structure | Color |
|---|---|---|
| (149) | 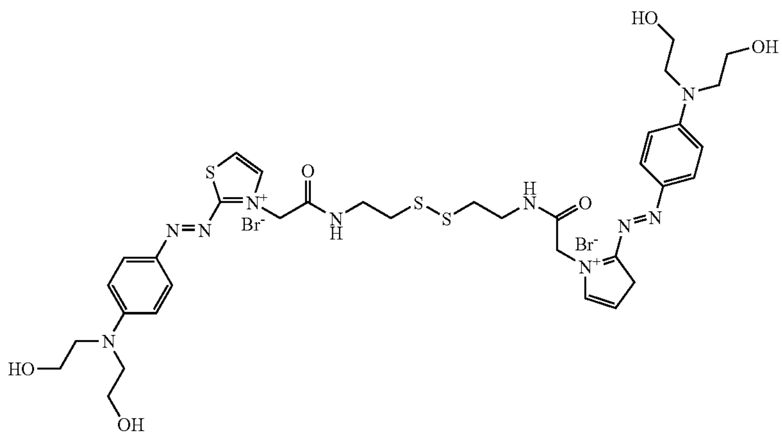 | violet |
| (150) | 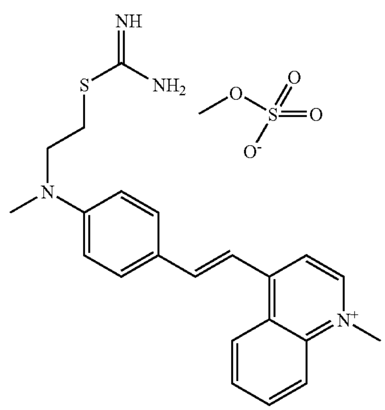 | violet |
| (151) | 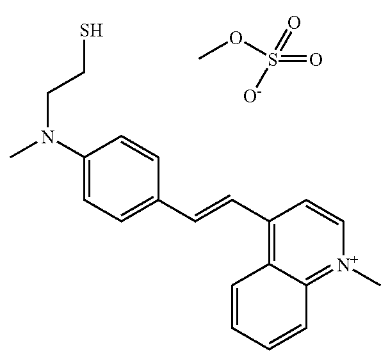 | violet |

TABLE EX-1-continued sulfide dyes USEFUL FOR HAIR DYEING MIXTURES

| Comp. Of formula | Structure | Color |
|---|---|---|
| (152) | 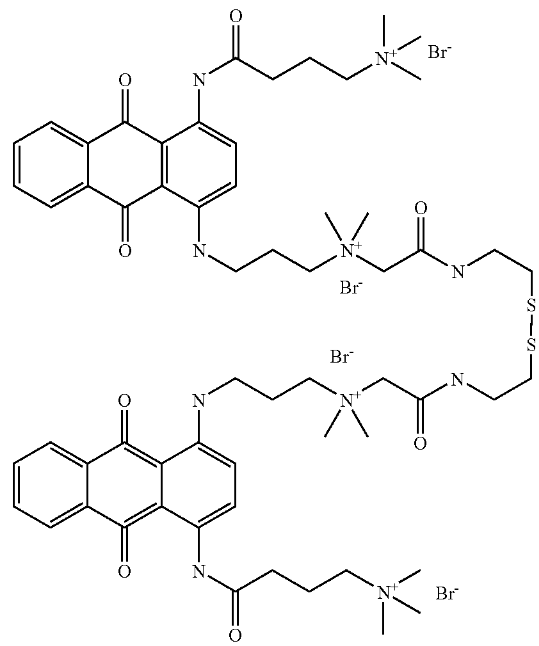 | violet |
| (153) | 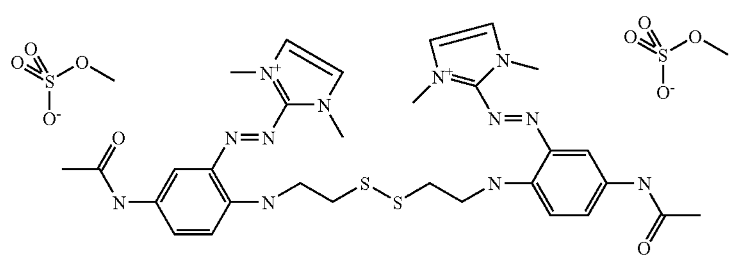 | blue |
| (154) | 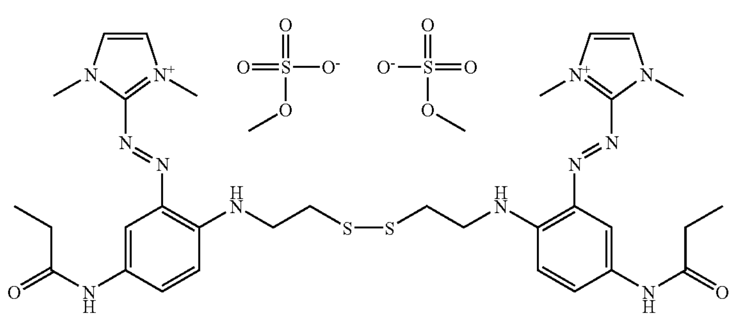 | blue |
| (155) | 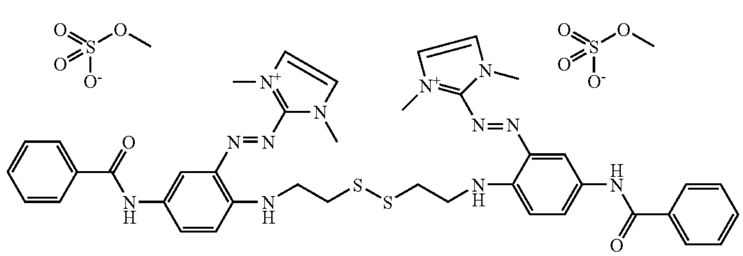 | blue |

TABLE EX-1-continued sulfide dyes USEFUL FOR HAIR DYEING MIXTURES

| Comp. Of formula | Structure | Color |
|---|---|---|
| (156) | 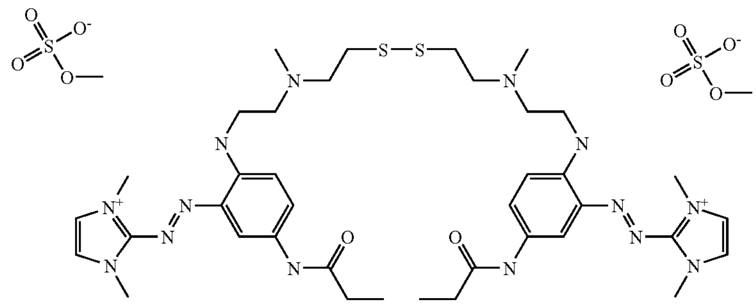 | blue |
| (157) | 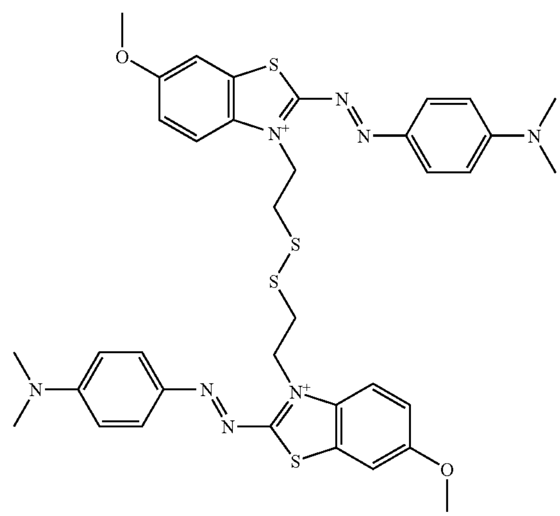 | blue |
| (158) | 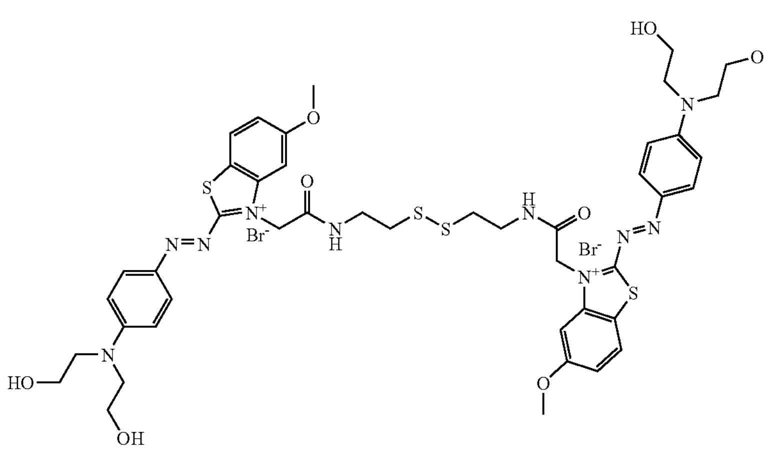 | blue |

TABLE EX-1-continued sulfide dyes USEFUL FOR HAIR DYEING MIXTURES

| Comp. Of formula | Structure | Color |
|---|---|---|
| (159) | 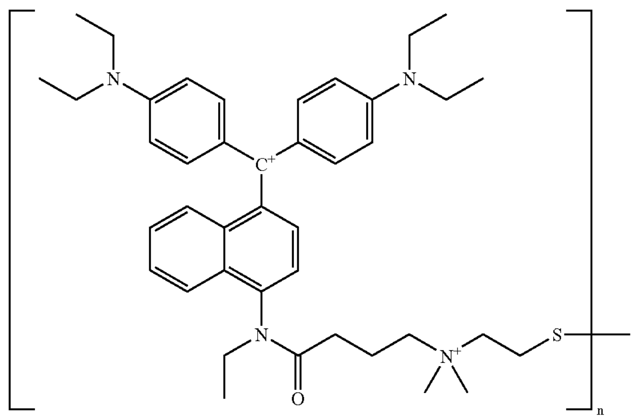 | blue |
| (160) | 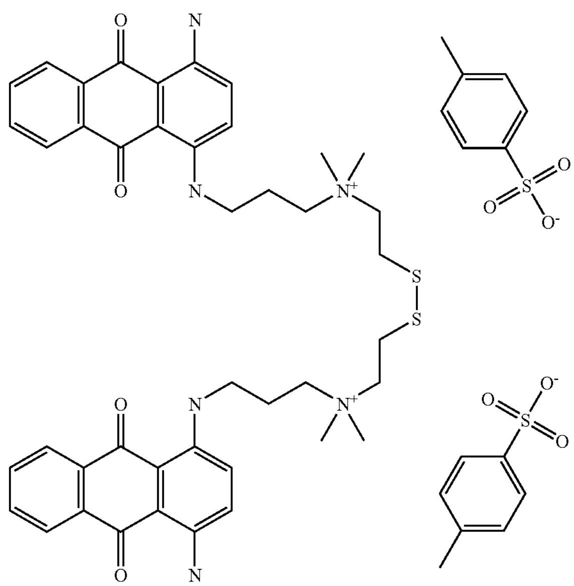 | blue |
| (161) | 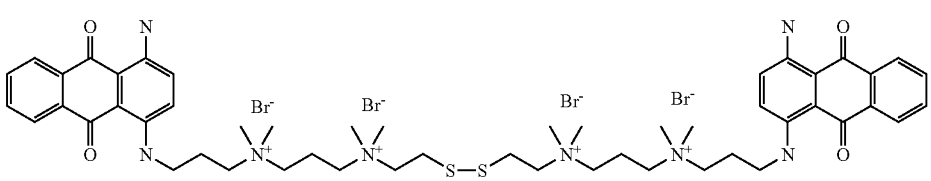 | blue |

TABLE EX-1-continued sulfide dyes USEFUL FOR HAIR DYEING MIXTURES

| Comp. Of formula | Structure | Color |
|---|---|---|
| (162) | 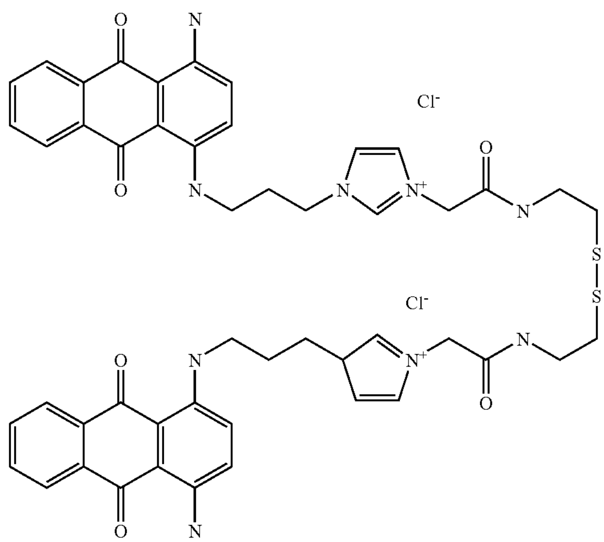 | blue |
| (163) | 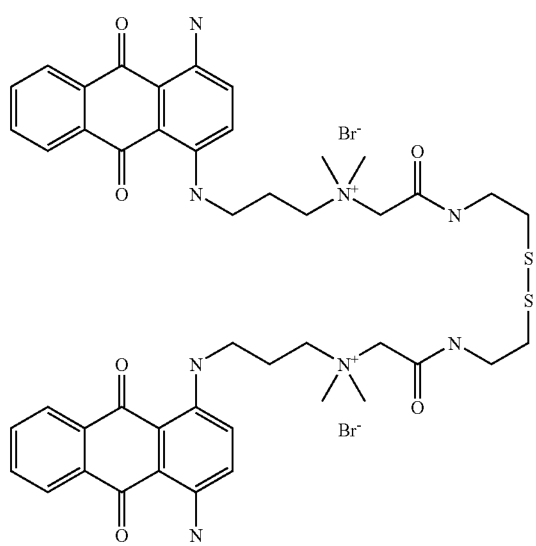 | blue |
| (164) | 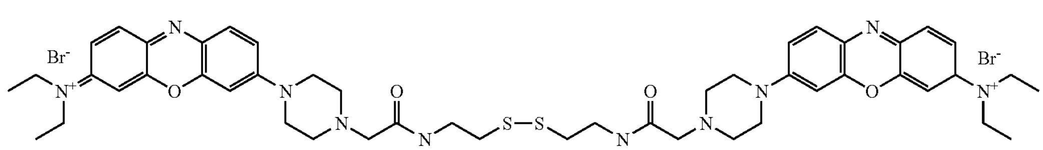 | blue |

For the treatment of hair the following compositions were used:

Composition (B-1)

Permanent-Formulation
(amounts in percent by weight)

| | |
|---|---|
| Ammonium Thioglycolate (71%) | 21.6 |
| Ammonium Hydrogencarbonate | 5.00 |
| Polyquaternium-11 | 1.00 |
| Hydrogenated Ricinus Oil Polyolester | 0.80 |
| Ethoxy Diglycol | 1.50 |
| Chlorophyllin | 0.05 |
| Perfume | 0.2 |
| Ammonia | pH 8.5 |
| Water | ad 100.00 |

Composition (B-2)

Dyeing-Formulation
(amounts in percent by weight)

| | |
|---|---|
| Dye mixture as described in tables 2 and 3. | X |
| cetyl stearyl alcohol | 11.00 |
| Oleth-5 | 5.0 |
| oleic acid | 2.5 |
| stearic acid monoethanolamide | 2.5 |
| coconut fatty acid monoethanolamide | 2.5 |
| sodium lauryl sulfate | 1.7 |
| 1,2-propanediol | 1.0 |
| ammonium chloride | 0.5 |
| EDTA, tetrasodium salt | 0.2 |
| perfume | 0.4 |
| wheat protein hydrolysate | 0.2 |
| Silica | 0.1 |
| Ammonia (25%) | 9.2 |

Composition (B-2)

Dyeing-Formulation
(amounts in percent by weight)

| | |
|---|---|
| composition: pH | 9.8 |
| Water | ad 100 |

Composition (B-3)

Permanent Fixation-Formulation
(amounts in percent by weight)

| | |
|---|---|
| Hydrogen Peroxide | 2.5 |
| Cetyl Stearylalcohol | 2.0 |
| Sodium Laurylethersulfate | 1.2 |
| $C_{12}$-$C_{14}$-Alkylpolyglykolether | 1.0 |
| Perfume | 0.2 |
| Water | ad 100.0 |

These three compositions (b-1)-(b-3) are applied to hair according to the following the general procedure:

A tress of bleached human hair is shampooed. Then the towel dried hair tress is put on the glass plate. The solution (B-1) (permanent solution) is applied to the wet hair tress. After 10 min the hair tress is rinsed under tap water and pressed out with a paper towel. Afterwards the tress is treated with a solution (B-2) containing the dye mixtures described in table 2 for 20 min and then rinsed with water. Then solution (B-3) (permanent fixation) is applied to the towel dried hair tress. After 10 min. the hair tress is rinsed under tap water again and dried.

The color result for each dye mixture is given in tables 2 and 3. In general all tresses showed an intense coloration and a very good wash fastness.

TABLE EX-2

Combinations of two sulfide dyes

| Comp. of formula | Color | Formulation No.: | | | | | | | | | |
|---|---|---|---|---|---|---|---|---|---|---|---|
| | | 1 | 2 | 3 | 4 | 5 | 6 | 7 | 8 | 9 | 10 |
| (101) | yellow | 0.05 | | | | | | | | | |
| (102) | yellow | | | | | | | | 0.05 | | |
| (103) | yellow | | 0.05 | | | | | | | 0.05 | |
| (104) | yellow | | | | | | | | | | |
| (105) | yellow | | | | | | | | | | |
| (106) | yellow | | | | | | | | | | |
| (107) | yellow | | | | 0.05 | | | | | | |
| (108) | yellow | | | | | | | | | | |
| (109) | yellow | | | | | 0.05 | | | | | |
| (110) | yellow | | | | | | 0.05 | | | | |
| (111) | yellow | | | | | | | 0.05 | | | |
| (112) | yellow | | | | | | | | 0.05 | | |
| (113) | orange | 0.05 | | | | | | | | | |
| (114) | orange | | | | | | | | | | |
| (115) | orange | | | 0.05 | | | | | | | 0.05 |
| (116) | orange | | | | | | | | | | |
| (117) | orange | | | | | | | | | | |
| (118) | orange | | | | | | | | | | |
| (119) | orange | | | | | 0.05 | | | | | |
| (120) | orange | | | | | | | | | | |
| (121) | orange | | | | | | | | | | |
| (122) | orange | | | | | | | | | | |
| (123) | orange | | | | | | | | | | |
| (124) | orange | | | | | | | | | | |

TABLE EX-2-continued

Combinations of two sulfide dyes

| Comp. of formula | Color | Formulation No.: | | | | | | | | | |
|---|---|---|---|---|---|---|---|---|---|---|---|
| | | 1 | 2 | 3 | 4 | 5 | 6 | 7 | 8 | 9 | 10 |
| (125) | orange | | | | | | | | | | |
| (126) | orange | | | | | | | | | | |
| (127) | orange | | | | | | | | | | |
| (128) | orange | | | | | | | | | | 0.05 |
| (129) | red | | | | | | | | | | 0.05 |
| (130) | red | | | | | | | | | | |
| (131) | red | | | | | | | | | | |
| (132) | red | | | | 0.05 | | | | | | |
| (133) | red | | | | | 0.05 | | | | | |
| (134) | red | | | | | | | | | | |
| (135) | red | | | | | | | | | | |
| (136) | red | | | | | | | | | | |
| (137) | red | | | | | | | | | | |
| (138) | red | | | | | | | | | | |
| (139) | red | | | | | | 0.05 | | | | |
| (140) | red | | | | | | | | | | |
| (141) | pink | | | | | | | | | | |
| (142) | pink | | | | | | | | | | |
| (143) | pink | | | | | | | 0.05 | | | |
| (144) | pink | | | | | | | | | | |
| (145) | pink | | | | | | | | | | |
| (146) | violet | | | | | | | | 0.05 | | |
| (147) | violet | | | | | | | | | | |
| (148) | violet | | | | | | | | | | |
| (149) | violet | | | | | | | | | | |
| (150) | violet | | | | | | | | | | |
| (151) | violet | | | | | | | | | | |
| (152) | violet | | | | | | | | | | |
| (153) | blue | | | | | | | | | 0.05 | |
| (154) | blue | | | | | | | | | | |
| (155) | blue | | | | | | | | | | |
| (156) | blue | | | | | | | | | | |
| (157) | blue | | | | | | | | | | |
| (158) | blue | | | | | | | | | | |
| (159) | blue | | | | | | | | | | |
| (160) | blue | | | | | | | | | | |
| (161) | blue | | | | | | | | | | |
| (162) | blue | | | | | | | | | | |
| (163) | blue | | | | | | | | | | |
| (164) | blue | | | | | | | | | | |
| Total dye content X | | 0.1 | 0.1 | 0.1 | 0.1 | 0.1 | 0.1 | 0.1 | 0.1 | 0.1 | 0.1 |
| Color result on bleached hair[1] | | C | C | C | O | O | O | B | B | G | R |

| Comp. of formula | Color | Formulation No.: | | | | | | | | | |
|---|---|---|---|---|---|---|---|---|---|---|---|
| | | 11 | 12 | 13 | 14 | 15 | 16 | 17 | 18 | 19 | 20 |
| (101) | yellow | | | | | | | | | | |
| (102) | yellow | | | | | | | | | | |
| (103) | yellow | | | | | | 0.1 | | | | |
| (104) | yellow | | | | | | | | | | |
| (105) | yellow | | | | | | | | | | |
| (106) | yellow | | | | | | | | | | |
| (107) | yellow | | | | | | | | | | |
| (108) | yellow | | | | | | | | | | |
| (109) | yellow | | | | | | | | | | |
| (110) | yellow | | | | | | | | | | |
| (111) | yellow | | | | | | | | | | |
| (112) | yellow | | | | | | | | | | |
| (113) | orange | | | | | | | | | | |
| (114) | orange | | | | | | 0.1 | | | | |
| (115) | orange | | | | | | | 0.5 | | | |
| (116) | orange | | | | | | | | | | |
| (117) | orange | | | | | | | | | | |

-continued

| Comp. of formula | Color | \multicolumn{10}{c}{Formulation No.:} | | | | | | | | | |
|---|---|---|---|---|---|---|---|---|---|---|---|
| | | 11 | 12 | 13 | 14 | 15 | 16 | 17 | 18 | 19 | 20 |
| (118) | orange | | | | | | | | | | |
| (119) | orange | 0.05 | | | | | | | | | |
| (120) | orange | | | | | | | | | | |
| (121) | orange | | | | | | | | | | |
| (122) | orange | | | | | | | | | | |
| (123) | orange | | | | | | | | | | |
| (124) | orange | | | | | | | | | | |
| (125) | orange | | | | | | | | | | |
| (126) | orange | | | | | | | | | | |
| (127) | orange | | 0.05 | | | | | | | | |
| (128) | orange | | | | | | | | | | |
| (129) | red | | | | | | | | | | |
| (130) | red | | | 0.05 | | | | | | | |
| (131) | red | | | | 0.05 | | | | | | |
| (132) | red | | | | | | | | | | |
| (133) | red | | | | | | | | | | |
| (134) | red | | | | | | | | | | 0.1 |
| (135) | red | | | | | | | | | | |
| (136) | red | | | | | | | | | | |
| (137) | red | | | | | | | | | | |
| (138) | red | | | | | | | | | | |
| (139) | red | | | | | | | | | | |
| (140) | red | | | | | | | | | 0.05 | |
| (141) | pink | 0.05 | | | | | | | | 0.05 | |
| (142) | pink | | | | | | | | | | |
| (143) | pink | | | | | | | | | | |
| (144) | pink | | | | | | | | | | |
| (145) | pink | | | | | | | | | | |
| (146) | violet | | | | | | | | | | |
| (147) | violet | | | 0.05 | | | | | | | |
| (148) | violet | | | | | 0.05 | | | | | |
| (149) | violet | | | | | | | 0.5 | | | |
| (150) | violet | | | | | | | | | | |
| (151) | violet | | | | | | | | | | |
| (152) | violet | | | | | | | | | | |
| (153) | blue | | | | | | | | | | |
| (154) | blue | | | | | | | | | | |
| (155) | blue | | | | 0.05 | | | | | | |
| (156) | blue | | | | | | | | | | 0.2 |
| (157) | blue | | | | | | | | 0.05 | | |
| (158) | blue | | 0.05 | | | | | | | | |
| (159) | blue | | | | | | | | | 0.05 | |
| (160) | blue | | | | | | | | | | |
| (161) | blue | | | | | 0.05 | | | | | |
| (162) | blue | | | | | | | | | | |
| (163) | blue | | | | | | | | | | |
| (164) | blue | | | | | | | | | | |
| Total dye content X | | 0.1 | 0.1 | 0.1 | 0.1 | 0.1 | 0.1 | 0.2 | 1.0 | 0.1 | 0.1 |
| Color result on bleached hair[1] | | C | B | B | V | V | V | C | B | B | B |

[1] C = copper, B = brown, G = green, V = violet

TABLE EX-3

Combinations of three and four sulfide dyes

| Comp. of formula | Color | \multicolumn{10}{c}{Formulation No.:} | | | | | | | | | |
|---|---|---|---|---|---|---|---|---|---|---|---|
| | | 21 | 22 | 23 | 24 | 25 | 26 | 27 | 28 | 29 | 30 |
| (101) | yellow | 0.1 | | | | | | | | | |
| (102) | yellow | | | | 0.3 | | | | | | |
| (103) | yellow | | 0.05 | | | | | | | 0.3 | |
| (104) | yellow | | | | | | | | | | |
| (105) | yellow | | | | | | | | | | |
| (106) | yellow | | | | | | | | | | |
| (107) | yellow | | | | | | | | | | |
| (108) | yellow | | | | | | | | | | |
| (109) | yellow | | | | | | | | 0.1 | | |
| (110) | yellow | | | | | | | | | | 0.1 |
| (111) | yellow | | | 0.07 | | | 0.06 | | | | |

TABLE EX-3-continued

Combinations of three and four sulfide dyes

| | Color | | | | | | | | | | |
|---|---|---|---|---|---|---|---|---|---|---|---|
| (112) | yellow | | | | | | 0.06 | | | | |
| (113) | orange | | | | 0.4 | | | | | | |
| (114) | orange | | | | | | | | | | 0.1 |
| (115) | orange | | | | | | | | | | |
| (116) | orange | | | | | | | | | | |
| (117) | orange | | | | | | | | | | |
| (118) | orange | | | | | | | | | | |
| (119) | orange | | | | | | | | | | |
| (120) | orange | | | | | | | | | | |
| (121) | orange | | | | | | | | | | |
| (122) | orange | | | | | | | | | | |
| (123) | orange | | | | | | | | | | |
| (124) | orange | | | | | | | | | | |
| (125) | orange | | | | | | | | | | |
| (126) | orange | | | | | | | | | | |
| (127) | orange | | | | | | | | | | |
| (128) | orange | | | | | | | | | | |
| (129) | red | | | | | | | 0.1 | | | |
| (130) | red | | | | | | | | | | |
| (131) | red | | | | | | | | | | |
| (132) | red | 0.1 | | | | 0.01 | | | | | |
| (133) | red | | | 0.1 | | 0.01 | 0.3 | | | | |
| (134) | red | | | | 0.3 | | | | | | |
| (135) | red | | | | | | | | | | |
| (136) | red | | | | | | | | | | |
| (137) | red | | | | | | | | | | |
| (138) | red | | | | | | | | | | |
| (139) | red | 0.05 | | | | | | | | | |
| (140) | red | | 0.01 | | | | | | | | |
| (141) | pink | | | | | | | | | | |
| (142) | pink | | | | | | | | | | |
| (143) | pink | | | | | | | | | | |
| (144) | pink | | | | | | | | | | |
| (145) | pink | | | | | | | | | | |
| (146) | violet | | | | | | | | | | 0.1 |
| (147) | violet | | | | | | | | | | |
| (148) | violet | | | | | | | | | | |
| (149) | violet | | | | | | | | | | |
| (150) | violet | | | | | | | | | | |
| (151) | violet | | | | | | | | | | |
| (152) | violet | | | | | | | | | | |
| (153) | blue | 0.1 | | | | | | | | | |
| (154) | blue | | | | | | | | | | |
| (155) | blue | | | | | | | | | | |
| (156) | blue | | | | | | | | | | |
| (157) | blue | 0.05 | | | | | | | | | |
| (158) | blue | | | | | | 0.03 | | | | |
| (159) | blue | | 0.03 | | | | | | | | |
| (160) | blue | | | | | 0.03 | | | | | |
| (161) | blue | | | 0.1 | | | | | 0.4 | 1.2 | |
| (162) | blue | | | | | | | | | | |
| (163) | blue | | | | | | | | | | |
| (164) | blue | | | | 0.3 | | | | | | |
| Total dye content X | | 0.1 | 0.3 | 0.15 | 0.11 | 0.5 | 1.0 | 0.1 | 0.1 | 0.6 | 1.8 |
| Color result on bleached hair[1)] | | C | B | B | B | B | B | B | B | S | S |

| Comp. of formula | Color | Formulation No.: | | | | | | | | | |
|---|---|---|---|---|---|---|---|---|---|---|---|
| | | 31 | 32 | 33 | 34 | 35 | 36 | 37 | 38 | 39 | 40 |
| (101) | yellow | | | | | | | | | | |
| (102) | yellow | | | | | | | | | | |
| (103) | yellow | | | | 0.5 | | | | | | |
| (104) | yellow | | | | | 0.03 | | | | | |
| (105) | yellow | | | | | | 0.03 | | | | |
| (106) | yellow | | | | | | | 0.06 | | | |
| (107) | yellow | | | | | | | | 0.1 | | |
| (108) | yellow | | | | | | | | | 0.2 | |
| (109) | yellow | | | | | | | | | | 0.4 |
| (110) | yellow | | | | | | | | | | |
| (111) | yellow | | | | | | | | | | |
| (112) | yellow | 0.07 | | | | | | | | | |
| (113) | orange | | 0.07 | | | | | | | | |
| (114) | orange | | | | | | | | | | |
| (115) | orange | | | 0.07 | | | | | | | |

TABLE EX-3-continued

Combinations of three and four sulfide dyes

| # | Color | C1 | C2 | C3 | C4 | C5 | C6 | C7 | C8 | C9 | C10 |
|---|---|---|---|---|---|---|---|---|---|---|---|
| (116) | orange | | | | | 0.03 | | | | | |
| (117) | orange | | | | | | | | | | |
| (118) | orange | | | | | | | | | | |
| (119) | orange | 0.02 | | | | | | | | | |
| (120) | orange | | | | | | 0.01 | | | | |
| (121) | orange | | | | | | | | | | |
| (122) | orange | | | | | | | | | | |
| (123) | orange | | | | | | | | | | |
| (124) | orange | | | | | | | | | | |
| (125) | orange | | | | | | | | | | |
| (126) | orange | | | | | | | | | | |
| (127) | orange | | | | | | | | | | |
| (128) | orange | | | | 0.03 | | | | | | |
| (129) | red | | | | | | | | | | |
| (130) | red | | 0.01 | | | | | | | | |
| (131) | red | | | | | | | | | | |
| (132) | red | | | | | | | 0.1 | | | |
| (133) | red | | | | 0.5 | | | | 0.2 | | |
| (134) | red | | | | | | | | | 0.4 | |
| (135) | red | | | 0.01 | | | | | | | |
| (136) | red | | | | | | | 0.01 | | | |
| (137) | red | | | | | 0.03 | | | | | |
| (138) | red | | | | | 0.03 | | | | | |
| (139) | red | | | | | | | | | | |
| (140) | red | | | | | | | | | | |
| (141) | pink | | | | | | | | | | |
| (142) | pink | | | | | | | | | | |
| (143) | pink | | | | | | | | | | |
| (144) | pink | | | | | | | | | | |
| (145) | pink | | | | | | | | | | |
| (146) | violet | 0.1 | | | | | | | | | |
| (147) | violet | | | | | | | | 0.4 | | |
| (148) | violet | | | | | | | | | | |
| (149) | violet | | 0.02 | | | | | | | | |
| (150) | violet | | | 0.03 | | | | | | | |
| (151) | violet | | | | | | | | | | 0.8 |
| (152) | violet | | | 0.03 | | | | | | | |
| (153) | blue | | | | | | | | | | |
| (154) | blue | | | | | 0.03 | | | | | |
| (155) | blue | | | | | | 0.03 | | | | |
| (156) | blue | | | | | | | | 0.4 | | |
| (157) | blue | | | | | | | | | | |
| (158) | blue | | | | | | | | | | |
| (159) | blue | | | | | | | | | | |
| (160) | blue | | | | | | | | | | |
| (161) | blue | | | | 2.0 | | | 0.03 | | | 1.6 |
| (162) | blue | | | | | | | | 0.8 | | |
| (163) | blue | | | | | | | | | | |
| (164) | blue | | | | | | | | | | |
| Total dye content X | | 0.11 | 0.11 | 0.11 | 3.0 | 0.12 | 0.12 | 0.11 | 1.0 | 2.0 | 4.0 |
| Color result on bleached hair[1] | | B | B | B | S | B | B | B | S | S | S |

[1] B = brown, S = black

The invention claimed is:

1. A mixture of dyes selected from the compounds of formula (1)

  (1), wherein

A is hydrogen; a radical of formula (1a) *—S—Y$_2$—(Z$_2$)$_r$-D$_2$; or a thio ester group of formula (1b)

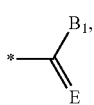

wherein

E is O; S; or N—R$_a$;

B$_1$ is —OR$_b$; —NR$_b$R$_c$; or —SR$_b$;

R$_a$, R$_b$ and R$_c$, independently from each other are hydrogen; C$_1$-C$_{12}$alkyl; C$_6$-C$_{12}$aryl; or C$_6$-C$_{12}$aryl-C$_1$-C$_{12}$alkyl;

D$_1$ and D$_2$ independently from each other is a radical of formula

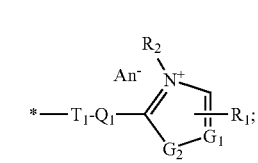  (1a$_1$)

-continued

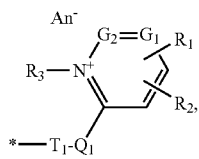
(1a₂)

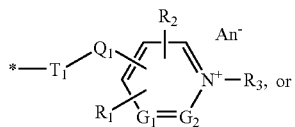
(1a₃)

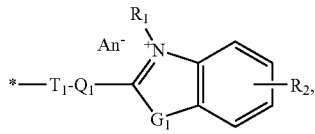
(1a₄)

and formula

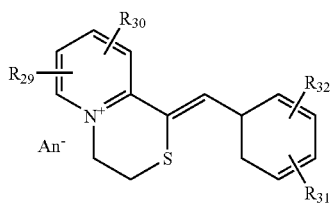
(2)

wherein the mixture comprises at least two compounds of formula (1), and/or at least two compounds of formula (2) and/or at least one compound of formula (1) and at least one compound of formula (2), wherein $R_1$, $R_2$ and $R_3$ independently from each other hydrogen; halogen; $C_1$-$C_{16}$alkyl, which is saturated or unsaturated, linear or branched, substituted or unsubstituted, or interrupted or uninterrupted with heteroatoms; phenyl, which substituted or unsubstituted; a carboxylic acid radical; sulfonic acid radical; hydroxy; nitrile; $C_1$-$C_{16}$alkoxy, (poly)-hydroxy-$C_2$-$C_4$-alkoxy; halogen; $SO_2NR_{33}R_{34}$; $SR_{33}$; $NR_{33}R_{34}$; $OR_{33}$; $SO_2$; $COOR_{33}$; $NR_{33}COR_{34}$; or $CONR_{33}$;

$Q_1$ is a bivalent radical selected from —N═N—; —$CR_d$═N—; —N═$CR_d$—; —$NR_d$—N═$CR_e$—; and —$R_dC$═N—$NR_e$—;

$T_1$ is a bivalent radical of an aromatic or heteroaromatic substituted or unsubstituted compound;

$R_d$ and $R_e$ independently from each other are hydrogen; unsubstituted or substituted $C_1$-$C_{14}$alkyl; $C_2$-$C_{14}$alkenyl; $C_5$-$C_{10}$aryl; $C_1$-$C_{10}$alkyl-$C_5$-$C_{10}$aryl; or $C_5$-$C_{10}$aryl-$C_1$-$C_{10}$alkyl;

$R_{33}$ and $R_{34}$ independently from each other are hydrogen; $C_1$-$C_{12}$alkyl, which may be substituted by one or more $C_1$-$C_5$alkyl, $C_1$-$C_5$-alkoxy, hydroxy or —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$Y_1$ and $Y_2$ independently from each other are unsubstituted or substituted, straight-chain or branched, interrupted or uninterrupted $C_1$-$C_{10}$alkylene; $C_5$-$C_{10}$cycloalkylene; $C_5$-$C_{10}$arylene; or —$C_5$-$C_{10}$arylene-($C_1$-$C_{10}$alkylene);

$Z_1$ and $Z_2$ independently from each other are *—$(CH_2)_q$—C(O)—**; *—$(CH_2CH_2$—O$)_w$—**; *—$(CH_2)_q$—C(O)O—**; *—$(CH_2)_q$—OCO—**; *—$(CH_2)_q$—N($R_{60}$)—**;

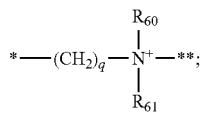

*—$(CH_2)_q$—CON($R_{60}$)—**; *—$(CH_2)_q$—($R_{60}$)NC(O)—**; —O—; —S—; —S(O)—; —S(O)$_2$—; or a cationic biradical of a substituted or unsubstituted aromatic or heteroaromatic compound of the formula

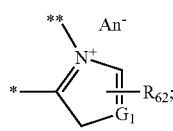
(1a)

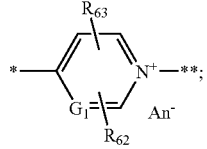
(1b)

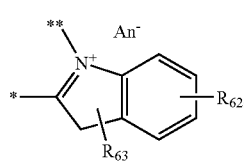
(1c)

(1d)

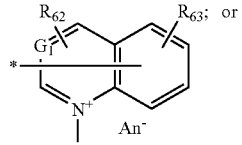

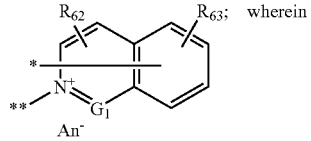
(1e)

$G_1$ and $G_2$ independently from each other are N; —O—; —S—; or a radical of $CR_{64}$;

the asterix * indicates the linkage to $D_1$ and/or $D_2$;
the asterix ** indicates the linkage to $Y_1$ and/or $Y_2$;

$R_{60}$, $R_{61}$, $R_{62}$, $R_{63}$ and $R_{64}$ independently from each other are hydrogen; $C_1$-$C_{14}$alkyl; $C_2$-$C_{14}$alkenyl; $C_6$-$C_{10}$aryl; $C_5$-$C_{10}$aryl-($C_1$-$C_{10}$alkyl); or —$C_1$-$C_{10}$alkyl($C_5$-$C_{10}$aryl);

$R_{29}$, $R_{30}$, $R_{31}$ and $R_{32}$ independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; —$NR_{65}R_{66}$; —$NO_2$; —(CO)H or (CO)—$C_1$-$C_5$alkyl; $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl; —$NR_{67}R_{68}$; —$NO_2$; —(CO)—H; or —(CO)—$C_1$-$C_5$alkyl;

$R_{65}$, $R_{66}$, $R_{67}$ and $R_{68}$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; phenyl or phenyl-$C_1$-$C_5$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

q is a number from 0 to 5;

w is a number from one to 5;

r is 0; or 1; and

An is an anion.

2. A dyeing mixture according to claim 1, wherein $Y_1$ and $Y_2$ are $C_1$-$C_5$alkylene.

3. A dyeing mixture according to claim 1, wherein $Z_1$ and $Z_2$ independently from each are other —$N(R_{60})$—;

$$-\overset{R_{60}}{\underset{R_{61}}{N^+}}-;$$

—$CON(R_{60})$—; —$(CH_2)_qNC(O)$—; —O—; or —S—; and $R_{60}$ $R_{61}$ and q are defined as in claim 1.

4. A dyeing mixture according to claim 1, wherein
A is a radical of formula (1a); and
$D_2$ has the same meaning as $D_1$;
$Y_2$ has the same meaning as $Y_1$; and
$Z_2$ has the same meaning as $Z_1$.

5. A dyeing mixture according to claim 1, wherein $D_1$ and $D_2$ independently from each other are a radical of formula (1a₈)

(1a₉)

-continued (1a₁₀)

(1a₁₁)

(1a₁₂)

$R_1$, $R_2$, $Q_1$, $T_1$ and $An^-$ independently from each other are defined as in claim 1.

6. A dyeing mixture according to claim 1, wherein the dyes are selected from the compounds of formula (AZO-01)

$R_{69}$, $R_{70}$, $R_{72}$ and $R_{73}$ independently from each other are hydrogen; unsubstituted or substituted $C_1$-$C_{14}$alkyl; $C_5$-$C_{10}$cycloalkyl; $C_2$-$C_{14}$alkenyl; $C_5$-$C_{10}$aryl-($C_1$-$C_{10}$alkyl); $C_1$-$C_{10}$alkyl-($C_5$-$C_{10}$aryl); $C_5$-$C_{10}$aryl;

$R_{71}$ is hydrogen; or a radical of formula (2a)

An is an anion; and $Y_1$ is defined as in claim 1.

7. A dyeing mixture according to claim 1, wherein $D_1$ is selected from the radicals of formulae (1h₃)

-continued (1h4)
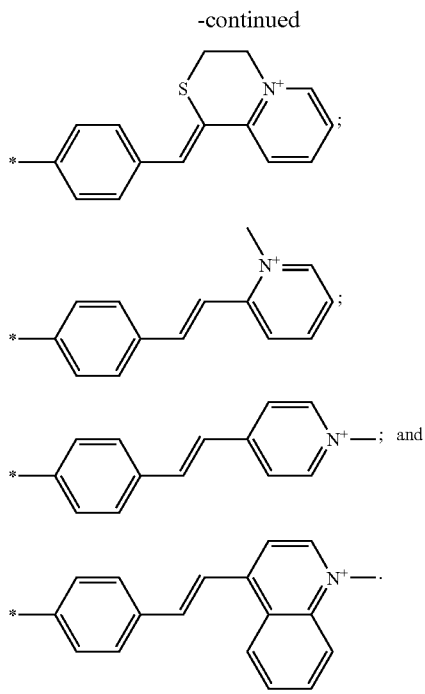
(1h5)

(1h6); and (1h7)

8. A dyeing mixture according to claim 1, wherein the dyes are selected from the compounds of formula (PYR-02)
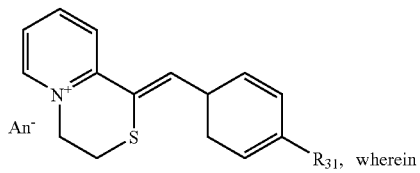
$R_{31}$, wherein $R_{31}$ is hydrogen; $C_1$-$C_5$-alkoxy; halogen; or —$NR_pR_q$, wherein $R_p$ and $R_q$, independently from each other are hydrogen; $C_1$-$C_{12}$alkyl; —(CO)—H; or —(CO)—$C_1$-$C_5$alkyl; and An is an anion.

9. A method of dyeing keratin-containing fibers comprising treating the fiber with a mixture of dyes according to formula (1) and formula (2) wherein $$D_1\text{-}(Z_1)_r\text{—}Y_1\text{—}S\text{-}A \quad (1)$$

wherein

A is hydrogen; a radical of formula (1a) *—S—$Y_2$—$(Z_2)_r$-$D_2$; or a thio ester group of formula (1b)
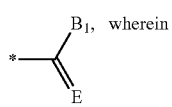
$B_1$, wherein E is O; S; or N—$R_a$;
$B_1$ is —$OR_b$; $NR_bR_c$; or —$SR_b$;
$R_a$, $R_b$ and $R_c$, independently from each other are hydrogen; $C_1$-$C_{12}$alkyl; $C_6$-$C_{12}$aryl; or $C_6$-$C_{12}$aryl-$C_1$-$C_{12}$alkyl;

$D_1$ and $D_2$ independently from each other is a radical of formula

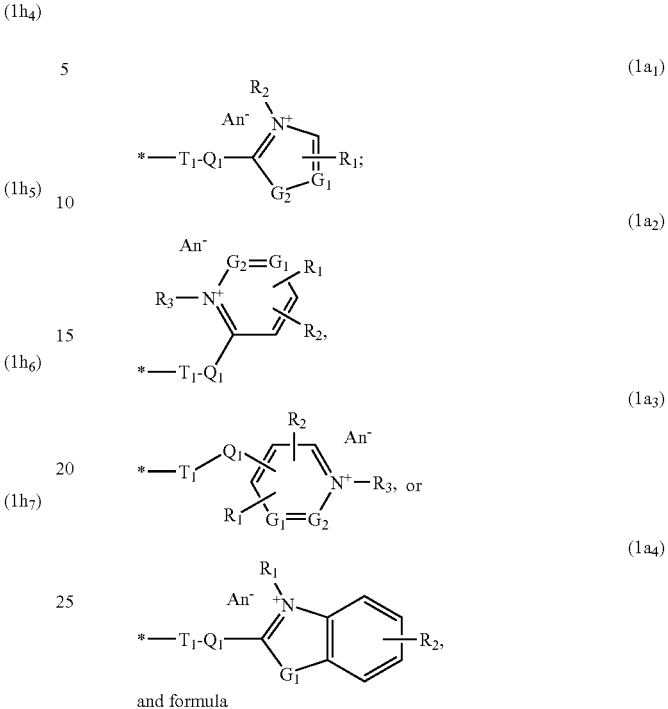

and formula (2)

wherein the mixture comprises at least two compounds of formula (1), and/or at least two compounds of formula (2) and/or at least one compound of formula (1) and at least one compound of formula (2), wherein $R_1$, $R_2$ and $R_3$ independently from each other hydrogen; halogen; $C_1$-$C_{16}$alkyl, which is saturated or unsaturated, linear or branched, substituted or unsubstituted, or interrupted or uninterrupted with heteroatoms; phenyl, which substituted or unsubstituted; a carboxylic acid radical; sulfonic acid radical; hydroxy; nitrile; $C_1$-$C_{16}$alkoxy, (poly)-hydroxy-$C_2$-$C_4$-alkoxy; halogen; $SO_2NR_{33}R_{34}$; $SR_{33}$; $NR_{33}R_{34}$; $OR_{33}$; $SO_2$; $COOR_{33}$; $NR_{33}COR_{34}$; or $CONR_{33}$;

$Q_1$ is a bivalent radical selected from —N═N—; —$CR_d$═N—; —N═$CR_d$—; —$NR_d$—N═$CR_e$—; and —$R_dC$═N—$NR_e$—;

$T_1$ is a bivalent radical of an aromatic or heteroaromatic substituted or unsubstituted compound;

$R_d$ and $R_e$ independently from each other are hydrogen; unsubstituted or substituted $C_1$-$C_{14}$alkyl; $C_2$-$C_{14}$alkenyl; $C_5$-$C_{10}$aryl; $C_1$-$C_{10}$alkyl-$C_5$-$C_{10}$aryl; or $C_5$-$C_{10}$aryl-$C_1$-$C_{10}$alkyl;

$R_{33}$ and $R_{34}$ independently from each other are hydrogen; $C_1$-$C_{12}$alkyl, which may be substituted by one or more $C_1$-$C_5$alkyl, $C_1$-$C_5$-alkoxy, hydroxy or —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$Y_1$ and $Y_2$ independently from each other are unsubstituted or substituted, straight-chain or branched, interrupted or uninterrupted $C_1$-$C_{10}$alkylene; $C_5$-$C_{10}$cycloalkylene; $C_5$-$C_{10}$arylene; or —$C_5$-$C_{10}$arylene-($C_1$-$C_{10}$alkylene);

$Z_1$ and $Z_2$ independently from each other are *—$(CH_2)_q$—C(O)—**; *—$(CH_2CH_2$—$O)_w$—**; *—$(CH_2)_q$—C(O)O—**; *—$(CH_2)_q$—OCO—**; *—$(CH_2)_q$—N($R_{60}$)—**;

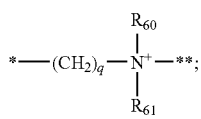

*—$(CH_2)_q$—CON($R_{60}$)—**; *—$(CH_2)_q$—$(R_{60})$NC(O)—**; —O—; —S—; —S(O)—; —S(O)$_2$—; or a cationic biradical of a substituted or unsubstituted aromatic or heteroaromatic compound of the formula

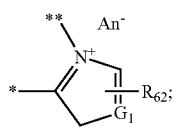 (1a)

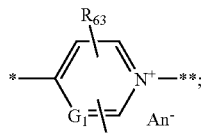 (1b)

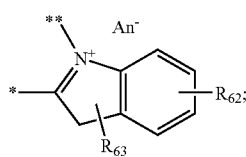 (1c)

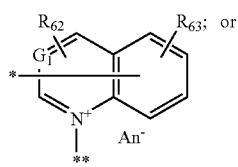 (1d)

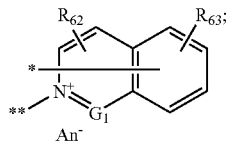 (1e)

wherein $G_1$ and $G_2$ independently from each other are N; —O—; —S—; or a radical of $CR_{64}$;

the asterix * indicates the linkage to $D_1$ and/or $D_2$;
the asterix ** indicates the linkage to $Y_1$ and/or $Y_2$;

$R_{60}$, $R_{61}$, $R_{62}$, $R_{63}$ and $R_{64}$ independently from each other are hydrogen; $C_1$-$C_{14}$alkyl; $C_2$-$C_{14}$alkenyl; $C_6$-$C_{10}$aryl; $C_5$-$C_{10}$aryl-($C_1$-$C_{10}$alkyl); or —$C_1$-$C_{10}$alkyl($C_5$-$C_{10}$aryl);

$R_{29}$, $R_{30}$, $R_{31}$ and $R_{32}$ independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; —$NR_{65}R_{66}$; —$NO_2$; —(CO)H or (CO)—$C_1$-$C_5$alkyl; $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl; —$NR_{67}R_{68}$; —$NO_2$; —(CO)—H; or —(CO)—$C_1$-$C_5$alkyl;

$R_{65}$, $R_{66}$, $R_{67}$ and $R_{68}$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; phenyl or phenyl-$C_1$-$C_5$alkyl, wherein the phenyl moiety may be substituted by one or more $C_1$-$C_5$alkyl; $C_1$-$C_5$alkoxy, halogen, —$NH_2$, mono-$C_1$-$C_5$alkylamino, di-$C_1$-$C_5$alkylamino, —$NO_2$, carboxy or hydroxy;

q is a number from 0 to 5;
w is a number from one to 5;
r is 0; or 1; and
An is an anion.

10. A method according to claim 9, wherein the dyeing is carried out in presence of a reducing agent.

11. A method according to claim 10, wherein the reducing agent is selected from the group consisting of thioglycol acid or salts thereof, gycerine monothioglycolate, cystein, 2-mercaptopropionic acid, 2-mercaptoethylamine, thiolactic acid, thioglycerine, sodium sulfite, dithionithe, ammonium sulfite, sodium bisulfite, sodium metabisulfite and hydrochinon.

12. A method according to claim 9, comprising treating the keratin-containing fiber
(a) optionally with a reduction agent, and
(b) with a mixture of dyes, and
(c) optionally with an oxidizing agent.

13. A composition comprising a mixture of dyes according to formula (1) and formula (2) wherein $$D_1\text{-}(Z_1)_r\text{—}Y_1\text{—}S\text{-}A \qquad (1)$$

wherein

A is hydrogen; a radical of formula (1a) *—S—$Y_2$—$(Z_2)_r$-$D_2$ or a thio ester group of formula

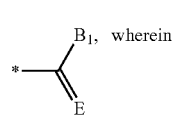 (1b)

E is O; S; or N—$R_a$;
$B_1$ is —$OR_b$; —$NR_bR_c$ or —$SR_b$;
$R_a$, $R_b$ and $R_c$ independently from each other are hydrogen; $C_1$-$C_{12}$alkyl; $C_6$-$C_{12}$aryl; or $C_6$-$C_{12}$aryl-$C_1$-$C_2$alkyl;
$D_1$ and $D_2$ independently from each other is a radical of formula

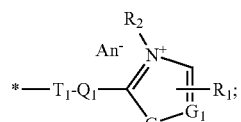 (1a$_1$)

-continued

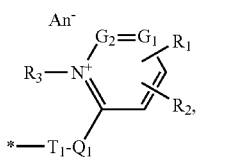
(1a₂)

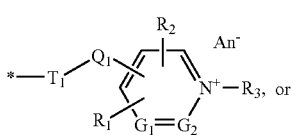
(1a₃)

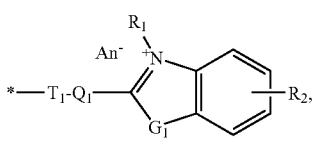
(1a₄)

and formula

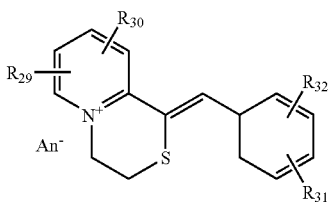
(2)

wherein the mixture comprises at least two compounds of formula (1), and/or at least two compounds of formula (2) and/or at least one compound of formula (1) and at least one compound of formula (2), wherein $R_1$, $R_2$ and $R_3$ independently from each other hydrogen; halogen; $C_1$-$C_{16}$alkyl, which is saturated or unsaturated, linear or branched, substituted or unsubstituted, or interrupted or uninterrupted with heteroatoms; phenyl, which substituted or unsubstituted; a carboxylic acid radical; sulfonic acid radical; hydroxy; nitrile; $C_1$-$C_{16}$alkoxy, (poly)-hydroxy-$C_2$-$C_4$-alkoxy; halogen; $SO_2NR_{33}R_{34}$; $SR_{33}$; $NR_{33}R_{34}$; $OR_{33}$; $SO_2$; $COOR_{33}$; $NR_{33}COR_{34}$; or $CONR_{33}$;

$Q_1$ is a bivalent radical selected from —N=N—; —$CR_d$=N—; —N=$CR_d$—; —$NR_d$—N=$CR_e$—; and —$R_dC$=N—$NR_e$—;

$T_1$ is a bivalent radical of an aromatic or heteroaromatic substituted or unsubstituted compound;

$R_d$ and $R_e$ independently from each other are hydrogen; unsubstituted or substituted $C_1$-$C_{14}$alkyl; $C_2$-$C_{14}$alkenyl; $C_5$-$C_{10}$aryl; $C_1$-$C_{10}$alkyl-$C_5$-$C_{10}$aryl; or $C_5$-$C_{10}$aryl-$C_1$-$C_{10}$alkyl;

$R_{33}$ and $R_{34}$ independently from each other are hydrogen; $C_1$-$C_{12}$alkyl, which may be substituted by one or more $C_1$-$C_5$alkyl, $C_1$-$C_5$-alkoxy, hydroxy or —(CO)—H; —(CO)—$C_1$-$C_5$alkyl; phenyl or phenyl-$C_1$-$C_4$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

$Y_1$ and $Y_2$ independently from each other are unsubstituted or substituted, straight-chain or branched, interrupted or uninterrupted $C_1$-$C_{10}$alkylene; $C_5$-$C_{10}$cycloalkylene; $C_5$-$C_{10}$arylene; or —$C_5$-$C_{10}$arylene-($C_1$-$C_{10}$alkylene);

$Z_1$ and $Z_2$ independently from each other are *—$(CH_2)_q$—C(O)—**; *—$(CH_2CH_2$—O$)_w$—**; *—$(CH_2)_q$—C(O)O—**; *—$(CH_2)_q$—OCO—**; *—$(CH_2)_q$—N($R_{60}$)—**;

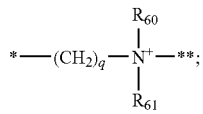

*—$(CH_2)_q$—CON($R_{60}$)—**; *—$(CH_2)_q$—($R_{60}$)NC(O)—**; —O—; —S—; —S(O)—; —$S(O)_2$—; or a cationic biradical of a substituted or unsubstituted aromatic or heteroaromatic compound of the formula

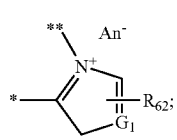
(1a)

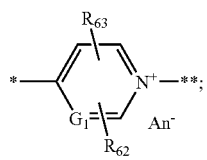
(1b)

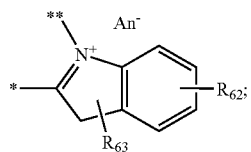
(1c)

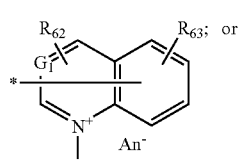
(1d)

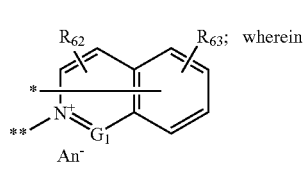
(1e)

wherein $G_1$ and $G_2$ independently from each other are N; —O—; —S—; or a radical of $CR_{64}$;

the asterix * indicates the linkage to $D_1$ and/or $D_2$;
the asterix ** indicates the linkage to $Y_1$ and/or $Y_2$;

$R_{60}$, $R_{61}$, $R_{62}$, $R_{63}$ and $R_{64}$ independently from each other are hydrogen; $C_1$-$C_{14}$alkyl; $C_2$-$C_{14}$alkenyl; $C_6$-$C_{10}$aryl; $C_5$-$C_{10}$aryl-($C_1$-$C_{10}$alkyl); or —$C_1$-$C_{10}$alkyl($C_5$-$C_{10}$aryl);

$R_{29}$, $R_{30}$, $R_{31}$ and $R_{32}$, independently from each other are hydrogen; hydroxy; —S—H; —S—$C_1$-$C_{12}$alkyl; halogen; $C_1$-$C_{12}$alkyl or $C_1$-$C_{12}$alkoxy, which may be substituted by one or more $C_1$-$C_5$alkyl, $C_1$-$C_5$-alkoxy, hydroxy, —(CO)—H or —(CO)—$C_1$-$C_5$alkyl; —$NR_{65}R_{66}$; —$NO_2$; —(CO)H or (CO)—$C_1$-$C_5$alkyl; $C_6$-$C_{12}$aryl, $C_6$-$C_{12}$aryl-$C_1$-$C_4$alkyl or $C_6$-$C_{12}$aryl-$C_1$-$C_4$alkoxy, wherein the aryl moiety may be substituted by one or more $C_1$-$C_5$alkyl, $C_1$-$C_5$alkoxy, —(CO)—H or —(CO)—$C_1$-$C_5$alkyl; —$NR_{67}R_{68}$; —$NO_2$; —(CO)—H; or —(CO)—$C_1$-$C_5$alkyl;

$R_{65}$, $R_{66}$, $R_{67}$ and $R_{68}$ independently from each other are hydrogen; hydroxy; $C_1$-$C_{12}$alkyl; hydroxy-$C_1$-$C_{12}$alkyl; —(CO)—H; —(CO)—$C_1$-$C_5$alkyl; phenyl or phenyl-$C_1$-$C_5$alkyl, wherein the phenyl moiety may be substituted by one or more $C_1$-$C_5$alkyl, $C_1$-$C_5$alkoxy, halogen, —$NH_2$, mono-$C_1$-$C_5$alkylamino, di-$C_1$-$C_5$alkylamino, —$NO_2$, carboxy or hydroxy;

q is a number from 0 to 5;
w is a number from one to 5;
r is 0; or 1; and
An is an anion.

14. A composition according to claim 13 in form of a shampoo, conditioner, gel or emulsion.

15. A composition according to claim 13 comprising mixture of dyes and a direct dye and/or a reactive dye.

\* \* \* \* \*